US007563947B2

(12) United States Patent
Ito et al.

(10) Patent No.: US 7,563,947 B2
(45) Date of Patent: Jul. 21, 2009

(54) PLANT CELLS AND PLANT BODIES WITH MODIFIED CELL GROWTH, DEVELOPMENT AND DIFFERENTIATION

(75) Inventors: Masaki Ito, Nagoya (JP); Satoshi Araki, Kusatsu (JP); Hiroaki Kodama, Matsudo (JP); Yasunori Machida, Nagoya (JP)

(73) Assignee: Ishihara Sangyo Kaisha, Ltd, Osaka (JP)

(*) Notice: Subject to any disclaimer, the term of this patent is extended or adjusted under 35 U.S.C. 154(b) by 219 days.

(21) Appl. No.: 10/548,484

(22) PCT Filed: Mar. 11, 2004

(86) PCT No.: PCT/JP2004/003228

§ 371 (c)(1),
(2), (4) Date: Nov. 10, 2005

(87) PCT Pub. No.: WO2004/081204

PCT Pub. Date: Sep. 23, 2004

(65) Prior Publication Data

US 2006/0107343 A1 May 18, 2006

(30) Foreign Application Priority Data

Mar. 12, 2003 (JP) ............................. 2003-066064

(51) Int. Cl.
*A01H 5/00* (2006.01)
(52) U.S. Cl. ...................................................... 800/298
(58) Field of Classification Search ....................... None
See application file for complete search history.

(56) References Cited

FOREIGN PATENT DOCUMENTS

| WO | 03/000905 | 1/2003 |
|---|---|---|
| WO | 03/007699 | 1/2003 |
| WO | 03/013227 | 2/2003 |

OTHER PUBLICATIONS

Wada et al (1997, Science 277(5329):1113-1116).*
Ito et al (2001, The Plant Cell 13:1891-1905).*
Stracke et al (2001, Current Opinion in Plant Biology 4:447-456).*
Lee et al (1999, Cell 99:473-483).*
Doerner et al (1996, Nature 5(Apr. 11):520-523).*
Yang et al (2001, PNAS 98(20):11438-11443).*
Ito, Masaki et al., "G2/M-Phase-Specific Transcription during the Plant Cell Cycle Is Mediated by c-Myb-Like Transcription Factors", *The Plant Cell*, vol. 13, pp. 1891-1905 (2001).
Stracke, Ralf et al., "The *R2R3-MYB* gene family in *Arabidopsis thaliana*", *Current Opinion in Plant Biology*, vol. 4, pp. 447 to 456 (2001).
Umeda, Masaaki, "Cell Division-Controlling Mechanisms in Organogenesis", *Protein, Nucleic Acid and Enzyme*, vol. 47, No. 12, pp. 1628-1632 (2002).

Okada, Masahiro et al., "Myb controls $G_2/M$ progression by inducing cyclin B expression in the *Drosphila* eye imaginal disc" *The EMBO Journal*, vol. 21, No. 4, pp. 675-684 (2002).
Sasaki, Takuji et al., "The genome sequence and structure or rice chromosome 1", *Nature*, vol. 420, pp. 312-316 (2002).
Database EMBL, Mar. 23, 2001, "Oryza sativa (japonica cultivar-group) genomic DNA, Chromosome 1, PAC clone: P0452F10." XP002445651, retrieved from EBI Accession No. EMBL:AP003434, Database Access No. AP003434.
Database EMBL, Dec. 16, 2002, "Oryza sativa (japonica cultivar-group) partial mRNA for MYB31 protein", XP002445652, retrieved from EBI Accession No. EMBL:AJ495800, Database Access No. AJ495800.
H. Kranz et al., "c-MYB Oncogene-Like Genes Encoding Three MYB Repeats Occur in all Major Plant Lineages", The Plant Journal, Blackwell Scientific Publications, Oxford GB, vol. 21, No. 2, pp. 231-235, Jan. 2000.
S. Araki et al., "Mitotic Cyclins Stimulate the Activity of c-Myb-like Factors for Transactivation of $G_2/M$ Phase-Specific Genes in Tobacco", The Journal of Biological Chemistry, vol. 279, No. 31, pp. 32979-32988, Jul. 30, 2004.
Database UniProt, Dec. 1, 2001,"Myb.", XP002452506, retrieved from EBI Accession No. UniProt: Q948S6, Database Accession No. Q948S6.
Database UniProt, Dec. 1, 2001, "Putative c-myb-like transcription factor MYB3R-4(MYB Transcription Factor)", XP002452507, retrieved from EBI Accession No. UniProt: Q94FL9, Database Accession No. Q94FL9.
Ito et al., "A Novel *cis*-Acting Element in Promoters of Plant B-Type Cyclin Genes Activates M Phase-Specific Transcription", *The Plant Cell*, vol. 10, pp. 331-341, 1998.
Doerner et al., "Control of root growth and development by cyclin expression", *Nature*, vol. 380, pp. 520-523, 1996.
Nishihama et al., "Expansion of the Cell Plate in Plant Cytokinesis Requires a Kinesin-like Protein/MAPKKK Complex", *Cell*, vol. 109, pp. 87-99, 2002.
Dash et al., "The EVES motif mediates both intermolecular and intramolecular regulation of c-Myb", *Genes & Development*, vol. 10, pp. 1858-1869, 1996.

* cited by examiner

*Primary Examiner*—Stuart F. Baum
(74) *Attorney, Agent, or Firm*—Wenderoth, Lind & Ponack, L.L.P.

(57) ABSTRACT

Control of cell cycle is important in crop breeding, and it is demanded to develop, through the control, techniques for modifying cell growth in plants, techniques for modifying the development/differentiation of plant individuals and plant genes for use therein. It has been successfully disclosed that plant gene 3Rmyb is a factor indispensable for the multiplication of plant cells. Thus, there are provided, with the gene as a target, techniques for modifying the multiplication of plant cells and techniques for modifying the development/differentiation of plant individuals, and there can be obtained plants and plant cells retaining modified cell growth and development/differentiation. These enable development of plants with desirable properties, such as specified organ enlargement, male sterility or improved stress resistance.

1 Claim, 32 Drawing Sheets

```
BAB78687    1:-MTSDNGKAPDKGEPSGPPSAPQEGEISNEPKRRRPLNGRTTGPTRRSTKGNWTPEEDA  59
Os3RmybA1   1:MMTSDNGKAPDKGEPSGPPSAPQEGEISNEPKRRRPLNGRTTGPTRRSTKGNWTPEEDA  60
              ***********************************************************

BAB78687   60:ILSRAVQTYNGKNWKKIAECFPDRTDVQCLHRWQKVLNPELVKGPWSKEEDEIIVQMVNK 119
Os3RmybA1  61:ILSRAVQTYNGKNWKKIAECFPDRTDVQCLHRWQKVLNPELVKGPWSKEEDEIIVQMVNK 120
              ************************************************************

BAB78687  120:LGPKKWSTIAQALPGRIGKQCRERWYNHLNPGINKEAWTQEEEITLIHAHRMYGNKWAEL 179
Os3RmybA1 121:LGPKKWSTIAQALPGRIGKQCRERWYNHLNPGINKEAWTQEEEITLIHAHRTYGNKWAEL 180
              ***************************************************  *******

BAB78687  180:TKFLPGRTDNSIKNHWNSSVKKKVNSYMSSGLLTQVSCLPLNEYSANCNSSPAMTQQNSE 239
Os3RmybA1 181:TKFLPGRTDNSIKNHWNSSVKKKVNSYMSSGLLTQVSCLPLNEYSANCNSSPAMTQQNSE 240
              ************************************************************

BAB78687  240:DSGCFAVREVENSSGCSQSSLAKVSCSQVHDTTVPLGCDLQVNANFDKNEAHDSQSSMGP 299
Os3RmybA1 241:DSGCFAVREVENSSGCSQSSLAKVSCSQVHDTTVPLGCDLQVNANFDKNEAHDSQSSMGP 300
              ************************************************************

BAB78687  300:QACYTSAEAVASALPAVHCHVSSSNLDPDQHLQEDFAQGLNLDMTIDEMPTVPSFADNQT 359
Os3RmybA1 301:QACYTSAEAVASALPAVHCHVSSSNLDPDQHLQEDFAQGLNLDMTIDEMPTVPSFADNQT 360
              ************************************************************
```

Fig. 1

```
BAB78687    360:VCSIENHERSLEPYDVAMEVPLSMLSSDSGAEQKLHFMSEADFNSPNCLKSELWQDISLQ 419
Os3RmybA1   361:VCSIENHERSLEPYDVAMEVPLSMLSSDSGAEQKLHFMSEADFNSPNCLKSELWQDISLQ 420
                ************************************************************

BAB78687    420:GLLSGPDAVEADSISRSNHQSDVYSSEADTHFLAPPYMPQTSNSSSVMGLADDQSPQMSV 479
Os3RmybA1   421:GLLSGPDAVEADSISRSNHQSDVYSSEADTHFLAPPYMPQTSNSSSVMGLADDQSPQMSV 480
                ************************************************************

BAB78687    480:PPSLICSNAMTDDAPFDNRPGRKEMPLSQAEVVTQSSSSSGDAEMFANPGCSNDRHVPSS 539
Os3RmybA1   481:PPSLICSNAMTDDAPFDNRPGRKEMPLSQAEVVTQSSSSSGDAEMFANPGCSNDRHVPSS 540
                ************************************************************

BAB78687    540:TMESIPECGDQQVTNAEEPEASLEKEPSLTQSVTAPDEQDKGALFYEPPRFPSLDVPFVS 599
Os3RmybA1   541:TMESIPECGDQQVTNAEEPEASLEKEPSLTQSVTAPDEQDKGALFYEPPRFPSLDVPFVS 600
                ************************************************************

BAB78687    600:CDLVTSGDLQEFSPLGIRQLMHSTMNVCTPMRLWGSPTHDESTGVLLKSAAKSFICTPSI 659
Os3RmybA1   601:CDLVTSGDLQEFSPLGIRQLMHSTMNVCTPMRLWGSPTHDESTGVLLKSAAKSFICTPSI 660
                ************************************************************

BAB78687    660:LKKRHRDLLSPIPDKRIEKKYGTEKDRGVSDTSSTGIQTSCINATKDDALITTVLRIERS 719
Os3RmybA1   661:LKKRHRDLLSPIPDKRIEKKYGTEKDRGVSDTSSTGIQTSCINATKDDALITTVLRIERS 720
                ************************************************************
```

Fig. 2

```
BAB78687   720:ASSKSLEKKLVFSDENKENLGYTTEQTKDGQSAGNDEHMDEQTTGERSSATNVATNDDLS 779
Os3RmybA1  721:ASSKSLEKKLVFSDENKENLGYTTEQTKDGQSAGNDEHMDEQTTGERSSATNVATNDDLS 780
               ************************************************************

BAB78687   780:GNLVSTSSF--------------------------------------------------- 788
Os3RmybA1  781:GNLQPAGILIEHSGDDPISPDYGKNTMNQKLNTNVKSLSVCKEGVCAKSKPTELIVEKSS 840
               ***

BAB78687   789:------------------------------------------------------------ 788
Os3RmybA1  841:PCINVDYEYVNILADTPGIKRGLESPSAWKSPWFVDMHFQGSYFTSPADSYDALGLMKQI 900

BAB78687   789:------------------------------------------------------------ 788
Os3RmybA1  901:NVQTAAALVEAREVLASGGQCDNISSDKENTGNPDAKKEPGTTKLQTKIMAEGRVLDFEC 960

BAB78687   789:----------------------------------- 788
Os3RmybA1  961:TTPERSSDKNAGSNLGRYLSSPIPSSHLLKSFR    993
```

Fig. 3

Fig. 7
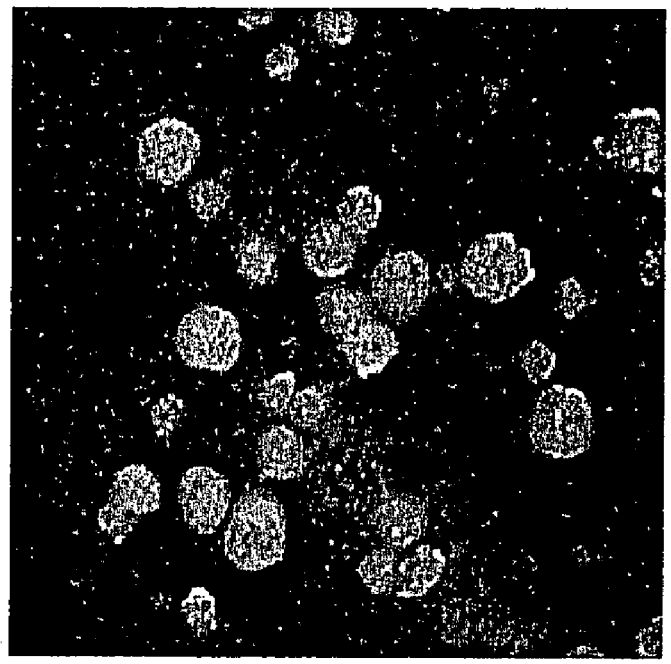
A2 RNAi
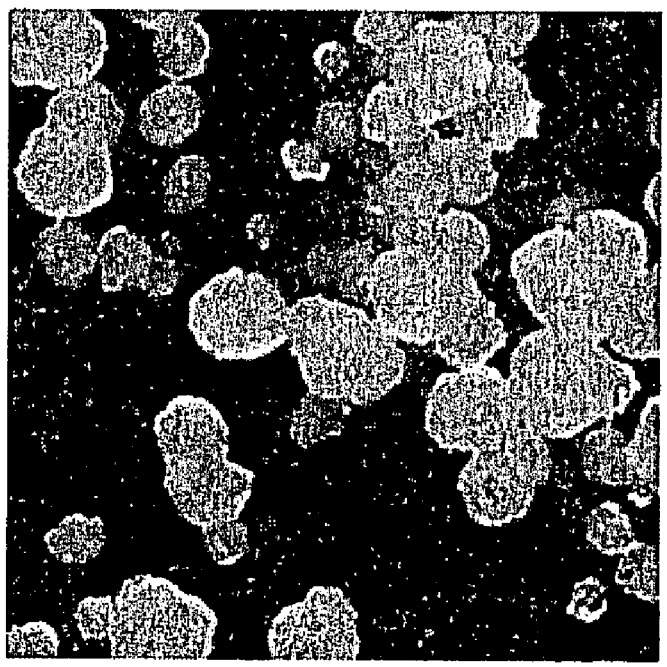
vector

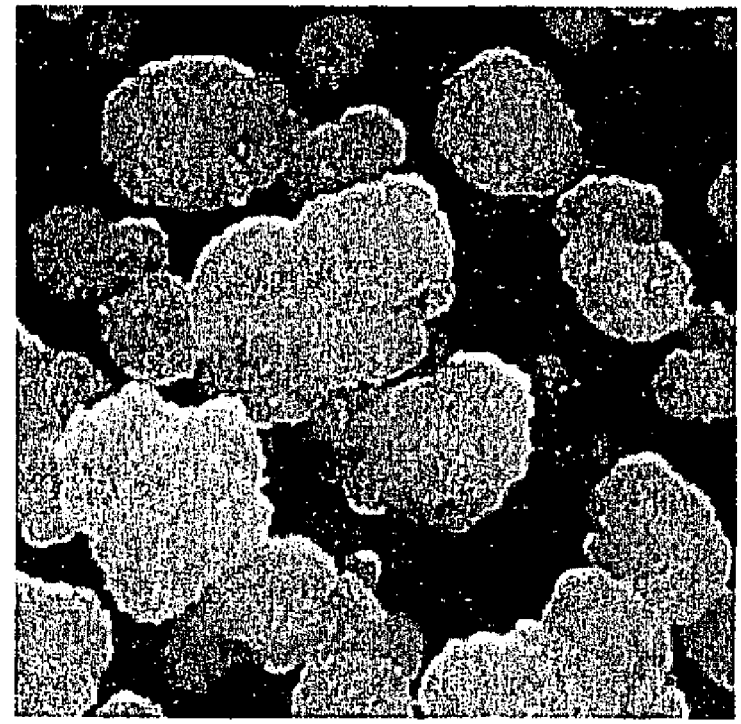
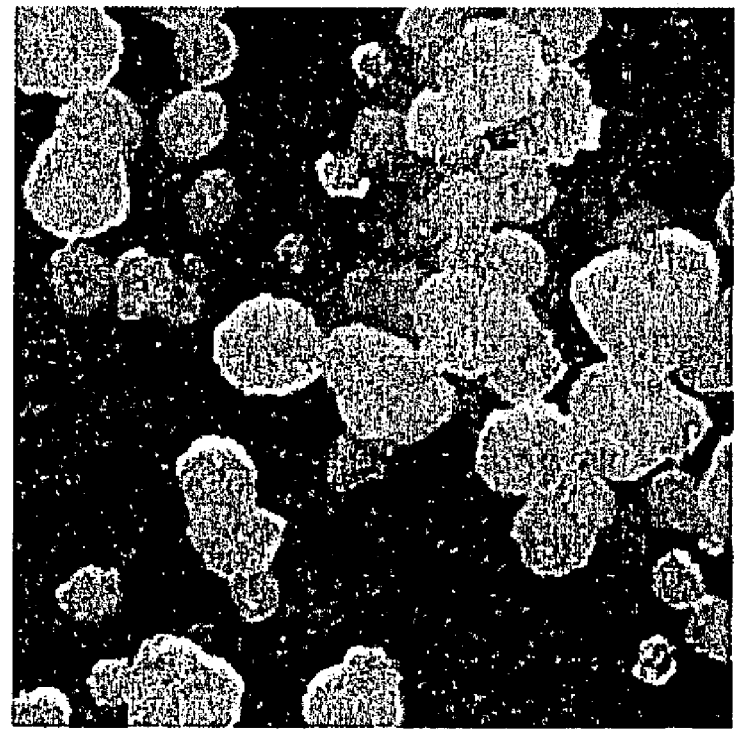
Fig. 9

```
NtmybA2    -MESDRISTPSDGT----------------SSSLQRVRPLHGRTSGPTRRSTKGQWTTEEDE      45
NtmybA1    -MESDKTSTPSDD-----------------ISSLQRVQPSHGRTSGPKRRSSQ--WTPEEDE      43
Os3RmybA1  MMTSDNGKAPDKDGEPSGPPSAPQEGEISNEPKRRRPLNGRTTGPTRRSTKGNWTPEEDA       60
            * **.                          .: * :***:** ***:: **.***

NtmybA2    ILRKAVQRFKGKNWKKIAECFKDRTDVQCLHRWQKVLNPELVKGPWSKEEDEVIVELVKK       105
NtmybA1    ILRQAVQQFKGKSWKRIAECFKDRTDVQCLHRWQKVLDPELVKGSWTKEEDDKLIELVNR       103
Os3RmybA1  ILSRAVQTYNGKNWKKIAECFPDRTDVQCLHRWQKVLNPELVKGPWSKEEDEIIVQMVNK       120
           ** :***  :.**.** **** ***********:******.*:****:: ::  :*:

NtmybA2    YGPKKWSTIAQHLPGRIGKQCRERWHNHLNPGINKEAWTQEEELTLIRAHQIYGNKWAEL       165
NtmybA1    YGPKKWSTIAQELAGRIGKQCRERWHNHLNPAINKEPWTQEEELTLIRAHQVYGNKWAEL       163
Os3RmybA1  LGPKKWSTIAQALPGRIGKQCRERWYNHLNPGINKEAWTQEEEITLIHAHRTYGNKWAEL       180
            ********** * .************:****.****.******:**:**: ********

NtmybA2T5(1~187)
                       NtmybA1(1~185)
                       Os3RmybA1(1~202)
                                        ↓
NtmybA2    TKYLPGRTDNAIKNHWNSSVKKKLDSYLASGLLAQFPALPNVNRQNQSIP----------       215
NtmybA1    AKVLHGRSDNAIKNHWHSSVKKKLDSYLASGLLAQFPALPNVNHQNQSVPSSSMTLQQNS       223
Os3RmybA1  TKFLPGRTDNSIKNHWNSSVKKKVNSYMSSGLLTQVSCLPLNEYSANCNSS---------       231
           :* * .*:**:****:******: .**::****:*   **.*  ...:*

NtmybA2    -----------------------------AKLQQSSEDD                       227
NtmybA1    EDESVHKEGTEAEDSSVHKKKLDSYSASGLLGQFSALPNVHQNQSVPSSSMTLQQNSEDE   283
Os3RmybA1  ----------------------------PAMTQQNSED                        241
                                        :  .: . :
```

Fig. 15

```
                NtmybA2T4(1~242)
                NtmybA1(1~298)
                Os3RmybA1(1~256)

NtmybA2   SVRKEGTEMEEASECSQGSNLAG-CSQSTSDMGNKFVHTREEGKLLEDSNYRKDPSSSSA         286
NtmybA1   SVHKEGMEAEEVPECSQGSNFAG-CSQSTSDLGNTFVHIRENGGMSEESICKKDATSSTA         342
Os3RmybA1 SGCFAVREVENSSGCSQSSLAKVSCSQVHDTTVPLGCDLQVNANFDKNEAHDSQSSMGPQ         301
           *  **    ***.*   *** .       . .   :: . .    :     : :

NtmybA2   PCSEYYTPAFEDITFSMAEVP-SELDESKLLEHTFSHDWAASIGKEWQFNPDDIPNISPL         345
NtmybA1   PCCRNYSPVFQDVSCSMLKVP-SELADSKFLEHNLSHDWGNSMEEDWQFNRDDIPNISPP         401
Os3RmybA1 ACYTSAEAVASALPAVHCHVSSSNLDPDQHLQEDFAQGLNLDMTIDEMPTVPSFADNQTV         361
           *        .   .  .*  .  *.* *. :. .  : ::  :

NtmybA2   ELMQ-DSSGLFMQCLTGNGNHDMVTFPQQNAVKFETTNVGSMVVGFDKPNEMFTSVEGCR         404
NtmybA1   EFIQ-ESSGISVHCLTGNDNHDHDMVATAN———————VGNVVEDPYKPNEMFVSVDGSM         450
Os3RmybA1 CSIENHERSLEPYDVAMEVPLSMLSSDS-G———AEQKLHFMSEADFNSPNCLKSELWQDI         417
          .  :   .:  :     :  .    . :       :::       . ..  **

NtmybA2 Δ EcoRI(1~412)
                NtmybA1(1~458)
                Os3RmybA1(1~425)
NtmybA2   MVYPEAGIPQYIPSEAGTNGADETADSLICQSSNYQISEGGNMSIENCNPLCSDVMGTSS         464
NtmybA1   MVYPEEGIIPQCSPSETGVNGCGQPSYSLFYQSSNYQIPEAGDMVPQNCNALNFDDFEASF        510
Os3RmybA1 SLQGLLSGPDAVEADSISRSNHQSDVYSSEADTHFLAPPYMPQTSNSSSVMGLADDQSPQ         477
           *                        .    ::                         ..

NtmybA2   GQPFSIPSQFSSEQSSLMFGTAANQFHNPLQGNPAQESHTSNSDGFLYPFESGTPCDNIM         524
NtmybA1   HQPFSVPSQFSSEDRSSVFDIVLNQFHNPP———————————————————————————————   540
Os3RmybA1 MSVPPSLICSNAMTDDAPFDNRPGRKEMPLSQAEVVTQSSSSSGDAEMFANPG—————————   530
             *
```

Fig. 16

```
                                                                    NtmybA2T3(1~568)
                                                                    NtmybA1(1~578)
                                                                    Os3RmybA1(1~574)
NtmybA2    DDPLLEEQLDQTKDSLQLVSVNDFRTTPSNTIQTCPLVN------ENSSIPVEQKDGGALYYE  581
NtmybA1    ------LEGPDHMKDSSRIVPVNDIGSTTSNTVQTCLLN------ENSFVQEEQKDGGALCYD  591
Os3RmybA1  ---CSNDRHVPSSTMESIPECGDQQVTNAEEPEASLEKEPSLTQSVTAPDEQDKGALFYE  587
                                                 *    : :: * *** * :
                                                                    NtmybA2T2(1~630)
                                                                    NtmybA1(1~640)
                            PPRFPSXDIPF                  NXXTPXRLWX  Os3RmybA1(1~634)
NtmybA2    PPRFPSLDIPFFSCDLIQSGTDAQQEYSPLGIRQLMMTSVNCLTPFRLWDSPSRDGSTDA   641
NtmybA1    PPRFPSSDVPFFCCDLIQSGSDTQEEYSPFGIRQLMMTSANCLTPLRLWDSPSRDDSPDA   651
Os3RmybA1  PPRFPSLDVPEVSCDLVTSG------DLQEFSPLGIRQLMHSTMVCTPMRLWGSPTHDESTGV  645
           ****** *:.***.**    *:  .: *:**:******* :  : **: :* * .. .
                                          TPSILKKRHR
NtmybA2    VLRSAAKTFTSITPSILKKRHRDLVSPLSEKRCEKKLGSDFRQESFSDLSKDFSRLDVMFD  701
NtmybA1    ILKSAAKTFTGITPSILKKRHRHLLSPLSEKRCEKKLESNLNQESFYNMSTNFSRPDDMFD  711
Os3RmybA1  LLKSAAKSFICITPSILKKRHRDLLSPIPDKRIEKKYGTEKDRGVSDTSSTGIQTSCINAT  705
           :*:****:*  :**********  * **:*  *** .::  .  **  .*  :   :

NtmybA2T1(1~704)
                                                                    NtmybA1(1~708)
                                                                    Os3RmybA1(1~714)
NtmybA2    EAANEKATKSSLTTDQTLELEASSEDKENINPTEDGSKEEDKVRNGLSNERQLDGGEVHY  761
NtmybA1    ESANEKASME------------------DKENLHPSSEDGRKE---------------  736
Os3RmybA1  KDDALITTVLR-------------IERSASSKSLEKKLVFSDENKEN          739
            :

NtmybA2    KEKGTREGTKGGANSAIGKIKQPSGVLVELNASDLFFSPDRFGAKSGRATYLSSKALGNQ  821
NtmybA1    EGEISGANDATGMVKQHPGVLVELSSNDLFFSPDRFLIKCDRATSLSNKALGRQ       790
Os3RmybA1  ---LGYTTEQTKDGGSAGNDEHMDEQTTGERSSATNVATNDDLSGNLQPAGILIEHSGDDP  797
                                *                 *       * *  ..
```

Fig. 17

```
NtmybA2    YARRLEAASNQGSVSSSFETSCFSVICSPRIRGKKDGSSFIITTSMQSAPAPTALDNSAE          881
NtmybA1    YARRLEAASNQVTVSSSFETSCLSVVCSPDICGKHRGSVVIATS----------TALENTAE          842
Os3RmybA1  ISPDYGKNTMNQKLNTNVKS------LSVCKEGVCAKSKPTELIVEK---------------SS          840
           ..          *:.:**     .  . *           ..      *        .:

NtmybA2    TSGNGVGAETVSISGETP-YKRSIESPSAWKSPWFINSLLSSPRLDNELNFEDLALFMSP          940
NtmybA1    DSENGFGAETLSIFGETP-FKRSFESPSAWKSPWFMSSFPPSTRYDTELEFEDFALFMSP          901
Os3RmybA1  P-CINVDYEYVNILADTPGIKRGLESPSAWKSPWFVDMHFQG------------SYFTSP          887
            .   *  :.:**  **. :**  ************           . *  **

NtmybA2    GDRSYDAIGLMKQLSEQTAGAFADAQEVLGG--------ETPESILRGRNSKNQKADENHSLLS          996
NtmybA1    GDRSYDAIGLMKQLSEQTAPSIADAHQILGS--------ETPETNLSKRNSKKPKADENCTLLA          957
Os3RmybA1  AD-SYDALGLMKQINVQTAAALVEAREVLASGGQCDNISSDKENTGNPDAKKEPGTTKLQ          946
           *  ****:******: .:**. :::  :.*.        . :.   .   .*   *

NtmybA2    ANVMSERRTLDFSECGSPGKGKETENFCTSNNSFSS--PSSYLLKGCR          1042
NtmybA1    SNATSERRTLDFNECGIPGKGKETTKFGSNNNSFSS--PSSYLLKYCR          1003
Os3RmybA1  TKIMAEGRVLDF-ECTTPERSSDKNAGSNLGRYLSSPIPSSHLLKSFR          993
           :  : *  :***  **  *.   :: .**   * **  *** ***  *
```

Fig. 18

```
NtmybA1     ------------------------------------MESDKTSTTPSDDISSLQRVQP-SHGRTSGPKRRSSQ---WTPEEDE
NtmybA2     ------------------------------------MESDRISTPSDGTSSSLQRVRP-LHGRTSGPTRRSTKGQWTTEEDE
AtMYB3R-1   ---------------------------MKREMKAPTTPLESLQGDLKG-KQGRTSGPARRSTKGQWTPEEDE
AtMYB3R-4   --------------------------------MEAESSTPQERIPKLR----HGRTSGPARRSTRGQWTAEEDE
Os3RmybA1   MMTSDNGKAPDKDGEPSGPPSAPQEGEISNEPKRRRPLNGRTTGPTRRSTKGNWTPEEDA
                                          ..   :.***.:** ***::. **.***

NtmybA1     ILRQAVQQFKGKSWKRIAECFKDRTDVQCLHRWQKVLDPELVKGSWTKEEDDKLIELVNR
NtmybA2     ILRKAVQRFKGKNWKKIAECFKDRTDVQCLHRWQKVLNPELVKGPWSKEEDEVIVELVKK
AtMYB3R-1   VLCKAVERFQGKNWKKIAECFKDRTDVQCLHRWQKVLNPELVKGPWSKEEDNTIIDLVEK
AtMYB3R-4   ILRKAVHSFKGKNWKKIAEYFKDRTDVQCLHRWQKVLNPELVKGPWTKEEDEMIVQLIEK
Os3RmybA1   ILSRAVQTYNGKNWKKIAECFPDRTDVQCLHRWQKVLNPELVKGPWSKEEDEIIVQMVNK
            :* :**. ::**:*** *********:*****::**:.  :   :    :

NtmybA1     YGPKKWSTIAQELAGRIGKQCRERWHNHLNPAINKEPWTQEEELTLIRAHQVYGNKWAEL
NtmybA2     YGPKKWSTIAQHLPGRIGKQCRERWHNHLNPGINKEAWTQEEELTLIRAHQIYGNKWAEL
AtMYB3R-1   YGPKKWSTISQHLPGRIGKQCRERWHNHLNPGINKNAWTQEEELTLIRAHQIYGNKWAEL
AtMYB3R-4   YGPKKWSTIARFLPGRIGKQCRERWHNHLNPAINKEAWTQEEELLLIRAHQIYGNRWAEL
Os3RmybA1   LGPKKWSTIAQALPGRIGKQCRERWYNHLNPGINKEAWTQEEEITLIHAHRTYGNKWAEL
            *******::   *******:*****:*****.***:.*****:.**:**: ***:****
```

Fig. 19

```
NtmybA1    AKVLHGRSDNAIKNHWHSSVKKKLDSYLASGLLAQFPALPNVHQNQSVPSSSMTLQQNS
NtmybA2    TKYLPGRTDNAIKNHWNSSVKKKLDSYLASGLLAQFPALPNVRQNQSIP----------
AtMYB3R-1  MKFLPGRSDNSIKNHWNSSVKKKLDSYYASGLLDQCQSSPLIALQNKSIASS-------
AtMYB3R-4  TKFLPGRSDNGIKNHWHSSVKKKLDSYMSSGLLDQYQAMPLAPYERSSTLQS-------
Os3RmybA1  TKFLPGRTDNSIKNHWNSSVKKKVNSYMSSGLLTQVSCLPLNEYSANCNSSP-------
           * * **:** ******:******::** :***** .  .   .  :

NtmybA1    EDESVHKEGTEAEDSSVKKKLDSYSASGLLGQFSALPNVNHQNQSVPSSSMTLQQNSEDE
NtmybA2    --------------------------------------------SS----AKLQQSSEDD
AtMYB3R-1  ------------------------------------------------SSWMHSNGDE
AtMYB3R-4  ------------------------------------------------TFMQSNIDG
Os3RmybA1  ------------------------------------------------AMTQQNSED
                                                                  .:

NtmybA1    SVHKEGMEAEEVPECSQGSNFAGCSQSTSDLGNTFVHIRENGGMSEESICKKDATSSTAP
NtmybA2    SVRKEGTEMEEASECSQGSNLAGCSQSTSDMGNKFVHTREEGKLLEDSNYRKDPSSSSAP
AtMYB3R-1  GSSRPGVDAEES--ECSQAS----TVFSQSTNDLQDEVQRGNEEYYMPEFHSGTEQQISNAAS
AtMYB3R-4  NGCLNGQAENEIDSRQNSS--MVGCSLSARDFQNGTINIGHDFHPCGNSQENEQ------TAYH
Os3RmybA1  SGCFAVREVENSSGCSQSS------LAKVSCSQVHDTTVPLGCDLQVNANFDKNEAHDSQSSM
                    *  .       .  :   *     .                     ..
```

Fig. 20

```
NtmybA1    CCRNYSPVFQDVSCSMLKVPSELADSKFLEHNLSHDWGNSMEEDWQFNRDDIPNISPPEF
NtmybA2    CSEYYTPAFEDITFSMAEVPSELDESKLLEHTFSHDWAASIGKEWQFNPDDIPNISPLEL
AtMYB3R-1  HAEPYYPSFKDVKIVVPEISCETECSKKFQNLN----CSHELRTTTATEDQLPGVSNDAK
AtMYB3R-4  SEQFYYPELEDISVSISEVSYDMEDCSQFPDHN----VSTSPSQDYQFDFQELSDISLEMR
Os3RmybA1  GPQACYTSAEAVASALPAVHCHVSSSNLDPDQH-LQEDFAQGLNLDMTIDEMPTVPSFAD
              .  .    .   .     .            :   : :      . :   :

NtmybA1    IQESSGISVHCLTGNDNHDMVATAN----------VGNVVEDPYKPNEMFVSVDGSMMVY
NtmybA2    MQDSSGLFMQCLTGNGNHDMVTFPQQNAVKFETTNVGSMVVGFDKPNEMFTSVEGCRMVY
AtMYB3R-1  QDRGLELLTHNMDNGGKNQALQQDFQSSVRLSDQPFLSNSDTDPEAQTLITDEECCRVLF
AtMYB3R-4  HNMSEIPMPYTKESKESTLGAPNSTLN----------IDVATYTNSANVLTPETECCRVLF
Os3RmybA1  NQTVCSIENHERSLEPYDVAMEVPLSMLS------SDSGAEQKLHFMSEADFNSPNCLKSEL
              .       .       .        .             .    :  :

NtmybA1    PEEGIPQCSPS-------ETGVNGCGQPS--YSLFYQSSNYQIPEAGDMVPQNCNALNFDD
NtmybA2    PEAGIPQYIPS-------EAGTNGADETA--DSLICQSSNYQISEGGNMSIENCNPLCSDV
AtMYB3R-1  PDNMKDSSTSSG-----EQGRNMVDPQNGKGSLCSQAAETHAHETGKVPALPWHPSSSSEG
AtMYB3R-4  PDQESEGHSVSRSLTQEPNEFNQVDRRD--PILYSSASDRQISEATKSPTQSSSSRFTAT
Os3RmybA1  WQDISLQGLLSGP-----DAVEADSISRSNHQSDVYSSEADTHFLAPPYMPQTSNSSSVMGL
              *
```

Fig. 21

```
NtmybA1     ----------------------------------------FEASFHQPFSVPSQFSSEDRSSVFDIVLNQFHNPP---------------------
NtmybA2     MGTSSGQPFSIPSQFSSEEQSSLMFGTAANQFHNPLQGNPAQESHTSNDGFLYPFESGTP
AtMYB3R-1   LAGHNCVPLLDSDLKDSLLPRNDSNAPIQGCRLFGATELECKTDTNDGFIDTYGHVTSHG
AtMYB3R-4   AASGKGTLRPAPLIISPDKYSKKSSGLICHPFEVEP----KCTTNGNGSFICIGDPSSSTC
Os3RmybA1   ADDQSPQMSVPPSLICSNAMTDDAPFDNRPGRKEMP----------LSQAEVVTQSSSSSG NtmybA1     --------LEGPDHMKDSSRIVPVNDIGSTTSNTVQTCLLN-E----NSFVQEEQKDG
NtmybA2     CDNIMDDPLLEEQLDQTKDSLQLVSVNDFRTTPSNTIQTCPLVNE----NSSIPVEQKDG
AtMYB3R-1   NDDNGGFPEQQGLSYIPKDSLKLVPLNSFSSPSRVNKIYFPID----------DKPAEKDK
AtMYB3R-4   VDEGTNNSSEEDQSYHVNDPKKLVPVNDFASLAEDRPHSLPKHEP-----NMTNEQHHEDM
Os3RmybA1   DAEMFANPGCSNDRHVPSSTMESIPECGDQQVTNAEEPEASLEKEPSLTQSVTAPDEQDK
                 .      :    .                  . .:  :   .      .:*

NtmybA1     GALCYDPPRFPSSDVPFFCCDLIQSGSDTQEEYSPFGIRQLMMTSANCLTPLRLWDSPSR
NtmybA2     GALYYEPPRFPSLDIPFFSCDLIQSGSDLIQSGTDAQQEYSPLGIRQLMMTSVNCLTPFRLWDSPSR
AtMYB3R-1   GALCYEPPRFPSADIPFFSCDLVPSNSDLRQEYSPFGIRQLMISSMNCTTPLRLWDSPCH
AtMYB3R-4   GASSSLG--FPSFDLPVFNCDLLQSKNDPLHDYSPLGIRKLLMSTMTCMSPLRLWESPTG
Os3RmybA1   GALFYEPPRFPSLDVPFVSCDLVTSG---DLQEFSPLGIRQLMHSTMNVCTPMRLWGSPTH
            **       **** *:**. ***.* *        . :***:*:*: ::   *:*** **

```
                    SILX₁KRXRXLUOPJXX₅X₁RXX₅KK

NtmybA1    DDSPDAILKSAAKTFTGTPSILKKRHRHLLSPLSEKRCEKKLESNLNQESFYNMSTNFSR
NtmybA2    DGSTDAVLRSAAKTFTSTPSILKKRHRDLVSPLSEKRCEKKLGSDFRQESFSDLSKDFSR
AtMYB3R-1  DRSPDVMLNDTAKSFSGAPSILKKRHRDLLSPVLDRRKDKKLKR------AATSSLANDFSR
AtMYB3R-4  ---------KKTLVGAQSILRKRTRDLLTPLSEKRSDKKLEID------IAASLAKDFSR
Os3RmybA1  DESTGVLLKSAAKSFICTPSILKKRHRDLLSPIPDKRIEKKYGTEKDRGVSDTSSTGIQT
           *::  : ***:** *.*::*: ::* :**                    ::

NtmybA1    PDDMFDESANEKASME-----------DKENLHPSSEDGRKE--------------------
NtmybA2    LDVMFDEAANEKATKSSLTTDQTLELEASSEDKENINPTEDGSKEEDKVRNGLSNERQLD
AtMYB3R-1  LDVMLDEGDDCMTSRP---------------------------------------------
AtMYB3R-4  LDVMFDETENRQSNFGNSTG---------VIHGDRENHFHILNGDGEE---------WS--
Os3RmybA1  SCINATKDDALITTVLR------------------IERSASSKSLEKKLVFS--------
           ::

NtmybA1    ---------------EGEISGANDATGMVKQHPGVLVELSSNDLFFSPDRFLIKCDRATSLSN
NtmybA2    GGEVHYKEKGTREGTKGGANSAIGKIKQPSGVLVELNASDLFFSPDRFGAKSGRATYLSS
AtMYB3R-1  -------------------------------------------------------------
AtMYB3R-4  -GKPSSLFSHRMPEETMHIRKSLEKVDQICMEANVREKDDSEQDVENVEFFSGILSEHNT
Os3RmybA1  ------------------DENKENLGYTTEQTKDGQSAGNDEHMDEQTTGERSSATNVATNDDLSG
```

```
NtmybA1    KALGRQYARRLEAASNQVTVSSSFETSCLSVVCSPDICGKHRGSVVIATS----------TA
NtmybA2    KALGNQYARRLEAASNQGSVSSSFETSCFSVICSPRIRGKKDGSSFIITTSMQSAPAPTA
AtMYB3R-1  ------------------------------------------------------------
AtMYB3R-4  GKPVLSTPGQSVTKAEKAQVSTPRNQLQRTLMATSNKEHHSPSSVCLVINSPS------RA
Os3RmybA1  N---LQPAGILIEHSGDDPISPDYGKNTMNQKLNTNVKSLSVCKEGVCAKSKP------TE NtmybA1    LENTAEDSENGFGAETLSIFGETP-FKRSFESPSAWKSPWFMSSFPPSTRYDTELEFEDF
NtmybA2    LDNSAETSGNGVGAETVSISGETP-YKRSIESPSAWKSPWFINSLLSSPRLDNELNFEDL
AtMYB3R-1  -----------------------------------S------------------------
AtMYB3R-4  ------------------------------------------------------------
Os3RmybA1  RNKEGHLVDNGTSNENFSIFCGTP-FRRGLESPSAWKSPFYINSLLPSPRFDTDLTIEDM
           LIVEKSSPCINVDYEYVNILADTPGIKRGLESPSAWKSPWFVDMHFQG------------
                                            .            .

NtmybA1    ALFMSPGDRSYDAIGLMKQLSEQTAPSIADAHQILGSETPETNL------SKRNSKKPKADE
NtmybA2    ALFMSPGDRSYDAIGLMKQLSEQTAGAFADADAQEVLGGETPESIL-----RGRNSKNQKADE
AtMYB3R-1  ----ESPEDKNICASPSIARDNRNCASARLYQEMIPIDEEPKETL------ESGGVTSMQNEN
AtMYB3R-4  GYIFSPGERSYESIGVMTQINEHTSAFAAFADAMEVSISP----------TNDDARQKKE
Os3RmybA1  -SYFTSPADSYDALGLMKQINVQTAAALVEAREVLASGGQCDNISSDKENTGNPDAKKEP
              .                  .                    .

Fig. 24
```

```
NtmybA1    NCTLLASNATSERRTLDFNECGIPGKGKETTKFGS-NNNSFSSPSSYLLKYCR-
NtmybA2    NHSLLSANVMSERRTLDFSECGSPGKGKETENFCT-SNNSFSSPSSYLLKGCR-
AtMYB3R-1  GCNDGGASAKNVSPSLSLHIIWYQL————————————————————————————
AtMYB3R-4  LDKENNDPLLAERRVLDFNDCESPIKATEEVS—————————SYLLKGCR-
Os3RmybA1  GTTKLQTKIMAEGRVLDFECTTPERSSDKNAGSNLGRYLSSPIPSSHLLKSFRL
                           *.:
```

Fig. 25

```
                                    SCSSXSX₆
                                   ▬▬▬▬▬

AtMYB3R-3  MSSTFNPAASSPDEEGTGEVKIEDQCVENKQSTPASCSSVSEGSAGSSHKSPTIASPATV
AtMYB3R-5  MSLSSNPPVCSPEKEERSEMKIEIQCMENKQPLAASCSSASEGSGCFFLKSPEIATPATV
NtmybB     ───────────────MIQVKEESQTLDFSGFASCSSFSDSS────────YEASTPRYS
                           :::..   .  *****  *:.  *          ::  *

AtMYB3R-3  SPTHRYLGRTSGPIRRAK-GGWTPEEDETLRQAVDTFKGKSWKNIAKSFPDRTEVQCLHR
AtMYB3R-5  SSFPR────RTSGPMRRAK-GGWTPEEDETLRRAVEKYKGKRWKKIAEFFPERTEVQCLHR
NtmybB     SEPGSSYRRSSGPTKRSSQAGWTEEEDNLLTEVVKRFKGRNWKKIAECMNGRTDVQCLHR
           *   *:***  * :*: .***  *** :  *..*:::*: *.**: ** ******

AtMYB3R-3  WQKVLNPDLIKGPWTHEEDEKIVELVEKYGPAKWSIIAQSLPGRIGKQCRERWHNHLNPD
AtMYB3R-5  WQKVLNPELVKGPWTQEEDDKIVELVKKYGPAKWSVIAKSLPGRIGKQCRERWHNHLNPG
NtmybB     WQKVLNPELVKGPWSKEEDDLIVELVEKYGCKKWSFIAKSMPGRIGKQCRERWHNHLDPT
           ******:*:****: :***: ****:.** .:** **:*:*******************:*

AtMYB3R-3  INKDAWTTEEEVALMNAHRSHGNKWAEIAKVLPGRTDNAIKNHWNSSLKKKSEFYLLTGR
AtMYB3R-5  IRKDAWTVEEESALMNSHRMYGNKWAEIAKVLPGRTDNAIKNHWNSSLKKKKLEFYLATGN
NtmybB     IKRDAWTEQEESVLCHYHQIYGNKWAEIARFLPGRTDNAIKNHWNSSVKKRLNLNLPSRL
           *.:****  :**.* ::*: ********: ************::**::  :  :
```

Fig. 26

```
AtMYB3R-3    LPPPTTRNGVPDSVTKRSSSAQKRVFGSVAQTSSVTTDVN----NLAEDGNGQINSSVPV
AtMYB3R-5    LPPPASKFIVLKDIADGDRDSKQSSATKPFKDSDSLTQTSSGNTDSNEVGRDHFDSSSAL
NtmybB       VLDTESEGSPNFSSDKKKIEIKKHPVQAQNAEQTIFLGKQTGLDNAAVALSTDLRIGYAY
                  :   .   :       :          .   . * . . .  :   :  .:

AtMYB3R-3    EEVVAASRMTSLNEYARS-------------------------PQLPNPEPLPE-----
AtMYB3R-5    LEEVAASRRIGVNEYACSPVE----------------------YKPQLPNLEPISEEVRINSKA
NtmybB       SAGNAKHKDTSLFGACISAEENVRDLIKPLGGIQFGKADVLPIGETDKPCQSNLSRTKIS
               *  :  .  :  * :                          * . .*   :

AtMYB3R-3    ----------------NGGAANNGYHLYYTPQIDYYRASEVDTQRMYGNECGCSPSASPV
AtMYB3R-5    YFERSIQR--------KVENGFGTPKHGNLYYKSPLDYYFPSEADLQHMYGYECGCSPGAASP
NtmybB       YPLSASSSDFPLDQLHHTSWSTSQVEAVHPTTFRSMYESPKRSRHDTVNDPNCDFLSLSL
                ::          :  :   : : . *  :  :  *     .: * .  . * :

AtMYB3R-3    SFFTPPPCRNVHSNGSTPRSPESYLREAGRTYPNTPSIFRKRR---------PRV
AtMYB3R-5    VSLMTTPCN-KDSGLTATRSPESFLREAARTFPNTPSIFRKRKVVLAAKTDAVVVNGV
NtmybB       ASFTEVHSQSTKKNKAYDTQSSLGLKQQGSLYYEPPQLKDMMIP--LTDEN----LSRDD
              * . . :       :  :   ::   *: :  .   .*:
```

Fig. 27

```
AtMYB3R-3   VVQDNNNAKKTDEAKEVDQKVNDGKDSSEIQNNGSNAYNLSPPYRIRSKRT------
AtMYB3R-5   VKEVDRKEESKDMRKSLLLETTDNCSDDEELGLNGNAFNLSPPYRLRAKRT------
NtmybB      LIRQQNGHPFCSTPPSLKLTVSANGSSPESVLRNSAMSYTRTPSIIRKKNSRFPEAATHS
             . :          . .    :       *    . :        .  *  :* *..

AtMYB3R-3   ------AVFKSRQLEFISREEEKADDETKSSEKDMLIDGDSQLLG---------------
AtMYB3R-5   ------AVIKSRQLEFTSEKEKQPDNEIEFTSAKEKQPDNEIKTSEEDKPV---------
NtmybB      RCTGTTSPTHIFPRASDREDTSNLKDRFSGCKSSASGKSLGRRLEYAFDMEWDASRCCTP
              :      : *.:  .  *.      ::  .

AtMYB3R-3   ------------------------
AtMYB3R-5   ------------------------
NtmybB      VSAASPCALRLGGNTMLTP
```

Fig. 28

```
                  V                                                                              V
                T D I                                                                          T D I
              WSXXEEXXL                      42 Amino Acids                                  WSXXEEXXL HvMYB3R-1    ————————————————————————————————ECFPGRTDVQCLHRWQKVLNPELIKGPWSKEEDDI
ScMYB3R-1    ————————————————————————————————————————————————PELVKGPWSKEEDDV
Os3RmybA1    WTPEEDAILSRAVQTYNGKNWKKIAECFPDRTDVQCLHRWQKVLNPELVKGPWSKEEDEI
NtmybA1      WTPEEDEILRQAVQQFKGKSWKRIAECFKDRTDVQCLHRWQKVLDPELVKGSWTKEEDDK
AtMYB3R-4    WTAEEDEILRKAVHSFKGKNWKKIAEYFKDRTDVQCLHRWQKVLNPELVKGPWTKEEDEM
NtmybA2      WTTEEDEILRKAVQRFKGKNWKKIAECFKDRTDVQCLHRWQKVLNPELVKGPWSKEEDEV
AtMYB3R-1    WTPEEDEVLCKAVERFQGKNWKKIAECFKDRTDVQCLHRWQKVLNPELVKGPWSKEEDNT
PhpMYB3R-1   WTPEEDETLRRAVQCFNGKAMWKKIAEFFTBRTDVQCLHRWQKVLNPDLVKGAWTKEEDDR
AtMYB3R-3    WTPEEDETLRQAVDTFKGKSWKNIAKSFPDRTEVQCLHRWQKVLNPDLIKGPWTHEEDEK
AtMYB3R-5    WTPEEDETLRRAVEKYKGKRWKKIAEFFPERTEVQCLHRWQKVLNPELVKGPWTQEEDDK
ParMYB3R-1   WTPEEDEKLRKAVESFKGKNWKKIAACLPHRTELQCLHRWQKVLHPDLVKGPWTLEEDDK
NtmybB       WTEEEDNLLTEVVKRFKGRNWKKIAECMNGRTDVQCLHRWQKVLNPELVKGPWSKEEDDL
AdrMYB3R-1   ————————————————————————————————DLLKDRSDVQCLHRWQKVLNPNLVKGPWTKEEDEK Consensus Sequence  WTXEEDXXLXXXXVXXXXUXGX₇XWKXIAXXXXXXROX₅JQCLHRWQKVLXPXLJKGXWOXEEDXX
```

Fig. 29

| | |
|---|---|
| HvMYB3R-1 | GNKWAELTKFLPGKTDNSIKNHWNSSVKKK |
| ScMYB3R-1 | GNKWAELSKFLPGRTDNAIKNHW———— |
| Os3RmybA1 | GNKWAELTKFLPGRTDNSIKNHWNSSVKKK |
| NtmybA1 | GNKWAELAKVLHGRSDNAIKNHWHSSVKKK |
| AtMYB3R-4 | GNRWAELTKFLPGRSDNGIKNHWHSSVKKK |
| NtmybA2 | GNKWAELTKYLPGRTDNAIKNHWNSSVKKK |
| AtMYB3R-1 | GNKWAELMKFLPGRSDNSIKNHWNSSVKKK |
| PhpMYB3R-1 | GNKWAEIAKFLPGRTDNSIKNHWNSTMKKK |
| AtMYB3R-3 | GNKWAEIAKVLPGRTDNAIKNHWNSSLKKK |
| AtMYB3R-5 | GNKWAEIAKVLPGRTDNAIKNHWNSSLKKK |
| ParMYB3R-1 | GNKWAEIAKVLPGRTDNAIKNLWNSSLKKK |
| NtmybB | GNKWAEIARFLPGRTDNAIKNHWNSSVKKR |
| AdrMYB3R-1 | GNKWAEIAKSLPGRTDNAIKNHWNSSLKKK |
| Consensus Sequence | GNX$_7$WAEJXX$_7$XLXGX$_7$ODNOIKNXWXSOXKKX$_7$ |

Fig. 31

PLANT CELLS AND PLANT BODIES WITH MODIFIED CELL GROWTH, DEVELOPMENT AND DIFFERENTIATION

This application is a U.S. national stage of International Application No. PCT/JP2004/003228 filed Mar. 11, 2004.

FIELD OF THE INVENTION

The present invention relates to methods for the control of cell growth and/or regulation of development and differentiation in plants, and molecules for applications thereof. Further, the present invention relates to produced and/or created plants with genetically controlled genes involved in their cell growth, and/or, development and differentiation, and application techniques thereof.

BACKGROUND OF THE INVENTION

Plants have distinctive embryologic characteristics different from those of other eukaryotes. Since plant cells do not migrate, cell division, extension, and program cell death are thought to determine morphogenesis. Cells proliferate in meristematic tissues existing at both poles of a shoot apex and a root apex. The proliferated cells differentiate and pile up to develop into a plant. The size of a plant is determined by the number and size of constituent cells for forming the plant. Plants control cell growth (cell proliferation) by regulating the cell cycle so that the sizes of plants are adapted to changed environmental conditions. The regulation of the cell cycle is important for differentiation of plants. For example, pericyclic cells of roots remain in a specific period (G2 phase) of the cell cycle, and differentiation of lateral roots is determined by whether or not the cells start to divide. The number of the hypocotyl cells is regulated in plants, but the cell cycle changes in the dark and the cell size changes by endoreduplication.

A method for controlling cell division of plants, in particular, a method for regulating the cell cycle is thought to be important as a new method of plant breeding which collectively treats matters such as growth, shapes, and stress response.

A cell is divided into two daughter cells through a series of processes called a cell cycle that consists of four phases; i.e. gap 1 phase (G1 phase), DNA synthesis phase (S phase), gap 2 phase (G2 phase), and mitosis phase (M phase). Mechanisms relating to the regulation of S and M phases of the cell cycle have been noticed and studied. In the two phases, M phase, called mitotic division phase, is a phase for equally distributing the chromosomes duplicated in the S phase into daughter cells. For entry into the M phase, cyclins (one representative is Cyclin B) bind to cyclin-dependent kinase (CDK) to form an activated complex for enhancing aggregation of chromosomes and disruption of nuclear membranes. The M phase terminates after a process called cytokinesis (cytoplasmic division) for dividing cytoplasm after the distribution of the chromosomes into two. In plant cells, phragmoplast which is a structure specific to plant is formed and the cytoplasmic division progresses. The formation of phragmoplasts is regulated by kinesin-like proteins; i.e. NACK1 and NACK2.

Cyclin B, NACK1, and NACK2 having important functions in the process from the entry into the M phase till the termination of the M phase in plant cells show gene expression patterns specific to G2/M phases. It is reported that a specific control sequence called M-specific activator (MSA) existing in a promoter region controls the phase-specific expression of these genes (Non-patent Document 1). In addition to a plant-specific CDK, CDKB, and genes having high similarities to cyclin-specific E2 enzymes among E2 enzymes relating to proteolysis, a variety of functionally unknown genes have been reported to have M phase-specific expression patterns. Many of these genes are analyzed to include MSA sequences in promoter regions. Therefore, it is thought that mechanisms for regulating G2/M phase-specific gene expression by MSA sequences are universally conserved in plants.

NtmybA1, NtmybA2, and NtmybB (hereinafter collectively referred to as "Ntmyb") have been identified from tobacco as MSA binding factors. The amino acid sequences of Ntmyb proteins characteristically have high similarities to the myb DNA binding region having a sequence composed of imperfect three repeats existing in animal c-myb and others (such proteins containing this DNA binding region are hereinafter referred to as "3Rmyb"). Many plants have genes carrying myb-like DNA binding regions, but most of them are constituted of two myb region repeats or non-repeated type myb regions. For example, *Arabidopsis thaliana* of which genome sequencing was completed has more than one hundred myb-like DNA binding region-containing genes, but only five genes contain the aforementioned myb-like DNA binding region composed of three imperfect myb repeats (3Rmyb). Thus, such genes are known as specific members among superfamilies constituting the plant myb-like protein group (Non-patent Document 2).

Transcription control experiments with reporter genes were conducted for investigations on Ntmyb functions using transient expression systems in plant cells. It was reported that NtmybA1 and NtmybA2 activated transcription of the Madagascar Periwinkle (*Catharanthus roseus*) cyclin B (CYM) promoter and the NACK 1 promoter, and vice versa NtmybB suppressed these transcription, thereby indicating that Ntmyb were capable of binding to MSA, and acted as transcription-controlling factors for genes exhibiting G2/M phase-specific expression (Non-patent Document 3). However, these reports are merely based on the results of reporter gene transcription activated by Ntmyb transiently expressed at one point in the cell cycle regulated by cyclic expression of numerous genes. Thus, there have been no reports disclosing functions of Ntmyb in the cell cycle and cell division yet.

There have been report examples disclosing that the growth and development of plants was modified by transformation with G2/M phase-specific expression genes. For example, the elongation of roots was enhanced in transformed plants which ectopically expressed cyclin B (Non-patent Document 4); and cytoplasmic division was incomplete to shorten plant height in plants having suppressed expression of NACK1 essential for the termination of the M phase or in transformed plants having dominant negative NACK1 constructs (Non-patent Document 5). However, these examples are the approaches for controlling the cell growth by utilizing individual genes relating to the progress of M phase. Therefore, there have been no reports disclosing transformed plants in which expression of G2/M phase-specific genes including functionally unknown genes, regulated by MSA sequences, is collectively regulated.

Ntmyb contains a myb DNA-binding region having high homology to c-myb. It is thought that the transcriptional function of c-myb is inactive when the EVES motif existing in said protein is binding to the myb DNA-binding domain, and is activated when phosphorylation of the EVES motif with a protein kinase leads to a change in the protein conformation, thereby allowing the binding of coactivator P100 to the myb DNA-binding region (Non-patent Document 6). Since regions other than the myb DNA-binding regions are observed to be nonsimilar between Ntmyb and c-myb, and regulating sequences such as the EVES motif are not conserved, the mechanism for controlling Ntmyb ability to activate transcription is thought to be different from that for c-myb protein. There have been no reports disclosing the presence of a region for controlling the transcription-activating ability of Ntmyb.

DNAs encoding full-length 3Rmyb have been reported in only tobacco and *Arabidopsis thaliana* which are dicotyledonous plants, but there have been no reports on full-length 3Rmyb from monocotyledonous plants. This means that there are no reports revealing whether or not mechanisms for regulating G2/M phase-specific gene expression, mediated by MSA sequence and 3Rmyb, are conserved in monocotyledonous plants and dicotyledonous plants.

Most of animals are diploid, but various ploidy levels are broadly known in plants. *Triticum* is hexaploid, and *Asterales* is decaploid. A large number of these polyploidy plants generally have characters or properties useful for agriculture, and creation of ploidy plants is used as a tool for breeding. Colchicine treatment has been broadly used as a technology for generating polyploids. Namely, colchicine treatment is performed to plant seeds, embryo plants, or tissue culture cells of organs, and then plants are selected from regenerated plants. Colchicine inhibits spindle formation of ploidy cells after DNA duplication, and ploidy cells are generated by skipping the mitosis phase. However, investigations of organs to be treated with colchicine and of timing for drug-treatment are necessary; thus, it is not readily performed in all plants.

[Non-patent Document 1] Ito et al., Plant Cell, 10: 331 (1998)

[Non-patent Document 2] Stracke et al., Curr. Opin. Plant Biol. 4: 447 (2001)

[Non-patent Document 3] Ito et al., Plant Cell, 13: 1891 (2001)

[Non-patent Document 4] Doerner et al., Nature, 380: 520 (1996)

[Non-patent Document 5] Nishihama et al., Cell, 109: 87 (2002)

[Non-patent Document 6] Dash et al., Genes Dev., 10: 1858 (1996)

SUMMARY OF THE INVENTION

As mentioned above, since regulation of the cell cycle is important for breeding plants, an object of the present invention is to provide a novel technology for modifying the growth or proliferation of plant cells. Namely, an object of the present invention is to provide a technology for modifying the development/differentiation of plants in combination with modifying the growth or proliferation of plant cells and to provide plant genes used therefor.

Another object of the present invention is to provide methods for dramatically modifying a function of plant 3Rmyb genes and novel 3Rmyb protein version molecules of which function is modified.

The inventors have extensively investigated to disclose that the plant 3Rmyb gene is a factor essential for the growth (or proliferation) of plant cells and to accomplish the technology for modifying the growth of plant cells by targeting on the 3Rmyb gene and the technology for modifying the development/differentiation of plants. Furthermore, the inventors have found that these technologies can be applied to a variety of plants.

Namely, plant cells and plants exhibiting modified plant 3Rmyb protein activities are generated. In these plant cells and plants, the cell growth (or cell proliferation) and/or cell development/differentiation can be clearly modified.

Furthermore, it has been firstly disclosed, by using the plant cells and plants that exert modified plant 3Rmyb protein activities, that a plant 3Rmyb member containing a specific amino acid sequence is a positively regulating factor in respect to the cell cycle and cell division (one representative of the plant 3Rmyb is "NtmybA2") and that another plant 3Rmyb member containing an amino acid sequence different from the foregoing sequence is a negatively regulating factor in respect to the cell cycle and cell division (one representative of the plant 3Rmyb is "NtmybB").

The inventors have also succeeded in creating variants of transcription factors, plant 3Rmyb proteins, and in finding that their functions are modified. The inventors have successfully found that these variants can be used to modify activities owned by the plant 3Rmyb proteins in plant cells and in plants. Namely, the inventors have found control regions for regulating activities of transcribing downstream genes among the amino acid sequences of plant 3Rmyb proteins, and have successfully generated molecules having modified ability to activate gene transcription. The inventors have successfully created plant 3Rmyb protein variants having dramatically enhanced ability to activate transcription (having dramatically enhanced transcription activating properties) and molecules dominant-negatively acting on transcripts of plant 3Rmyb genes.

The inventors have also succeeded in isolating a novel monocotyledonous plant rice-derived plant 3Rmyb gene, i.e., DNA encoding Os3RmybA1 protein; and in finding that Os3RmybA1 protein is functionally equivalent to that of tobacco 3Rmyb protein, NtmybA2 protein.

Based on the foregoing findings, the present inventors have been accomplished the present invention.

The present invention relates to control techniques for regulating the cell growth of plants, and/or regulating the development and differentiation of plant individuals wherein the target gene is selected from plant 3Rmyb genes, the Os3RmybA1 gene involved in the cell division of plants as well as analog genes thereof, and proteins encoded by these genes.

As used herein, the score, "Aligned Score" indicating the similarity between a certain amino acid or amino acid sequence and a specific one of interest, refers to the percentage of identical or similar amino acids, which has resulted from multiple amino acid sequence alignment analysis using ClustalW program (www.ddbj.nig.ac.jp/E-mail/clustalw-j.html). Further, the aforementioned amino acid sequence comparison is conducted under optimal alignment of amino acid sequences to be targeted. Two amino acid sequences are optimally aligned herein unless otherwise disclosed herein specifically. The program runs under the following conditions: parameters are set to default (def), OUTPUT=clustal, OUTORDER=aliged, MATRIX=blosum, GAPDIST=8, MAXDIV=40, ENDGAPS=OFF, NOPGAPS=OFF, and NOHGAPS=OFF.

In a more specific aspect, the present invention provides the following:

(1) A plant cell having a (genetically) modified plant 3Rmyb protein activity, as compared to the corresponding wild type plant cell.

(2) The plant cell according to the above (1), wherein said plant cell harbors, or has been transformed with, a DNA selected from the following (a) to (f), or a recombinant DNA construct or vector as set forth in the following (g):

(a) a DNA coding for any amino acid sequence of plant 3Rmyb proteins, (b) a DNA not only hybridizing with a DNA coding for any amino acid sequence of the plant 3Rmyb proteins under stringent conditions, but also coding for a functionally equivalent protein to any of the plant 3Rmyb proteins;

(c) a DNA coding for ribozyme catalytic RNA which specifically cleaves a transcript of DNA coding for any of the plant 3Rmyb proteins;

(d) a DNA not only coding for RNA which suppresses the expression of DNA coding for any of the plant 3Rmyb proteins by co-suppression mechanisms when expressed in a plant cell, but also being at least 90% homologous to the 3Rmyb DNA;

(e) a DNA coding for RNA which suppresses the expression of DNA coding for any of the plant 3Rmyb proteins by RNA interference mechanisms when expressed in a plant cell;

(f) a DNA coding for antisense RNA which is complementary to a transcript of DNA coding for any of the plant 3Rmyb proteins;

(g) a recombinant DNA construct or vector comprising at least a member selected from the group consisting of the following (i) to (iii):

(i) a promoter transcribable in a plant cell, (ii) a DNA wherein the DNA according to any of the above (a) to (f) is linked to said promoter sequence in a sense or antisense direction, and (iii) a signal for transcription termination and polyadenylation of an RNA molecule.

(3) The plant cell according to the above (1) or (2), wherein the plant 3Rmyb protein is a transcription factor for activating G2/M phase-specific transcription mediated by the MSA sequence.

(4) The plant cell according to the above (1) or (2), wherein the plant 3Rmyb protein, which is a transcription factor for activating G2/M phase-specific transcription mediated by the MSA sequence, is a protein comprising at least an amino acid sequence of

SILX$_1$KRXRXLX$_3$X$_4$PX$_2$XX$_5$X$_1$RXX$_5$KK        (SEQ ID NO: 94)

wherein X is any amino acid, X$_1$ is K or R, X$_2$ is L, I or V, X$_3$ is L or V, X$_4$ is S or T, and X$_5$ is D or E.

(5) The plant cell according to any of the above (1) to (4), wherein the plant 3Rmyb protein is an amino acid sequence selected from SEQ ID NO:32, SEQ ID NO:51, SEQ ID NO:53, SEQ ID NO:75 and SEQ ID NO:76.

(6) The plant cell according to the above (1) or (2), wherein the plant 3Rmyb protein is a transcription factor for suppressing or inhibiting G2/M phase-specific transcription mediated by the MSA sequence.

(7) The plant cell according to the above (1) or (2), wherein the plant 3Rmyb protein, which is a transcription factor for suppressing or inhibiting G2/M phase-specific transcription mediated by the MSA sequence, is a protein comprising at least an amino acid sequence of

SCSSXSX$_6$        (SEQ ID NO: 95)

wherein X is any amino acid, and X$_6$ is K, R, D, E or H.

(8) The plant cell according to the above (1), (2), (6) or (7), wherein the plant 3Rmyb protein is an amino acid sequence selected from SEQ ID NO:55, SEQ ID NO:77 and SEQ ID NO:78.

(9) The plant cell according to any of the above (1) to (8), wherein the amount of expressed plant 3Rmyb proteins is modified as compared to the corresponding wild type plant cell.

(10) The plant cell according to any of the above (1) to (8), wherein its cell growth is modified as compared to the corresponding wild type plant cell.

(11) A plant comprising or harboring the plant cell according to any of the above (1) to (10).

(12) A plant which is a progeny, descendant or clone of the transgenic plant according to the above (11).

(13) The plant according to the above (11) or (12), wherein the cell growth and/or development/differentiation is modified as compared to the corresponding wild type plant.

(14) The plant according to the above (11) or (12), which is used for modifying its cell growth and/or development/differentiation.

(15) A DNA encoding a 3Rmyb protein with an enhanced transcription activating property as compared to the corresponding wild type protein.

(16) The DNA according to the above (15), wherein the 3Rmyb protein with an enhanced transcription activating property carries a loss of the function exerted by the control region for regulating the transcription activating property.

(17) The DNA according to the above (16), wherein said loss-of-function control region is located at a position closer to the C-terminal side than the amino acid sequence of TPSILKKRHR as shown in SEQ ID NO: 89.

(18) The DNA according to the above (16), wherein said loss-of-function control region is located at a position closer to the C-terminal side than the amino acid residue W in the amino acid sequence of

NXXTPXRLWX wherein X is any amino acid, as shown in SEQ ID NO: 90.

(19) The DNA according to the above (16), wherein said loss-of-function control region is ranging from the amino acid sequence of

```
PPRFPSXDXPF
``` wherein X is any amino acid, as shown in SEQ ID NO: 91, to the C-terminal end.

(20) The DNA according to any of the above (15) to (19), which encodes a plant 3Rmyb protein wherein the loss-of-function mutation is attributable to the substitution, deletion (or disruption), and/or addition (or insertion) of at least one or more amino acids.

(21) The DNA according to any of the above (15) to (19), which encodes a plant 3Rmyb protein wherein the loss-of-function mutation is attributable to the deletion or disruption of at least one or more amino acids.

(22) A DNA coding for a dominant negative protein against the endogenous plant 3Rmyb protein.

(23) The DNA according to the above (22), which codes for a protein comprising the amino acid sequence of a plant 3Rmyb DNA-binding region.

(24) A recombinant DNA construct or vector comprising a member selected from the group consisting of the following (i) to (iii):
  (i) a promoter transcribable in a plant cell,
  (ii) a DNA wherein the DNA according to any of the above (15) to (23) is linked to said promoter sequence in a sense or antisense direction, and
  (iii) a signal for transcription termination and polyadenylation of an RNA molecule.

(25) A plant cell which harbors, or has been transformed with, a DNA, recombinant DNA construct or vector according to any of the above (15) to (24).

(26) The plant cell according to the above (25), wherein the cell growth is modified, as compared to the corresponding wild type plant cell.

(27) A transgenic plant comprising or harboring the plant cell according to the above (25).

(28) A plant which is an off-spring, descendant or clone of the transgenic plant according to the above (27).

(29) The plant according to the above (27) or (28), wherein the cell growth and/or development/differentiation is modified, as compared to the corresponding wild type plant.

(30) A DNA selected from the following (a) to (i):
  (a) a DNA coding for a protein comprising an amino acid sequence of SEQ ID NO: 32,
  (b) a DNA comprising a nucleotide sequence of SEQ ID NO: 31,
  (c) a DNA coding for a protein not only comprising an amino acid sequence with an amino acid substitution, deletion (or disruption) or addition (or insertion) of one or plural amino acids in the amino acid sequence of SEQ ID NO: 32, but also being functionally equivalent to a protein with the SEQ ID NO: 32 amino acid sequence,
  (d) a DNA not only hybridizing with a DNA with the SEQ ID NO: 31 nucleotide sequence under stringent conditions, but also coding for a functionally equivalent protein to a protein with the SEQ ID NO: 32 amino acid sequence,
  (e) a DNA coding for a protein not only comprising an amino acid sequence with the Aligned Score of 60 or more, as compared to the SEQ ID NO: 32 amino acid sequence, but also being functionally equivalent to a protein with the SEQ ID NO: 32 amino acid sequence,
  (f) a DNA coding for antisense RNA which is complementary to a transcript of DNA selected from the above (a) to (e),
  (g) a DNA coding for ribozyme catalytic RNA which specifically cleaves a transcript of DNA selected from the above (a) to (e),
  (h) a DNA not only coding for RNA which suppresses the expression of DNA selected from the above (a) to (e), according to co-suppression mechanisms when expressed in a plant cell, but also being at least 90% homologous to said DNA selected from the above (a) to (e), and
  (i) a DNA not only coding for RNA which suppresses the expression of DNA selected from the above (a) to (e) according to RNA interference mechanisms when expressed in a plant cell, but also being identical over 20 or more contiguous nucleotides to said DNA selected from the above (a) to (e).

In the present invention, the plant 3Rmyb protein is a group of proteins characterized in that the c-Myb-like Myb domain comprises an amino acid sequence including imperfect 3 repeats in the DNA binding domain. The desirable plant 3Rmyb proteins are those comprising an amino acid sequence with the Aligned Score of at least 60 (i.e. 60 or higher) in comparison with the human c-myb protein myb DNA binding domain amino acid sequence (i.e. the amino acid sequence with residues at amino acids 43 to 192 of SEQ ID NO: 88) wherein the Aligned Score indicates similarity when aligned amino acid sequences are compared. Further, the desirable species include proteins comprising an amino acid sequence with three repeats of the c-Myb-like Myb DNA binding domain-conservative SEQ ID NO:92 amino acid sequence, i.e.,

```
W[S,T]XXE[D,E]XX[L,I,V]           (SEQ ID NO: 92)
``` wherein X is any amino acid, and [ ] stands for one specific amino acid selected from the listed amino acids in square brackets, accompanied with intervening 42 arbitrary amino acid residues located between said repeats. More preferably, such species include proteins comprising a sequence, with 150 amino acids, of the following formula:

```
                                                              (SEQ ID NO: 93)
WTXEEDXXLXXXVXXUXGX₇XWKXIAXXXXXROX₅JQCLHRWQKVLXPXLJKGXWOXEED

XXJXXXJXX₇XGXXKWSXJOXXXXXGRIGKQCRERWUNHLXPXIXX₇XXWTXXEX₅XXLXX

XHXXXGNX₇WAEJXX₇XLXGX₇ODNOIKNXWXSOXKKX₇
``` wherein X is any amino acid, J is one amino acid selected from I, V, and L, O is one amino acid selected from G, S, T, C, and A, X$_7$ is one amino acid selected from K, R, and H, U is one amino acid selected from H, W, Y, and F, and X$_5$ is one amino acid selected from D, and E, as shown in SEQ ID NO: 93.

More desirably, the plant 3Rmyb protein species include proteins wherein said sequence with 150 amino acids is a sequence of the following formula:

```
                                                     (SEQ ID NO: 101)
WTXEEDXXLXX[A,V]VXX[F,Y]XG[K,R][N,S,R]WK[K,R,N]IAXXXXXR[S,T]

[D,E][V,L]QCLHRWQKVL[N,D,H]P[D,E,N]L[V,I]KG[P,S,A]W[S,T]XE

ED[D,E,N]X[I,L]X[E,D,Q][L,M][V,I]X[K,R][Y,N,L]G[P,A,C]XKWSX

[I,V][A,S]XX[L,M][P,A]GRIGKQCRERW[H,Y]NHL[D,N]PXI[K,N,R][K,

R][D,E,N][A,P]WTX[E,Q]E[E,D]XXL[I,M,C]X[A,S,Y]H[Q,R]X[N,Y,H]

GN[K,R]WAE[I,L]X[K,R]XL[P,H]G[R,K][S,T]DN[S,A,G]IKN[H,L]W[H,N]

S[S,T][L,V,M]KK[K,R]
``` wherein X is any amino acid, and [ ] stands for one specific amino acid selected from the listed amino acids in square brackets, in [K,R] for instance, it is K or R.

Further, the more desirable plant 3Rmyb protein is a protein represented by an amino acid sequence selected from the group consisting of SEQ ID NO: 32, SEQ ID NO: 51, SEQ ID NO: 53, SEQ ID NO: 55, SEQ ID NO: 75, SEQ ID NO: 76, SEQ ID NO: 77 and SEQ ID NO: 78. Still the more desirable plant 3Rmyb protein include a protein represented by an amino acid sequence selected from the group consisting of SEQ ID NO: 32, SEQ ID NO: 51, SEQ ID NO: 53, and SEQ ID NO: 55.

Therefore, the present invention also encompasses the following:

(1) A transformed cell comprising or harboring a DNA selected from the following (a) to (f):
- (a) a DNA selected from the group consisting of SEQ ID NO: 31, SEQ ID NO: 50, SEQ ID NO: 52, and SEQ ID NO: 54,
- (b) a DNA coding for antisense RNA which is complementary to a transcript of DNA selected from the group consisting of SEQ ID NO: 31, SEQ ID NO: 50, SEQ ID NO: 52, and SEQ ID NO: 54,
- (c) a DNA coding for ribozyme catalytic RNA which specifically cleaves a transcript of DNA selected from the group consisting of SEQ ID NO: 31, SEQ ID NO: 50, SEQ ID NO: 52, SEQ ID NO: 54,
- (d) a DNA not only coding for RNA which suppresses the expression of DNA selected from the group consisting of SEQ ID NO: 31, SEQ ID NO: 50, SEQ ID NO: 52, SEQ ID NO: 54, according to co-suppression mechanisms when expressed in a plant cell, but also being 90% or more homologous to the DNA selected from the group consisting of SEQ ID NO: 31, SEQ ID NO: 50, SEQ ID NO: 52, SEQ ID NO: 54,
- (e) a DNA not only coding for RNA which suppresses the expression of DNA selected from the group consisting of SEQ ID NO:31, SEQ ID NO:50, SEQ ID NO:52, and SEQ ID NO:54 according to RNA interference mechanisms when expressed in a plant cell, but also being identical over 20 or more contiguous nucleotides to the DNA selected from the group consisting of SEQ ID NO: 31, SEQ ID NO: 50, SEQ ID NO: 52, SEQ ID NO: 54,
- (f) a DNA coding for a dominant negative protein against a protein encoded by an endogenous DNA selected from the group consisting of SEQ ID NO: 31, SEQ ID NO: 50, SEQ ID NO: 52, and SEQ ID NO: 54, or a recombinant DNA construct or vector as set forth in the following (g):

- (g) a recombinant DNA construct or vector selected from the group consisting of:
  - (i) a promoter transcribable in a plant cell,
  - (ii) a DNA wherein the DNA selected from the above (a) to (f) is linked to said promoter sequence in a sense or antisense direction, and
  - (iii) a signal for transcription termination and polyadenylation of an RNA molecule.

(2) A transformed plant cell comprising or harboring a DNA selected from (1) (a) to (f) or a recombinant DNA construct or vector of (1) (g)

(3) The transformed plant cell according to (2), which is used for modifying its cell growth.

(4) The transformed plant cell according to (2), wherein the cell growth is modified or altered.

(5) A transgenic plant comprising or harboring the transformed plant cell according to any of (2) to (4).

(6) A transgenic plant which is an off-spring, descendant or clone of the transgenic plant according to (5).

(7) The transgenic plant according to (5) or (6), wherein the plant cell growth is modified or altered.

(8) The transgenic plant according to (5) or (6), which is used for modifying the development and differentiation of plant individuals.

(9) The transgenic plant according to (5) or (6), the development and/or differentiation of plant individuals is modified or altered.

(10) A food and/or feed composition which is manufactured or produced from the plant cell according to any of (2) to (4) or the plant according to any of (5) to (8).

(11) A chemical product which is manufactured or produced from the plant cell according to (2) to (4) or the plant according to any of (5) to (8).

(12) A protein which is isolated or produced from the plant cell according to (2) to (4) or the plant according to any of (5) to (8).

(13) A nucleic acid which is isolated or produced from the plant cell according to (2) to (4) or the plant according to any of (5) to (8).

Further, the present invention provides the following:

(14) A DNA selected from the group consisting of the following (a) to (e):

(a) a DNA coding for a protein with an amino acid sequence of SEQ ID NO:32, (b) a DNA with a nucleotide sequence of SEQ ID NO:31, (c) a DNA coding for a protein with a sequence having an amino acid substitution, deletion (or disruption), or addition (or insertion) of one or plural amino acids in the amino acid sequence of SEQ ID NO:32, said protein being functionally equivalent to the amino acid sequence of SEQ ID NO:32, (d) a DNA not only hybridizing with a DNA having the nucleotide sequence of SEQ ID NO: 31 under stringent conditions, but also coding for a functionally equivalent protein to the amino acid sequence of SEQ ID NO: 32, and (e) a DNA coding for a protein having an amino acid sequence with the Aligned Score of 60 or more, as compared to the SEQ ID NO: 32 amino acid sequence, said protein being functionally equivalent to a protein with the SEQ ID NO: 32 amino acid sequence.

(15) A DNA coding for antisense RNA which is complementary to a transcript of DNA selected from (14) (a) to (e).

(16) A DNA coding for ribozyme catalytic RNA which specifically cleaves a transcript of DNA selected from (14) (a) to (e).

(17) A DNA not only coding for RNA which suppresses the expression of DNA selected from (14) (a) to (e), according to co-suppression mechanisms when expressed in a plant cell, but also being 90% or more homologous to the DNA selected from (14) (a) to (e).

(18) A DNA (i) coding for RNA which suppresses the expression of DNA selected from (14) (a) to (e) according to RNA interference mechanisms when expressed in a plant cell, and (ii) being identical over 20 or more contiguous nucleotides to the DNA selected from (14) (a) to (e).

(19) A DNA coding for a dominant negative protein against a protein encoded by endogenous plant cell DNA selected from (14) (a) to (e).

(20) The DNA according to any of (14) to (19), which is used to modify the cell growth, and/or development/differentiation of plants.

(21) A recombinant DNA construct or vector comprising an element selected from the following (i) to (iii):

(i) a promoter transcribable in a plant cell, (ii) a DNA wherein the DNA selected from (14) to (19) is linked to said promoter sequence in a sense or antisense direction, and (iii) a signal for transcription termination and polyadenylation of an RNA molecule.

(22) A transformed cell which harbors a DNA selected from (14) to (19), or a recombinant DNA construct or vector as set forth in (21).

(23) A peptide encoded by a DNA as set forth in (14), or a peptide thereof; or a dominant negative protein directed to a protein encoded by endogenous plant cell DNA selected from (14) (a) to (e), or a peptide thereof.

(24) A process for producing a protein according to (23), which comprises steps of culturing a transformed cell harboring the DNA of (14) or a vector carrying said DNA, and recovering the resulting expressed protein product from said transformed cells or culture supernatants thereof.

(25) A transformed plant cell which harbors a DNA according to any of (14) to (19) or a recombinant DNA construct or vector as set forth in (21).

(26) The transformed plant cell according to (25), which is used for modifying the growth of plant cells.

(27) The transformed plant cell according to (25), wherein the plant cell growth is modified.

(28) A transgenic plant comprising or harboring the transformed plant cell according to any of (25) to (27).

(29) A transgenic plant which is an off-spring, descendant or clone of the transgenic plant according to (28).

(30) The transgenic plant according to (28) or (29), wherein the plant cell growth is modified.

(31) The transgenic plant according to (28) or (29), which is used for modifying the development and/or differentiation of plant individuals.

(32) The transgenic plant according to (28) or (29), wherein the development and/or differentiation of plant individuals is modified.

(33) A food and/or feed composition which is manufactured or produced from the plant cell according to any of (25) to (27) or the plant according to any of (28) to (32).

(34) A chemical product which is manufactured or produced from the plant cell according to (25) to (27) or the plant according to any of (28) to (32).

(35) A protein which is isolated or produced from the plant cell according to (25) to (27) or the plant according to any of (28) to (32).

(36) A nucleic acid which is isolated or produced from the plant cell according to (25) to (27) or the plant according to any of (28) to (32).

(37) A transcript of the DNA selected from (14) (a) to (e).

(38) A method for quantitatively assaying for the transcript according to (37).

(39) A method for making a relative comparison among plural samples for amounts of the transcript according to (37).

(40) A method for quantitatively assaying a protein encoded by DNA according to (14).

(41) A method for making a relative comparison among plural samples for amounts of a protein encoded by DNA according to (14).

The present inventor et al. have found that the C-terminal region of protein NtmybA2 is a portion responsible for regulating negatively transcription activator properties, and there is a transcription activator domain located at a middle site of the NtmybA2 protein. Based on these findings, the present inventor et al. have succeeded in modifying the functions of protein NtmybA2, thereby allowing the construction and production of NtmybA2 mutants having enhanced transcription activating properties, and other NtmybA2 mutants having reduced transcription activating properties. Thus, they have succeeded in manufacturing NtmybA2 mutants which function dominant-negatively.

The present invention also provided the following:

(42) A DNA coding for an amino acid sequence owned by a molecule having a loss of the function exerted by an NtmybA2 control region for regulating a transcription activating property in connection with the NtmybA2 protein of SEQ ID NO: 53.

(43) The DNA according to (42), which encodes the amino acid sequence of a molecule with the loss-of-function control region being an amino acid portion with residues at amino acids 705 to 1042 of SEQ ID NO: 53.

(44) The DNA according to (42), which encodes the amino acid sequence of a molecule with the loss-of-function control region being an amino acid portion with residues at amino acids 631 to 1042 of SEQ ID NO: 53.

(45) The DNA according to (42), which encodes the amino acid sequence of a molecule with the loss-of-function control region being an amino acid portion with residues at amino acids 569 to 1042 of SEQ ID NO: 53.

(46) The DNA according to (42), which encodes the amino acid sequence of a molecule with the loss-of-function control region being an amino acid portion with residues at amino acids 413 to 1042 of SEQ ID NO: 53.

(47) The DNA according to (42), which encodes the amino acid sequence of a molecule with the loss-of-function control region being an amino acid portion with residues at amino acids 243 to 1042 of SEQ ID NO: 53.

(48) The DNA according to (42), which encodes the amino acid sequence of a molecule with the loss-of-function control region being an amino acid portion with residues at amino acids 188 to 1042 of SEQ ID NO: 53.

(49) The DNA according to any of (42) to (48), wherein the loss-of-function control region is produced by substitution, deletion (or disruption), and/or addition (or insertion) of one or more amino acids in sequence.

(50) The DNA according to any of (42) to (48), wherein the loss-of-function control region is produced by deletion (or disruption) of one or more amino acids in sequence.

(51) A DNA coding for an amino acid sequence with residues at amino acids 1 to 704 of SEQ ID NO: 53, said amino acid sequence serving as the molecule wherein the function of protein NtmybA2 as shown in SEQ ID NO: 53 is modified (or altered).

(52) A DNA coding for an amino acid sequence with residues at amino acids 1 to 630 of SEQ ID NO: 53, said amino acid sequence serving as the molecule wherein the function of protein NtmybA2 as shown in SEQ ID NO: 53 is modified (or altered).

(53) A DNA coding for an amino acid sequence with residues at amino acids 1 to 568 of SEQ ID NO: 53, said amino acid sequence serving as the molecule wherein the function of protein NtmybA2 as shown in SEQ ID NO: 53 is modified (or altered).

(54) A DNA coding for an amino acid sequence with residues at amino acids 1 to 412 of SEQ ID NO: 53, said amino acid sequence serving as the molecule wherein the function of protein NtmybA2 as shown in SEQ ID NO: 53 is modified (or altered).

(55) A DNA coding for an amino acid sequence with residues at amino acids 1 to 242 of SEQ ID NO: 53, said amino acid sequence serving as the molecule wherein the function of protein NtmybA2 as shown in SEQ ID NO: 53 is modified (or altered).

(56) A DNA coding for an amino acid sequence with residues at amino acids 1 to 187 of SEQ ID NO: 53, said amino acid sequence serving as the molecule wherein the function of protein NtmybA2 as shown in SEQ ID NO: 53 is modified (or altered).

(57) A DNA coding for an amino acid sequence owned by a molecule having a loss of the function exerted by an NtmybA1 control region for regulating a transcription activating property in connection with the NtmybA1 protein of SEQ ID NO: 51.

(58) The DNA according to (57), which encodes the amino acid sequence of a molecule with the loss-of-function control region being an amino acid portion with residues at amino acids 715 to 1003 of SEQ ID NO: 51.

(59) The DNA according to (57), which encodes the amino acid sequence of a molecule with the loss-of-function control region being an amino acid portion with residues at amino acids 641 to 1003 of SEQ ID NO: 51.

(60) The DNA according to (57), which encodes the amino acid sequence of a molecule with the loss-of-function control region being an amino acid portion with residues at amino acids 579 to 1003 of SEQ ID NO: 51.

(61) The DNA according to (57), which encodes the amino acid sequence of a molecule with the loss-of-function control region being an amino acid portion with residues at amino acids 459 to 1003 of SEQ ID NO: 51.

(62) The DNA according to (57), which encodes the amino acid sequence of a molecule with the loss-of-function control region being an amino acid portion with residues at amino acids 299 to 1003 of SEQ ID NO: 51.

(63) The DNA according to (57), which encodes the amino acid sequence of a molecule with the loss-of-function control region being an amino acid portion with residues at amino acids 186 to 1003 of SEQ ID NO: 51.

(64) The DNA according to any of (57) to (63), wherein the loss-of-function control region is produced by substitution, deletion (or disruption), and/or addition (or insertion) of one or more amino acids in sequence.

(65) The DNA according to any of (57) to (63), wherein the loss-of-function control region is produced by deletion (or disruption) of one or more amino acids in sequence.

(66) A DNA coding for an amino acid sequence with residues at amino acids 1 to 714 of SEQ ID NO: 51, said amino acid sequence serving as the molecule wherein the function of protein NtmybA1 as shown in SEQ ID NO: 51 is modified (or altered).

(67) A DNA coding for an amino acid sequence with residues at amino acids 1 to 640 of SEQ ID NO: 51, said amino acid sequence serving as the molecule wherein the function of protein NtmybA1 as shown in SEQ ID NO: 51 is modified (or altered).

(68) A DNA coding for an amino acid sequence with residues at amino acids 1 to 578 of SEQ ID NO: 51, said amino acid sequence serving as the molecule wherein the function of protein NtmybA1 as shown in SEQ ID NO: 51 is modified (or altered).

(69) A DNA coding for an amino acid sequence with residues at amino acids 1 to 458 of SEQ ID NO: 51, said amino acid sequence serving as the molecule wherein the function of protein NtmybA1 as shown in SEQ ID NO: 51 is modified (or altered).

(70) A DNA coding for an amino acid sequence with residues at amino acids 1 to 298 of SEQ ID NO: 51, said amino acid sequence serving as the molecule wherein the function of protein NtmybA1 as shown in SEQ ID NO: 51 is modified (or altered).

(71) A DNA coding for an amino acid sequence with residues at amino acids 1 to 185 of SEQ ID NO: 51, said amino acid sequence serving as the molecule wherein the function of protein NtmybA1 as shown in SEQ ID NO: 51 is modified (or altered).

(72) A DNA coding for an amino acid sequence owned by a molecule having a loss of the function exerted by an Os3RmybA1 control region for regulating a transcription activating property in connection with the Os3RmybA1 protein of SEQ ID NO: 32.

(73) The DNA according to (72), which encodes the amino acid sequence of a molecule with the loss-of-function control region being an amino acid portion with residues at amino acids 709 to 993 of SEQ ID NO: 32.

(74) The DNA according to (72), which encodes the amino acid sequence of a molecule with the loss-of-function control region being an amino acid portion with residues at amino acids 635 to 993 of SEQ ID NO: 32.

(75) The DNA according to (72), which encodes the amino acid sequence of a molecule with the loss-of-function control region being an amino acid portion with residues at amino acids 575 to 993 of SEQ ID NO: 32.

(76) The DNA according to (72), which encodes the amino acid sequence of a molecule with the loss-of-function control region being an amino acid portion with residues at amino acids 426 to 993 of SEQ ID NO: 32.

(77) The DNA according to (72), which encodes the amino acid sequence of a molecule with the loss-of-function control region being an amino acid portion with residues at amino acids 257 to 993 of SEQ ID NO: 32.

(78) The DNA according to (72), which encodes the amino acid sequence of a molecule with the loss-of-function control region being an amino acid portion with residues at amino acids 203 to 993 of SEQ ID NO: 32.

(79) The DNA according to any of (72) to (78), wherein the loss-of-function control region is produced by substitution, deletion (or disruption), and/or addition (or insertion) of one or more amino acids in sequence.

(80) The DNA according to any of (72) to (78), wherein the loss-of-function control region is produced by deletion (or disruption) of one or more amino acids in sequence.

(81) A DNA coding for an amino acid sequence with residues at amino acids 1 to 708 of SEQ ID NO: 32, said amino acid sequence serving as the molecule wherein the function of protein Os3RmybA1 as shown in SEQ ID NO: 32 is modified (or altered).

(82) A DNA coding for an amino acid sequence with residues at amino acids 1 to 634 of SEQ ID NO: 32, said amino acid sequence serving as the molecule wherein the function of protein Os3RmybA1 as shown in SEQ ID NO: 32 is modified (or altered).

(83) A DNA coding for an amino acid sequence with residues at amino acids 1 to 574 of SEQ ID NO: 32, said amino acid sequence serving as the molecule wherein the function of protein Os3RmybA1 as shown in SEQ ID NO: 32 is modified (or altered)

(84) A DNA coding for an amino acid sequence with residues at amino acids 1 to 425 of SEQ ID NO: 32, said amino acid sequence serving as the molecule wherein the function of protein Os3RmybA1 as shown in SEQ ID NO: 32 is modified (or altered).

(85) A DNA coding for an amino acid sequence with residues at amino acids 1 to 256 of SEQ ID NO: 32, said amino acid sequence serving as the molecule wherein the function of protein Os3RmybA1 as shown in SEQ ID NO: 32 is modified (or altered).

(86) A DNA coding for an amino acid sequence with residues at amino acids 1 to 202 of SEQ ID NO: 32, said amino acid sequence serving as the molecule wherein the function of protein Os3RmybA1 as shown in SEQ ID NO: 32 is modified (or altered).

(87) A recombinant DNA (or recombinant DNA construct) or vector selected from the group consisting of the following (i) to (iii):
　(i) a promoter transcribable in a plant cell,
　(ii) a DNA wherein the DNA according to any of (42) to (86) is linked to said promoter sequence in a sense or antisense direction, and
　(iii) a signal for transcription termination and polyadenylation of an RNA molecule.

(88) A transformed plant cell which harbors a DNA according to any of (42) to (86) or a recombinant DNA construct or vector as set forth in (87).

(89) The transformed plant cell according to (88), which is used for modifying the growth of plant cells.

(90) The transformed plant cell according to (88), wherein the plant cell growth is modified.

(91) A transgenic plant comprising or harboring the transformed plant cell according to any of (88) to (90).

(92) A transgenic plant which is an off-spring, descendant or clone of the transgenic plant according to (91).

(93) The transgenic plant according to (91) or (92), wherein the plant cell growth is modified.

(94) The transgenic plant according to (91) or (92), which is used for modifying the development and differentiation of plant individuals.

(95) The transgenic plant according to (91) or (92), wherein the development and/or differentiation of plant individuals is modified.

(96) A food and/or feed composition which is manufactured or produced from the plant cell according to any of (88) to (90) or the plant according to any of (91) to (95).

(97) A chemical product which is manufactured or produced from the plant cell according to (88) to (90) or the plant according to any of (91) to (95).

(98) A protein which is isolated or produced from the plant cell according to (88) to (90) or the plant according to any of (91) to (95).

(99) A nucleic acid which is isolated or produced from the plant cell according to (88) to (90) or the plant according to any of (91) to (95).

Further, the present invention also encompasses the following:

(100) A transformed cell which harbors a DNA selected from the following (a) to (f), or a recombinant DNA construct or vector as set forth in the following (g):
 (a) a DNA coding for plant 3Rmyb protein,
 (b) a DNA coding for antisense RNA which is complementary to a transcript of DNA coding for plant 3Rmyb protein,
 (c) a DNA coding for ribozyme catalytic RNA which specifically cleaves a transcript of DNA coding for plant 3Rmyb protein,
 (d) a DNA not only coding for RNA which suppresses the expression of DNA coding for plant 3Rmyb protein according to co-suppression mechanisms when expressed in a plant cell, but also being at least 90% homologous to the plant 3Rmyb protein-coding DNA,
 (e) a DNA not only coding for RNA which suppresses the expression of DNA coding for plant 3Rmyb protein according to RNA interference mechanisms when expressed in a plant cell, but also being identical over 20 or more contiguous nucleotides to said plant 3Rmyb protein-coding DNA.
 (f) a DNA coding for a dominant negative protein against a protein encoded by an endogenous plant cell DNA coding for plant 3Rmyb protein,
 (g) a recombinant DNA (or recombinant DNA construct) or vector selected from the group consisting of the following (i) to (iii):
  (i) a promoter transcribable in a plant cell,
  (ii) a DNA wherein the DNA according to any of (a) to (f) is linked to said promoter sequence in a sense or antisense direction, and
  (iii) a signal for transcription termination and polyadenylation of an RNA molecule.

(101) A transformed plant cell which harbors a DNA according to any of (100) (a) to (f) or a recombinant DNA construct or vector as set forth in (100) (g).

(102) The transformed plant cell according to (101), which is used for modifying the growth of plant cells.

(103) The transformed plant cell according to (101), wherein the plant cell growth is modified.

(104) A transgenic plant comprising or harboring the transformed plant cell according to any of (101) to (103).

(105) A transgenic plant which is an off-spring, descendant or clone of the transgenic plant according to (104).

(106) The transgenic plant according to (104) or (105), wherein the plant cell growth is modified.

(107) The transgenic plant according to (104) or (105), which is used for modifying the development and/or differentiation of plant individuals.

(108) The transgenic plant according to (104) or (105), wherein the development and/or differentiation of plant individuals is modified.

(109) A food and/or feed composition which is manufactured or produced from the plant cell according to any of (101) to (103) or the plant according to any of (104) to (108).

(110) A chemical product which is manufactured or produced from the plant cell according to (101) to (103) or the plant according to any of (104) to (108).

(111) A protein which is isolated or produced from the plant cell according to (101) to (103) or the plant according to any of (104) to (108).

(112) A nucleic acid which is isolated or produced from the plant cell according to (101) to (103) or the plant according to any of (104) to (108).

Still the present invention encompasses plant 3Rmyb proteins with an enhanced transcription activating property (or gain-of-function plant 3Rmyb proteins). Embodiments of such proteins are listed herein below. Also, gain-of-function plant 3Rmyb protein-coding DNAs are encompassed by the present invention.

(113) A loss-of function plant 3Rmyb protein wherein the control region for regulating a transcription activating property has lost its function.

(114) The loss-of-function plant 3Rmyb protein according to (113), wherein the loss-of-function region is a range with 600 amino acid residues from the C-terminal end.

(115) The loss-of-function plant 3Rmyb protein according to (113), wherein the loss-of-function region is a range with 500 amino acid residues from the C-terminal end.

(116) The loss-of-function plant 3Rmyb protein according to (113), wherein the loss-of-function region is a range with 420 amino acid residues from the C-terminal end.

(117) The loss-of-function plant 3Rmyb protein according to (113), wherein the loss-of-function region is a range with 350 amino acid residues from the C-terminal end.

(118) The loss-of-function plant 3Rmyb protein according to (113), wherein the loss-of-function region is a range with 280 amino acid residues from the C-terminal end.

Desirably, listed are the following proteins:

(119) The loss-of-function plant 3Rmyb protein according to (113), wherein the loss of functions is attributable to deletion or disruption of one or more amino acid in sequence.

(120) The plant 3Rmyb protein according to (113), wherein the amino acid deletion takes place within the range of 280 to 600 amino acids from the C-terminal end in sequence.

(121) The plant 3Rmyb protein according to (113), wherein the amino acid deletion takes place within the range of 280 to 500 amino acids from the C-terminal end in sequence.

More desirably, (122) The plant 3Rmyb protein according to (113), wherein the amino acid deletion takes place within the range of 350 to 420 amino acids from the C-terminal end in sequence.

(123) The protein according to any of (113) to (122), wherein the plant 3Rmyb protein is an amino acid sequence selected from the group consisting of SEQ ID NO: 32, SEQ ID NO: 51, SEQ ID NO: 53, SEQ ID NO: 75, and SEQ ID NO: 76.

(124) The protein according to any of (113) to (122), wherein the plant 3Rmyb protein is an amino acid sequence selected from the group consisting of SEQ ID NO: 32, SEQ ID NO: 51, and SEQ ID NO: 53.

ADVANTAGEOUS PROFILES OF THE INVENTION

The present invention provides plant cells having modified cell growth (or modified cell proliferation). These plant cells allow production of plants having modified development/ differentiation. Thus, provided are novel techniques for generating plants having desirable properties, such as specific organ enlargement, male sterility, and improved stress resistance.

The above objects and other objects, features, advantages, and aspects of the present invention are readily apparent to those skilled in the art from the following disclosures. It should be understood, however, that the description of the specification including the following best modes of carrying out the invention, examples, etc. is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BRIEF DESCRIPTION OF THE DRAWINGS

FIG. 1 shows comparison results from multiple amino acid sequence alignment analysis when both the putative rice protein amino acid sequence registered with ACCESSION NO: BAB78687 on DDBJ (DNA Data Bank of Japan) and the amino acid sequence of protein Os3RmybA1 are optimally aligned. Continued on FIGS. 2 and 3.

FIG. 2 shows comparison results from multiple amino acid sequence alignment analysis when both the putative rice protein amino acid sequence registered with ACCESSION NO: BAB78687 on DDBJ and the amino acid sequence of protein Os3RmybA1 are optimally aligned. Continued from FIG. 1 on FIG. 3.

FIG. 3 shows comparison results from multiple amino acid sequence alignment analysis when both the putative rice protein amino acid sequence registered with ACCESSION NO: BAB78687 on DDBJ and the amino acid sequence of protein Os3RmybA1 are optimally aligned. Continued from FIGS. 1 and 2.

FIG. 7 is a set of photos exhibiting each size of pPZP211-35S:A2RNAi-transfromed BY2 calli, wherein levels of endogenously expressed NtmybA2 decreased by RNA interference mechanisms, and pPZP211-transfromed BY2 calli. Vector: pPZP211-transfromed BY2 calli; and A2 RNAi: pPZP211-35S:A2RNAi-transfromed calli.

FIG. 9 is a set of photos exhibiting each size of pPZP211-35S:BRNAi-transformed BY2 calli, wherein levels of endogenous NtmybB expressed decreased by RNA interference mechanisms, and pPZP211-transformed calli. Vector & vector control: pPZP211-transfromed calli; and B RNAi: pPZP211-35S:BRNAi-transfromed calli.

FIG. 15 shows comparison results from multiple amino acid sequence alignment analysis when the amino acid sequences of proteins, NtmybA1, NtmybA2, and Os3RmybA1, are optimally aligned.

In FIGS. 15 to 17, arrows indicate areas for respective C-terminal deletion NtmybA2 mutant constructs and the corresponding amino acid regions related to NtmybA1, and Os3RmybA1. In the drawings, "*" means that the amino acid residues in that column are identical in all sequences in the alignment (completely conserved amino acid site), ":" means that conserved substitutions have been observed (highly conserved amino acid site), and "." means that semi-conserved substitutions are observed (moderately conserved amino acid site), in connection with amino acid similarity output results from multiple sequence alignment analysis by ClustalW program. Continued on FIGS. 16 to 18.

FIG. 16 shows comparison results from multiple amino acid sequence alignment analysis when the amino acid sequences of proteins, NtmybA1, NtmybA2, and Os3RmybA1, are optimally aligned. Continued from FIG. 15 on FIGS. 17 & 18.

FIG. 17 shows comparison results from multiple amino acid sequence alignment analysis when the amino acid sequences of proteins, NtmybA1, NtmybA2, and Os3RmybA1, are optimally aligned. In the drawings, the sequence segments enclosed by the rectangular box indicate positions of consensus amino acids with NtmybA1 and Os3RmybA1, observed at or near the deletion region of NtmybA2. The amino acid sequences shown over the rectangular boxes signify conserved sequences wherein X stands for any amino acid. Continued from FIGS. 15 & 16 on FIG. 18.

FIG. 18 shows comparison results from multiple amino acid sequence alignment analysis when the amino acid sequences of proteins, NtmybA1, NtmybA2, and Os3RmybA1, are optimally aligned. Continued from FIGS. 15 to 17.

FIG. 19 shows comparison results from multiple amino acid sequence alignment analysis when the amino acid sequences of proteins, NtmybA1, NtmybA2, Os3RmybA1, AtMYB3R1 (in FIGS. 19 to 25, designated "AtMYB3R-1"), and AtMYB3R4 (in FIGS. 19 to 25, designated as "AtMYB3R-4"), are optimally aligned. In the drawings, "*" means that the amino acid residues in that column are identical in all sequences in the alignment (completely conserved amino acid site), ":" means that conserved substitutions have been observed (highly conserved amino acid site), and "." means that semi-conserved substitutions are observed (moderately conserved amino acid site), in connection with amino acid similarity output results from multiple sequence alignment analysis by ClustalW program. Continued on FIGS. 20 to 25.

FIG. 20 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. Continued from FIG. 19 on FIGS. 21 to 25.

FIG. 21 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. Continued from FIGS. 19 & 20 on FIGS. 22 to 25.

FIG. 22 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. Continued from FIGS. 19 to 21 on FIGS. 23 to 25.

FIG. 23 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. In the drawing, the black crossbar indicates a particular sequence region wherein amino acids are highly conserved, except the myb DNA binding domain. The consensus sequence observed in the black crossbar region is written by bold letters, wherein X is any amino acid; J is an amino acid selected from I, V, and L; O is an amino acid selected from S, and T; $X_1$ is an amino acid selected from K, and R; U is an amino acid selected from V, and L; and $X_5$ is an amino acid selected from D, and E. Continued from FIGS. 19 to 22 on FIGS. 24 & 25.

FIG. 24 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. Continued from FIGS. 19 to 23 on FIG. 25.

FIG. 25 shows comparison results from multiple amino acid sequence alignment analysis when the amino acid sequences of proteins, NtmybA1, NtmybA2, Os3RmybA1, AtMYB3R-1, and AtMYB3R-4, are optimally aligned. Continued from FIGS. 19 to 24.

FIG. 26 shows comparison results from multiple amino acid sequence alignment analysis when the amino acid sequences of proteins, NtmybB, AtMYB3R3 (in FIGS. 26 to 28, designated "AtMYB3R-3"), and AtMYB3R5 (in FIGS. 26 to 28, designated "AtMYB3R-5"), are optimally aligned. In the drawings, "*" means that the amino acid residues in that column are identical in all sequences in the alignment (completely conserved amino acid site), ":" means that conserved substitutions have been observed (highly conserved amino acid site), and "." means that semi-conserved substitutions are observed (moderately conserved amino acid site), in connection with amino acid similarity output results from multiple sequence alignment analysis by ClustalW program. In the drawing, the black crossbar indicates a particular sequence region wherein amino acids are highly conserved, except the myb DNA binding domain. The consensus sequence observed in the black crossbar region is written by bold letters, wherein X is any amino acid, and $X_6$ is an amino acid selected from K, R, D, E, and H. Continued on FIGS. 27 & 28.

FIG. 27 shows comparison results from multiple amino acid sequence alignment analysis when the amino acid sequences of proteins, NtmybB, AtMYB3R-3, and AtMYB3R-5, are optimally aligned. Continued from FIG. 26 on FIG. 28.

FIG. 28 shows comparison results from multiple amino acid sequence alignment analysis when the amino acid sequences of proteins, NtmybB, AtMYB3R-3, and AtMYB3R-5, are optimally aligned. Continued from FIGS. 26 & 27.

FIG. 29 shows comparison results from multiple amino acid sequence alignment analysis when the constituent amino acid sequences of respective 3-repeat myb-like DNA binding domains are optimally aligned in connection with proteins, MYB3R-1 (isolated from *Physcomitrella patens*; in FIGS. 29 to 31, designated as "PhpMYB3R-1"), MYB3R-1 (isolated from *Adiantum raddianum*; in FIGS. 29 to 31, designated as "AdrMYB3R-1"), MYB3R-1 (isolated from *Hordeum vulgare*; in FIGS. 29 to 31, designated as "HvMYB3R-1"), MYB3R-1 (isolated from *Secale cereale*; in FIGS. 29 to 31, designated as "ScMYB3R-1"), putative Myb-related domain (isolated from *Papaver rhoeas*; in FIGS. 29 to 31, designated as "ParMYB3R-1"), AtMYB3R1 (in FIGS. 29 to 31, designated as "AtMYB3R-1"), AtMYB3R3 (in FIGS. 29 to 31, designated as "AtMYB3R-3"), AtMYB3R4 (in FIGS. 29 to 31, designated as "AtMYB3R-4"), AtMYB3R5 (in FIGS. 29 to 31, designated as "AtMYB3R-5"), NtmybA1, NtmybA2, NtmybB, and Os3RmybA1. Among 13 amino acid sequences, the conservative amino acid sites are expressed on the consensus sequence in the drawings, wherein X is any amino acid; J is an amino acid selected from I, V, and L; O is an amino acid selected from G, S, T, C, and A; $X_7$ is an amino acid selected from, K, R, and H; U is an amino acid selected from H, W, Y, and F; and $X_5$ is an amino acid selected from D, and E. In the drawings, black crossbars indicate consensus segments observed in the c-myb 3-repeat myb DNA binding domains, which are expressed with "MYB#1 (Myb DNA-binding domain repeat signature 1.)" based on search results obtained by MOTIF program (motif.genome.ad.jp/). Arrows between the black crossbars stand for the number of amino acids existing between the aforementioned consensus sequences. Continued on FIGS. 30 & 31.

FIG. 30 shows comparison results from multiple amino acid sequence alignment analysis when the constituent amino acid sequences of respective 3-repeat myb-like DNA binding domains are optimally aligned in connection with proteins, PhpMYB3R-1, AdrMYB3R-1, HvMYB3R-1, ScMYB3R-1, ParMYB3R-1, AtMYB3R1, AtMYB3R3, AtMYB3R4, AtMYB3R5, NtmybA1, NtmybA2, NtmybB, and Os3RmybA1. Continued from FIG. 29 on FIG. 31.

FIG. 31 shows comparison results from multiple amino acid sequence alignment analysis when the constituent amino acid sequences of respective 3-repeat myb-like DNA binding domains are optimally aligned in connection with proteins, PhpMYB3R-1, AdrMYB3R-1, HvMYB3R-1, ScMYB3R-1, ParMYB3R-1, AtMYB3R1, AtMYB3R3, AtMYB3R4, AtMYB3R5, NtmybA1, NtmybA2, NtmybB, and Os3RmybA1. Continued from FIGS. 29 & 30.

BEST MODES OF CARRYING OUT THE INVENTION

Figure 4:
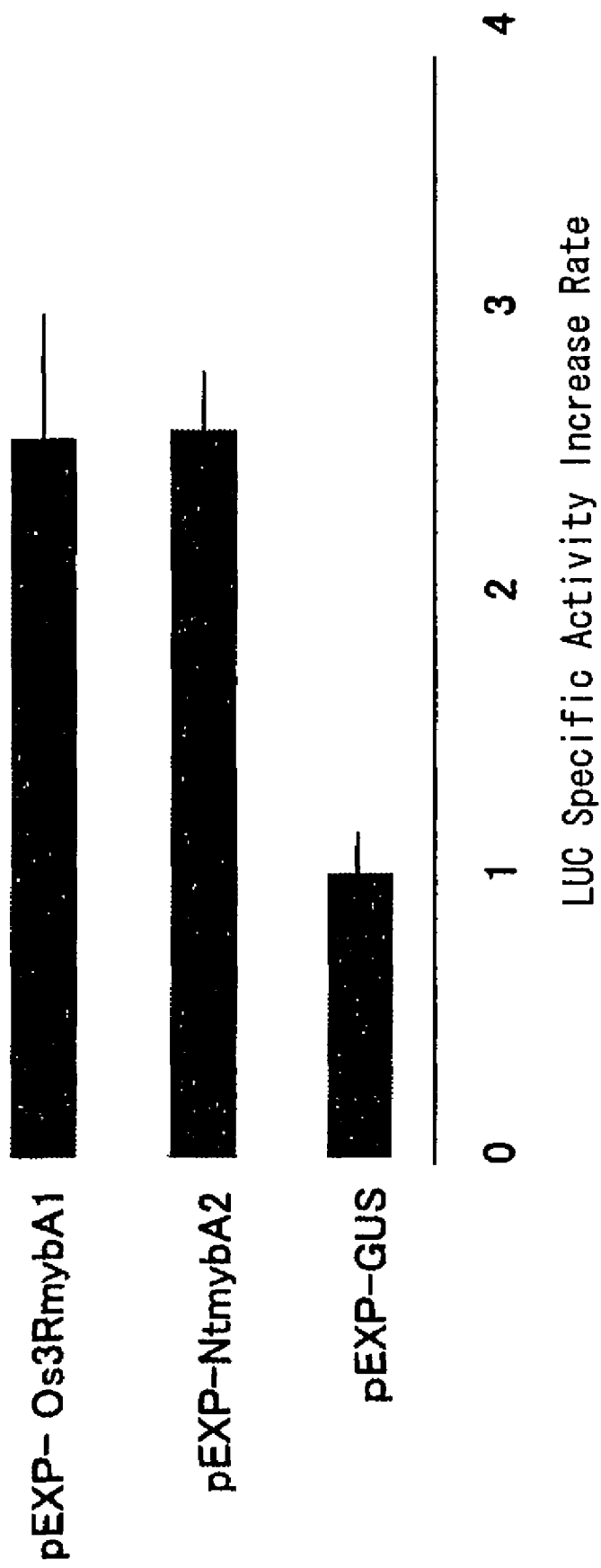
FIG. 4 is a diagram showing LUC specific activity increase ratios wherein Os3RmybA1 and NtmybA2 abilities to activate transcription of the CYM promoter-LUC fused gene were examined using expression plasmids for Os3RmybA1 and NtmybA2 in combination with the CYM promoter-LUC reporter plasmid. All LUC activities are expressed relative to the control (taken as 1.0). Data represent the mean of quintuplicate experiments. Error bars indicate S.D.

In the present invention, utilization of "gene recombination techniques" enables not only acquisition, isolation, and sequencing of targeted nucleic acids, peptides and fragments thereof, but also construction and production of recombinants thereof. Gene recombination techniques (including recombinant DNA techniques) as can be used herein include those known in the art, and can be carried out by the methods described in, for example, J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vol. 1 to 4, (The Practical Approach Series), IRL Press, Oxford University Press (1995); The Japanese Biochemical Society (JBS) ed., "Zoku-Seikagaku Jikken Koza 1, Idenshi Kenkyu-Hou II", Tokyo Kagaku Dozin Co. Ltd., Japan, (1986); JBS ed., "Shin-Seikagaku Jikken Koza 2, Kakusan III (Recombinant DNA technique)", Tokyo Kagaku Dozin Co. Ltd., Japan, (1992); "Methods in Enzymology" series, Academic Press, New York, including, for example, R. Wu ed., "Methods in Enzymology", Vol. 68 (Recombinant DNA), Academic Press, New York (1980); R. Wu et al. ed., "Methods in Enzymology", Vol. 100 (Recombinant DNA, Part B) & 101 (Recombinant DNA, Part C), Academic Press, New York (1983); R. Wu et al. ed., "Methods in Enzymology", Vol. 153 (Recombinant DNA, Part D), 154 (Recombinant DNA, Part E) & 155 (Recombinant DNA, Part F), Academic Press, New York (1987); J. H. Miller ed., "Methods in Enzymology", Vol. 204, Academic Press, New York (1991); R. Wu ed., "Methods in Enzymology", Vol. 216 (Recombinant DNA, Part G), Academic Press, New York (1992); R. Wu ed., "Methods in Enzymology", Vol. 217 (Recombinant DNA, Part H) & 218 (Recombinant DNA, Part I), Academic Press, New York (1993); G. M. Attardi et al. ed., "Methods in Enzymology", Vol. 260 (Mitochondrial Biogenesis and Genetics, Part A), Academic Press, New York (1995); J. L. Campbell ed., "Methods in Enzymology", Vol. 262 (DNA Replication), Academic Press, New York (1995); G. M. Attardi et al. ed., "Methods in Enzymology", Vol. 264 (Mitochondrial Biogenesis and Genetics, Part B), Academic Press, New York (1996); P. M. Conn ed., "Methods in Enzymology", Vol. 302 (Green Fluorescent Protein), Academic Press, New York (1999); S. Weissman ed., "Methods in Enzymology", Vol. 303 (cDNA Preparation and Characterization), Academic Press, New York (1999); J. C. Glorioso et al. ed., "Methods in Enzymology", Vol. 306 (Expression of Recombinant Genes in Eukaryotic Systems), Academic Press, New York (1999); M. Ian Phillips ed., "Methods in Enzymology", Vol. 313 (Antisense Technology, Part A: General Methods, Methods of Delivery and RNA Studies) & 314 (Antisense Technology, Part B: Applications), Academic Press, New York (1999); J. Thorner et al. ed., "Methods in Enzymology", Vol. 326 (Applications of Chimeric Genes and Hybrid Proteins, Part A: Gene Expression and Protein Purification), 327 (Applications of Chimeric Genes and Hybrid Proteins, Part B: Cell Biology and Physiology) & 328 (Applications of Chimeric Genes and Hybrid Proteins, Part C: Protein-Protein Interactions and Genomics), Academic Press, New York (2000) etc., or by methods described in the references cited therein or methods substantially equivalent thereto or modified methods thereof, the disclosures of which are incorporated herein by reference.

The present invention provides plant cells and plants comprising said plant cell, which have modified activities of plant 3Rmyb proteins. The modification of plant 3Rmyb protein activities according to the present invention includes modification of plant 3Rmyb gene expression and modification of plant 3Rmyb protein functions.

The aforementioned modification of plant 3Rmyb gene expression includes stable expression, overexpression, ectopic expression, and induced expression of said genes, and includes suppression of said expression. Preferably, the modification is stable expression, overexpression, or suppression of said expression.

The present invention also provides molecules capable of inhibiting or suppressing the expression (particularly including in vivo expression) of the plant 3Rmyb gene(s) in plants. The term "suppressing the expression" of the plant 3Rmyb gene(s) or of plant gene 3Rmyb, or "suppressed expression" or "repressed expression" of the plant 3Rmyb gene(s) includes suppression of gene transcription and suppression of translation to protein, as well as not only completely silencing of DNA expression but also reduction in DNA expression.

Methods utilizing antisense techniques are most employed among persons skilled in the art in suppression of specific endogenous gene expression in plants. Antisense effects in plant cells were first evidenced experimentally by Ecker et al. using transient expression analysis wherein antisense RNA was transformed into plants by electroporation and the antisense effect exerted by said antisense RNA was observed in the transgenic plants (J. R. Ecker and R. W. Davis, Proc. Natl. Acad. USA. 83: 5372 (1986)). Thereafter, embodiments of tobacco and petunia were reported where the expression of antisense RNA led to reduction in target gene expression (A. R. van der Krol et al., Nature 333: 866 (1988)). Thus, the techniques have currently been established in order to inhibit or suppress gene expression in plants.

Antisense nucleic acid-mediated gene expression inhibition or suppression includes plural actions as follows: namely, inhibition of transcription initiation, induced by triplex-formation; suppression of transcription, induced by hybridization to sites at which an open loop structure is locally created with RNA Polymerase; inhibition of transcription, induced by hybridization to RNA being synthesized in progress; suppression of splicing, induced by hybridization at intron-exon junctions; suppression of splicing, induced by hybridization to spliceosome-forming sites; suppression of transfer from nuclei to cytoplasms, induced by hybridization with mRNA; suppression of splicing, induced by hybridization to capping sites and polyadenylated sites; suppression of translation initiation, induced by hybridization to translation initiator-binding sites; suppression of translation, induced by hybridization to ribosome-binding sites near initiation codons; inhibition of peptide chain elongation, induced by hybridization to mRNA translation regions or polysome-binding sites; and silencing of gene expression, induced by hybridization with nucleic acid-protein interacting sites; and the like. These inhibit transcription, splicing, or translation processes to suppress the expression of target genes.

The antisense sequences as used herein may suppress or inhibit expression of target genes relying on any of the aforementioned actions or activities. In an embodiment, when designed to be complementary to the untranslated region (UTR) near the 5' end of target gene mRNA, antisense sequences will be effective in inhibition of gene translation. However, sequences complementary to the coding region or the 3' untranslated region (3'-UTR) are also applicable. Thus, DNA containing an antisense sequence on a sequence not limited to regions for translation but including untranslated regions is also encompassed by the antisense DNA utilized in the present invention. Antisense DNA which is used herein is ligated to the downstream site of a suitable promoter, preferably followed by ligation with a sequence containing a transcription termination signal at the 3' side. The DNA thus prepared can be transfected or transformed into desired plants by known techniques. It is preferable that the sequence of antisense DNA is complementary to an endogenous gene owned by plants to be transformed, or part thereof. However, it is not necessary that it is completely complementary, as long as it can inhibit effectively expression of the gene. Transcript RNA is preferably at least 90%, most preferably at least 95%, complementary to the transcript product of a target gene. The sequence homology can be determined by the aforementioned searching.

For inhibiting effectively expression of target genes by using antisense sequences, the length of antisense DNA is at least 15 nucleotides, preferably at least 100 nucleotides or more, and further preferably at least 500 nucleotides or more. Usually, the length of antisense DNA used herein is shorter than 5 kb, preferably less than 2.5 kb.

Suppression of endogenous gene expression can be carried out using DNA coding for a ribozyme. The ribozyme refers to a catalytic RNA molecule. There are ribozymes with a variety of activities. Among them, studies on ribozymes serving as enzymes which cleave RNA enable designs of ribozymes which allow site-specific cleavage of RNA. The ribozymes are not only those with a size of about 400 or more nucleotides, such as the group I intron and RNase P including M1 RNA, but also those having an active domain with about 40 nucleotides, denoted as the hammerhead ribozyme and the hairpin ribozyme.

For instance, the self-cleaver domain of hammerhead ribozymes cleaves G13U14C15 at the 3' side of C15; however, it is considered that the formation of base pairs between U14 and A9 is crucial for the catalysis, and it is shown that the nucleotide at the 15 position, A or U, in addition to C, can be cleaved (M. Koizumi et al. (1988), FEBS Lett. 228: 225). When the substrate-binding site of a ribozyme is designed to be complementary to the RNA sequence near the target site, it will be possible to produce ribozymes which cleave RNA in a restriction enzyme manner and recognize the sequence of UC, UU or UA within the target RNA (M. Koizumi et al. (1988), FEBS Lett. 239: 285, M. Koizumi et al. (1989), Nucleic Acids Res. 17: 7059). For example, plural potential target sites exist within the coding region of the NtmybA2 gene (SEQ ID NO: 2).

Also, hairpin ribozymes are useful for the purpose of practicing the present invention. The hairpin ribozyme is observed, for example, within the minus chain of tobacco ringspot virus satellite RNA (J. M. Buzayan, Nature, 323: 349, 1986). It is also shown that this ribozyme can be designed to allow cleavage of target-specific RNA (Y. Kikuchi and N. Sasaki, Nucleic Acids Res., 19: 6751 (1992)).

The ribozyme designed to allow cleavage of targets will be ligated to a promoter such as the cauliflower mosaic virus (CaMV) 35S promoter and a transcription termination sequence to provide transcription in plant cells. In such cases, however, when extra sequences are added to the 5' or 3' end of transcript RNA, the ribozyme activity will or will not vanish. In these cases, for cutting a ribozyme portion out of RNA containing a transcript ribozyme with accuracy, another cis acting trimming-ribozyme can also be placed on the 5' or 3' side of the ribozyme portion to allow trimming (K. Taira et al., Protein Eng., 3: 733 (1990); A. M. Dzianott and J. J. Bujarski, Proc. Natl. Acad. Sci. USA., 86: 4823 (1989); C. A. Grosshans and R. T. Cech, Nucleic Acids Res., 19: 3875 (1991); K. Taira et al., Nucleic Acids Res., 19: 5125 (1991)). Also, it is possible to place such constituent units in a tandem manner to allow cleavage of plural sites within target genes, thereby enhancing effects more (N. Yuyama et al., Biochem. Biophys. Res. Commun., 186: 1271, 1992). The transcript products of genes to be targeted in the present invention can be specifically cleaved with such ribozymes, thereby leading to suppression of said gene expression.

Suppression of endogenous gene expression can be achieved by co-suppression induced by transformation with DNA having a sequence identical or analogous to the sequence of target genes. The term "co-suppression" refers to a phenomenon where introduction of a gene comprising a sequence identical or similar to the sequence of a target endogenous gene into plants suppresses expression of both the incorporated foreign gene and the target endogenous gene. Details of co-suppression mechanism have been not yet apparent but the co-suppression is often observed among plants (Curr. Biol., 7: R793, 1997; Curr. Biol., 6: 810, 1996). For example, plants wherein the NtmybA2 gene is co-suppressed may be obtained by transforming or transfecting target plants with vector DNA constructed to allow expression of DNA comprising the NtmybA2 gene or an analogous sequence thereof followed by selection of plants with more suppressed cell growth from the resultant plants. Genes used in co-suppression are not necessary to be entirely identical with the target gene, but they are at least 70% (70% or more), preferably 80% or more, and still preferably at least 90% (e.g., 95% or more) identical in sequence. The identity of sequences can be determined using the aforementioned retrieval.

The suppression of endogenous gene expression can be achieved via RNA interference (RNAi) induced by transformation with DNA wherein a sequence identical or analogous to the sequence of target genes is arranged in an inverted repeat manner. The "RNA interference" or "RNAi" indicates a phenomenon where introduction of DNA wherein a sequence identical or analogous to a target endogenous gene is arranged in an inverted repeat manner, induced by transformation of plants, causes the expression of double-stranded RNA (dsRNA) derived from the foreign DNA, thereby suppressing the expression of the target gene. It is thought that the mechanism of RNA interference includes the initial step of forming a complex of targeted gene mRNA and double-stranded RNA derived from an introduced sequence followed by synthesis of complementary RNA using the associated sequences as primers, the second step of fragmenting the complex with endogenous RNase, and the third step of operating fragmented double-stranded RNAs with a length of 20 to 30 base pairs as signals for secondary RNA interference to allow redegradation of the targeted endogenous gene mRNA (Curr. Biol., 7: R793, 1997; Curr. Biol., 6: 810, 1996). For instance, the process for obtaining plants wherein the NtmybB gene is suppressed by RNA interference may include transformation of targeted plants with vector DNA constructed to allow expression of DNA wherein a DNA sequence having the NtmybB gene or an analogous sequence thereof is arranged in an inverted repeat manner followed by selection of transformed plants with enhanced or accelerated cell growth from the resultant transformed plants. It is not necessary that genes applied to RNA interference are entirely identical to targeted genes, but they are those with at least 10 continuous nucleotides, preferably 20 to 100 continuous nucleotides, and more preferably 50 or more continuous nucleotides, identical in sequence to the targeted gene. The genes applied to RNA interference may be those having a sequence at least 70%, preferably at least 80%, and further preferably at least 90% (e.g., 95% or more) identical in sequence to the targeted gene of interest. Further, the more preferable genes applied to RNA interference include those having a sequence which is not only at least 70%, preferably at least 80%, and further preferably at least 90% (e.g., 95% or more) identical in sequence to the targeted gene of interest but also arranged in an inverted repeat manner. Among them, the desirable genes applied to RNA interference are those having a sequence which has an identity in sequence to the targeted gene and arranged via a spacer sequence in an inverted repeat manner. The identity of sequences can be determined using the aforementioned retrieval. For the length of the gene applied to RNA interference, they may be full-length form target genes. However, it is sufficient that they have at least 25 nucleotides, preferably 50 nucleotides, more preferably 100 nucleotides, further preferably 500 nucleotides.

In addition, RNAi is practicable via plant virus infection. A plant virus having single strand RNA as a genome takes a double stranded form in the process of replication. Therefore, when the sequence of a targeted gene is inserted together with a suitable promoter into a plant virus genome, followed by transfection of plants with the resultant recombinant virus, the double stranded RNA of the targeted gene sequence will be produced in association with replication of said virus. As a result, RNAi effects will be achievable (Angell et al., Plant J. 20, 357-362 (1999)).

Further, the suppression of endogenous gene expression according to the present invention can be achieved by transformation of plants with genes having dominant negative properties against targeted genes. The "DNA coding for a protein having dominant negative properties" refers to DNAs coding for proteins which function as silencers or reducers against the activities of proteins encoded by the inventive endogenous genes intrinsically possessed by plants when said DNAs are expressed. Whether or not the DNA of interest functions as a silencer or reducer against the activity of the endogenous gene according to the present invention can be judged, as aforementioned, depending on whether or not the DNA of interest inhibits or suppresses the amount of gene transcripts from plant cyclin B genes, NACK1 genes or ortholog genes thereof.

Reduction induced by dominant negative molecules in the functions of endogenous 3Rmyb proteins may be transformed into plant species different from those from which the NtmybA1 proteins, the NtmybA2 proteins, or the Os3RmybA1 proteins are isolated.

The plants having modified activities of plant 3Rmyb proteins are herein those members having altered expression of plant 3Rmyb genes or altered functions of the 3Rmyb proteins. Preferably, the plants exhibit changes in expression amounts of said genes or in functions of expressed proteins at a level detectably different from those in wild-type plants. Examples of the change in expression amounts include stable expression, induced expression, overexpression, ectopic expression, and suppression of said expression. These plants exhibiting altered expression or functions may be created by traditional mutagenesis and selection techniques besides genetic engineering techniques via transformation.

The present invention still provides recombinant DNAs and vectors (vector constructs) comprising an insert of DNA which suppresses or inhibits the aforementioned DNA of the present invention, expression of the DNA of the present invention, and the expression of proteins encoded by the DNA of the present invention. The recombinant DNAs and vectors (vector constructs) include, besides the aforementioned vectors (vector constructs) utilized in production of recombinant proteins, vectors or vector constructs to allow expression of DNAs in plant cells for production of transgenic plants, said DNAs which suppress or inhibit the DNA of the present invention, expression of the DNA of the present invention, and the expression of proteins encoded by the DNA of the present invention. Such recombinant DNAs or vectors (vector constructs) are not limited to, but include any as long as they comprise a promoter sequence transcribable in plant cells and a terminator sequence containing a polyadenylation site required for stabilization of transcript products. Examples of the recombinant DNAs or vectors (vector constructs) are plasmids, "pBI121", "pBI221", "pBI101" (all, Clontech), "pTA7001", "pTA7002" (Aoyama et al. (1997) Plant J. 11: 605), "pPZP211" (Hajdukiewicz et al., Plant Mol. Biol. 25: 989 (1994), etc.

The aforementioned recombinant DNA or vector (vector construct) of the present invention may comprise any of promoters designed to allow stable or inducible expression of the proteins according to the present invention. The promoters expressible in vivo herein are desirably those as listed herein below. Examples of promoters designed to allow stable expression are the cauliflower mosaic virus (CaMV) 35S promoter (Odell et al., Nature, 313: 810 (1985)), the rice actin promoter (Zhang et al., Plant Cell, 3: 1155 (1991)), the maize ubiquitin promoter (Cornejo et al., Plant Mol. Biol., 23: 567 (1993)), etc.

Promoters designed to allow inducible expression include, for example, those known as elements which are expressible by exogenous factors including filamentous fungal, bacterial, or viral infection or invasion, low temperatures, elevated temperatures, dry conditions, UV light radiation, and applications of specific compounds. Examples of such promoters are those for expression induced by filamentous fungal, bacterial, or viral infection or invasion, such as the rice chitinase gene promoter (Xu et al., Plant Mol. Biol., 30: 387 (1996)) and the tobacco PR protein gene promoter (Ohshima et al., Plant Cell 2: 95 (1990)); the rice "lip19" gene promoter inducible by low temperatures (Aguan et al., Mol. Gen Genet., 240: 1 (1993)); the rice "hsp80" gene or "hsp72" gene promoter inducible by high temperatures (Van Breusegem et al., Planta, 193: 57 (1994)); the *Arabidopsis thaliana* "rab16" gene promoter inducible by desiccation (Nundy et al., Proc. Natl. Acad. Sci. USA, 87: 1406 (1990)); the parsley chalcone synthase gene promoter inducible by UV light radiation (Schulze-Lefert et al., EMBO J., 8: 651 (1989)); the maize alcohol dehydrogenase gene promoter inducible by anaerobic conditions (Walker et al., Proc. Natl. Acad. Sci. USA, 84: 6624 (1987)); etc. Also, the rice chitinase gene promoter and the tobacco PR protein gene promoter can be induced by specific compounds such as salicylic acid. The "rab16" can also be induced by applications of phytohormone abscisic acid. Included is use of vector systems comprising glucocorticoid- or estrogen-responsive systems to allow inducible expression of genes in plants. The glucocorticoid-responsive vectors to allow inducible expression include pTA7001, pTA7002 (Aoyama et al., Plant J., 11: 605 (1997)). The estrogen-responsive vectors to allow inducible expression include pER10 (Zuo et al., Plant J., 24: 265 (2000)). Also, examples of the promoters to allow growing cell-specific expression of genes in plants are the tobacco NPK1 gene promoter expressible during S to M phases (Nishihama et al., Genes Dev., 15: 352 (2000)), the tobacco NACK1 gene promoter as a promoter expressible at M phase (Nishihama et al., Cell, 109: 87 (2002)), the *Catharanthus roseus* CYM gene promoter (Ito et al., Plant J., 11: 983 (1997)), the *Catharanthus roseus* CYS gene promoter expressible at S phase (Ito et al., Plant J., 11: 983 (1997)), the *Arabidopsis thaliana* cdc2a gene promoter which is observed to be active in growing cells throughout cell cycle (Chung et al., FEBS Lett., 362: 215 (1995)), etc. Examples of the tissue-specific promoters can be found in the following documents:

U.S. Pat. No. 5,459,252 and U.S. Pat. No. 5,633,363 (root-specific), U.S. Pat. No. 5,097,025 ((i) seed, (ii) mature plant), U.S. Pat. No. 5,391,725 ((i) chloroplast, (ii) cytosol), U.S. Pat. No. 4,886,753 (root nodule), U.S. Pat. No. 5,646,333 (epidermis), U.S. Pat. No. 5,110,732 ((i) root, (ii) storage root), U.S. Pat. No. 5,618,988 (storage organ), U.S. Pat. No. 5,401,836 and U.S. Pat. No. 5,792,925 (root), U.S. Pat. No. 4,943,674 (fruit or nut), U.S. Pat. No. 5,495,007 (phloem), U.S. Pat. No. 5,824,857 (vascular tissue), the disclosures of which are incorporated herein by reference. Besides these promoters, the applicable promoters include the *Arabidopsis thaliana* AtHB8 promoter which acts as a vascular bundle procambium-specific promoter (Baima et al. Development 121: 4171 (1995)), the stem- or root-specific *Arabidopsis thaliana* ACL5 promoter (Hanzawa et al. The EMBO Journal, 19: 4248 (2000)), the terrestrial body-specific tomato RBCS3A promoter (Meier et al. Plant Physiol. 107: 1105 (1995)), etc.

The promoters which are active at high gene expression levels in the male reproductive organs or cells, include the *Arabidopsis thaliana* AtNACK2 gene promoter (PCT/JP02/12268), the *Arabidopsis thaliana* AVP1 gene promoter (Mitsuda et al., Plant Mol. Biol, 46: 185 (2001)), the *Arabidopsis thaliana* DAD 1 gene promoter (Ishiguro et al., Plant Cell, 13: 2191 (2001)), the tobacco TA20 & TA29 gene promoters (Goldberg et al., Science, 240: 1460 (1988)), the rice Osg6B gene promoter (Tuchiya et al., Plant Mol. Biol, 26: 1737 (1994)), the tomato Lat52 gene promoter (Twellr et al., Development, 109: 705 (1990)), the tobacco g10 gene promoter (Rogers et al., Plant Mol. Biol., 45: 577 (2001)), and artificial promoters derived by insertion of an anther-specific regulatory sequence for gene expression into the cauliflower mosaic virus 35S promoter (Ingrid et al., Plant Cell, 4: 253 (1992)), etc.

Also, the present invention provides transformed plant cells into which the aforementioned recombinant DNA or vector (or vector construct) of the present invention is incorporated. The plant cells into which the vector (or vector construct) of the present invention is incorporated includes those plant cells for giving transformed plant bodies (plant transformants). The plant cell into which the vector or vector construct of the present invention is transferred includes plant cells for producing or constructing transgenic plants or plant bodies. The applicable plant cell is not limited to but selected from known plants, including for example cultivated plants, useful or valuable plants and other plants. Such plants include those known as cereal crops, beans, root and tuber crops, nuts, seeds, vegetables, berries, fruits, or orchard trees, further derived from garden crops, garden trees or grasses, horticultural species, flowering trees and ornamental species. Examples of the plant cells are those selected from the group consisting of Solanaceous species, Cruciferous (Brassicaceous) species, Graminaceous species, Leguminous species, Liliaceous species, Umbelliferous species, Cucurbitaceous species and other species, preferably tobacco (*Nicotiana tabacum*), *Arabidopsis thaliana*, soybean (*Glycine max*), Aduki bean (small red bean), green beans (*Phaseolus vulgaris*), peas (*Lathyrus* spp. including snow pea (*Pisum sativum*)), broad bean (*Vicia faba*), peanuts (*Arachis hypogaea*), sesame (*Sesamum indicum* LINNE), rice (*Oryza sativa*), wheat (*Triticum aestivum*), barley, rye (*Secale cereale*), oat (*Avena sativa*), corn (*Zea mays*), sorghum (*Sorghum bicolor, Sorghum vulgare*), potato (*Solanum tuberosum*), tomato, green pepper, cabbage, broccoli, parsley, spinach, sweet potato (*Ipomoea batatus*), taro (*Colocasia* spp. including *C. esculenta*), konjac (*Amorphophallus rivieri* var. *konjac*), cassava (*Manihot* spp. including *M. esculenta*), grapes, apple, peach, pear (*Pyrus* spp. including *Pyrus pyrifolia* var. *culta* and *Pyrus communis*), persimmon (*Diospyros kaki*), strawberries, blueberries, plum, melon, cucumber, sugar cane (*Saccharum officinarum* L.), tangerine, lemon, orange, olive (*Olea europaea*), cotton (*Gossypium arboretum*) and other plant cells. The plant cells of the present invention include not only culture cells (cell lines) but also individual cells present in plant bodies. They also include protoplasts, shoot primordia, multiple shoots, and hairy roots. Applicable incorporation of a vector or vector construct into a plant cell includes, for example, *Agrobacterium*-mediated transformation (Hood et al., Transgenic Res., 2: 218 (1993); Hiei et al., Plant J., 6: 271 (1994)), electroporation (Tada et al., Theor. Appl. Genet, 80: 475 (1990)), polyethylene glycol method (Lazzeri et al., Theor. Appl. Genet, 81: 437 (1991)), particle bombardment (Sanford et al., J. Part. Sci. tech., 5: 27 (1987)). The incorporation (introduction) technique is suitably selected those known in the art and well described in the scientific and patent literature.

Transformed plant cells can be redifferentiated to regenerate plant bodies. Redifferentiation varies depending on plant cell species, but includes, for example, Fujimura et al. method (Plant Tissue Culture Lett., 2: 74 (1995)) for rice; Shillito et al. method (Bio/Technology, 7: 581 (1989)) and Gorden-Kamm et al. method (Plant Cell, 2: 603 (1990)) for corn; Visser et al. method (Theor. Appl. Genet, 78: 594 (1989)) for potato; Nagata & Takebe method (Planta, 99: 12 (1971)) for tobacco; and Akama et al. method (Plant Cell Reports, 12: 7-11 (1992)) for *Arabidopsis thaliana*.

Once transgenic plants are produced into which inhibitory or suppressive DNA is incorporated against the DNA of the present invention or expression of the inventive DNA, it is possible to obtain off-springs from the plants via sexual or asexual (vegetative) reproduction. It is possible to propagate plants in a mass scale on the basis of propagation materials (for example, seeds, nuts, fruits, cuttings, tubers, rhizomes, bulbs, shoots, roots, offsets, plant calli, protoplasts, etc.) obtained from the plant of interest, and off-springs or clones thereof. The present invention encompasses plant cells into which suppressive DNA has been incorporated against the DNA of the present invention or expression of the inventive DNA, plants harboring the same plant cell, off-springs and clones derived from the same plant, said plants or plant bodies, their propagation materials (sources) such as off-springs and clones.

The plants of the present invention can change their cell growth and development/differentiation by controlling the expression of inventive DNA, in comparison with normal plant individuals.

The term "modification of cell growth", "modification of cell proliferation", or "modified cell growth" refers to, for example, events including a reduction or delay in time required for the cell cycle; a reduction or delay in time required for each of constituent G1, S, G2, and M phases for the cell cycle; inhibition or arresting of entry into each of the constituent G1, S, G2, and M phases for the cell cycle; suppression of termination of each of the constituent G1, S, G2, and M phases for the cell cycle; suppression of occurrence of each of the constituent G1, S, G2, and M phases for the cell cycle; a change in cell size; a change in phragmoplast expansion; a change in phragmoplast formation; a change in cell plate expansion; a change in cell plate formation; a change in cell division frequency; a change in the number of nuclei contained in a cell; and a change in the content level of DNA in a nucleus. Preferable examples thereof are events including a reduction or delay in time required for the cell cycle, a change in cell size; a change in phragmoplast formation; a change in cell plate formation; a change in cell division frequency; and a change in the content level of nuclear DNA. The change in the content level of nuclear DNA as used herein covers a change in polyploidy, preferably, an increase in polyploidy.

The term "modification of development/differentiation" or "modified development/differentiation" as used herein refers to, for example, events including an increase in the number of constituent cells for a plant due to the enhanced cell growth, a decrease in the number of constituent cells for a plant due to the suppressed cell growth, an increase in the rate of plant growth and development due to the enhanced cell growth, a decrease in the rate of plant growth and development due to the suppressed cell growth, increasing the rate of plant growth and development to shorten a period required for flowering, decreasing the rate of plant growth and development to prolong a period required for flowering, increasing the rate of plant growth and development free of altering regulatory machinery in the flowering to form floral buds in a large size plant, decreasing the rate of plant growth and development free of altering regulatory machinery in the flowering to form floral buds in a small size plant, increasing the rate of plant growth and development to shorten a period required until senescence, decreasing the rate of plant growth and development to prolong a period until senescence, increasing the rate of plant growth and development free of altering regulating machinery until initiation of senescence to grow up to be a large size plant until the initiation of senescence, decreasing the rate of plant growth and development free of altering regulating machinery until initiation of senescence to start senescence after growing up to be a small size plant, a change in tissue morphologic form due to the enhanced or suppressed cell growth, a change in tissue size due to the enhanced or suppressed cell growth, a change in organ morphologic form due to the enhanced or suppressed cell growth, a change in organ size due to the enhanced or suppressed cell growth, a change in plant morphologic form due to the enhanced or suppressed cell growth, and a change in plant size due to the enhanced or suppressed cell growth. Preferable examples thereof are events including increasing the rate of plant growth and development without changing regulatory machinery in the flowering to form floral buds in a large size plant, a decrease in the number of constituent cells for a plant due to the suppressed cell growth, decreasing the rate of plant growth and development without changing floral bud formation-regulating machinery to form floral buds in a small size plant, a change in organ size due to the enhanced or suppressed cell growth, and a change in plant size due to the enhanced or suppressed cell growth. A more preferable example thereof is a change in plant size due to the enhanced or suppressed cell growth. In the present invention, the change in plant size due to the enhanced or suppressed cell growth is an increase in plant size because of the enhanced cell growth or a decrease in plant size due to the suppressed cell growth.

The creation of plants allowing a decline in gene expression levels of endogenous NtmybA1 and NtmybA2 herein leads to production of plants having suppressed growth and development or proliferation, accompanied with cells having their suppressed or inhibited cell division or cytokinesis, and the creation of cultured cells having decreased gene expression levels of endogenous NtmybA2 results in their modified cell cycle. These show that NtmybA1 and NtmybA2 are positively regulating factors in respect to the cell cycle and cell division, and that it is possible to generate plants having their suppressed growth and development properties.

In the present invention, the creation of transgenic plants and transformed cells which allow stable expression of NtmybA2 results in production of plants or culture cells which are slowly grown. This shows that the ectopic expression of NtmybA2 allows the creation of plants having their delayed cell cycle and suppressed growth and development.

In transgenic plants and transformed cells having decreased gene expression levels of endogenous NtmybB, their growth and development is herein suppressed or inhibited. This shows that NtmybB is a negatively regulating factor in respect to the cell cycle and cell division, and that it is possible to create plants having enhanced growth and development properties.

In plants which allow stable expression of NtmybB, their growth and development is herein suppressed or inhibited. This shows that NtmybB is a negatively regulating factor in respect to the cell cycle and cell division, and that it is possible to provide plants having suppressed growth and development properties.

The present invention provides rice Os3RmybA1 genes which serve as transcription activators for cyclin B genes and NACK-related genes. From rice (*Oryza sativa*), cDNA of Os3RmybA1 which is the plant 3Rmyb gene is isolated and its nucleotide sequence is successfully disclosed herein. The nucleotide sequence of Os3RmybA1 cDNA is shown in SEQ ID NO: 31, and the amino acid sequence of protein Os3RmybA1 encoded by this gene is also shown in SEQ ID NO: 32.

The present invention provides Monocotyledonae plant 3Rmyb proteins which are functionally equivalent to the protein Os3RmybA1. As used herein, the term "equivalently functional" or "functionally equivalent" indicates that a protein acts or functions as a transcription activator for the cyclin B genes and NACK-related genes. It is possible to assess whether or not proteins serve as factors for controlling the transcription of the cyclin B genes and NACK-related genes, through functional complementation assay based on the expression of such proteins in mutant strains, and activation of cyclin B gene and NACK-related gene transcription by such proteins which are transiently expressed in plant cells.

Utilizable plants for isolation or separation of proteins functionally equivalent to the plant 3Rmyb proteins characterized in the present invention can be selected from Monocotyledonae plants. These plants can also be used as gene sources.

In an embodiment of methods for obtaining or isolating the aforementioned functionally equivalent protein, techniques for incorporating an amino acid mutation into a protein are well known to persons skilled in the art. It is possible for a person skilled in the art to incorporate an amino acid substitution, deletion (disruption), and/or insertion (addition) into the amino acid sequence of a naturally occurring "Os3RmybA1" protein (e.g., the protein shown in SEQ ID NO: 32) according to a conventional technique to produce a mutated protein (mutein) functionally equivalent to such a naturally occurring protein. Amino acid mutations may also occur naturally. The proteins of the present invention include those having an amino acid sequence containing at least one substitution, deletion (disruption), or insertion (addition) of one or plural amino acid residues in the amino acid sequence of such a naturally occurring "Os3RmybA1" protein. The number of altered amino acid residues in sequence is usually 50 or less per total of amino acid residues present in a protein, preferably 30 or less, still preferably 10 or less and more preferably 3 or less. Amino acid modifications can be performed using for example "Transformer Site-directed Mutagenesis Kit" and "ExSite PCR-Based Site-directed Mutagenesis Kit" (Clontech) for mutations and substitutions, and "Quantum leap Nested Deletion Kit" (Clontech) for deletions.

Such mutations, conversions and modifications include those described in JBS (Ed.), "Zoku-Seikagaku Jikken Koza 1, Idenshi Kenkyuhou II", p105 (Susumu Hirose), Tokyo Kagaku Dozin Co. Ltd., Japan (1986); JBS (Ed.), "Shin-Seikagaku Jikken Koza 2, Kakusan III (Recombinant DNA technique)", p233 (Susumu Hirose), Tokyo Kagaku Dozin Co. Ltd., Japan (1992); R. Wu, L. Grossman, ed., "Methods in Enzymology", Vol. 154, p. 350 & p. 367, Academic Press, New York (1987); R. Wu, L. Grossman, ed., "Methods in Enzymology", Vol. 100, p. 457 & p. 468, Academic Press, New York (1983); J. A. Wells et al., Gene, 34: 315, 1985; T. Grundstroem et al., Nucleic Acids Res., 13: 3305, 1985; J. Taylor et al., Nucleic Acids Res., 13: 8765, 1985; R. Wu ed., "Methods in Enzymology", Vol. 155, p. 568, Academic Press, New York (1987); A. R. Oliphant et al., Gene, 44: 177, 1986, etc. For example, included are methods such as site-directed mutagenesis (site-specific mutagenesis) utilizing synthetic oligonucleotides (Zoller et al., Nucl. Acids Res., 10: 6487, 1987; Carter et al., Nucl. Acids Res., 13: 4331, 1986), cassette mutagenesis (Wells et al., Gene, 34: 315, 1985), restriction selection mutagenesis (Wells et al., Philos. Trans. R. Soc. London Ser A, 317: 415, 1986), alanine scanning (Cunningham & Wells, Science, 244: 1081-1085, 1989), PCR mutagenesis, the Kunkel method, dNTP[αS] method (Eckstein), region directed mutagenesis using sulfurous acid and nitrous acid and the like.

The substitution, deletion (disruption) or insertion (addition) of amino acids may produce a desirable modification, and can cause an alteration in physiological or chemical properties of a constituent polypeptide for the protein of interest. There are often cases where a polypeptide with substitution, deletion or insertion will be considered to be substantially identical to a polypeptide without such substitution, deletion or insertion. Substantially identical substituents of amino acids in the amino acid sequence can be selected from other amino acids in the class to which the amino acid belongs. For instance, non-polar (hydrophobic) amino acids include alanine, phenylalanine, leucine, isoleucine, valine, proline, tryptophan, methionine and the like, polar (neutral) amino acids include glycine, serine, threonine, cysteine, tyrosine, asparagine, glutamine and the like, amino acids having a positive charge (basic amino acids) include arginine, lysine, histidine and the like, and amino acids having a negative charge (acidic amino acids) include aspartic acid, glutamic acid and the like. In some cases, cysteine may be replaced with serine; glycine with alanine or leucine; and leucine with alanine, isoleucine, valine, or others. In the proteins of the present invention, amino acid residues contained therein can be modified by chemical techniques. Also, they can be modified and partially degraded with enzymes such as peptidases (e.g., pepsin, chymotrypsin, papain, bromelain, endopeptidase, exopeptidase, etc.) to make derivatives or mutants thereof.

And, the proteins may be expressed as fusion proteins when produced by gene recombination techniques, and may be in vivo or in vitro converted or processed into those products having substantially equivalent biological activity as compared to those which naturally occur. The fusion protein expression system usually used in gene engineering can be applied. Such fusion proteins can be purified by an affinity chromatography and the like, taking advantage of their fusion moieties. Such fusion proteins include those fused to a histidine tag, and those fused to the amino acid sequence of β-galactosidase (β-gal), maltose-binding protein (MBP), glutathione S-transferase (GST), thioredoxin (TRX) or Cre Recombinase. Similarly, the polypeptide can be united with a tag of heterogeneous epitope, and can be isolated/purified by an immunoaffinity chromatography using an antibody specifically binding to the epitope. In more suitable embodiments, the representatives include, for example, AU5, c-Myc, CruzTag 09, CruzTag 22, CruzTag 41, Glu-Glu, HA, Ha.11, KT3, FLAG (registered trademark, Sigma-Aldrich), Omni-probe, S-probe, T7, Lex A, V5, VP16, GAL4, VSV-G, and others (Field et al., Molecular and Cellular Biology, 8: pp. 2159-2165 (1988); Evan et al., Molecular and Cellular Biology, 5: pp. 3610-3616 (1985); Paborsky et al., Protein Engineering, 3(6): pp. 547-553 (1990); Hopp et al., BioTechnology, 6: pp. 1204-1210 (1988); Martin et al., Science, 255: pp. 192-194 (1992); Skinner et al., J. Biol. Chem., 266: pp. 15163-15166 (1991); Lutz-Freyermuth et al., Proc. Natl. Acad. Sci. USA, 87: pp. 6393-6397 (1990); etc.). Yeast two-hybrid systems are also applicable.

Besides, the fusion proteins can be those tagged with a marker such that they become detectable proteins. In more suitable embodiments, the detectable markers may be Biotin-Avi Tag which is a biotin/streptavidin system, and fluorescent substances. The fluorescent substances include green fluorescent proteins (GFP) derived from luminescent jelly fish such as *Aequorea victorea* and the like, modified variants thereof (GFP variants) such as EGFP (enhanced-humanized GFP) and rsGFP (red-shift GFP), yellow fluorescent proteins (YFP), green fluorescent proteins (GFP), cyan fluorescent proteins (CFP), blue fluorescent proteins (BFP), GFP derived from *Renilla reniformis*, and the like (Atsushi Miyawaki ed., Jikken Igaku, suppl., Postgenome Jidai no Jikken Kouza 3. GFP and Bioimaging, Youdosha, Japan, 2000). Also, detection can be carried out using antibodies (including monoclonal antibodies and fragments thereof) which specifically recognize the above fusion tag.

The methods known in the peptide synthetic art, for example, chemical synthetic methods such as liquid phase synthetic methods, and solid phase synthetic methods can be used for the synthesis of the proteins and peptide fragments thereof according to the present invention. In such methods, using a resin for synthesis of proteins or peptides, an appropriately protected amino acid is sequentially attached to the desired amino acid sequence on the resin according to various condensation methods as known in the art. Various activating reagents as known in the art are preferably used for the condensation reactions. For example, carbodiimides such as dicyclohexylcarbodiimide can be preferably used as such reagents. An objective reagent can be obtained by appropriately removing a protecting group when a product has the protecting group.

The proteins of the present invention can be produced as naturally occurring proteins (native proteins) by methods known to a person skilled in the art or alternatively as recombinant proteins which are prepared using gene recombination techniques. Such native proteins can be produced, for example, by the following steps: a small animal such as a rabbit is immunized with recombinant proteins prepared by the method disclosed herein below to raise antibodies, which are then coupled to suitable adsorbents (CNBr-activated agarose or tosyl-activated agarose), and a rice leaf protein extract is subjected to purification using a column containing the resultant immunoadsorbent to afford the native protein. The recombinant proteins can be prepared by conventional methods, for example by insertion of the inventive protein-coding DNA into a suitable expression vector, introduction of said vector construct into a suitable cell, and purification from the resultant transformed cell.

Host cells employed for production of recombinant proteins include, for example, plant cells, microorganism cells such as *Escherichia coli* and yeast, animal cells, insect cells and others. Vectors (or vector constructs) for in vivo expression of recombinant proteins include, for example, plasmids "pBI121" and "pBI101" (Clontech) for plant or yeast cells; plasmids "pET Expression system" (Stratagene) and "GST gene fusion Vectors" (Pharmacia) for *E. coli*; plasmid "pMAM" (Clontech) for mammal cells; plasmid "pBac-PAK8.9" (Clontech); etc.

Insertion of DNA into a vector may be carried out using conventional techniques such as methods disclosed in Molecular Cloning (Maniatis et al., Cold Spring harbor Laboratory Press). The vector or vector construct may be incorporated into the host cell using conventional techniques such as electroporation, microinjection, and particle bombardment. The introduction of vector constructs may be conducted with a suitable technique depending on a particular host cell used.

Purification of recombinant proteins from the resultant transformed cells can be performed using salting out or precipitation with organic solvents, ion exchange chromatography, affinity chromatography, column chromatography using an immunoadsorbent column, gel filtration, SDS electrophoresis, isoelectric electrophoresis, and other purification and separation techniques alone or optionally in combination with any other method, depending on the properties of target proteins. When the recombinant protein of the present invention is expressed as a fusion protein with a tag such as glutathione S-transferase (GST), it can be purified by an affinity chromatography directed to said tag.

The present invention also provides DNA coding for each of the aforementioned proteins according to present invention. The DNA of the present invention is not limited to but includes genomic DNA, cDNA, chemically synthesized DNA, and others as long as it is capable of encoding the protein of the present invention. Genomic DNA can be prepared, for example by conducting a polymerase chain reaction (PCR) wherein template genome DNA prepared according to the method disclosed in the document (Rogers and Bendich, Plant Mol. Biol. 5: 69 (1985)) is used in combination with primers constructed on the basis of the DNA sequences (e.g., the nucleotide sequence of SEQ ID NO: 31) of the present invention. For cDNA, mRNA prepared from plants according to conventional techniques (Maniatis et al. Molecular Cloning Cold Spring harbor Laboratory Press) is subjected to reverse transcription followed by PCR using the aforementioned primers to prepare the cDNA. Also, genomic DNA and cDNA can be prepared by production of genomic DNA libraries or cDNA libraries according to conventional techniques, and screening for the resultant genomic DNA libraries or cDNA libraries with probes synthesized on the bases of the nucleotide sequence of the present invention (e.g., the nucleotide sequence of SEQ ID NO: 31).

Other embodiments of functionally equivalent protein isolation include hybridization techniques (Southern, J. Mol. Biol. 98: 503 (1975); Maniatis et al., "Molecular Cloning", Cold Spring harbor Laboratory Press) and PCR techniques (H. A. Erlich (ed.), "PCR technology", Stockton Press, New York (1989)). In other words, it is possible for a person skilled in the art to obtain proteins functionally equivalent to the "Os3RmybA1" protein via using isolated DNA highly homologous to the nucleotide sequence of the "Os3RmybA1" gene (SEQ ID NO: 31) wherein said isolated DNA is obtained using the nucleotide sequence of the "Os3RmybA1" gene (SEQ ID NO: 31) or part thereof as a probe as well as using oligonucleotides hybridizable with part of the nucleotide sequence of the "Os3RmybA1" gene (SEQ ID NO: 31) as primers. Hence, the protein of the present invention also encompasses proteins which are encoded by DNA isolated according to hybridization or PCR techniques and are functionally equivalent to the "Os3RmybA1" protein.

The term "polymerase chain reaction" or "PCR" used herein usually refers to techniques described in Saiki et al., Science, 239: 487 (1988); U.S. Pat. No. 4,683,195 and other documents. For example, the PCR is an in vitro method for the enzymatic amplification of desired specific nucleotide sequences. In general, the PCR includes repetitive series of cycles wherein a primer elongation synthesis is constructed using two oligonucleotide primers capable of preferentially hybridizing with a template nucleic acid. Typically, the primers used in PCR may include those which are complementary to the internal nucleotide sequence of interest in the template. For example, preferable primer pairs as used herein may be those which are complementary to both ends of said nucleotide sequence to be amplified, or flanking regions adjacent to said nucleotide sequence. It is preferred to select a 5'-terminal primer such that at least an initiation codon is contained or the amplification can be performed including the initiation codon, and to select a 3'-terminal primer such that at least a stop codon is contained or the amplification can be performed including the stop codon. The primers include oligonucleotides made up of preferably 5 or more nucleotide bases, more preferably 10 or more nucleotide bases, and still preferably 18 to 25 nucleotide bases.

The PCR reactions can be carried out by methods known in the art or methods substantially equivalent thereto and modified methods thereof. For example, the PCR can be performed according to methods described in the aforementioned documents as well as R. Saiki, et al., Science, 230: 1350, 1985; H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995); M. A. Innis et al. ed., "PCR Protocols: a guide to methods and applications", Academic Press, New York (1990)); M. J. McPherson, P. Quirke and G. R. Taylor (Ed.), PCR: a practical approach, IRL Press, Oxford (1991); M. A. Frohman et al., Proc. Natl. Acad. Sci. USA, 85, 8998-9002 (1988), and modified methods or variants thereof. The PCR methods can also be performed using commercially available kits suitable therefor, and can also be carried out according to protocols disclosed by manufacturers or distributors of the kits.

For the PCR, in a representative case, for example, a template (e.g., DNA synthesized using mRNA as a template; 1st strand DNA) and primers synthesized according to designs on said gene are mixed with a 10× reaction buffer (attached with a Taq DNA polymerase kit), dNTPs (deoxyribonucleoside triphosphates; dATP, dGTP, dCTP and dTTP mix), Taq DNA polymerase and deionized distilled water. The mixture is subjected to 25 to 60 cycles of amplification using an automated thermal cycler such as GeneAmp 2400 PCR system (Perkin-Elmer/Cetus) under general PCR cycle conditions. The number of amplification cycles can be suitably set to an appropriate value depending on purposes. The PCR cycle includes, for example, denaturation at 90 to 95° C. for 5 to 100 sec, annealing at 40 to 60° C. for 5 to 150 sec and extension at 65 to 75° C. for 30 to 300 sec, and preferably denaturation at 94° C. for 15 sec, annealing at 58° C. for 15 sec and extension at 72° C. for 45 sec. For the annealing temperature and reaction time, an appropriate value is suitably selected by experimentation. For the denaturation and extension time, an appropriate value suitably varies according to the strand length of expected PCR products. In general, the time of annealing preferably varies depending on the Tm value of primer-template DNA hybrids. The time period of extension is usually set with the aim of getting about 1 min per 1000 bp in strand length, but it may be possible to select a shorter time period in some cases.

The nucleotide sequence of DNA thus obtained can be readily sequenced, for example, using "Sequencer Model 310" (ABI). The DNA of the present invention can be used, for example in preparation of recombinant proteins as aforementioned. It is also possible that the DNA according to the present invention is expressed in vivo in plants to produce transgenic plants wherein the cell growth is altered and transgenic plants with modified development and differentiation.

For isolation or separation of genes coding for proteins functionally equivalent to Os3RmybA1, hybridization can be performed under conditions of hybridization at 55° C. followed by totally 3 times washing for 10 min at 55° C. in 0.1% SDS-containing 2×SSC (3M NaCl, 0.3M sodium citrate) or 2×SSPE (3.6M NaCl, 0.2M sodium phosphate solution (pH 7.7), 0.02M Na$_2$-EDTA). More stringent hybridization may include preferably hybridization at 65° C. followed by totally 3 times washing for 10 min at 65° C. in 0.1% SDS-containing 2×SSC or 2×SSPE. Further more stringent hybridization includes preferably hybridization at 65° C., then washing for 10 min at 65° C. in 0.1% SDS-containing 2×SSC or 2×SSPE followed by totally 2 times washing for 10 min at 65° C. in 0.1% SDS-containing 1×SSC or 1×SSPE. Applicable hybridization buffers may be those disclosed in "Molecular cloning (Maniatis T. et al., Cold Spring Harbor Laboratory Press)", and others.

The related proteins, fragments thereof, and nucleic acids (including mRNA and oligonucleotides) as disclosed herein can be applicable, alone or in admixture with a variety of the other elements, to the technology of genomics & proteomics, optionally in combination with antisense techniques, antibodies including monoclonal antibodies, transgenic plants and other technologies or materials. Also, they may be applied to RNA interference (RNAi) technology using double strand RNA (dsRNA). Thus, the following will be available: gene polymorphism analysis including core "single nucleotide polymorphism (SNP)" analysis; gene expression analysis, gene function analysis, protein-protein interaction analysis, related gene analysis, and analysis of agrochemicals, using nucleic acid arrays and protein arrays. For example, in the nucleic acid array technology, samples are analyzed using cDNA libraries, arranging DNA obtained by PCR on a support plate at a high density with a spotting apparatus, and utilizing hybridization.

The arraying can be performed by immobilization of DNA at each defined site on a support plate such as a slide glass, a silicon plate, and a plastic plate, with needles or pins or using an ink jet printing technique and others. Data are acquired by observation of signals which have resulted from hybridization on the nucleic acid arrays. The signals may be those obtained from labels such as fluorescent dyes (e.g., Cy3, Cy5, BODIPY, FITC, Alexa Fluor dyes (trade name), and Texas red (trade name). Detection can be conducted with a laser scanner and the like. The resultant data may be processed with a computer system installed with programs according to an appropriate algorithm. Also, tagged recombinant expression protein products may be utilized in protein array technology. The instruments and techniques utilizable in the protein array technology may include dimensional electrophoresis (2-DE); mass analysis (MS), including techniques such as electrospray ionization (ESI), and matrix-assisted laser desorption/ionization (MALDI), wherein MALDI-TOF analyzers, ESI-triple quadrupole analyzers, ESI-ion trap analyzers and others may be employed, for protein substances including enzymatically digested fragments; staining techniques; isotope labeling and analysis; image processing techniques; and the like. Therefore, the present invention can encompass softwares, databases and others obtainable or utilizable in the preceding in connection with not only NACK1 and NACK2 but also antibodies against NACK2, and related substances thereof.

As used herein, the term "antibody" can be used in the broadest sense and may cover a single species of desirable monoclonal antibodies against any of Os3RmybA1 proteins, Os3RmybA1-constituent polypeptides and Os3RmybA1-related peptide fragments; antibody compositions (or mixtures) having a specificity to various epitopes thereof; further monovalent or polyvalent antibodies and polyclonal and monoclonal antibodies, and also those which are intact molecules or fragments and derivatives thereof, including F(ab')$_2$, Fab' and Fab fragments; and also chimeric antibodies, hybrid antibodies each having at least two antigen or epitope binding sites, or bispecific recombinant antibodies (e.g., quadromes, triomes, etc.), interspecies hybrid antibodies, anti-idiotypic antibodies and those which have been chemically modified or processed and must be regarded as derivatives of these antibodies and further which may be produced either by adopting cell fusion or hybridoma techniques or antibody engineering or by using synthetical or semi-synthetical techniques in a known manner, which may be prepared either by the known conventional methods in view of antibody production or by recombinant DNA techniques, and which have neutralizing or binding properties with respect to the target antigen substances or target epitopes described and defined herein. Specifically, the preferable antibody of the present invention includes those capable of specifically recognizing a polypeptide selected from the group consisting of domains ranging from amino acid residues 53 to 202 of SEQ ID NO: 32.

Monoclonal antibodies prepared against antigenic substances are produced by any method capable of providing production of antibody molecules by a series of cell lines in culture. The modifier "monoclonal" indicates the character of the antibody as being obtained from a substantially homogeneous population of antibodies, and is not to be construed as requiring production of the antibody by any particular method. The individual antibodies are those containing a population of identical antibodies except for possible naturally occurring mutations that may be present in minor amounts. Monoclonal antibodies are highly specific, being directed against a single antigenic site. In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The monoclonal antibodies include hybrid and recombinant antibodies. They are obtainable by substituting a constant domain of an antibody for a variable domain, or a heavy chain for a light chain, by substituting a chain from one species with a chain from another species, or by fusing to heterogeneous proteins, regardless of species of origin or immunoglobulin class or subclass designation, so long as they exhibit the desired biological activity (e.g., U.S. Pat. No. 4,816,567; Monoclonal Antibody Production Techniques and Applications, pp. 79-97, Marcel Dekker, Inc., New York, 1987; etc.).

Preferable techniques for producing monoclonal antibodies include, for example, the methods using hybridoma cells (G. Kohler and C. Milstein, Nature, 256, pp. 495-497 (1975)); the methods using human B cell hybridomas (Kozbor et al., Immunology Today, 4, pp. 72-79 (1983); Kozbor, J. Immunol., 133, pp. 3001 (1984); Brodeur et al., Monoclonal Antibody Production Techniques and Applications, pp. 51-63, Marcel Dekker, Inc., New York (1987); triome methods; EBV-hybridoma methods (Cole et al., Monoclonal Antibodies and Cancer Therapy, Alan R. Liss, Inc., pp. 77-96 (1985)) (techniques for production of human monoclonal antibodies); U.S. Pat. No. 4,946,778 (techniques for production of single-chain antibodies), as well as the following documents in connection with antibodies: S. Biocca et al., EMBO J, 9, pp. 101-108 (1990); R. E. Bird et al., Science, 242, pp. 423-426 (1988); M. A. Boss et al., Nucl. Acids Res., 12, pp. 3791-3806 (1984); J. Bukovsky et al., Hybridoma, 6, pp. 219-228 (1987); M. DAINO et al., Anal. Biochem., 166, pp. 223-229 (1987); J. S. Huston et al., Proc. Natl. Acad. Sci. USA, 85, pp. 5879-5883 (1988); P. T. Jones et al., Nature, 321, pp. 522-525 (1986); J. J. Langone et al. (ed.), "Methods in Enzymology", Vol. 121 (Immunochemical Techniques, Part I: Hybridoma Technology and Monoclonal Antibodies), Academic Press, New York (1986); S. Morrison et al., Proc. Natl. Acad. Sci. USA, 81, pp. 6851-6855 (1984); V. T. Oi et al., BioTechniques, 4, pp. 214-221 (1986); L. Riechmann et al., Nature, 332, pp. 323-327 (1988); A. Tramontano et al., Proc. Natl. Acad. Sci. USA, 83, pp. 6736-6740 (1986); C. Wood et al., Nature, 314, pp. 446-449 (1985); Nature, 314, pp. 452-454 (1985) or documents cited therein (the disclosures of which are incorporated herein by reference). The antibodies of the present invention are utilizable not only in analyzing and detecting the expression products of genes concerned herein but also in a variety of applications.

It is convenient to isolate DNAs coding for plant 3Rmyb proteins according to the present invention with the aforementioned methods relying on hybridization and methods relying on PCR. In cases where the isolation is carried out with PCR, it is possible to isolate DNA coding for the myb DNA-binding region exhibiting a 3 repeat frame by PCR using, for example, degenerated primers as disclosed in Example 1. To enhance the specificity of PCR, it is also convenient to design a second pair of PCR primers which have annealing sites at a more internal location than the first PCR primer annealing sites of the target sequence. Nested-PCR with the second primer pair can be applied. After nucleotide sequence determination of the resulting DNA products, application of Rapid amplification of cDNA ends (RACE, Dorit en al., Current protocols in molecular biology. Unit15.6 (1992)) allows isolation and determination of 5'- and 3'-terminal cDNA sequences.

Utilizable plants from which the plant 3Rmyb protein characterized in the present invention is isolated or separated can be selected from Dicotyledonae plants. These plants can also be used as gene sources.

The applicable Dicotyledonae and Monocotyledonae plants characterized in the present invention are not limited to, but may be selected from any species including those widely known as cultivated plants or useful plants. The plants include cereal crops, beans, root and tuber crops, nuts, seeds, vegetables, berries, fruits, or orchard trees, as well as garden crops, garden trees or grasses, horticultural species, flowering trees and ornamental species. Exemplary plants include Solanaceous species, Cruciferous (*Brassicaceous*) species, *Graminaceous* species, *Leguminous* species, *Liliaceous* species, *Umbelliferous* species, *Cucurbitaceous* species and other species, preferably tobacco (*Nicotiana tabacum*), *Arabidopsis thaliana*, soybean (*Glycine max*), Aduki bean (small red bean), green beans (*Phaseolus vulgaris*), peas (*Lathyrus* spp. including snow pea (*Pisum sativum*)), broad bean (*Vicia faba*), peanuts (*Arachis hypogaea*), rice (*Oryza sativa*), wheat (*Triticum aestivum*), barley, rye (*Secale cereale*), oat (*Avena sativa*), bentgrass (*Agrostis* spp.), corn (*Zea mays*), sorghum (*Sorghum bicolor, Sorghum vulgare*), canola (*Brassica napus, Brassica rapa* ssp.), rape (*Brassica napus*), potato (*Solanum tuberosum*), sweet potato (*Ipomoea batatus*), taro (*Colocasia* spp. including *C. esculenta*), konjac (*Amorphophallus rivieri* var. *konjac*), cassava (*Manihot* spp. including *M. esculenta*), and others.

The present invention provides methods for constructing or producing molecules with at least an enhanced transcription-activating property as compared to that inherently owned by a member selected from the group consisting of proteins, NtmybA1, NtmybA2, Os3RmybA1, AtMYB3R1 and AtMYB3R4, which comprises modifying the function of said protein selected from NtmybA1, NtmybA2, Os3RmybA1, AtMYB3R1 and AtMYB3R4, and selecting said desirable molecule with at least such an enhanced activating property for the transcription activator function of said protein.

In the present invention, the NtmybA1 protein (including modified NtmybA1 and NtmybA1-related protein) which serves as a molecule with an enhanced transcription activating property as compared to that inherently owned by protein NtmybA1 is at least one member selected from the group consisting of:

(a) a molecule wherein a sequence with residues at amino acids 459 to 1003 of SEQ ID NO: 51 is deleted from the NtmybA1 protein shown in SEQ ID NO: 51, (b) more desirably, a molecule wherein a sequence with residues at amino acids 579 to 1003 of SEQ ID NO: 51 is deleted from the NtmybA1 protein shown in SEQ ID NO: 51, or a molecule wherein a sequence with residues at amino acids 715 to 1003 of SEQ ID NO: 51 is deleted from the NtmybA1 protein shown in SEQ ID NO: 51, and (c) most desirably a molecule wherein a sequence with residues at amino acids 641 to 1003 of SEQ ID NO: 51 is deleted from the NtmybA1 protein shown in SEQ ID NO: 51.

In the present invention, the NtmybA2 protein (including modified NtmybA2 and NtmybA2-related protein) which serves as a molecule with an enhanced transcription activating property as compared to that inherently owned by protein NtmybA2 is at least one member selected from the group consisting of:

(a) a molecule wherein a sequence with residues at amino acids 413 to 1042 of SEQ ID NO: 53 is deleted from the NtmybA2 protein shown in SEQ ID NO: 53, (b) more desirably, a molecule wherein a sequence with residues at amino acids 569 to 1042 of SEQ ID NO: 53 is deleted from the NtmybA2 protein shown in SEQ ID NO: 53, or a molecule wherein a sequence with residues at amino acids 705 to 1042 of SEQ ID NO: 53 is deleted from the NtmybA2 protein shown in SEQ ID NO: 53, and (c) most desirably a molecule wherein a sequence with residues at amino acids 631 to 1042 of SEQ ID NO: 53 is deleted from the NtmybA2 protein shown in SEQ ID NO: 53.

In the present invention, the Os3RmybA1 protein (including modified Os3RmybA1 and Os3RmybA1-related protein) which serves as a molecule with an enhanced transcription activating property as compared to that inherently owned by protein Os3RmybA1 is at least one member selected from the group consisting of:

(a) a molecule wherein a sequence with residues at amino acids 426 to 993 of SEQ ID NO: 32 is deleted from the Os3RmybA1 protein shown in SEQ ID NO: 32, (b) more desirably, a molecule wherein a sequence with residues at amino acids 575 to 993 of SEQ ID NO: 32 is deleted from the Os3RmybA1 protein shown in SEQ ID NO: 32, or a molecule wherein a sequence with residues at amino acids 709 to 993 of SEQ ID NO: 32 is deleted from the Os3RmybA1 protein shown in SEQ ID NO: 32, (c) most desirably a molecule wherein a sequence with residues at amino acids 635 to 993 of SEQ ID NO: 32 is deleted from the Os3RmybA1 protein shown in SEQ ID NO: 32.

In the present invention, the AtMYB3R1 protein (including modified AtMYB3R1 and AtMYB3R1-related protein) which serves as a molecule with an enhanced transcription activating property as compared to that inherently owned by protein AtMYB3R1 is at least one member selected from the group consisting of:

(a) a molecule wherein a sequence with residues at amino acids 583 to 776 of SEQ ID NO: 75 is deleted from the AtMYB3R1 protein shown in SEQ ID NO: 75, or a molecule wherein a sequence with residues at amino acids 691 to 776 of SEQ ID NO: 75 is deleted from the AtMYB3R1 protein shown in SEQ ID NO: 75, and (b) desirably, a molecule wherein a sequence with residues at amino acids 621 to 776 of SEQ ID NO: 75 is deleted from the AtMYB3R1 protein shown in SEQ ID NO: 75.

In the present invention, the AtMYB3R4 protein (including modified AtMYB3R4 and AtMYB3R4-related protein) which serves as a molecule with an enhanced transcription activating property as compared to that inherently owned by protein AtMYB3R4 is at least one member selected from the group consisting of:

(a) a molecule wherein a sequence with residues at amino acids 570 to 961 of SEQ ID NO: 76 is deleted from the AtMYB3R4 protein shown in SEQ ID NO: 76, or a molecule wherein a sequence with residues at amino acids 667 to 961 of SEQ ID NO: 76 is deleted from the AtMYB3R4 protein shown in SEQ ID NO: 76, and (b) desirably, a molecule wherein a sequence with residues at amino acids 608 to 961 of SEQ ID NO: 76 is deleted from the AtMYB3R4 protein shown in SEQ ID NO: 76.

The present invention provides methods for constructing or producing molecules which serve as dominant negative agents against endogenous plant 3Rmyb molecules, which comprises modifying the function of a member selected from the group consisting of proteins, NtmybA1, NtmybA2, Os3RmybA1, AtMYB3R1 and AtMYB3R4, and selecting said desirable molecule with at least a dominant negative activity on said endogenous plant 3Rmyb molecule, wherein said dominant negative molecule includes those with at least a diminished or extinguished transcription activating property as compared to the property inherently owned by said wild type protein selected from the group consisting of NtmybA1, NtmybA2, Os3RmybA1, AtMYB3R1 and AtMYB3R4.

In the present invention, the NtmybA1, NtmybA2, Os3RmybA1, AtMYB3R1, or AtMYB3R4 protein (including modified NtmybA1, NtmybA2, Os3RmybA1, AtMYB3R1, or AtMYB3R4 as well as NtmybA1-, NtmybA2-, Os3RmybA1-, AtMYB3R1-, or AtMYB3R4-related protein) which serves as a dominant negative molecule against at least one of the endogenous 3Rmyb genes is at least one member selected from the group consisting of:

(a) a molecule wherein a sequence with residues at amino acids 299 to 1003 of SEQ ID NO: 51 is deleted from the NtmybA1 protein shown in SEQ ID NO: 51, (b) more desirably, a molecule wherein a sequence with residues at amino acids 186 to 1003 of SEQ ID NO: 51 is deleted from the NtmybA1 protein shown in SEQ ID NO: 51, (c) a molecule wherein a sequence with residues at amino acids 243 to 1042 of SEQ ID NO: 53 is deleted from the NtmybA2 protein shown in SEQ ID NO: 53, (d) more desirably, a molecule wherein a sequence with residues at amino acids 188 to 1042 of SEQ ID NO: 53 is deleted from the NtmybA2 protein shown in SEQ ID NO: 53, (e) a molecule wherein a sequence with residues at amino acids 257 to 993 of SEQ ID NO: 32 is deleted from the Os3RmybA1 protein shown in SEQ ID NO: 32, (f) more desirably, a molecule wherein a sequence with residues at amino acids 203 to 993 of SEQ ID NO: 32 is deleted from the Os3RmybA1 protein shown in SEQ ID NO: 32, (g) a molecule wherein a sequence with residues at amino acids 241 to 776 of SEQ ID NO: 75 is deleted from the AtMYB3R1 protein shown in SEQ ID NO: 75, (h) more desirably, a molecule wherein a sequence with residues at amino acids 187 to 776 of SEQ ID NO: 75 is deleted from the AtMYB3R1 protein shown in SEQ ID NO: 75

(i) a molecule wherein a sequence with residues at amino acids 235 to 961 of SEQ ID NO: 76 is deleted from the AtMYB3R4 protein shown in SEQ ID NO: 76, and (j) more desirably, a molecule wherein a sequence with residues at amino acids 181 to 961 of SEQ ID NO: 76 is deleted from the AtMYB3R4 protein shown in SEQ ID NO: 76.

The transcription activator properties exerted by the NtmybA2-related molecule having an amino acid sequence deletion with residues at amino acids 242 to 1042 or 188 to 1042 of the NtmybA2 protein, was diminished as compared to that inherently owned by the wild type NtmybA2 protein; besides, when the full-length form NtmybA2 protein was co-expressed with the NtmybA2-related molecule having an amino acid sequence deletion with residues at amino acids 188 to 1042 of the NtmybA2 protein, the transcription activator property exerted by the NtmybA2 protein alone was suppressed, and further when the full-length form NtmybB was co-expressed with the molecular having an amino acid sequence deletion with residues at amino acids 188 to 1042 of the NtmybA2 protein, the transcription supressor property exerted by the NtmybB protein alone was suppressed. These facts evidence that the NtmybA2-related molecule having an amino acid sequence deletion with residues at amino acids 243 to 1042 or 188 to 1042 of the NtmybA2 protein dominant-negatively functions against the endogenous plant 3Rmyb protein.

For terms (words), symbols and/or abbreviations used in the specification and in the drawings, they must conform to the "IUPAC-IUB Commission on Biochemical Nomenclature" or are based on the meanings of the definitions or standards which are commonly or conventionally used in the art. Representative abbreviations have meanings as follows:

Regarding symbols for amino acids:

A: Alanine (Ala)

C: Cysteine (Cys)

D: Aspartic acid (Asp)

E: Glutamic acid (Glu)

F: Phenylalanine (Phe)

G: Glycine (Gly)

H: Histidine (His)

I: Isoleucine (Ile)

K: Lysine (Lys)

L: Leucine (Leu)

M: Methionine (Met)

N: Asparagine (Asn)

P: Proline (Pro

Q: Glutamine (Gln)

R: Arginine (Arg)

S: Serine (Ser)

T: Threonine (Thr)

V: Valine (Val)

W: Tryptophan (Trp)

Y: Tyrosine (Tyr)

X: Any amino acid from the aforementioned amino acids or any specific amino acid (when indicated specifically) (Xaa)

Regarding symbols for nucleotides:

A,a: Adenine

C,c: Cytosine

R,r: Guanine or Adenine

M,m: Adenine or Cytosine

S,s: Guanine or Cytosine

D,d: Adenine or Guanine or Thymine/Uracil

H,h: Adenine or Cytosine or Thymine/Uracil

V,v: Adenine or Guanine or Cytosine

N,n: Adenine or Guanine or Cytosine or Thymine/Uracil, Unknown, Any other nucleotide or Any specific nucleotide (when indicated specifically)

G,g: Guanine

T,t: Thymine

Y,y: Thymine/Uracil or Cytosine

K,k: Guanine or Thymine/Uracil

W,w: Adenine or Thymine/Uracil

EXAMPLES

Details of the present invention are described by the following examples but such examples are provided only for illustrative purposes, and for referential embodiments of the present invention. These examples have been described herein for the purpose of illustrating specific embodiments of the present invention but should in no way be construed as limiting and restricting the scope of the invention disclosed herein. It should be understood in the present invention that various embodiments can be made or executed within the spirit, scope and concept disclosed herein.

It should be noted that general methods required for gene recombination, including disconnection and ligation of DNA, transformation or transfection of E. coli, nucleotide sequencing of genes, hybridization, and others are in principle according to user manuals and handbooks attached to commercially available reagents, devices, instruments or machines useful in each operation, and guide books for experiments (e.g., "Molecular cloning (Maniatis T. et al., Cold Spring Harbor Laboratory Press)" including J. Sambrook et al., Molecular Cloning: A Laboratory Manual, Cold Spring Harbor Laboratory Press, Cold Spring Harbor, N.Y. (2nd Edition, 1989 & 3rd Edition, 2001)). All the examples were carried out or can be carried out, unless otherwise disclosed herein specifically, by standard techniques which are well known and conventional to those skilled in the art.

Example 1

Isolation and Sequencing of Rice Os3RmybA1 Gene

Isolation of rice 3Rmyb coding cDNA from rice was performed, followed by sequencing.

To isolate cDNA, degenerated primers were designed based on amino acid sequences in each myb DNA binding domain of tobacco 3Rmyb proteins, NtmybA1, NtmybA2, and NtmybB. PCR was performed with the degenerated primers in combination with as a template cDNA prepared from rice calli. To enhance the specificity of degenerated PCR, Nested PCR was conducted. As a result, the isolation of cDNA fragments having 3 repeats in the myb DNA binding domain was a success.

The resultant fragments were subjected to 5' RACE and 3'RACE, and each terminal sequence of full-length cDNA was sequenced.

The isolation of cDNA including the full-length structural gene was a success with primers designed from the 5'-terminal sequence and the 3'-terminal sequence. Details are disclosed below.

(1) Purification of mRNA and Synthesis of cDNA

Cultivated rice var. *Nipponbare* (japonica) seeds were subjected to removal of husks, sterilized with antiformin, then placed on N6CI medium (N6 inorganic salts and N6 vitamins (Chu et al. (1975), Sientia Sinica 18: 659) supplemented with 30 g/l sucrose, 2 mg/l 2,4-D and 2 g/l Gelrite™, pH5.8), and incubated to induce scutellum-derived embryogenic calli.

Total RNA was extracted from the calli (130 mg) with RNeasy™ Plant Mini Kit (QIAGEN). The resulting total RNA (50 μg) was subjected to purification with PolyATtract™ mRNA Isolation Systems (Promega) to give mRNA. The purified mRNA was concentrated by precipitation with ethanol, and then applied to cDNA synthesis with Superscript™ First-strand synthesis system for RT-PCR (Invitrogen).

(2) Cloning by PCR with Degenerated Primers Based on Myb Domains

PCR was performed with an aliquot (2 μl) of the synthesized cDNA (50 μl).

Primers used in PCR were

```
DEGmybF:                                 (SEQ ID NO: 1)
5'- GAIGTICARTGYYWICAYMGNTGG -3',
and DEGmybR:                                 (SEQ ID NO: 2)
5'- YTTYTTDAVIGAISWRTKCCA -3'.
```

The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 10 μM each of DEGmybF and DEGmybR. The amplification was performed using GeneAmp™ PCR system 9700 (PE Applied Biosystems) set to repeat steps at 94° C. for 30 sec, at 42° C. for 30 sec, and at 72° C. for 30 sec for a total of 35 cycles. After the reaction was finished, the products were subjected to purification with QIAquick™ PCR Purification Kit (QIAGEN).

Nested PCR was performed with an aliquot (1 μl) of the purified PCR reaction solution as a template.

Primers used in the second PCR were degenerated primers (designed on regions inside DEGmybF and DEGmybR),

```
DEGmybF2:                                (SEQ ID NO: 3)
5'- CARTGYYTICAYMGITGGCARAARG -3',
and DEGmybR2:                                (SEQ ID NO: 4)
5'- ACISWISWRTTCCARTTRTGYTT -3'.
```

The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 10 μM each of DEGmybF2 and DEGmybR2. The amplification was performed using GeneAmp™ PCR system 9700 (PE Applied Biosystems) set to repeat steps at 94° C. for 30 sec, at 58° C. for 30 sec, and at 72° C. for 30 sec for a total of 35 cycles. After the reaction was finished, the PCR reaction solution was subjected to purification with QIAquick™ PCR Purification Kit (QIAGEN).

Further, Nested PCR was performed with an aliquot (1 μl) of the purified second PCR reaction solution as a template.

Primers used in the third PCR were degenerated primers (designed on regions inside DEGmybF2 and DEGmybR2),

```
DEGmybF3:                                (SEQ ID NO: 5)
5'- CAYMGITGGCARAARGTIYTIRAYCC -3',
and DEGmybR3:                                (SEQ ID NO: 6)
5'- HIGCRTTITCISWICKICCIKGIA -3'
```

The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 10 μM each of DEGmybF3 and DEGmybR3. The amplification was performed using GeneAmp™ PCR system 9700 (PE Applied Biosystems) set to repeat steps at 94° C. for 30 sec, at 56° C. for 30 sec, and at 72° C. for 30 sec for a total of 30 cycles. After the reaction was finished, the PCR reaction solution was subjected to purification with QIAquick™ PCR Purification Kit (QIAGEN). The resultant PCR reaction solution was analyzed using agarose gels. As a result, it was verified that the amplified product was a DNA of about 300 bp. Next, this DNA fragment was subjected to TA cloning into pCR4-TOPO™ (Invitrogen). DNA inserts from 3 clones were sequenced at a nucleotide level with T7 primer, 5'-TAATACGACTCACTATAGGG-3' (SEQ ID NO: 7) to give SEQ ID NO: 8, SEQ ID NO: 9, and SEQ ID NO: 10.

(3) Sequencing of the 5'-Terminal Sequence of Rice 3Rmyb cDNA

In order to obtain full-length rice 3Rmyb gene cDNA including the 3Rmyb DNA binding domain fragment, which was isolated in the above (1), the amplification of 5'-ends was conducted for said cDNA. The isolation of 5'-terminal DNA ends was performed by 5' RACE with GeneRacer™ Kit (Invitrogen). Briefly, total RNA was extracted from rice scutellum-derived embryogenic calli (130 mg) (derived according to the aforementioned method (1)) with RNeasy™ Plant Mini Kit (QIAGEN). The synthesis of cDNA was performed using GeneRacer™ Kit (Invitrogen) with an aliquot (3 μg) of the extracted total RNA as a template. PCR was performed with this cDNA as a template in combination with primers (designed on SEQ ID NO: 8, SEQ ID NO: 9, and SEQ ID NO: 10),

```
78687-R1:                                (SEQ ID NO: 11)
5'- CAGCTCGGCCCATTTATTTCCATACATT -3'
and GeneRacer 5' Primer (contained in the GeneRacer ™
Kit, Invitrogen):                        (SEQ ID NO: 12)
5'- CGACTGGAGCACGAGGACACTGA
-3'.
```

The reaction was done in a total volume of 50 μl, using TaKaRa Ex Taq™ (Takara, Japan). The amplification was performed using GeneAmp™ PCR system 9700 (PE Applied Biosystems) set to carry out an initial step at 94° C. for 2 min, then to repeat steps at 94° C. for 30 sec, and at 72° C. for 3 min for a total of 5 cycles, next steps at 94° C. for 30 sec, and at 70° C. for 3 min for a total of 5 cycles, and steps at 94° C. for 30 sec, at 68° C. for 30 sec and at 72° C. for 3 min for a total of 25 cycles, and to carry out a final step at 72° C. for 10 min. PCR was performed with an aliquot (1 μl) of the resultant PCR reaction solution as a template in combination with primers,

```
78687-R2:                              (SEQ ID NO: 13)
5'- CTTCTTGTGTCCATGCCTCCTTGTTTAT -3'
and GeneRacer 5' Nested Primer (contained in the
GeneRacer ™ Kit, Invitro-             (SEQ ID NO: 14)
gen):
5'- GGACACTGACATGGACTGAAGGAGTA -3'
```

The reaction was done in a total volume of 50 µl, using TaKaRa Ex Taq™ (Takara, Japan). The amplification was performed using GeneAmp™ PCR system 9700 (PE Applied Biosystems) set to carry out an initial step at 94° C. for 2 min, then to repeat steps at 94° C. for 30 sec, and at 72° C. for 3 min for a total of 5 cycles, next steps at 94° C. for 30 sec, and at 70° C. for 3 min for a total of 5 cycles, and steps at 94° C. for 30 sec, at 68° C. for 30 sec and at 72° C. for 3 min for a total of 25 cycles, and to carry out a final step at 72° C. for 10 min. After the reaction was finished, the PCR reaction solution was subjected to purification with QIAquick™ PCR Purification Kit (QIAGEN). The amplified DNA was subjected to TA cloning into pCR4-TOPO™ (Invitrogen). The resulting DNA insert from the plasmid was sequenced at a nucleotide level with

```
T7 primer:                             (SEQ ID NO: 7)
5'- TAATACGACTCACTATAGGG -3'
and T3 primer:                             (SEQ ID NO: 15)
5'- AATTAACCCTCACTAAAGGG -3'.
```

The nucleotide sequence of clone #26 is shown in SEQ ID NO: 16. SEQ ID NO: 17 is the nucleotide sequence of clone #27.

(4) Sequencing of the 3'-Terminal Sequence of Rice 3Rmyb cDNA

In order to obtain full-length rice 3Rmyb gene cDNA including the 3Rmyb DNA binding domain fragment, which was isolated in the above (1), the amplification of 3'-ends was conducted for said cDNA. The 3'-end was sequenced by 3' RACE with GeneRacer™ Kit (Invitrogen). Briefly, total RNA was extracted from rice scutellum-derived embryogenic calli (130 mg) (derived according to the aforementioned method (1)) with RNeasy™ Plant Mini Kit (QIAGEN). The synthesis of cDNA was performed using GeneRacer™ Kit (Invitrogen) with an aliquot (5 µg) of the extracted total RNA as a template. PCR was performed with this cDNA as a template in combination with primers (designed on SEQ ID NO: 8, SEQ ID NO: 9, and SEQ ID NO: 10),

```
78687-F1:                              (SEQ ID NO: 18)
5'- AGGAGGCATGGACACAAGAAGAGGAAAT -3'
and GeneRacer 3' Primer (contained in the GeneRacer ™
Kit, Invitrogen):                      (SEQ ID NO: 19)
5'- GCTGTCAACGATACGCTACGTAACG -3'.
```

The reaction was done in a total volume of 50 µl, using TaKaRa Ex Taq™ (Takara, Japan). The amplification was performed using GeneAmp™ PCR system 9700 (PE Applied Biosystems) set to carry out an initial step at 94° C. for 2 min, then to repeat steps at 94° C. for 30 sec, and at 72° C. for 3 min for a total of 5 cycles, next steps at 94° C. for 30 sec, and at 70° C. for 3 min for a total of 5 cycles, and steps at 94° C. for 30 sec, at 68° C. for 30 sec and at 72° C. for 3 min for a total of 25 cycles, and to carry out a final step at 72° C. for 10 min. PCR was performed with an aliquot (1 µl) of the resultant PCR reaction solution as a template in combination with primers,

```
78687-F2:                              (SEQ ID NO: 20)
5'- GGAAATAAATGGGCCGAGCTGACAAAAT -3'
and GeneRacer 3' Nested Primer (contained in the
GeneRacer ™ Kit, Invitro-             (SEQ ID NO: 21)
gen):
5'- CGCTACGTAACGGCATGACAGTC -3'.
```

The reaction was done in a total volume of 50 µl, using TaKaRa Ex Taq™ (Takara, Japan). The amplification was performed using GeneAmp™ PCR system 9700 (PE Applied Biosystems) set to carry out an initial step at 94° C. for 2 min, then to repeat steps at 94° C. for 30 sec, and at 72° C. for 3 min for a total of 5 cycles, next steps at 94° C. for 30 sec, and at 70° C. for 3 min for a total of 5 cycles, and steps at 94° C. for 30 sec, at 68° C. for 30 sec and at 72° C. for 3 min for a total of 25 cycles, and to carry out a final step at 72° C. for 10 min. After the reaction was finished, the PCR reaction solution was subjected to purification with QIAquick™ PCR Purification Kit (QIAGEN). The amplified DNA was subjected to TA cloning into pCR4-TOPO™ (Invitrogen). The resulting DNA insert from the plasmid was sequenced at a nucleotide level with

```
T7 primer:                             (SEQ ID NO: 7)
5'- TAATACGACTCACTATAGGG -3',
and T3 primer:                             (SEQ ID NO: 15)
5'- AATTAACCCTCACTAAAGGG -3'.
```

As a result, each nucleotide sequence of both 5'- and 3'-ends of the DNA insert fragment was determined. The 5'-side nucleotide sequence of clone #31 is shown in SEQ ID NO: 22. SEQ ID NO: 23 is the 3'-side nucleotide sequence of clone #23.

(5) Isolation of cDNA Including the Full-Length Rice 3Rmyb Structural Gene and Nucleotide Sequencing Total RNA was extracted from rice scutellum-derived embryogenic calli (130 mg) (derived according to the aforementioned method (1)) with RNeasy™ Plant Mini Kit (QIAGEN). The synthesis of cDNA was performed using Superscript™ First-strand synthesis system for RT-PCR (Invitrogen) with an aliquot (5 µg) of the extracted total RNA as a template.

PCR was performed with an aliquot (1 µg) of the synthesized cDNA (50 µl). Primers used in PCR were

```
OsA1-1F:                               (SEQ ID NO: 24)
5'- TGTCTTCAGTCATGATGACAAGCGA -3',
and OsA1-2R:                               (SEQ ID NO: 25)
5'- CAAGCTATCTAAAACTTTTCAGAAGATGG -3'.
```

The reaction was done in a total volume of 50 µl, using PfuTurbo™ Hotstart DNA Polymerase (Stratagene), a reaction buffer attached to PfuTurbo™ Hotstart DNA Polymerase, 200 µM each of dATP, dTTP, dCTP and dGTP, and 1 µM each of OsA1-1F and OsA1-2R. The amplification was performed using GeneAmp™ PCR system 9700 (PE Applied Biosystems) set to carry out an initial step at 95° C. for 2 min, then to repeat steps at 95° C. for 30 sec, at 60° C. for 30 sec, and at 72° C. for 4 min for a total of 40 cycles, and to carry out a final step at 72° C. for 10 min. After the reaction was finished, the PCR reaction solution was subjected to purification with QIAquick™ PCR Purification Kit (QIAGEN).

When the PCR reaction solution was analyzed on agarose gels, it was verified that the amplified DNA was a single fragment of about 3 kbp. Therefore, this DNA fragment was subjected to TA cloning into pCR4-TOPO™ (Invitrogen). The resultant plasmid pCR4-Os3RmybA1 with this DNA insert was sequenced with the following primers:

```
T7 primer:                          (SEQ ID NO: 7)
5'- TAATACGACTCACTATAGGG -3', T3 primer:                          (SEQ ID NO: 15)
5'- AATTAACCCTCACTAAAGGG -3', primer 78687-F1:                    (SEQ ID NO: 18)
5'- AGGAGGCATGGACACAAGAAGAGGAAAT -3', primer OsA1-4F:                     (SEQ ID NO: 26)
5'- GATCAACACTTGCAAGAGGA-3', primer OsA1-3F:                     (SEQ ID NO: 27)
5'- ACAGGGCCTTCTTTTCTGGAC -3', primer OsA1-5F:                     (SEQ ID NO: 28)
5'- AGCATACCTGAATGTGGGGA -3', primer OsA1-6F:                     (SEQ ID NO: 29)
5'- TACTCATGATGAAAGCACGG -3', primer OsA1-7F:                     (SEQ ID NO: 30)
5'- ATCTCCTTCACATGGAAGTC -3'.
```

The resulting nucleotide sequence is shown in SEQ ID NO: 31.

Example 2

The amino acid sequence encoded by the DNA of SEQ ID NO: 31 is shown in SEQ ID NO: 32. The amino acid sequence of SEQ ID NO: 32 includes three myb DNA binding domain repeats, and the gene for this coding sequence is designated as "Os3RmybA1". When both the amino acid sequence of protein Os3RmybA1 and the putative amino acid sequence (SEQ ID NO: 49) presumed from the genome information data registered with ACCESSION NO: BAB78687 on DDBJ (DNA Data Bank of Japan) are optimally aligned, it is apparently found that the N-terminal regions are highly analogous between the amino acid sequence encoded by Os3RmybA1 cDNA and the BAB78687 amino acid sequence while the C-terminal regions are different each other. The downstream region at or from amino acid position 783 of BAB78687 differs from Os3RmybA1, and BAB78687 is a protein composed of 787 amino acids while Os3RmybA1 is composed of 993 amino acids. Therefore, it is conceived that the splicing sites of BAB78687 were erroneously assumed when the structural region of BAB78687 was determined from the genomic sequence (FIGS. 1 to 3).

Example 3

Transcription Activator Property of Os3RmybA1

The function of isolated Os3RmybA1 was confirmed through a transcription activator ability exerted by the CYM gene carrying the MSA sequence in the promoter region. In brief, tobacco cell line BY2 protoplasts were co-transfected with plasmids optimized for cauliflower mosaic virus (CaMV) 35S promoter-driven expression of Os3RmybA1, and plasmids carrying the reporter gene wherein the CYM promoter is fused to the luciferase gene. Transient expression assay was performed by monitoring luciferase activities for transcription activator property quantitation of Os3RmybA1.

(1) Construction of Plasmids

Construction of Expression Plasmids

Construction of pEXP-Os3RmybA1

A DNA fragment (containing Os3RmybA1), cut out from pCR4-Os3RmybA1 by cleavage with EcoRI, was inserted in a sense direction into the site derived by cleavage with EcoRI from pEXP35S to create pEXP-Os3RmybA1. This pEXP-Os3RmybA1 is a plasmid optimized for cauliflower mosaic virus (CaMV) 35S promoter-driven expression of full-length Os3RmybA1 ORF.

Plasmids which are substantially functionally equivalent to pEXP-Os3RmybA1 can also be constructed as follows:

A protruded end of DNA, cut out from pBI221 (Clontech) by cleavage with EcoRI and SacI, is blunt-ended with the Klenow fragment, and then inserted into the site derived by XhoI cleavage followed by blunt-ending with the Klenow fragment at the XhoI-cut end from pBluescript (SK−) to create plasmid pTN. A DNA fragment, which is cut out from pBI221 by PstI cleavage, and blunt-ending at the resultant protruded end with the Klenow fragment followed by XbaI cleavage, is inserted into the site, derived by NotI cleavage, and blunt-ending with the Klenow fragment at the protruded end followed by XbaI cleavage from pTN, to create plasmid pP35S. That is, plasmid pP35S is a plasmid with plural restriction sites between the CaMV 35S promoter and the nopaline synthetase (NOS) terminator. A DNA fragment (containing Os3RmybA1), cut out from pCR4-Os3RmybA1 by cleavage with EcoRI, is inserted in a sense direction into the site derived by EcoRI cleavage from pP35S to create pP35S-Os3RmybA1. pP35S-Os3RmybA1 is a plasmid optimized for CaMV 35S promoter-driven expression of full-length Os3RmybA1 ORF.

Construction of Plasmid pEXP-GUS

A DNA fragment, produced by SacI cleavage, and blunt-ending at the resultant protruded end with the Klenow fragment followed by HindIII cleavage from pBI-121 (Clontech), was inserted into the site, derived by EcoRI cleavage, and blunt-ending at the resultant protruded end with the Klenow fragment followed by HindIII cleavage from pEXP35S, to create pEXP-GUS. pEXP-GUS is a plasmid optimized for CaMV 35S promoter-driven expression of GUS. Applicable plasmids which are substantially functionally equivalent to pEXP-GUS include pBI221 (Clontech).

Construction of Plasmid R-LUC

A DNA fragment produced by cleavage with BamHI and NheI from plasmid pRL-null Vector (Promega) was inserted into the site produced by cleavage with XbaI and BamHI from pBI-221 (Clontech). The resulting plasmid was cleaved with XbaI and SacI, blunt-ended with the Klenow fragment at the resultant protruded end, followed by removal of DNA fragments. The resulting product was subjected to self-ligation to create plasmid R-LUC. The plasmid R-LUC is a plasmid optimized for CaMV 35S promoter-driven expression of Renilla-derived luciferase (R-LUC).

Construction of Plasmid CYM Promoter-LUC

A DNA fragment produced by cleavage with HindIII and SacI from plasmid pDO432 (Nishiuchi et al., Plant Mol. Biol., 29: 599 (1995)) was inserted into the site derived by cleavage with HindIII and SacI followed by removal of DNA fragments containing the CaMV 35S promoter region from pBI221 (Clontech) to create pUC-LUC. CYM promoter regions were amplified by PCR using genomic DNA (prepared from *Catharanthus roseus* according to conventional techniques) as a template. Primers used in PCR are

```
CYM3:                                    (SEQ ID NO: 56)
5'- CCGGATCCTTCAATAGAATTTCTTCCA -3'
and CYM5 -1:                                 (SEQ ID NO: 57)
5'- CCAAGCTTACCCATAAATTGTTGGTAAA -3'.
```

The amplified CYM promoter region was cleaved with BamHI and HindIII, and inserted into the site derived by cleavage with BamHI and HindIII from pUC-LUC to create plasmid CYM promoter-LUC. That is, the plasmid CYM promoter-LUC is a plasmid optimized for expression of luciferase (LUC), driven by the CYM promoter including the MSA sequence as a control sequence at three positions.

(2) Preparation of BY-2 Protoplasts, Gene Transfer with Plasmids, and LUC Activity Assay Protoplasts were prepared from cultured tobacco cell line BY2 (3-day-old; from culture passage in fresh LSD liquid medium (100 ml, Nagata et al. (1981), Mol. Gen. Genet. 184: 161)) according to the Evans et al. method (Evans et al. (1983), Int. Rev. Cytol. 33: 53).

In brief, BY2 cells were collected from LSD liquid medium by centrifugation at 2,000 rpm at room temperature, then admixed with 100 ml of N2 medium (1% Cellulase "ONOZUKA" RS (Yakult Honsha Co., Ltd., Japan), 0.5% Hemicellulase (SIGMA), 0.1% Pectolyase Y-23 (Kikkoman Co., Japan), 7.4 g/l $CaCl_2.2H_2O$, 1.6 g/l sodium acetate, 45 g/l Mannitol, pH5.7), and subjected to gently rotary culture at 27° C. in the dark to digest cell walls. Three hours later, the cells were collected by centrifugation at 500 rpm at room temperature. The collected cells were admixed with 50 ml of N3 medium (7.4 g/l $CaCl_2.2H_2O$, 1.6 g/l sodium acetate, 45 g/l Mannitol, pH5.7), and washed. The cells were collected by centrifugation at 500 rpm at room temperature, and suspended in 40 ml of N4 medium (4.6 g/l Murashige and Skoog Plant Salt Mixture (Wako Pure Chemical Industries, Ltd, Japan), 100 mg/l casamino acids, 100 mg/l myo-inositol, 2.8 g/l L-proline, 97.6 mg/l MES, 1 mg/l Thiamin-HCl, 357 mg/l $KH_2PO_4$, 102.6 g/l Sucrose, pH5.7). The cell suspension was centrifuged at 700 rpm at room temperature for 10 min to separate protoplasts from the upper layer of the medium.

Transfection of plasmid DNA into the protoplasts was performed by PEG-mediated direct gene transfer (Bilang et al. (1994), In Plant Molecular Biology Manual, pp. A1, 1-16).

In brief, the resultant protoplasts were washed with 40 ml of W5 (154 mM NaCl, 124 mM $CaCl_2$, 5 mM KCl, 5 mM glucose, pH5.8), subjected to centrifugation at 500 rpm for 3 min at room temperature to separate protoplasts. This washing step was repeated 3 times. After washing, the protoplast suspension was adjusted with MMM (15 mM $MgCl_2$, 0.1% MES, 0.5M Mannitol, pH5.8) to the cell concentration of $2 \times 10^5$ cells/ml. An aliquot (250 µl) of the protoplast suspension in MMM was dispensed to each of test tubes, and admixed with 20 µl of the plasmid DNA solution. After gentle stirring, a PEG solution (250 µl; PEG4000 was added to a 0.4M mannitol-0.1M $Ca(NO_3)_2$ solution to form a 40% w/v PEG solution, which was adjusted to pH8 and then autoclaved) was added to the plasmid DNA-treated protoplast suspension, and then stirred gently. Finally, 5 ml of LSD medium supplemented with 0.4M mannitol was added to the protoplast suspension, and incubated for 20 hr in the dark.

After cultivation, cells were collected by centrifugation at 500 rpm for 3 min, and subjected to LUC and R-LUC activity assays. The substrate used in these assays is Dual-Luciferase Reporter assay system (Promega). Monitoring was conducted with luminometer LB955 (BERTHOLD).

(3) Activation of the CYM Promoter by Os3RmybA1

Co-transfection with plasmid R-LUC for the CaMV 35S promoter-driven expression of *Renilla* luciferase was performed to provide an internal control for the efficiency of transfection among gene transferred samples. Each LUC activity was calibrated with the control *Renilla* luciferase activity. The plasmids used herein are pEXP-Os3RmybA1 for the CaMV 35S promoter-driven expression of full-length Os3RmybA1, pEXP-GUS for the CaMV 35S promoter-driven expression of GUS, the aforementioned plasmid CYM promoter-LUC, and the plasmid R-LUC. The transfection was performed in quintuplicate. The plasmid combinations were as follows:

(i) Effector Plasmid-Free Combination:

plasmid CYM promoter-LUC (10 µg/1 sample)+plasmid pEXP-GUS (10 µg/1 sample)+plasmid R-LUC (1 µg/1 sample)

(ii) Combination with pEXP-Os3RmybA1 as an Effector Plasmid:

plasmid CYM promoter-LUC (10 µg/1 sample)+plasmid pEXP-Os3RmybA1 (10 µg/1 sample)+plasmid R-LUC (1 µg/1 sample)

(iii) Combination with pEXP-NtmybA2 as an Effector Plasmid:

plasmid CYM promoter-LUC (10 µg/1 sample)+plasmid pEXP-NtmybA2 (10 µg/1 sample)+plasmid R-LUC (1 µg/1 sample).

When the LUC specific enzymatic activity is taken as "1" in case of transfection with the combination (i) (levels of luciferase activity are standardized according to levels of *Renilla* luciferase activity), the LUC specific activity in the combination (ii) increases about 2.5 fold higher. Similarly, the LUC specific activity in the combination (iii) also increases about 2.5 fold higher (FIG. 4). It has been disclosed that Os3RmybA1 activates the transcription of the CYM promoter. Surprisingly, although Os3RmybA1 is cDNA cloned from rice, it exerts an ability of activating transcription in tobacco cells to an extent of tobacco NtmybA2. The fact that Os3RmybA1, isolated from rice, functions in tobacco cells equivalently to tobacco NtmybA2 clearly indicates that control mechanisms for G2/M phase-specific gene expression are conservative between Dicotyledonae and Monocotyledonae plants.

Example 4

Isolation of DNA Coding for Each of NtmybA1, NtmybA2, and NtmybB

The nucleotide sequence of DNA coding for NtmybA1 as used herein, is shown in SEQ ID NO: 50, and the amino acid sequence of NtmybA1 in SEQ ID NO: 51. The nucleotide sequence of DNA coding for NtmybA2 is also shown in SEQ ID NO: 52, and the amino acid sequence of NtmybA2 in SEQ ID NO: 53. Besides, the nucleotide sequence of DNA coding for NtmybB as used herein, is shown in SEQ ID NO: 54, and the amino acid sequence of NtmybB in SEQ ID NO: 55.

Each coding DNA for NtmybA1, NtmybA2, and NtmybB, was isolated with a Yeast One-hybrid system (Clontech) (Ito et al., Plant Cell, 13:1891 (2001)). Plant cDNA, prepared from cultured 2-day-old BY2 cells, was inserted into plasmid pGAD10 to construct cDNA libraries. Created was the HIS-deficient yeast strain that harbors chromosomes carrying an insert of reporter genes wherein the MSA-containing promoter, NACK1 promoter, was functionally fused to the gene responsible for histidine biosynthesis (HIS3), and transfected with the aforementioned cDNA libraries. The transformed yeast cells were subjected to selection with histidine-free medium, and three clones (plasmids, OH53, OH60, and OH88) were recovered from grown colonies. Each nucleotide sequence of cDNA inserts in the three plasmids (OH53, OH60, and OH88) was sequenced and NtmybA1, NtmybA2, and NtmybB-encoding DNAs were obtained. An insert in plasmid OH53 is a DNA fragment coding for NtmybA1. A DNA insert in plasmid OH60 is a DNA coding for full-length NtmybA2. A DNA coding for full-length NtmybB is contained in plasmid OH88 as an insert. Since OH53 did not include the full-length coding region, the determination of 3'-ends was performed by 3'RACE. As a result, plasmid pGEMe-OH53i6 having an insert of full-length NtmybA1 cDNA was obtained.

It can be simply convenient to isolate these DNAs by PCR or hybridization techniques. When hybridization is applied, cDNA may be prepared from BY2 cells during exponential growth, and then cloned into plasmids or phages to construct libraries, which will be conveniently subjected to screening steps. Applicable probes can be produced on information about the DNA of SEQ ID NO: 50 for NtmybA1, the DNA of SEQ ID NO: 52 for NtmybA2, and the DNA of SEQ ID NO: 54 for NtmybB.

When the isolation is carried out by PCR, cDNA prepared from BY2 cells during exponential growth, may be used as a template. Primers can be designed on information about the DNA of SEQ ID NO: 50 for NtmybA1, the DNA of SEQ ID NO: 52 for NtmybA2, and the DNA of SEQ ID NO: 54 for NtmybB. In Examples after those where the construction of plasmids are disclosed herein, NtmybA2 and NtmybB can be cut out from OH60, OH88 and others, and DNA fragments coding for NtmybA2 and NtmybB can be conveniently obtained using PCR primers with a suitable restriction site incorporation.

Example 5

Construction of Plasmids, pEXP-NtmybA2 and pEXP-NtmybB

Plasmids, pEXP-NtmybA2 and pEXP-NtmybB, for CaMV 35S promoter-driven expression of NtmybA2 and NtmybB, respectively, were constructed. Briefly, DNA fragments, cut out by SalI digestion from OH60 and OH88, were inserted in a sense direction into the site derived by SalI digestion from pEXP35S to construct plasmids, pEXP-NtmybA2 and pEXP-NtmybB for CaMV 35S promoter-driven expression of NtmybA2 and NtmybB, respectively.

Plasmids which are substantially functionally equivalent to these plasmids can also be constructed as follows:

A DNA fragment, cut out by SalI-cleavage of OH60 or OH88, is inserted into the site derived by SalI-cleavage of plasmid pP35S to create pP35S-NtmybA2, or pP35S-NtmybB. That is, pP35S-NtmybA2, and pP35S-NtmybB are plasmids for the CaMV 35S promoter-driven expression of NtmybA2 and NtmybB, respectively.

Example 6

NtmybA2 Functional Region Modulates its Transcription Activating Ability

NtmybA2 is a transcription activator for the NACK1 gene and the CYM gene. However, it was unknown what was a functional region involved in the transcription activating ability of protein NtmybA2. For making a search for this functional region, a series of C-terminally truncated mutant versions of NtmybA2 was constructed. The ability of activating transcription of the NACK1 gene was assayed for these mutants and the NtmybA2 functional region that modulates the transcription activating ability was determined.

(1) Construction of Plasmids

Construction of Respective Plasmids for Each C-Terminally Truncated Mutant of Protein NtmybA2

For examining the NtmybA2 region that functions in gene transcription activation, the following C-terminal deletion mutant NtmybA2 proteins wherein the amino acid sequence of NtmybA2 was C-terminally truncated were created:

(i) pEXP-NtmybA2T1 (lacking a region from amino acid 705 to the C-terminal end)

(ii) pEXP-NtmybA2T2 (lacking a region from amino acid 631 to the C-terminal end)

(iii) pEXP-NtmybA2T3 (lacking a region from amino acid 569 to the C-terminal end)

(iv) pEXP-NtmybA2ΔEcoRI (lacking a region from amino acid 413 to the C-terminal end)

(v) pEXP-NtmybA2T4 (lacking a region from amino acid 243 to the C-terminal end)

(vi) pEXP-NtmybA2T5 (lacking a region from amino acid 188 to the C-terminal end)

For the plasmids, (i), (ii), (iii), (v), and (vi), each deletion DNA fragment was produced by PCR using pEXP-NtmybA2 as a template. Primers used in the PCR are as follows:

```
primer 35S0:                       (SEQ ID NO: 48)
5'- TATCCTTCGCAAGACCCTTC -3'
in combination with, for (i), primer A2-T1-TAG:         (SEQ ID NO: 43)
5'- CCGTCGACTATGCAGCCTCGTCAAACATAA -3', for (ii), primer A2-T2-           (SEQ ID NO: 44)
TAG:
5'- CCGTCGACTACCACAGCCTAAATGGAGTA -3', for (iii), primer A2-T3-          (SEQ ID NO: 45)
TAG:
5'- CCGTCGACTATATGCTCGAATTTTCGTTCAC -3', for (v), primer A2-T4-TAG:         (SEQ ID NO: 46)
5'- CCGTCGACTAGCATTCTGAAGCTTCCTCC -3',
and, for (vi), primer A2-T5-           (SEQ ID NO: 47)
TAG:
5'- CCGTCGACTACTTTTTGACGGAACTATTCC -3'.
```

PCR-amplified DNA fragments coding for respective C-terminal deletion NtmybA2 mutants were digested with SalI, and then inserted in a sense direction into the site derived by SalI digestion of pEXP35S to create plasmids, (i), (ii), (iii), (v), and (vi), respectively.

The plasmid (iv) was generated by cleaving pEXP-NtmybA2 with EcoRI, followed by self-ligation after removing the resulting cut out DNA.

Also, plasmids which are substantially functionally equivalent to any of plasmids (i) to (vi) can be constructed as follows:

(vii) pP35S-NtmybA2T1 (lacking a region from amino acid 705 to the C-terminal end)
(viii) pP35S-NtmybA2T2 (lacking a region from amino acid 631 to the C-terminal end)
(ix) pP35S-NtmybA2T3 (lacking a region from amino acid 569 to the C-terminal end)
(x) pP35S-NtmybA2ΔEcoRI (lacking a region from amino acid 413 to the C-terminal end)
(xi) pP35S-NtmybA2T4 (lacking a region from amino acid 243 to the C-terminal end)
(xii) pP35S-NtmybA2T5 (lacking a region from amino acid 188 to the C-terminal end)

For plasmids, (vii), (viii), (ix), (xi), and (xii), deletion DNA fragments are amplified by PCR using pP35S-NtmybA2 as a template.

Primers used in the PCR are:

```
primer 35S0:                        (SEQ ID NO: 48)
5'- TATCCTTCGCAAGACCCTTC -3',
in combination with for (vii), primer A2-T1-           (SEQ ID NO: 43)
TAG:
5'- CCGTCGACTATGCAGCCTCGTCAAACATAA -3', for (viii), primer A2-T2-          (SEQ ID NO: 44)
TAG:
5'- CCGTCGACTACCACAGCCTAAATGGAGTA -3', for (ix), primer A2-T3-            (SEQ ID NO: 45)
TAG:
5'- CCGTCGACTATATGCTCGAATTTTCGTTCAC -3', for (xi), primer A2-T4-            (SEQ ID NO: 46)
TAG:
5'- CCGTCGACTAGCATTCTGAAGCTTCCTCC -3',
and for (xii), primer A2-T5-           (SEQ ID NO: 47)
TAG:
5'- CCGTCGACTACTTTTTGACGGAACTATTCC -3'.
```

PCR-amplified DNA fragments coding for respective C-terminal deletion NtmybA2 mutants are digested with SalI, and then inserted in a sense direction into the site derived by SalI digestion of pP35S to create plasmids, (vii), (viii), (ix), (xi), and (xii), respectively. The plasmid (x) is generated by cleaving partially pP35S-NtmybA2 with EcoRI, followed by self-ligation after blunt-ending the protruded end with the Klenow fragment.

Construction of Plasmid for NACK1 Promoter-LUC

A DNA fragment, derived by cleavage with HindIII and SacI from plasmid pDO432 (Nishiuchi et al., Plant Mol. Biol., 29:599 (1995)), was inserted into the site, derived by HindIII-SacI digestion of pBI221 (Clontech) followed by removal of DNA fragments including the CaMV 35S promoter region, to create pUC-LUC. The NACK1 promoter region was amplified by PCR using genomic DNA (prepared from cultured tobacco BY2 cells according to a conventional technique) as a template.

Primers used in the PCR are:

```
NAK1P-3:                            (SEQ ID NO: 58)
```

```
                    -continued
5'- CCGGATCCTCTAGATTTGCGCCTGAGATCTGAG -3',
and NAK1P-5:                            (SEQ ID NO: 59)
5'- CCAAGCTTCATAAGCCGATAGAATTCACC -3'.
```

The amplified NACK1 promoter region was digested with BamHI and HindIII, and then inserted into the site, derived by cleavage with BamHI and HindIII of pUC-LUC, to create plasmid NACK1 promoter-LUC. That is, the plasmid NACK1 promoter-LUC is a plasmid for expression of LUC, driven by the NACK1 promoter including as control sequences the MSA motifs at two positions.

(2) Change in Transcription Activating Property of C-Terminal Deletion NtmybA2 Mutant Proteins Transfection of the plasmids into BY-2 protoplasts was performed according to the method of Example 3 (2). The effector plasmids used herein were the aforementioned plasmids, (1) (i) to (vi), for expression of the deletion NtmybA2 mutants, pEXP-NtmybA2 for expression of full-length NtmybA2, and pEXP-GUS for expression of GUS. The reporter used herein was plasmid, NACK1 promoter-LUC. The transcription activation of the reporter gene was evaluated by measuring levels of LUC activity. LUC and R-LUC activities were assayed in the same manner as in Example 3. Each LUC specific activity is expressed relative to the standardized value of LUC activity according to the level of R-LUC activity.

When the LUC specific activity was taken as "1" in case of effector plasmid pEXP-GUS, it was observed that the LUC specific activity of pEXP-NtmybA2 was about 4 fold higher. When plasmids (i) to (iii) were used, it was observed that the LUC specific activity increased relative to the pEXP-NtmybA2 case; in particular, it did about 45-fold higher in case of plasmid (ii). In case of transfection with plasmid (iv), the LUC specific activity decreased to an extent of the pEXP-NtmybA2 level, as compared to the case (iii). For (v) and (vi), the LUC activity decreased more than the pEXP-NtmybA2.

Figure 5:
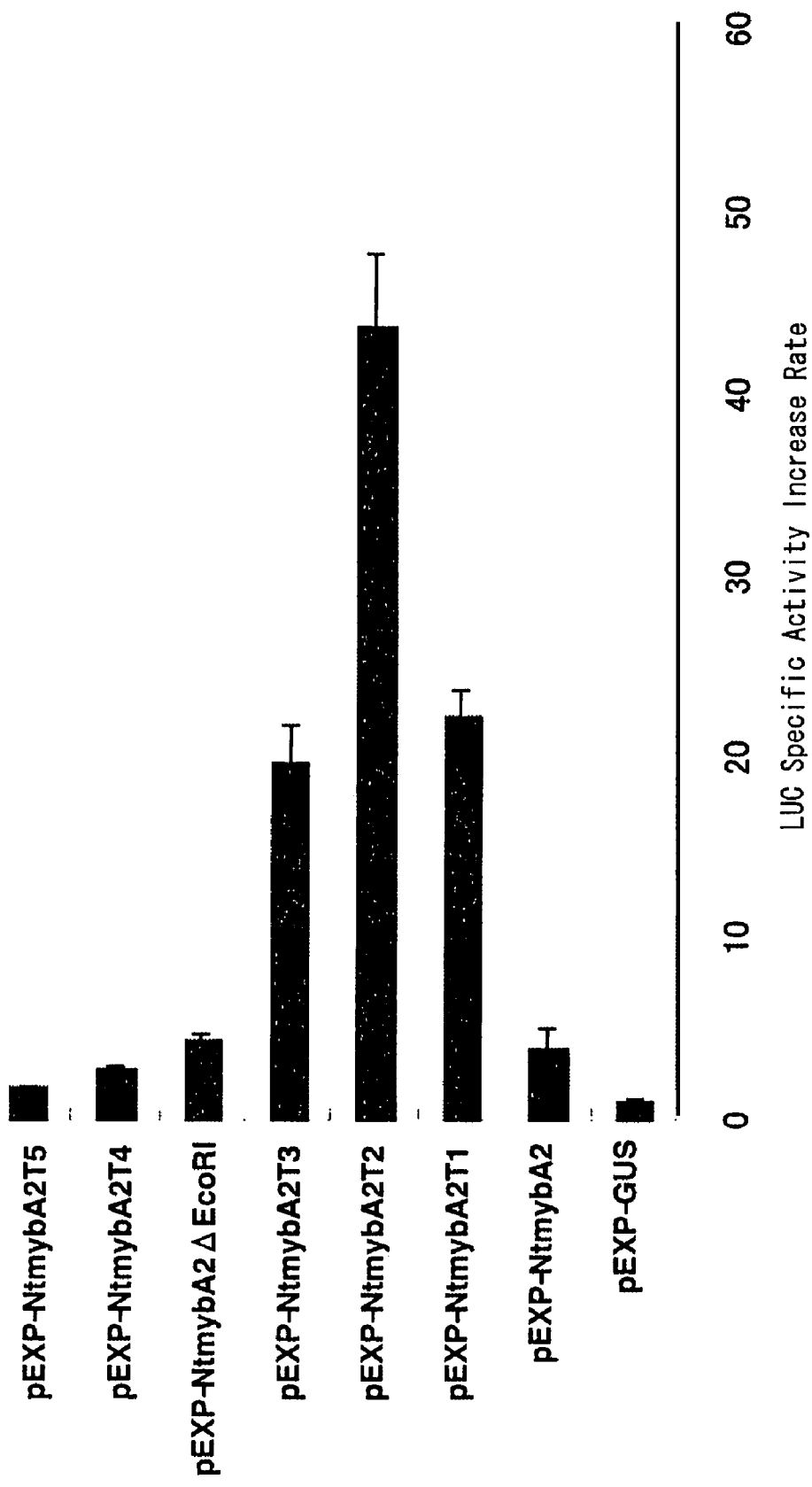
FIG. 5 is a diagram showing LUC specific activity increase ratios wherein C-terminally truncated NtmybA2- and NtmybA2-mutant version abilities to activate transcription of the NACK1 promoter-LUC fused gene were examined using various expression plasmids for C-terminally truncated mutant versions of NtmybA2 and NtmybA2 in combination with the NACK1 promoter-LUC reporter plasmid. All LUC activities are expressed relative to the control (taken as 1.0). Data represent the mean of quintuplicate experiments. Error bars indicate S.D.

From the foregoing results, it is apparent that the C-terminal NtmybA2 region ranging from amino acid 631 to the C-end is the region that negatively regulates the transcription activating property owned by protein NtmybA2. It is obvious that the amino acid sequence ranging from residues 413 to 630 will acts as an enhancer region of activating transcription. It has been demonstrated that the amino acid deletion of residues ranging from amino acid 569 to the C-terminal end, particularly from amino acid 631 to the C-end, allows a remarkable increase in NtmybA2 ability of activating transcription while the amino acid deletion of residues ranging from amino acid 188 to the C-end, or from amino acid 243 to the C-end, allows a decrease in NtmybA2 ability of activating transcription (FIG. 5).

Example 7

NtmybA2T5 Dominant Negative Actions on NtmybA2 or NtmybB

In Example 6, the levels of ability to activate transcription decreased in cases of NtmybA2T4 for use of a polypeptide with residues ranging from amino acids 1 to 242 of protein NtmybA2 and NtmybA2T5 for use of a polypeptide with residues ranging from amino acids 1 to 187 of protein NtmybA2 more than in case of full-length NtmybA2. These facts indicate that NtmybA2T4 and NtmybA2T5 wherein each ability to activate transcription is reduced or lost bind to the MSA sequence of target promoters, thereby inhibiting the binding of endogenous NtmybA1, NtmybA2 and NtmybB to the MSA sequence whereby NtmybA2T4 and NtmybA2T5 act dominant negatively. To demonstrate the dominant negative function of NtmybA2T5, the transcription activation driven by the CYM promoter was quantitated in cases of coexpression of NtmybA2 in combination with NtmybA2T5, and coexpression of NtmybB in combination with NtmybA2T5.

BY-2 protoplasts prepared according to the method described in Example 3 (2) were transformed with a set of plasmids, NACK1 promoter:LUC (10 µg/sample), R-LUC (1 µg/sample), pEXP-NtmybA2 (10 µg/sample) and pEXP-NtmybA2T5 (10 µg/sample), or another set of plasmids, NACK1 promoter:LUC (10 µg/sample), R-LUC (1 µg/sample), pEXP-NtmybA2 (10 µg/sample) and pEXP-GUS (10 µg/sample). The resultant transformed BY2 cells were assayed for LUC activity and R-LUC activity according to the method described in Example 3 (4). The transfection with plasmids was preformed in quintuplicate. The level of LUC specific activity (which is expressed relative to the level of LUC activity standardized according to the level of R-LUC activity) decreased in the combination of pEXP-NtmybA2+pEXP-NtmybA2T5 more than in the combination of pEXP-NtmybA2+pEXP-GUS.

These results support that NtmybA2T5 acts on NtmybA2 dominant-negatively.

Figure 6:
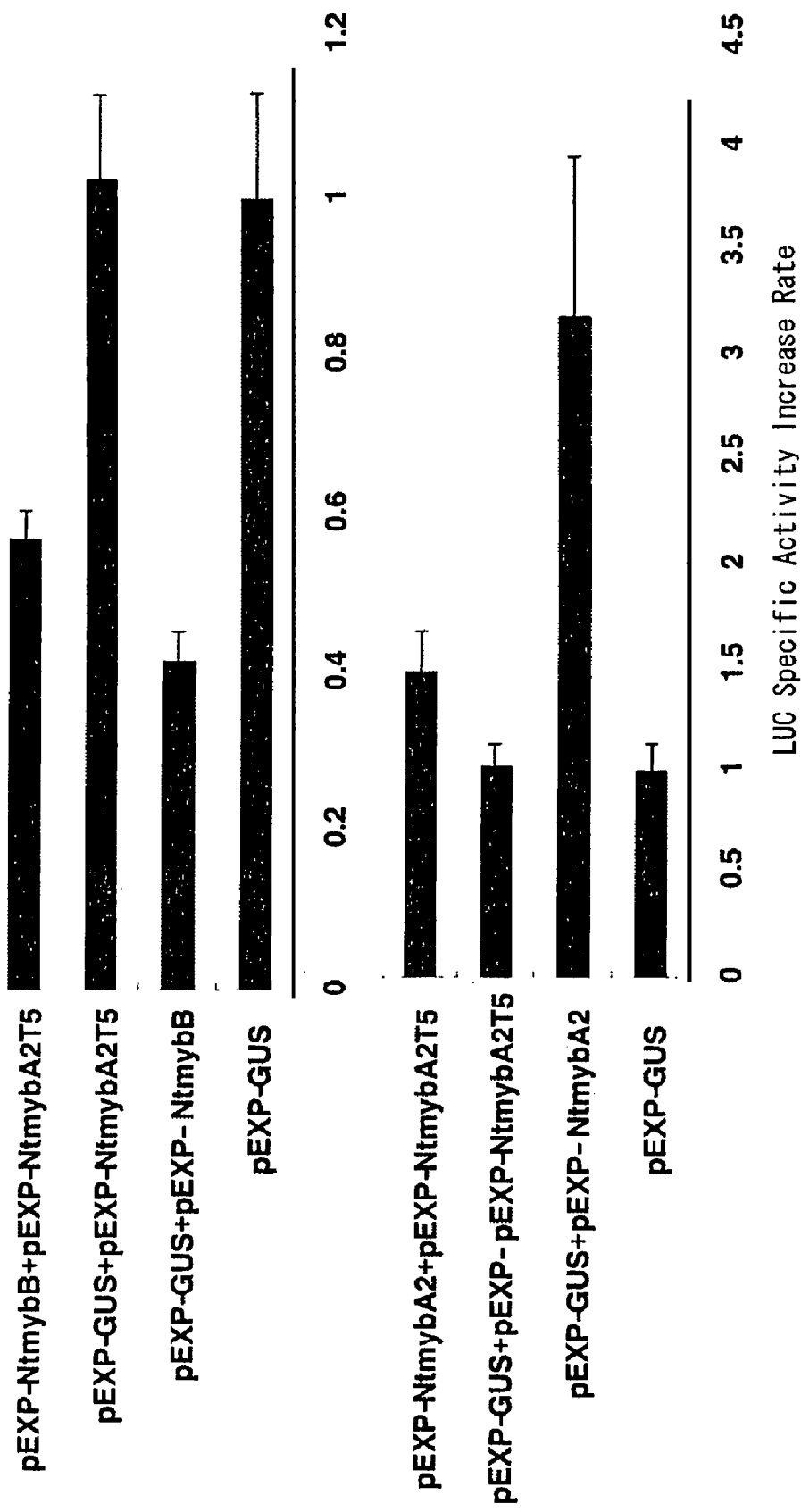
FIG. 6 is a diagram showing LUC specific activity increase ratios wherein (NtmybA2+NtmybA2T5)- or (NtmybB+ NtmybA2T5)-coexpression abilities to activate transcription of the CYM promoter-LUC fused gene were examined using the CYM promoter-LUC reporter plasmid. All LUC activities are expressed relative to the control (taken as 1.0). Data represent the mean of quintuplicate experiments. Error bars indicate S.D.

Also, to BY-2 protoplasts was added plasmid NACK1 promoter:LUC (10 µg/sample), R-LUC (1 µg/sample), followed by a gene transfer with pEXP-NtmybB (10 µg/sample)+pEXP-NtmybA2T5 (10 µg/sample), or pEXP-NtmybB (10 µg/sample)+pEXP-GUS (10 µg/sample). The resultant transformed BY2 cells were assayed for LUC activity and R-LUC activity according to the method described in Example 3 (4). The level of LUC specific activity (which is expressed relative to the level of LUC activity standardized according to the level of R-LUC activity) increased in the combination of pEXP-NtmybB+pEXP-NtmybA2T5 more than in the combination of pEXP-NtmybB+pEXP-GUS. These results support that NtmybA2T5 acts on NtmybB dominant-negatively (FIG. 6).

Example 8

Modification of Plant Growth and Development in NtmybA2-, NtmybA2T2-, and NtmybB-Transformed *Arabidopsis thaliana*

Generated were transgenic *Arabidopsis thaliana* plants which stably express transcription activator form NtmybA2, NtmybA2T2 which is a mutant construct with remarkably enhanced NtmybA2 ability to activate transcription, and transcription repressor form NtmybB, by an action of the CaMV 35S promoter, and compared for their growth and development, respectively.

(1) Construction of Plasmids for Transformation

A DNA fragment, derived by KpnI cleavage of pEXP-NtmybA2T2, then blunt-ending with the Klenow fragment followed by XhoI-cleavage, was inserted into the site, derived by digestion with SalI and SmaI of pBI-RHL as disclosed in PCT/JP02/12268 (2002), to create pBIHm-NtmybA2T2. Into the site, derived by SalI-cleavage of pBIHm-NtmybA2T2, followed by removal of a cut out DNA fragment including NtmybA2T2, were inserted DNA fragments, derived by SalI-cleavage of pEXP-NtmybB and pEXP-NtmybA2, to create pBIHm-NtmybB, and pBIHm-NtmybA2, respectively. An sGFP-containing DNA fragment, derived by NotI-cleavage of plasmid pTH2 (Chiu et al., Curr Biol 1996 Mar. 1; 6(3): 325-30), and blunt-ending with the Klenow fragment followed by cleavage with SalI, was inserted into the site, derived by SalI-SmaI digestion of pBIHm-NtmybA2T2 followed by removal of a DNA fragment including NtmybA2T2, to create pBIHm-GFP.

That is, the aforementioned (i) pBIHm-NtmybA2T2, (ii) pBIHm-NtmybB, (iii) pBIHm-NtmybA2 and (iv) pBIHm-GFP are binary vectors for CaMV 35S promoter-driven expression of respective NtmybA2T2, NtmybB, NtmybA2, and sGFP, respectively, which can transform plants according to *Agrobacterium*-mediated transformation techniques. These plasmids can be genetically transferred into plants which can be subjected to selection with hygromycin to obtain transformant plants.

Plasmids which are substantially functionally equivalent to any of plasmids (i) to (iv) can be constructed as follows:

A DNA fragment, derived by SacI-ApaI cleavage of pP35S-NtmybA2T2 followed by blunt-ending with the Klenow fragment at the resultant protruded end, is inserted into the site, derived by SalI cleavage of pBI-RHL as disclosed in PCT/JP02/12268 (2002), followed by blunt-ending the resultant protruded end with the Klenow fragment, to create pBIHm35S-NtmybA2T2. DNA fragments, derived by SalI cleavage of pP35S-NtmybB and pP35S-NtmybA2, are inserted into the site, derived by SalI cleavage of pBIHm35S-NtmybA2T2 followed by removal of the resultant cut out DNA fragment including NtmybA2T2, to create pBIHm35S-NtmybB, and pBIHm35S-NtmybA2, respectively. An sGFP-containing DNA fragment, derived by NotI-SalI cleavage of plasmid pTH2 (Chiu et al., Curr Biol 1996 Mar. 1; 6(3): 325-30) and blunt-ending the resultant protruded end with the Klenow fragment, is inserted into the site derived by SalI cleavage of pBIHm35S-NtmybA2T2, blunt-ending with the Klenow fragment at the protruded end followed by removal of the resultant DNA fragment including NtmybA2T2, to create pBIHm35S-GFP.

That is, the aforementioned (v) pBIHm35S-NtmybA2T2, (vi) pBIHm35S-NtmybB, (vii) pBIHm35S-NtmybA2 and (viii) pBIHm35S-GFP are plasmid vectors for CaMV 35S promoter-driven expression of NtmybA2T2, NtmybB, NtmybA2, and sGFP, respectively. They are binary vectors which allow *Agrobacterium*-mediated transformation of plants. These plasmids can be genetically transferred into plants which can be subjected to selection with hygromycin to obtain plant transformants.

(2) Transformation of *Arabidopsis thaliana*

*Agrobacterium tumefaciens* strain EHA101 was transformed with a binary vector selected from plasmids (1) (i) to (iv) as created in the aforementioned (1). Next, *Arabidopsis thaliana* ecotype Col-0 was transformed by the floral dip method for *Agrobacterium*-mediated transformation (Clough et al. (1998), Plant J. 16: 735) using *Agrobacterium* harboring the aforementioned plasmid. Seeds collected from *Agrobacterium*-infected floral buds were sterilized with hypochloric acid and sterile water, and seeded in MS medium supplemented with 25 µg/ml hygromycin and 100 µg/ml carbenicillin. Transgenic plants capable of growing in hygromycin-added medium were selected.

(3) Modification of Plant Growth and Development in NtmybA2-, NtmybA2T2-, and NtmybB-Transformed *Arabidopsis thaliana*

Selected plant transformants were transplanted on MS medium (MS inorganic salts, 30% sucrose, and 0.4% Gellan gum) solidified in a Petri dish (rectangular container #2, Eiken Chemical Co., Ltd., Japan), allowed to stand vertically, and cultivated at 21° C. for 16 hr under continuous light, and then in darkness for 8 hr. At 25 days post-transplantation, the length of taproots was measured. The most predominant plantlets were transformant lines with the taproot length of 31 mm to 35 mm in the control group (transformation with pBIHm-GFP), while the most predominantly distributed plantlets were those transformant lines with the taproot length of 21 mm to 25 mm in the cases of transformation with pBIHm-NtmybA2, pBIHm-NtmybA2T2, and pBIHm-NtmybB. Thus, the plants with repressed growth and development were successfully produced. From the foregoing results, it is apparent that transgenic *Arabidopsis thaliana* plants which stably express NtmybA2, NtmybB, or NtmybA2T2 have modified growing and developing properties.

Example 9

Modification of Plant Growth and Development in NtmybA2T2- and NtmybA2T5-Transformed *Arabidopsis thaliana*

Generated were transgenic *Arabidopsis thaliana* plants which stably express dominant negative form NtmybA2T5, by an action of the CaMV 35S promoter, and compared for their growth and development.

Generated were transgenic *Arabidopsis thaliana* plants which express NtmybA2T2 mutant constructs with remarkably enhanced NtmybA2 ability of activating transcription, by an action of the cyclin B (CYM) promoter, and compared for their growth and development.

(1) Construction of Plasmids for Transformation

Construction of Plasmid pDBIHm-NtmybA2T5

A DNA fragment for Reading Frame A, commercially supplied by Invitrogen, was inserted into the site by SmaI cleavage of pUC19 (Takara, Japan) to create pUC-RFA. A Reading Frame A, cut out by BamHI-SpeI digestion of pUC-RFA, was inserted into the site, derived by BamHI-SpeI digestion of plasmid pBI-RHL as disclosed in PCT/JP02/12268 (2002), to create pDESTBI-1.

A DNA fragment, cut out by KpnI-XhoI cleavage of plasmid pEXP-NtmybA2T5, was inserted into the site derived by KpnI-XhoI cleavage of plasmid pENTR2B (Invitrogen) to create pENTR-NtmybA2T5. A mixture of pDESTBI-1 and pENTR-NtmybA2T5 was subjected to site-specific recombination using Gateway™ LR Clonase™ mix (Invitrogen) to construct pDBIHm-NtmybA2T5. The reaction with Gateway™ LR Clonase™ mix was done according to protocols enclosed in the reagent. The vector, pDBIHm-NtmybA2T5, is a plasmid vector for CaMV 35S promoter-driven expression of NtmybA2T5. It is also a binary vector which allows *Agrobacterium*-mediated transformation of plants. This plasmid can be genetically transferred into plants which can be subjected to selection with hygromycin to obtain plant transformants.

Plasmids which are substantially functionally equivalent to pDBIHm-NtmybA2T5 can also be constructed as follows:

The plasmid, pP35S-NtmybA2T5, is digested with SacII and ApaI followed by blunt-ending the protruded end with the Klenow fragment. The resulting cut out DNA fragment is inserted into the site, derived by KpnI-XhoI cleavage of pENTR2B (Invitrogen) followed by blunt-ending with the Klenow fragment at the resultant protruded end, to create pENTR35S-NtmybA2T5. A mixture of pDESTBI-1 and pENTR35S-NtmybA2T5 is subjected to site-specific recombination using Gateway™ LR Clonase™ mix (Invitrogen) to construct pDBIHm35S-NtmybA2T5. The reaction with Gateway™ LR Clonase™ mix is done according to protocols enclosed in the reagent. The vector, pDBIHm35S-NtmybA2T5, is a plasmid vector for CaMV 35S promoter-driven expression of NtmybA2T5. It is also a binary vector which allows *Agrobacterium*-mediated transformation of plants. This plasmid can be genetically transferred into plants which can be subjected to selection with hygromycin to obtain plant transformants.

Construction of Plasmid pPCYM-NtmybA2T2

A CYM promoter region was prepared by PCR using as a template a genomic DNA prepared from *Catharanthus roseus* according to customary techniques.

Primers used in the PCR were

```
CYM3Pst:                                 (SEQ ID NO: 60)
5'- AACTGCAGTCTTCAATAGAATTTCTTCCAG -3';
and CYM5-1:                                  (SEQ ID NO: 57)
5'- CCAAGCTTACCCATAAATTGTTGGTAAA -3'.
```

The amplified CYM promoter region was digested with PstI and HindIII, and then was inserted into the site, derived by PstI-HindIII cleavage of pPZP211 (Hajdukiewicz et al., Plant Mol. Biol. 25: 989 (1994)), to create plasmid pPZP211-CYM. A fragment cut out by SalI cleavage of pEXP-NtmybA2T2 was inserted into the site derived by SalI cleavage of pPZP211-CYM to create pPCYM-NtmybA2T2. The vector, pPCYM-NtmybA2T2, is a plasmid vector for CYM promoter-driven expression of NtmybA2T2. It is also a binary vector which allows *Agrobacterium*-mediated transformation of plants. This plasmid can be genetically transferred into plants which can be subjected to selection with kanamycin to obtain plant transformants. The plasmid pPCYM-NtmybA2T2 can also be constructed as follows:

It can be constructed by inserting a DNA fragment, cut out by SalI cleavage of pP35SNtmybA2T2, into the site derived by SalI cleavage of pPZP211-CYM.

(2) Transformation of *Arabidopsis thaliana*

*Arabidopsis thaliana* ecotype Col-0 plants were transformed with pDBIHm-NtmybA2T5, pPCYM-NtmybA2T2 (constructed in the above (1)), and pBIHm-GFP (control group) according to the method disclosed in Example 5, and subjected to selection, respectively. The selection of transgenic plants transformed with pDBIHm-NtmybA2T5 and pBIHm-GFP was done on MS medium containing hygromycin (25 μg/ml) and carbenicillin (100 μg/ml) to give plant transformants capable of growing on the medium, respectively. The selection of transgenic plants transformed with pPCYM-NtmybA2T2 was done on MS medium containing kanamycin (50 μg/ml) and carbenicillin (100 μg/ml) to give viable plant transformants. The resultant transformant lines were transplanted on vermiculite:peat-moss (1:1) mix soil, acclimated, and cultivated at 21° C. for 16 hr under continuous light, and then in darkness for 8 hr. These lines were self-fertilized to provide first filial generation seeds which were used for analysis.

(3) Modification of Plant Growth Rate in *Arabidopsis thaliana* by an Action of NtmybA2 Mutants The first filial generation seeds from self-fertilized of plants resulting from the transformation were sterilized with hypochloric acid and sterile water, seeded on MS medium (MS inorganic salts, 30% sucrose, and 0.4% Gellan gum) solidified in a Petri dish (rectangular container #2, Eiken Chemical Co., Ltd., Japan), and vernalized at 4° C. in darkness for 4 days. After vernalization, plants were allowed to stand vertically, and cultivated at 21° C. for 16 hr under continuous light, and then in darkness for 8 hr. Three days after the vernalization, each main root length was measured.

Plural transformant lines with repressed growth phenotypes were observed among pDBIHm-NtmybA2T5- and pPCYM-NtmybA2T2-transformed lines, as compared to the control pBIHm-GFP-transformed line.

Example 10

Suppression of Plant Growth and Development by Repressed Expression of NtmybA1 and NtmybA2

Virus Induced Gene silencing (VIGS) was used as a tool for suppressing the expression of endogenous genes in order to assess the phenotype of plants with repressed expression of NtmybA1 and NtmybA2. Plasmids, LgJ, and LGFPJ, used in VIGS were presented by courtesy of distributor, Yuichiro Watanabe, Department of Life Sciences (Multi-Disciplinary Sciences), Graduate School of Arts and Sciences, The University of Tokyo, Japan. LgJ is a plasmid having an insert of DNA coding for virus derived by modification of plant RNA virus, tomato mosaic virus (ToMV). The modification of ToMV includes an introduction of amino acid substitution mutations into the replication enzyme-coding region to ameliorate the virus-induced symptoms due to reduction in levels of replicated virus; an incorporation of a new promoter sequence to allow the expression of foreign DNA; and an insert of Gateway™ system recombination sites downstream of the promoter for expression of foreign DNA to allow an insertion of foreign DNA by reaction with LR (available from Invitrogen). The LgJ plasmid can be subjected to In Vitro RNA Transcription to generate recombinant viral RNA which is infectious against plants. In plants infected with this recombinant virus, foreign DNA-derived double-stranded RNA is expressed as a replication intermediate in the plants. When the foreign DNA used in the recombinant virus is a DNA derived from the plant for viral infection, the expression of the corresponding endogenous plant gene will be suppressed. LGFPJ is derived by insertion of GFP-coding DNA into LgJ and allows detection of virus infection by monitoring the expression of GFP.

(1) Construction of Plasmids

Construction of LA1A2J

A DNA fragment including part of NtmybA1 cDNA was amplified by PCR using as a template pGEMe-OH53i6 in combination with primers,

```
primer VA1-F:                           (SEQ ID NO: 37)
5'- ATAGTTCTGTTAAAAAGAAACTG -3'
and primer VA1-R:                           (SEQ ID NO: 38)
5'- TAACATTGAACAAGAAACATCTTG -3'.
```

A DNA fragment including part of NtmybA2 cDNA was amplified by PCR using as a template OH60 in combination with primers,

```
primer VA2-F:                           (SEQ ID NO: 39)
5'- ACAAAGTCTTCTCTAACTACG -3'
and primer VA2-R:                           (SEQ ID NO: 40)
5'- AGCTTCGAGTCGTCTAGCG -3'.
```

The PCR reaction was done using Pyrobest™ (Takara, Japan). The resultant DNA fragments were inserted into the EcoRV site of pBluescript™ (Stratagene) to create pBS-VA1, and pBS-VA2, respectively. A DNA fragment, cut out by SmaI-SalI cleavage of PBS-VA2, was inserted into the site, derived by HindIII cleavage of pBS-VA1, blunt-ending with the Klenow fragment followed by cleavage with SalI, to create pBS-VA1A2. PCR was performed with pBS-VA1A2 as a template in combination with

```
primer B1T3:                                                    (SEQ ID NO: 41)
5'- GGGGACAAGTTTGTACAAAAAAGCAGGCTCAATTAACCCTCACTAAAGGG -3'
and primer B2T7:                                                    (SEQ ID NO: 42)
5'- GGGGACCACTTTGTACAAGAAAGCTGGGTCGTAATACGACTCACTATAGGGC -3'
``` to provide a DNA fragment carrying a tandem linked DNA segment coding for part of NtmybA1 and a tandem linked DNA segment coding for part of NtmybA2, wherein the sequence attB1 (Gateway™ system, Invitrogen) was added to one end and the sequence attB2 (Gateway™ system, Invitrogen) to another end. A mixture of this DNA fragment and plasmid pDONR201 (Invitrogen) was subjected to BP reaction using BP Clonase™ (Invitrogen) to give pDONOR-VA1A2. A mixture of pDONR-VA1A2 and LgJ was reacted with LR Clonase™ (Invitrogen) to give LA1A2J. The reactions with BP Clonase™, and LR Clonase™ were done according to protocols enclosed in the reagent.

An aliquot (5 µg) of LA1A2J was cleaved with MluI to produce a linearized plasmid. After treated with phenol/chloroform, the plasmid was precipitated with ethanol, and resolved in sterilized water (10 µl).

The resultant linearized LA1A2J was used as a template for in vitro transcription.

In brief, a mixture of 10×T7 buffer (5 µl, Roche, attachment of T7 RNA Polymerase), 0.1M DTT (2.5 µl), Rnase-Inhibitor (1 µl, Roche, 40 units/µl), A/C/U/G mixture (5 µl, each 20 mM for ATP, CTP, and UTP, and 2 mM for GTP), 5 mM m$^7$G[5'] ppp[5']G (2.5 µl, CAP, Roche), sterilized water (14 µl), and linearized LA1A2J (10 µl) was incubated at 37° C. for 5 min. To the mixture was added 10 µl of T7 RNA Polymerase (20 units/µl, Roche), and the resulting mixture was incubated at 37° C. for 25 min, followed by addition of 20 mM GTP (5 µl). The mixture was then incubated at 37° C. for 35 min. After the reaction was finished, an aliquot (2 µl) of the reaction solution was subjected to electrophoresis on agarose gels to confirm the transcription of RNA.

LA1A2J RNA was used to inoculate *Nicotiana benthamiana*. In brief, plants were cultivated at 25° C., and upper 2 leaves of 4 to 5 leaf stage *Nicotiana benthamiana* were dusted with carborundum powder, and inoculated with LA1A2J RNA (5 µl/leaf). Within 5 minutes after inoculation, inoculated leaves were rinsed with distilled water. Five plant individuals were inoculated, and cultivated at 23° C. after the inoculation.

In vitro RNA transcription was performed using LGFPJ as the control group, like LA1A2J, and LGFPJ RNA was used to inoculate plants.

(2) Suppression of Plant Growth and Development in Plants with Repressed Expression of NtmybA1 and NtmybA2

The levels of expressed NtmybA1 mRNA and NtmybA2 mRNA are checked by RT-PCR. In brief, the levels of expressed NtmybA1 mRNA and NtmybA2 mRNA are checked by RT-PCR in LA1A2J- and LGFPJ-infected plants. Total RNA is extracted from each shoot tip of LA1A2J RNA-inoculated plants with repressed grass height, and LGFPJ RNA-inoculated plants with RNeasy™ Plant Mini Kit (QIAGEN). The synthesis of cDNA is performed using Superscript™ First-strand synthesis system for RT-PCR (Invitrogen) with the extracted total RNA as a template. The synthesized cDNA is used as a template and the detection of NtmybA1 and NtmybA2 was done with

```
primer A2-583F:                     (SEQ ID NO: 33)
5'- GTACAATGCTTGCACCGGTGG-3'
and primer A2-1089R:                    (SEQ ID NO: 34)
5'- TGTAGACTGGGAACAGCCAGC-3'.
```

The level of cDNA is standardized according to the amount expressed by EF1α mRNA in combination with

```
primer EFF:                         (SEQ ID NO: 35)
5'- AGACCACCAAGTACTACTGC-3'
and primer EF R:                        (SEQ ID NO: 36)
5'- GTCAAGAGCCTCAAGGAGAG-3'.
```

The PCR is performed using an aliquot (1 µl) of the synthesized cDNA (50 µl), thereby allowing the standardization of cDNA amounts applied and the expression level analysis for NtmybA1, and NtmybA2.

The plant growth and development is extremely suppressed in LA1A2J RNA-inoculated *Nicotiana benthamoiana* plants with repressed levels of endogenously expressed NtmybA1 mRNA and NtmybA2 mRNA, as compared to the control group, LGFPJ RNA-inoculated group.

From the foregoing observations, it will be apparent that reduction in expression levels of endogenous NtmybA1 and NtmybA2 allows the suppression of plant growth and development.

(3) Suppression of Cytokinesis and M Phase Progress in Plants with Repressed Expression of NtmybA1 and NtmybA2

Leaf epidermal cells and stomata guard cells were examined for leaves of plant individuals with repressed expression of endogenous NtmybA1 and NtmybA2 as disclosed in the above (2).

Epidermal cells are peeled off the undersurface of leaves with a pair of tweezers, and subjected to nuclear staining with a lactic acid-propionic acid (1:1) mixture containing 1% Orcein. These cells are examined with a Differential Interference Contrast Microscope. As a result, multinucleated cells that have plural nuclei are observed. Large and small nuclei are also found among nuclei existing in the multinucleated cells. The multinucleated cell indicates that nuclear division processes are in progress and cytokinesis is inhibited. The fact that there are nuclei which differ in size indicates that nuclear chromosomes multiply due to the occurrence of aberrant nuclear division and M phase skipping. That is, steps for entry into, progress in and termination of the M phase are affected in cells with repressed expression of NtmybA1 and NtmybA2. From the foregoing, it is disclosed that NtmybA1 and NtmybA2 are genes essential for normal progress in the M phase.

(4) Changes in Cell Cycle of Plants with Repressed Expression of NtmybA1 and NtmybA2

The levels of nuclear DNA are assayed for leaves of tobacco plant individuals with repressed expression of endogenous NtmybA1 and NtmybA2 as disclosed in the above (2). The third upper leaf above the inoculated leaf is cut, admixed with 1 ml of a nuclei extraction buffer contained in Cystain™ UV Precise P (High Resolution DNA staining kit, Partec) on a Petri dish, and minced with the blade of a razor for 1 min. After maintained at room temperature for 10 min, the resultant sample is filtered through Partec Cell Trics™ Disposable filter units (50 µm mesh, Partec) to give a filtrate to which was added 2 ml of a staining buffer contained in Cystain™ UV Precise P (High Resolution DNA staining kit, Partec). Measurements are performed with the Ploidy Analyser PA (Partec).

In nuclear samples prepared from leaves of tobacco plant individuals with repressed expression of NtmybA1 and NtmybA2, 4C peaks (indicating S, G2 phases) increase, as compared to the control group, and further 8C peaks (which were not observed in the control group) indicating multiplied nuclei are also observed. The fact that 4C peaks increase indicates delayed progress in the S, G2 phases, or delayed entry into the M phase. The fact that there are 8C peaks for multiplied ones indicates inhibition of entry into the M phase or M phase skipping. From the foregoing, it is disclosed that NtmybA1 and NtmybA2 are genes essential for normal progress in the M phase and silencing expression of these genes allows modulation of the cell cycle.

Example 11

Modification of Cell Growth Rate in Transformed Tobacco BY2 Cell Lines with Repressed Expression of Ntmyb (1) Construction of Plasmid for Each RNAi Against NtmybA1, NtmybA2, and NtmybB A DNA fragment, cut out by KpnI cleavage of pEXP35S, blunt-ending with T4 DNA Polymerase at the protruded end followed by EcoRV cleavage, was inserted into the site, derived by EcoRI-HindIII cleavage of pPZP211 followed by blunt-ending with the Klenow fragment at the protruded end, to create pPZP211-35S.

PCR was performed using pBI121 (Clontech) as a template in combination with primers,

```
SEQ ID NO: 61,                      (SEQ ID NO: 61)
5'- GGAATTCGTGTGATATCTACCCGCTTCG -3',
and SEQ ID NO: 62,                      (SEQ ID NO: 62)
5'- CGGGATCCGTTTTTCACCGAAGTTCATGC -3'
``` to amplify a DNA fragment carrying GUS ORF.

This DNA fragment was cleaved with EcoRI and BamHI, and then inserted into the site, derived by EcoRI-BamHI cleavage of pBluescript™II (SK+, Stratagene), to create pGUS1.0.

PCR was performed with OH60 as a template in combination with

```
primer A2ia3:                        (SEQ ID NO: 63)
5'- TTGAATTCCAAGTCTTGGGCTTGACAGAAGAG -3'
and primer A2ia5:                        (SEQ ID NO: 64)
5'- TTCTCGAGAAGCTTCGTCAAGAATCATTCTCTGATCTG -3'
``` to amplify a DNA fragment coding for part of NtmybA2, which was then cleaved with EcoRI and XhoI. The resultant DNA fragment was inserted into the site derived by EcoRI-XhoI cleavage of pGUS1.0 to create pGUS-A2.RNAi-a.

PCR was performed with OH60 as a template in combination with

```
    primer A2ib3:                    (SEQ ID NO: 65)
    5'- TTGGATCCAAGTCTTGGGCTTGACAGAAGAG -3'
    and primer A2ib5:                    (SEQ ID NO: 66)
    5'- CCTCTAGACTAGTGTCGACCGTCAAGAATCATTCT
    CTGATCTG -3'
``` to amplify a DNA fragment coding for part of NtmybA2, which was then cleaved with BamHI and XbaI. The resultant DNA fragment was inserted into the site, derived by BamHI-XbaI cleavage of pGUS-A2.RNAi-a, to create pGUS-A2.RNAi.

PCR was performed with OH88 as a template in combination with

```
    primer Bia3:                     (SEQ ID NO: 67)
    5'- TTGAATTCTTGTTGCCTGATAAGGTCGTCTC -3'
    and primer Bia5:                     (SEQ ID NO: 68)
    5'- TTCTCGAGAAGCTTGAATTTGCCTAGTAGGTTAGTGC -3'
``` to amplify a DNA fragment coding for part of NtmybB, which was cleaved with EcoRI and XhoI. The resultant DNA fragment was inserted into the site, derived by EcoRI-XhoI cleavage of pGUS1.0, to create pGUS-B.RNAi-a.

PCR was performed with OH88 as a template in combination with

```
primer Bib3:                         (SEQ ID NO: 69)
5'- TTGGATCCTTGTTGCCTGATAAGGTCGTCTC -3'
and primer Bib5:                         (SEQ ID NO: 70)
5'- CCTCTAGACTAGTGTCGACGAATTTGCCTAGTAGGTTAGTGC -3'
``` to amplify a DNA fragment coding for part of NtmybB, which was cleaved with BamHI and XbaI. The resultant DNA fragment was inserted into the site, derived by BamHI-XbaI cleavage of pGUS-B.RNAi-a, to create pGUS-B.RNAi.

A DNA fragment, cut out by HindIII cleavage of pGUS-A2.RNAi, was inserted into the site, derived by HindIII cleavage of pPZP211-35S, to create pPZP211-35S:A2RNAi.

A DNA fragment, cut out by HindIII-SalI cleavage of pGUS-B.RNAi, was inserted into the site, derived by HindIII-SalI cleavage of pPZP211-35S, to create pPZP211-35S:B:RNAi.

The vectors, pPZ P211-35S:A2RNAi, and pPZP211-35S:B:RNAi, are plasmid vectors for CaMV 35S promoter-driven expression of a partial sequence of NtmybA2, and a partial sequence of NtmybB in the form of inverted repeats, wherein NtmybA2 partial sequences and NtmybB partial sequences will form double-stranded RNA configurations in plants, respectively. They are binary vectors which allow *Agrobacterium*-mediated transformation of plants. The plasmids can be genetically transferred into plants which can be subjected to selection with kanamycin to obtain plant transformants.

In tobacco plants and tobacco culture cells transformed with these plasmids, RNAi actions on NtmybA2 and NtmybB are obtainable by an action of expressed double-stranded RNA.

Plasmids which are substantially functionally equivalent to pPZP211-35S:A2RNAi, and pPZP211-35S:B:RNAi can be constructed as follows:

A DNA fragment, cut out by SacII and KpnI cleavage of pP35S followed by blunt-ending with T4 DNA Polymerase at the protruded end, is inserted into the site, derived by EcoRI-HindIII cleavage of pPZP211 followed by blunt-ending with the Klenow fragment at the protruded end, to create pPZP211-P35S. A DNA fragment, cut out by HindIII cleavage of pGUS-A2.RNAi, is inserted into the site, derived by HindIII cleavage of pPZP211-P35S, to create pPZP211-P35S:A2RNAi. A DNA fragment, cut out by HindIII-SalI cleavage of pGUS-B.RNAi, is inserted into the site, derived by HindIII-SalI cleavage of pPZP211-P35S to create pPZP211-P35S:B:RNAi. The vectors, pPZP211-P35S:A2RNAi, and pPZP211-P35S:B:RNAi, are plasmid vectors for CaMV 35S promoter-driven expression of a partial sequence of NtmybA2, and a partial sequence of NtmybB in the form of inverted repeats, wherein. NtmybA2 partial sequences and NtmybB partial sequences will form double-stranded RNA configurations in plants, respectively. They are binary vectors which allow *Agrobacterium*-mediated transformation of plants. The plasmids can be genetically transferred into plants which can be subjected to selection with kanamycin to obtain plant transformants.

(2) Transformation of Tobacco BY2 Cell Line

To determine the effects of repressed NtmybA2 and NtmybB expression on cell growth, tobacco BY2 cells were transformed with *Agrobacterium tumefaciens* strain LBA4404 harboring a member selected from pPZP211-35S:A2RNAi, pPZP211-35S:B:RNAi and pPZP211 (as a control vector). In brief, a mixture of 3-day-old passage tobacco BY-2 cells, cultured in fresh LSD liquid medium, and 2-day-old YEB medium cultures of *Agrobacterium tumefaciens* strain LBA4404 harboring a member selected from pPZP211-35S:A2RNAi, pPZP211-35S:B:RNAi and pPZP211 (as a vector control), was cocultured at 25° C. under dark conditions. Two days later, the BY-2 cells were rinsed with LSD liquid medium, seeded in LSD-0.2% Gelrite™ medium containing 200 µg/ml kanamycin and 300 µg/mL carbenicillin, and incubated at 25° C. in the dark. Twenty two days later, the resulting kanamycin-resistant calli were assayed for levels of expressed NtmybA2 and NtmybB by RT-PCR. Total RNA was extracted from these calli with Invitrogen Trizol™ reagent (Invitrogen). The synthesis of cDNA was performed using Superscript™ First-strand synthesis system for RT-PCR (Invitrogen) with the extracted total RNA as a template.

The amplification and detection of NtmybA2 cDNA was done using the resulting cDNA as a template in combination with primer OH60 DB1:

```
                                        (SEQ ID NO: 73)
5'- CCGGATCCTTCCAGTTCAGCACCATGCTCTG -3' and primer OH60DS6:                     (SEQ ID NO: 74)
5'- CCGTCGACCTAAGAGATCTGATAGTTCGATG -3'.

The amplification and detection of NtmybB cDNA was
done with primer OH88Bam5:                   (SEQ ID NO: 71)
5'- CCGGATCCTTCCTCAGTAAAGAAAAGATTGAACTTG -3' and primer OH88DS2:                     (SEQ ID NO: 72)
5'- CCGTCGACTTAACAGTTAGGATCATTAACAG -3'.
```

PCR was performed with an aliquot (1 μl) of the synthesized cDNA (50 μl). The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 1 μM each of primers. The step consisting of incubation at 93° C. for 30 sec, incubation at 56° C. for 1 min, and incubation at 73° C. for 2 min was repeated 27 cycles for detection of NtmybB, and 26 cycles for detection of NtmybA2, respectively. These PCR products were analyzed by agarose gel electrophoresis. As a result, the levels of expressed NtmybA2 declined in pPZP211-35S:A2RNAi-transformed calli, as compared to those in the vector control pPZP211-transformed calli, and the levels of expressed NtmybB declined in pPZP211-35S:B.RNAi-transformed calli, as compared to those in the vector control.

(3) Change in Cell Growth Rate of Transgenic BY2 Cells with Repressed Levels of Expressed NtmybA2

When the sizes of the aforementioned pPZP211-35S: A2RNAi-transformed calli with repressed levels of expressed NtmybA2 were compared with those of the vector control group, it was disclosed that the callus size reduced (FIG. 7).

Levels of nuclear DNA were assayed to examine the cell cycle of constituent cells for these calli. The assay was conducted as follows:

To each of frozen and stored calli was added 1 ml of a nuclei extraction buffer, contained in CyStain™ UV Precise P (High Resolution DNA staining kit, Partec), dissolved, and then mixed. After maintained at room temperature for 10 min, the resultant sample was filtered through Partec Cell Trics™ Disposable filter units (50 μm mesh, Partec) to give a filtrate to which was added 2 ml of a staining buffer contained in Cystain™ UV Precise P (High Resolution DNA staining kit, Partec). Measurements were performed with the Ploidy Analyser PA (Partec).

Figure 8:
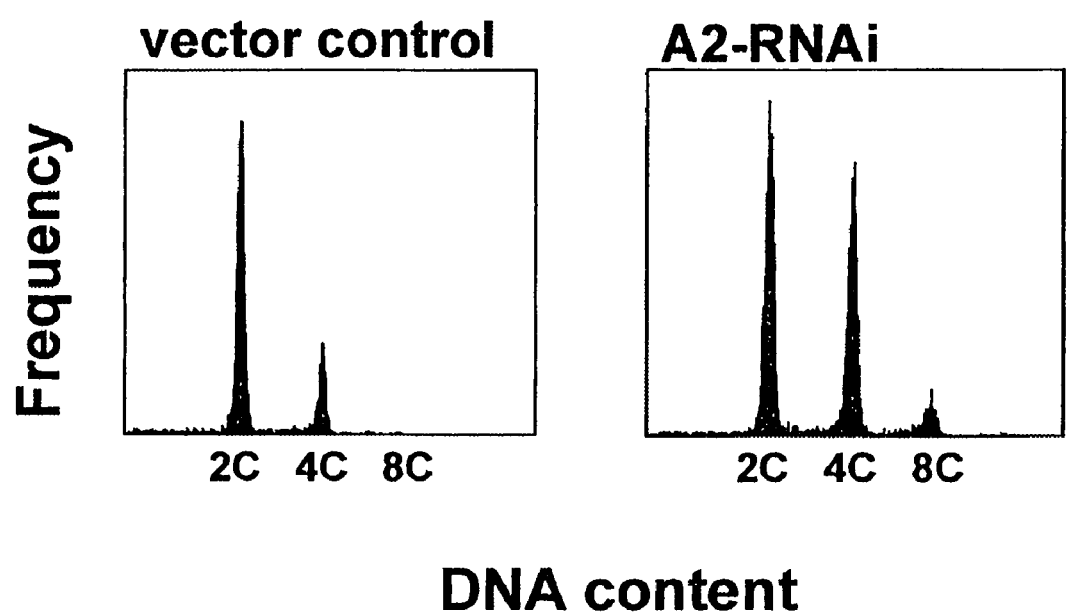
FIG. 8 shows nuclear DNA content assay results for pPZP211-35S:A2 RNAi-transformed BY2 calli, wherein levels of endogenously expressed NtmybA2 decreased by RNA interference mechanisms, and pPZP211-transformed BY2 calli. Vector & vector control: pPZP211-transfromed BY2 calli; and A2 RNAi: pPZP211-35S:A2RNAi-transfromed calli.

As compared to the vector control group, 4C peaks (indicating the S, G2 phases) increased, and further 8C peaks (which were not observed in the vector control group) indicating duplicated chromosomes were also observed in pPZP211-35S:A2RNAi-transformed calli with repressed levels of expressed NtmybA2 mRNA (FIG. 8). The fact that 4C peaks increase indicates prolongation of the S, G2 phase periods, because it is hard to enter into the M phase in cells with repressed expression of NtmybA2. The fact that there are 8C peaks indicates that inhibition of entry into the M phase takes place and the M phase is skipped, thereby leading to duplication of chromosomes. As a result of these, it is disclosed that the cell cycle is delayed and the cell growth is suppressed, thereby leading to the formation of smaller calli.

(4) Change in Cell Growth Rate of Transgenic BY2 Cells with Repressed Levels of Expressed NtmybB When the sizes of the aforementioned pPZP211-35S: BRNAi-transformed calli with repressed levels of expressed NtmybB mRNA were compared with those of the vector control group, it was disclosed that the callus size increased (FIG. 9).

Figure 10:
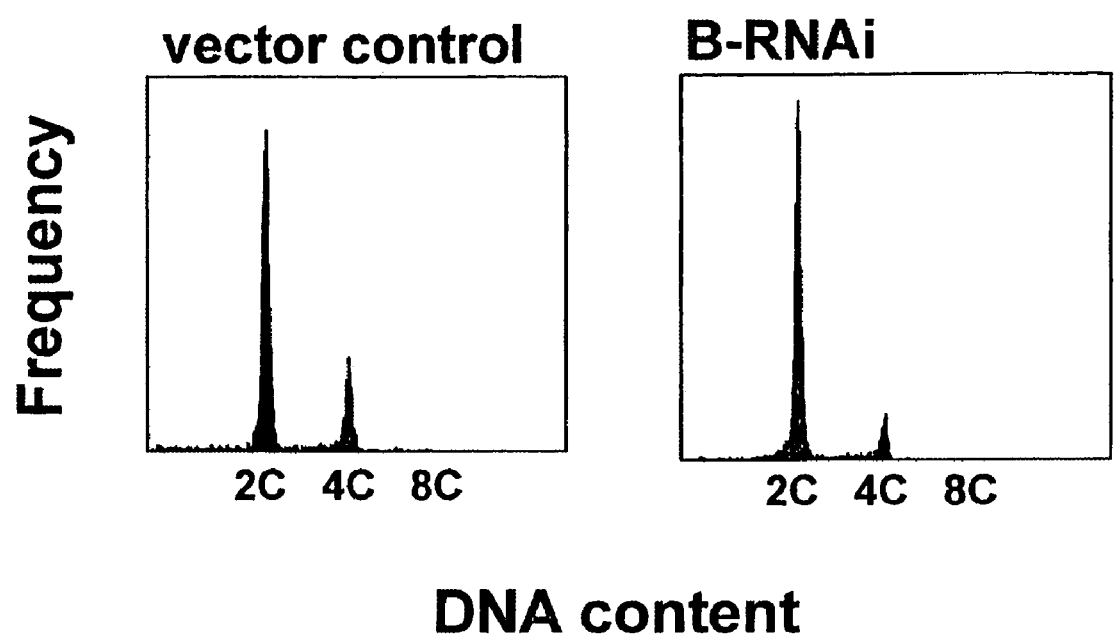
FIG. 10 shows nuclear DNA content assay results for pPZP211- and pPZP211-35S:BRNAi-transformed BY2 calli, wherein levels of endogenously expressed NtmybB decreased by RNA interference mechanisms, and pPZP211-transformed BY2 calli. Vector & vector control: pPZP211-transfromed calli; and B RNAi: pPZP211-35S:BRNAi-transfromed calli.

Levels of nuclear DNA were assayed to examine the cell cycle of constituent cells for these calli. The assay was done in the same manner as in the aforementioned (4). As compared to the vector control group, 4C peaks (indicating S, G2 phase chromosomes) reduced in pPZP211-35S:BRNAi-transformed calli with repressed levels of expressed NtmybB (FIG. 10). The fact that 4C peaks reduce indicates shortening of the S, M phases, i.e., speedup of entry into the M phase. The inhibition of NtmybB expression leads to advanced expression of genes or increase in levels of expressed genes, which are essential for the entry into the M phase. As a result of forwarding the entry into the M phase, it is disclosed that the cell cycle is shortened, and the cell growth is enhanced, thereby allowing the formation of larger calli.

Example 12

Modification of Cell Growth Rates in Transgenic Tobacco BY2 Cells with Stable Expression of NtmybA2 and NtmybA2T2

(1) Construction of Stable Expression Plasmids for NtmybA2, and NtmybA2T2

A DNA fragment, cut out by SalI cleavage of OH60, was inserted into the site, derived by SalI cleavage of pPZP211-35S, to create pPZP211-35S:A2.

A DNA fragment, cut out by SalI cleavage of pEXP-NtmybA2T2, was inserted into the site, derived by SalI cleavage of pPZP211-35S, to create pPZP211-35S:A2T2.

In brief, the vectors, pPZP211-35S:A2, and pPZP211-35S: A2T2, are plasmid vectors for CaMV 35S promoter-driven expression of NtmybA2, and NtmybA2T2, respectively. They are binary vectors which allow *Agrobacterium*-mediated transformation of plants. The plasmids can be genetically transferred into plants which can be subjected to selection with kanamycin to obtain plant transformants.

Plasmids which are substantially functionally equivalent to pPZP211-35S:A2T2 can be constructed as follows:

DNA fragments, cut out by SalI cleavage of pP35S-NtmybA2T2, and OH60, are inserted into the site, derived by SalI cleavage of pPZP211-35S, to create pPZP211-P35S: A2T2, and pPZP211-P35S:A2, respectively.

(2) Transformation of Tobacco Cell Line BY2

To determine the effects of stable NtmybA2, and NtmybA2T2 expression on cell growth, tobacco BY2 cells were transformed by mediation with *Agrobacterium tumefaciens* strain LBA4404 harboring a member selected from pPZP211-35S:A2, pPZP211-35S:A2T2 and pZP211 (as a control vector). The transformation of tobacco BY-2 cells was preformed according to the method disclosed in Example 11 (2). Twenty two days later, the resulting kanamycin-resistant calli were assayed for levels of expressed NtmybA2 mRNA and NtmybA2T2 mRNA by RT-PCR. Total RNA was extracted from these calli with Invitrogen Trizol™ reagent (Invitrogen). The synthesis of cDNA was performed using Superscript™ First-strand synthesis system for RT-PCR (Invitrogen) with the extracted total RNA as a template. The amplification and detection of NtmybA2 and NtmybA2T2 was done using the resulting cDNA as a template in combination with

```
primer OH60DB1:                    (SEQ ID NO: 73)
5'- CCGGATCCTTCCAGTTCAGCACCATGCTCTG -3',
and primer OH60DS6:                    (SEQ ID NO: 74)
5'- CCGTCGACCTAAGAGATCTGATAGTTCGATG -3'.
```

PCR was performed with an aliquot (1 μl) of the synthesized cDNA (50 μl). The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 1 μM each of primers. The step consisting of incubation at 93° C. for 30 sec, incubation at 56° C. for 1 min, and incubation at 73° C. form 1 min was repeated 24 cycles. These PCR products were analyzed by agarose gel electrophoresis. As a result, the levels of expressed NtmybA2 increased in pPZP211-35S:A2-transformed calli, as compared to the vector control group, and the expression of NtmybA2T2 was observed in pPZP211-35S:A2T2-transformed calli.

Figure 11:
FIG. 11 is a set of photos exhibiting each size of pPZP211-35S:A2-transformed BY2 calli, wherein NtmybA2 was stably expressed, pPZP211-35S:A2T2-transformed BY2 calli, wherein NtmybA2T2 was stably expressed, and pPZP211-transformed BY2 calli. Vector: pPZP211-transformed calli; 35S:A2: pPZP211-35S:A2-transformed calli; & 35S:A2T2: pPZP211-35S:A2T2-transformed calli.

(3) Change in Cell Growth Rates of Transgenic BY2 Cells Stably Expressing NtmybA2 and NtmybA2 Mutants The sizes of the aforementioned pPZP211-35S:A2-or pPZP211-35S:A2T2-transformed calli with verified expression of NtmybA2 mRNA or NtmybA2T2 mRNA were compared with those of the vector control group, it was disclosed that the callus size reduced (FIG. 11).

Levels of nuclear DNA were assayed to examine the cell cycle of constituent cells for these calli. The assay was done in the same manner as in the aforementioned Example 11 (3).

Figure 13:
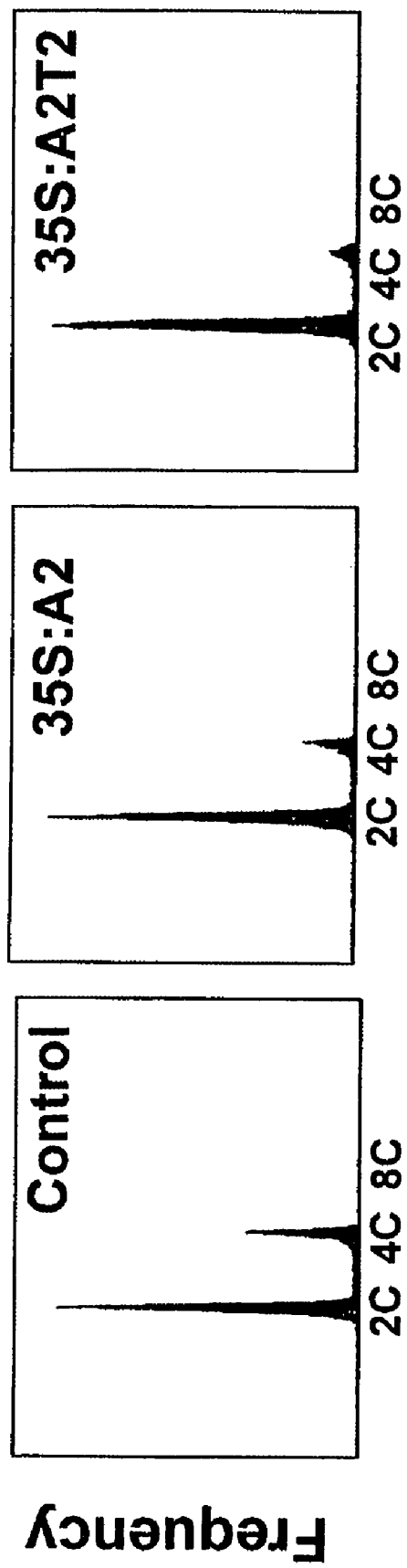
FIG. 13 shows nuclear DNA level assay results for pPZP211-35S:A2-transformed BY2 calli, wherein NtmybA2 was stably expressed, pPZP211-35S:A2T2-transformed BY2 calli wherein NtmybA2T2 was stably expressed, and pPZP211-transformed BY2 calli. Control: pPZP211-transformed calli; 35S:A2: pPZP211-35S:A2-transformed calli; & 35S:A2T2: pPZP211-35S:A2T2-transformed calli.

As compared to the vector control group, 4C peaks (indicating S, G2 phase chromosomes) decreased in stably NtmybA2-expressing calli. This tendency was also observed in the calli that stably express NtmybA2T2 which was a mutant with enhanced NtmybA2 ability to activate transcription (FIG. 13).

Figure 12:
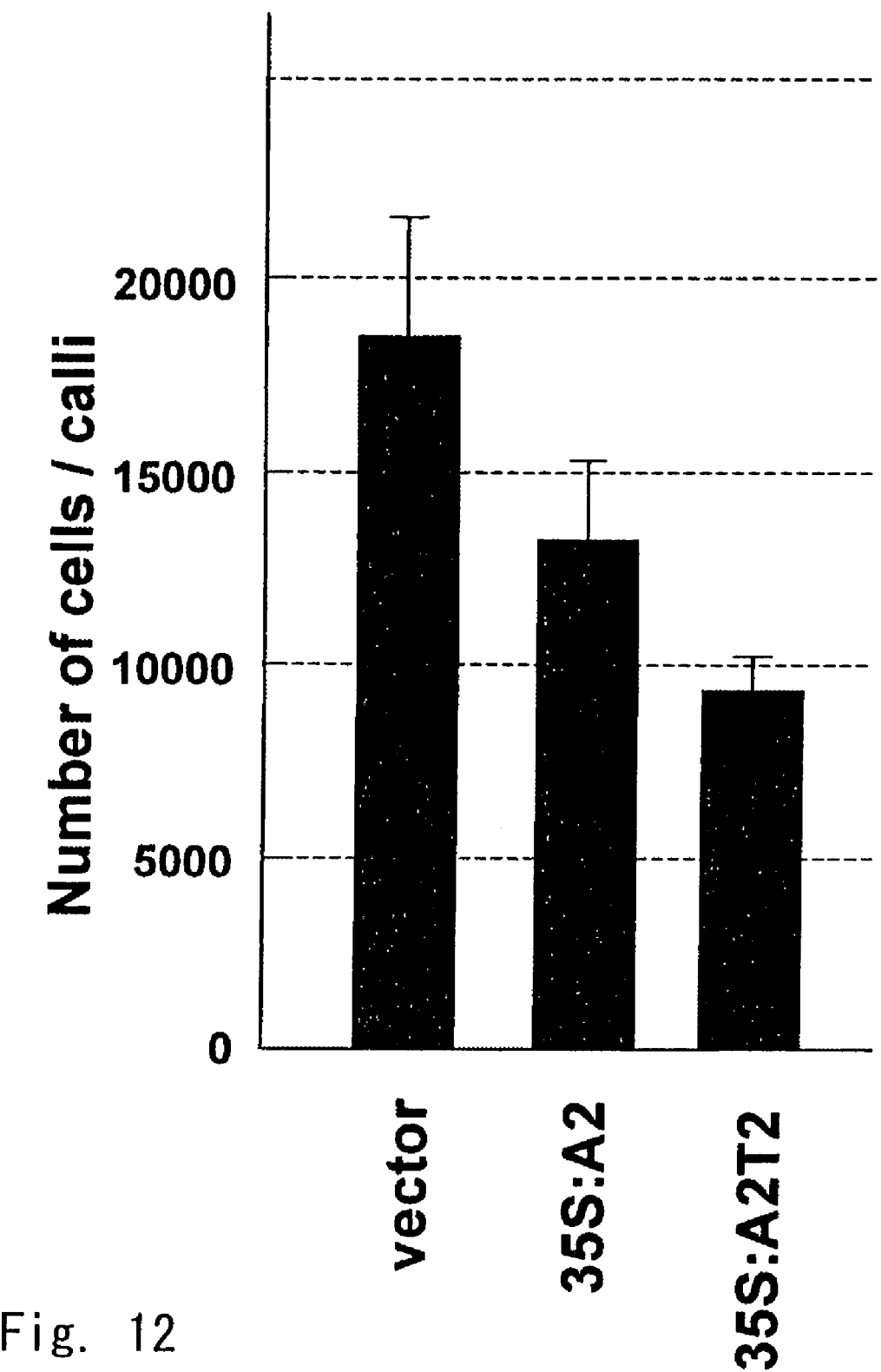
FIG. 12 shows each cell number of constituent cells for pPZP211-35S:A2-transformed BY2 calli, wherein NtmybA2 was stably expressed, pPZP211-35S:A2T2-transformed BY2 calli, wherein NtmybA2T2 was stably expressed, and pPZP211-transformed BY2 calli. Vector: pPZP211-transformed calli; 35S:A2: pPZP211-35S:A2-transformed calli; & 35S:A2T2: pPZP211-35S:A2T2-transformed calli.

These transformant cells were examined with a microscope. As a result, no polynucleated cells were observed, and the number of detected nuclei therefore indicated the cell number. The resulting cell numbers were compared among the vector control group, NtmybA2-transformed calli and NtmybA2T2-transformed calli. As a result, it has been disclosed that the cell number reduces for NtmybA2 in correlation with the callus size and further a decrease in the cell number is remarkable for NtmybA2T2 (FIG. 12).

These indicate that the cell growth is suppressed and the cell number decreases, thereby leading to the formation of smaller calli, although the entry into the M phase is brought forward in calli with stable expression of NtmybA2 and NtmybA2 mutants.

Example 13

Change in Growth and Development of Transgenic Tobacco Plants with Modulated Levels of Expressed NtmybB (1) Construction of Plasmids A DNA fragment derived by SalI cleavage of OH88 was inserted into the site derived by SalI cleavage of pPZP211 to create pPZP211-35S:B.

(2) Production of Transgenic Tobacco Plants

The plasmid, pPZP211-35S:B.RNAi (as disclosed in Example 11 (3)), was used to produce transgenic tobacco plants with RNAi machinery-repressed expression of endogenous NtmybB RNAi. The plasmid, pPZP211-35S:B, was used to produce transgenic tobacco plants which express NtmybB in a stable fashion. *Agrobacterium tumefaciens* strain LBA4404 harboring a member selected from pPZP211-35S:B.RNAi, pPZP211-35S:B and pPZP211 (as a control vector) was used according to a standard leaf-disc transformation method to generate transformants of *Nicotiana tabacum* ver. SR1.

(3) Growth Change in Transgenic Tobacco Plants

The resulting kanamycin-resistant plant individuals were cultivated to give self-fertilized seeds. The resultant seeds were sterilized with ethanol and hypochloric acid, then seeded in MS-0.2% Gelrite™ medium containing 50 μg/mL kanamycin, and grown at 28° C. under continuous light to generate plants. After cultivation for 12 days, the resulting kanamycin-resistant plant individuals were transplanted on soil, and grown at 28° C. under continuous light conditions for 25 days.

The resultant kanamycin-resistant plant individuals were assayed by RT-PCR to verify changes in the level of expressed NtmybB mRNA. Total RNA was extracted with Invitrogen Trizol™ reagent (Invitrogen) from plants (raw weight 0.5 to 0.8 g) at 22 days post-sowing. The synthesis of cDNA was performed using Superscript™ First-strand synthesis system for RT-PCR (Invitrogen) with the extracted total RNA as a template. The amplification and detection of NtmybB cDNA was done using the resulting cDNA as a template in combination with

```
primer OH88Bam5:                   (SEQ ID NO: 71)
5'-CCGGATCCTTCCTCAGTAAAGAAAAGATTGAACTTG-3'
and primer OH88DS2:                    (SEQ ID NO: 72)
5'-CCGTCGACTTAACAGTTAGGATCATTAACAG-3'.
```

The level of cDNA was standardized according to the level of expressed EF1α mRNA, in combination with

```
primer EFF:                        (SEQ ID NO: 35)
5'- AGACCACCAAGTACTACTGC
-3'
and primer EFR:                        (SEQ ID NO: 36)
5'- GTCAAGAGCCTCAAGGAGAG
-3'.
```

PCR was performed with an aliquot (1 μl) of the synthesized cDNA (50 μl). The reaction was done in a total volume of 50 μl, using TaKaRa Ex Taq™ (Takara, Japan), a reaction buffer attached to TaKaRa Ex Taq™, 200 μM each of dATP, dTTP, dCTP and dGTP, and 1 μM each of primers. The step consisting of incubation at 93° C. for 30 sec, incubation at 56° C. for 1 min, and incubation at 73° C. form 1 min was repeated 27 cycles. The same step was repeated 18 cycles for detection of EF1α. These PCR products were analyzed by agarose gel electrophoresis. As a result, a high level of amplified NtmybB cDNA was observed in the pPZP211-35S:B-transformed cell line #6, relative to the vector control group, although EF1α was equivalently detected among all the samples and elevation of the expression level was verified. Also, the level of amplified NtmybB cDNA was scarcely observed in the pPZP211-35S:B.RNAi-transformed cell line #2, relative to the vector control group, and reduction in the expression level was verified.

Figure 14:
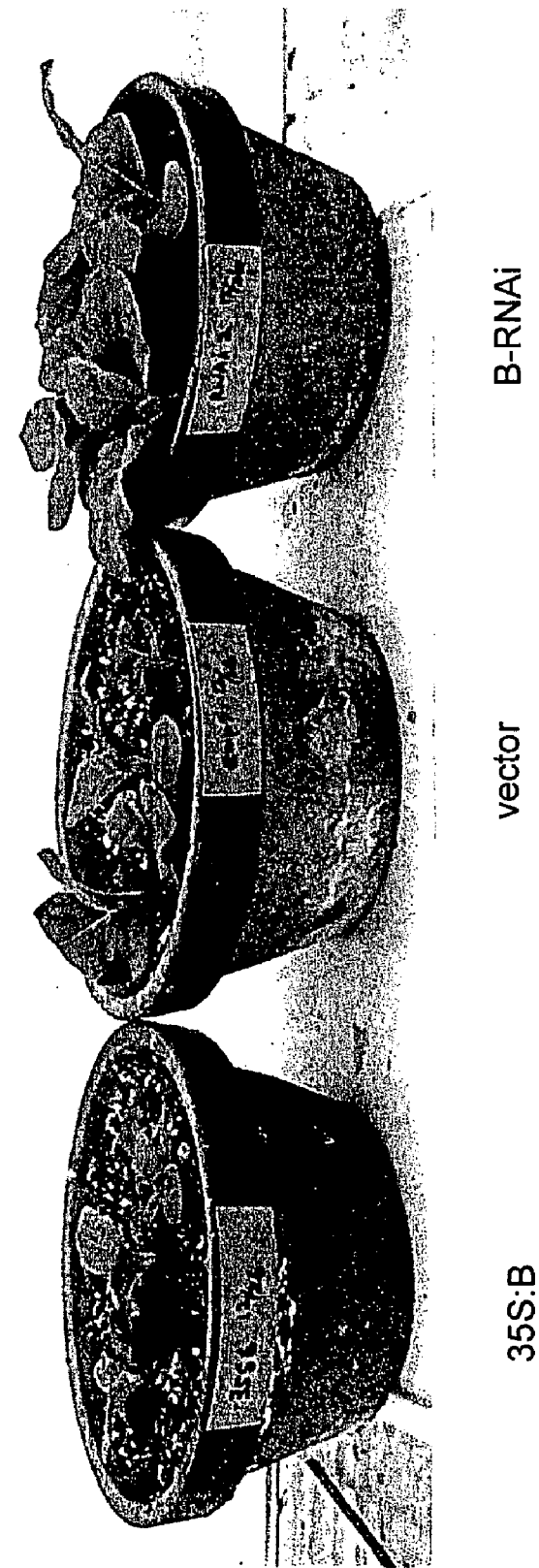
FIG. 14 is a set of photos exhibiting each growth of pPZP211-35S:B-transformed tobacco, wherein NtmybB was stably expressed, pPZP211-35S:B.RNAi-transformed tobacco, wherein the expression of endogenous NtmybB was suppressed by RNAi mechanisms, and pPZP211-transformed tobacco. Vector: pPZP211-transformed calli; 35S:B: pPZP211-35S:B -transformed calli; & B RNAi: pPZP211-35S:B.RNAi-transformed calli.

The growth and development is suppressed in the stably NtmybB-expressing transgenic tobacco line (#6), relative to the vector control group, while the growth and development is enhanced in the transgenic tobacco line (#2) with RNAi-repressed expression of endogenous NtmybB, relative to the vector control group (FIG. 14). It is thought that, since NtmybB represses the expression of genes indispensable for progress in the M phase, the entry into, and/or progress in, the M phase is delayed in NtmybB-overexpressing transgenic plants, thereby leading to inhibition of the cell division and extension of time required for the cell cycle, with the result that the lines display a phenotype of suppressed growth and development. Reversely, it is thought that the expression of endogenous NtmybB is repressed, thereby bringing forward the expression of genes necessary for progress in the M phase, or increasing the expression level, with the result that the entry into, and/or progress in, the M phase is accelerated and the time required for the cell cycle is shortened, whereby the lines display a phenotype of enhanced growth and development.

Example 14

Amino Acid Sequence Similarity Among Proteins, NtmybA1, NtmybA2, and Os3RmybA1

The amino acid sequences of proteins, NtmybA1, NtmybA2, and Os3RmybA1, are optimally aligned and multiple amino acid sequence alignment analysis is conducted. The comparison results are shown in FIGS. 15 to 18. The high amino acid sequence similarity is found not only at the myb DNA binding region composed of 3 repeats but also at the region (amino acid positions 631 to 1042) negatively regulating, and region (amino acid positions 413 to 630) enhancing, the transcription activating ability owned by protein NtmybA2, as disclosed in Example 6. The members acting as transcription activators, NtmybA1, NtmybA2, and Os3RmybA1, are highly similar at an amino acid level among the regions regulating the transcription activating ability, and it is therefore shown that they have the similar control machinery. In FIGS. 15 to 18, arrows indicate areas for respective deletion NtmybA2 mutant constructs as disclosed in Example 6 and the corresponding amino acid regions related to NtmybA1, and Os3RmybA1. It is recognized that the NtmybA2 deletion portions for creating the NtmybA2 mutants with high transcription activating ability, NtmybA2T1, NtmybA2T2, and NtmybA2T3, are highly similar to NtmybA1, and Os3RmybA1, and conserved amino acids are found among these three proteins. That is, for NtmybA2T1, the sequence of TPSILKKRHR (SEQ ID NO: 89), is found near the deletion region; for NtmybA2T2, the sequence of NXXTPXRLWX (SEQ ID NO: 90); and for NtmybA2T3, the sequence of PPRFPSXDXPF (SEQ ID NO: 91), wherein X is any amino acid. For NtmybA1 and Os3RmybA1, deletion of the C-terminal portion ranging from any of these conserved sequences to the C-terminal end will allow creation of mutants functionally equivalent to NtmybA2T1, NtmybA2T2, and NtmybA2T3.

Example 15

Amino Acid Sequence Similarity Among *Arabidopsis thaliana* 3Rmyb, NtmybA1, NtmybA2, NtmybB, and Os3RmybA1

Although 100 or more myb-like DNA binding motif-containing proteins are known in the whole *Arabidopsis thaliana* genome, it is reported that only 5 members are 3Rmyb proteins having a structural configuration composed of imperfect 3 myb sequence repeats (Stracke et al., Curr. Opin. Plant Biol. 4: 447 (2001)). However, there have been no proteins with revealed functions among these 3Rmyb proteins yet.

(1) Amino Acid Sequence Similarity Among Transcription Activator Form Plant 3Rmyb The reported *Arabidopsis thaliana* 3Rmyb members, AtMYB3R (GenBank™ Accession No. AAD46772, SEQ ID NO: 75), and AtMYB3R4 (GenBank™ Accession No. AAK54739, SEQ ID NO: 76) amino acid sequences and the amino acid sequences of NtmybA1, NtmybA2, and Os3RmybA1 were optimally aligned and multiple amino acid sequence alignment analysis was conducted. The similarity comparison results are shown in FIGS. 19 to 25. It is recognized that the amino acid sequences of AtMYB3R1 and AtMYB3R4 are highly similar to those of NtmybA1, NtmybA2, and Os3RmybA1 not only at the myb-like DNA binding domains but also at the regions important for NtmybA2 to regulate the activation of transcription. In particular, the characteristic consensus sequence composed of 22 constituent amino acids of the formula:

SILX$_1$KRXRXLUOPJXX$_5$X$_1$RXX$_5$KK,                    (SEQ ID NO: 94)

wherein X is any amino acid; J is an amino acid selected from the group consisting of I, V, and L; O is an amino acid selected from S, and T; X$_1$ is an amino acid selected from K, and R; U is an amino acid selected from V, and L; and X$_5$ is an amino acid selected from D, and E, is observed among segments with high similarity. This consensus sequence indicates that AtMYB3R1 and AtMYB3R4 can function as transcription activators for the cyclin B gene and the NACK1 gene in a similar fashion to NtmybA1, NtmybA2, and Os3RmybA1.

(2) Amino Acid Sequence Similarity Among Transcription Repressor Form Plant 3Rmyb Since the amino acid sequence similarity is not found between a member selected from *Arabidopsis thaliana* 3Rmyb members, AtMYB3R3 (GenBank™ Accession No. AAF25950, SEQ ID NO: 77), and AtMYB3R5 (GenBank™ Accession No. AAK54740, SEQ ID NO: 78), and a member selected from the aforementioned transcription activator form plant 3Rmyb, except for the myb DNA binding domains, it is expected that AtMYB3R3 and AtMYB3R5 would not function as transcription activators. Therefore, the amino acid sequences of AtMYB3R3 and AtMYB3R5, and the amino acid sequence of NtmybB were optimally aligned. As a result, amino acid sequence similarities were found among the AtMYB3R3, AtMYB3R5 and NtmybB amino acid sequences. The comparison results are shown in FIGS. 26 to 28. It is recognized that not only the amino acid sequences of AtMYB3R3 and AtMYB3R5 are highly similar to the NtmybB amino acid sequence at the myb-like DNA binding domain but also a large number of similar amino acids are present in other domains, and further the characteristic consensus sequence composed of 7 constituent amino acids (including four Ser core residues), of the formula:

$$SCSSXSX_6, \qquad \text{(SEQ ID NO: 95)}$$

wherein X is any amino acid, and $X_6$ is an amino acid selected from the group consisting of K, R, D, E, and H, is located at a position closer to the N-terminal side than the myb DNA binding domain. This consensus sequence is not observed in the AtMYB3R1, AtMYB3R4, NtmybA1, NtmybA2, and Os3RmybA1 amino acid sequences. This fact indicates that this consensus sequence is, like NtmybB, a transcription repressor for the cyclin B gene and the NACK1 gene.

(3) Members in the Plant 3Rmyb Family, Classified into Activator Form and Repressor Form Subfamilies It is apparent from the above (1) and (2) that the 3Rmyb members occupy structurally and functionally special positions even in the plant myb superfamily, and act as factors for controlling the transcription of the cyclin B gene and the NACK1 gene. It has also been found that they can be classified, based on their similarity, into transcription activator form and transcription repressor form subfamilies, even within the 3Rmyb family.

The optimal amino acid sequence alignment was performed by ClustalW program (www.ddbj.nig.ac.jp/E-mail/clustalw-j.html) with all parameters set to default. In the drawings illustrating ClustalW program output results, the symbols signifying amino acid similarity and identity, "*" means that the amino acid residues in that column are identical in all sequences in the alignment (completely conserved amino acid site); ":" means that conserved substitutions have been observed (highly conserved amino acid site); and "." means that conserved substitutions are observed (moderately conserved amino acid site).

Example 16

Conservativeness in myb DNA Binding Motif-Constituent Amino Acid Segments among Divergent Plant 3Rmyb Members Up to now, it has been reported that cDNA fragments for 3Rmyb with a structural configuration composed of three myb motif repeats are isolated from various plant members (Kranz et al., Plant J. 21: 231 (2000)). The myb DNA binding motif amino acid sequences of these divergent plant 3Rmyb members were compared with the full-length amino acid sequence of human c-myb.

The 3Rmyb members from these divergent plants were compared at their myb DNA binding motif amino acid segment. The 3Rmyb used in the amino acid sequence comparison includes *Physcomitrella patens*-derived MYB3R-1 (GenBank™ accession no. AAF78888, SEQ ID NO: 79, denoted as "PhpMYB3R-1" in FIGS. 29 to 31), *Adiantum raddianum*-derived MYB3R-1 (GenBank™ accession no. AAF67053, SEQ ID NO: 80, denoted as "AdrMYB3R-1" in FIGS. 29 to 31), *Hordeum vulgare*-derived MYB3R-1 (GenBank™ accession no. AAF78890, SEQ ID NO: 81, denoted as "HvMYB3R-1" in FIGS. 29 to 31), *Secale cereale*-derived MYB3R-1 (GenBank™ accession no. AAF67050, SEQ ID NO: 82, denoted as "ScMYB3R-1" in FIGS. 29 to 31), *Papaver rhoeas*-derived putative Myb-related domain (GenBank™ accession no. AAF43043, SEQ ID NO: 83, denoted as "ParMYB3R-1" in FIGS. 29 to 31), AtMYB3R1 (denoted as "AtMYB3R-1" in FIGS. 29 to 31), AtMYB3R3 (denoted as "AtMYB3R-3" in FIGS. 29 to 31), AtMYB3R4 (denoted as "AtMYB3R-4" in FIGS. 29 to 31), AtMYB3R5 (denoted as "AtMYB3R-5" in FIGS. 29 to 31), NtmybA1, NtmybA2, NtmybB, Os3RmybA1, human c-myb (SWISS-PROT accession no. P10242, SEQ ID NO: 88). Since *Adiantum raddianum*-, *Hordeum vulgare*-, and *Secale cereale*-derived cDNAs are fragments, initial constituent repeats for the myb DNA biding motifs are not shown in perfect length forms.

The myb DNA binding motif amino acid sequence ranging from positions 43 to 192 of human c-myb protein (SWISS-PROT accession no. P10242, SEQ ID NO: 88) and the amino acid sequences of 3Rmyb members, isolated from the aforementioned plants, were optimally aligned. The already-reported full-length sequences were compared among other plant 3Rmyb members than *Adiantum raddianum*, *Hordeum vulgare*, and *Secale cereale* ones with failure in covering the full-length myb DNA binding motif. Each Aligned Score indicating the amino acid similarity relative to c-myb is shown as follows:

The Aligned Score is 62 for NtmybA1; 65 for NtmybA2; 60 for NtmybB; 64 for AtMYB3R1; 64 for AtMYB3R3; 63 for AtMYB3R4; 66 for AtMYB3R5; 66 for PhpMYB3R-1; 66 for ParMYB3R-1; and 60 for Os3RmybA1. It is apparent from the above that the myb DNA binding domains of plant 3Rmyb members are highly conservative in comparison with c-myb. It is also disclosed that the myb DNA binding domains of plant 3Rmyb members have the Aligned Score of 60 or higher, relative to c-myb.

Figure 30:
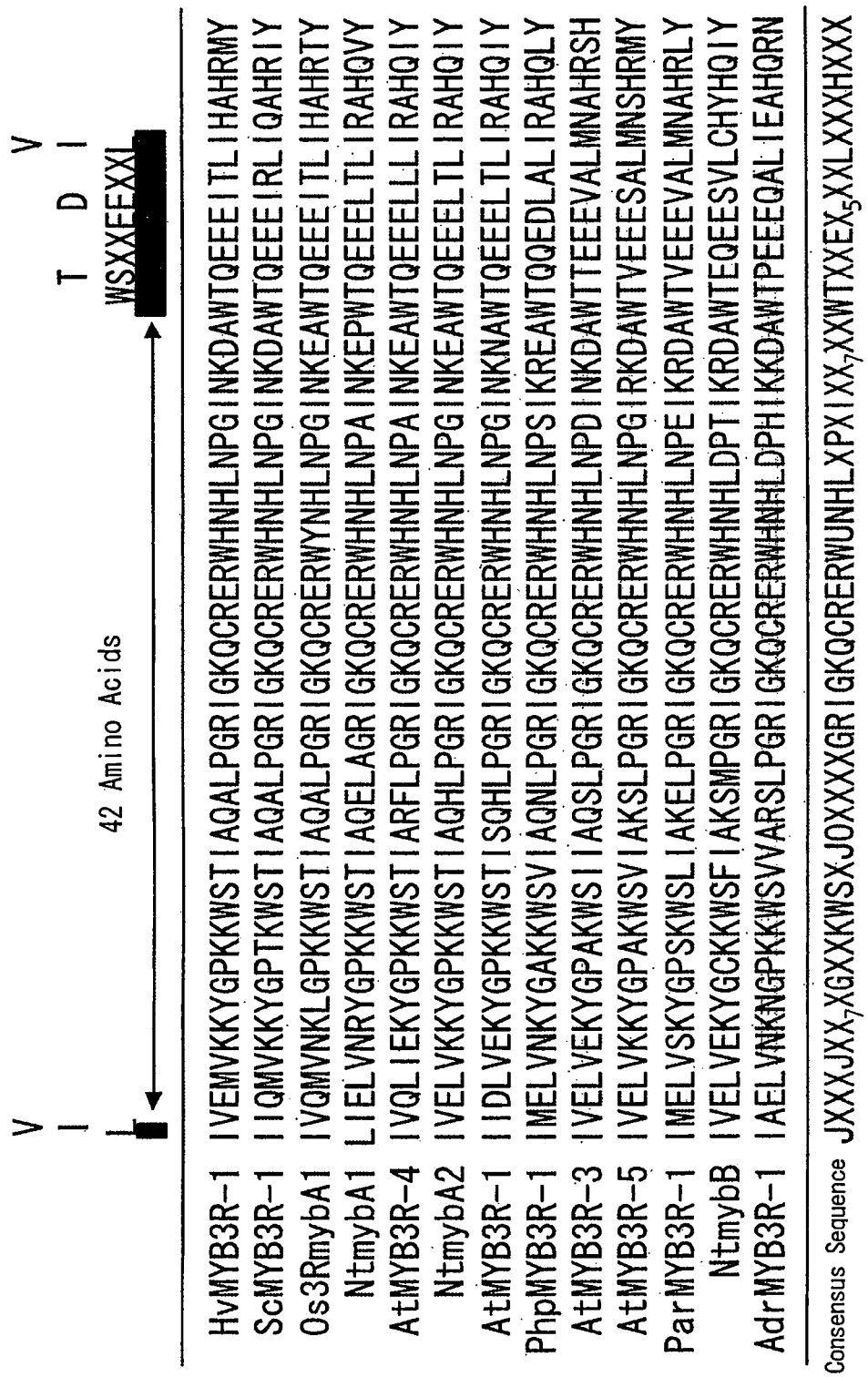

Through optimal amino acid sequence alignment analysis of NtmybA1, NtmybA2, NtmybB, AtMYB3R1, AtMYB3R3, AtMYB3R4, AtMYB3R5, PhpMYB3R-1, ParMYB3R-1, Os3RmybA1, HvMYB3R-1, AdrMYB3R-1, and ScMYB3R-1 c-myb-like DNA binding motifs, the present inventor et al. have succeeded in finding conserved common sequences at said motifs among these 13 plant 3Rmyb members (FIGS. 29 to 31).

The common amino acid sequence (consensus amino acid sequence) conserved at the myb DNA binding motif among various plant 3Rmyb members contains three c-myb myb motif repeats, accompanied with intervening 42 arbitrary amino acids (amino acids between arrows in the drawings) located between said repeats, wherein said c-myb myb motif is a sequence, composed of 9 amino acid residues, of the formula:

(corresponding to SEQ ID NO: 92)
(i) W[S,T]XXE[D,E]XX[L,I,V]

wherein X is any amino acid, and [ ] stands for one amino acid selected from amino acids set forth in square brackets, (each of consensus segments (marked with black crossbars in the drawing) constituting the c-myb 3-repeat myb DNA binding region, indicated by the symbol, MYB#1 (Myb DNA-binding domain repeat signature 1.), in retrieval results obtained by using MOTIF program-(motif.genome.ad.jp/)).

More specifically, when sites constituted of consensus amino acids or chemically analogous amino acids among the 13 amino acid sequences are expressed in the "Consensus Sequence", the potential sequence is a sequence (denoted as "Consensus Sequence" in the drawings) with 150 amino acids, of the following formula:

(corresponding to SEQ ID NO: 93)
(ii) WTXEEDXXLXXXVXXUXGX₇XWKXIAXXXXXROX₅JQCLHRWQKV

LXPXLJKGXWOXEEDXXJXXXJXX₇XGXXKWSXJOXXXXGRIGKQCRERW

UNHLXPXIXX₇XXWTXXEX₅XXLXXXHXXXGNX₇WAEJXX₇XLXGX₇ODN

OIKNXWXSOXKKX₇ wherein X is any amino acid; J is an amino acid selected from the group consisting of I, V, and L; 0 is an amino acid selected from the group consisting of G, S, T, C, and A; X₇ is an amino acid selected from the group consisting of K, R, and H; U is an amino acid selected from the group consisting of H, W, Y, and F; and X₅ is an amino acid selected from D, and E.

The optimal alignment of the amino acid sequences was conducted with ClustalW program (www.ddbj.nig.ac.jp/E-mail/clustalw-j.html) wherein all parameters were set to default.

Example 17

Isolation of Plant 3Rmyb

In order to isolate DNA coding for proteins comprising an amino acid sequence of (i), specifically (ii), as disclosed in Example 16, the process of Example 1 can be performed.

In brief, the amplification can be performed with cDNA prepared from target plant tissues or cells with vigorous cell growth as a template by PCR using degenerated primers in combination with Nested PCR. The degenerated primers used in the first PCR are a primer set of SEQ ID NO: 1 and SEQ ID NO: 2. The resulting first reaction solution is used as a template for second PCR. The second PCR, Nested PCR, is performed with a primer set of SEQ ID NO: 3 and SEQ ID NO: 4. The second reaction solution is used as a template for third PCR. The third PCR, Nested PCR, is performed with a primer set of SEQ ID NO: 5 and SEQ ID NO: 6 to allow the amplification of DNA coding for part of the myb DNA binding domain. It is possible to sequence the 5'- and 3'-end nucleotide sequences of full-length cDNA by adaptations of 5'RACE, and 3'RACE based on the nucleotide sequences of the resulting DNA fragments. PCR can be performed with primers designed on the terminal sequences characterized by RACE to amplify full-length cDNA. The tissue and cell with vigorous cell growth includes calli, culture cells, seedlings, or plantlets, derived from target plants; apical shoots, apical roots; and others.

Example 18

Determination of Plant 3Rmyb Functions

In order to determine the function of plant 3Rmyb as isolated according to the process of Example 17, plant 3Rmyb plasmids for CaMV 35S promoter-driven expression of targeted cDNA are constructed, and protoplasts, prepared from tobacco BY2 cells, are then co-transfected with a plasmid combination selected from the following (i) and (ii):

(i) plant 3Rmyb plasmid (10 µg/sample), NACK1 promoter-LUC plasmid (10 µg/sample), and R-LUC plasmid (1 µg/sample)

(ii) pBI221 plasmid (10 µg/sample), NACK1 promoter-LUC plasmid (10 µg/sample), and R-LUC plasmid (1 µg/sample).

The resultant protoplasts are assayed for LUC activity and R-LUC activity. The level of LUC activity is standardized (LUC specific activity) according to the level of R-LUC activity. When the LUC specific activity is elevated in the combination (i) relative to that in the combination (ii), it can be determined that plant 3Rmyb members used are transcription activator forms. When the LUC specific activity decreases in the combination (i) relative to that in the combination (ii), it can be determined that plant 3Rmyb members used are transcription repressor forms. Preparation of protoplasts, gene transfer of plasmids, and LUC and R-LUC activity assays can be conducted according to the methods disclosed in Example 3.

Example 19

Creation of Male-Sterile Plants by Male Reproductive Organ-Specific Expression of NtmybB Plants can be transformed with plasmids for male reproductive organ-specific expressible promoter-driven expression of the NtmybB gene that represses the transcription of G2/M phase-specific expressible genes. The modification of cell growth in the male reproductive organ leads to the inhibition or suppression of normal pollen formation, thereby allowing the production of transgenic plants with decreased seed fertility.

(1) Construction of Plasmids

Described below is an embodiment of constructing plasmids for transformation, which allow male reproductive organ-specific expression of NtmybB. The plasmids disclosed in PCT/JP02/12268 (2002), pENTRAVP1 and pENTR0.6, are plasmids carrying an insert of the *Arabidopsis thaliana* AtNACK2 gene promoter and the *Arabidopsis thaliana* AVP1 gene promoter, respectively. PCR is performed using each of these plasmids as a template in combination with

```
primer HindIII-AVP1-298S:
                                      (SEQ ID NO: 84)
5'- CCCAAGCTTAAATTCGGACAAATAGAGCGTAGTCAAC-3',
and primer AVP1+5A:
                                      (SEQ ID NO: 85)
5'- GCCATCTTCTCTCCTCCGTATAAGAG-3'
for pENTRAVP1,
or primer HindIII-NACK2-575S:
                                      (SEQ ID NO: 86)
5'- CCCAAGCTTCTCGTTAAGAACCCTTGATC-3',
and primer NACK2+3A+2:
                                      (SEQ ID NO: 87)
5'- GCCATCTTCTACACACAAAATCGAAACC-3'
for pENTR0.6.
```

The amplified DNA fragments are cleaved with HindIII, and then inserted together with a DNA fragment for NtmybB, cut out by SalI and EcoRV from pEXP-NtmybB, into the SalI-HindIII site of pUC18 (Takara, Japan) to create pUC-AVP1-NtmybB and pUC-0.6-NtmybB, respectively. DNA fragments, cut out by SacI cleavage of pUC-AVP1-NtmybB and pUC-0.6-NtmybB, then blunt-ending with T4 DNA polymerase at the protruded end followed by HindIII cleavage, are inserted into the site, derived by SacI cleavage of pBI121 (Clontech), then blunt-ending with T4 DNA polymerase at the protruded end followed by HindIII cleavage, to create pBI-PAVP1-NtmybB and pBI-N0.6-NtmybB, respectively.

The plasmid pBI-PAVP1-NtmybB is a binary vector for AVP1 promoter-driven expression of NtmybB. This plasmid allows *Agrobacterium*-mediated transformation of plants. The plasmid pBI-N0.6-NtmybB is a plasmid vector for AtNACK2 promoter-driven expression of NtmybB. This plasmid allows *Agrobacterium*-mediated transformation of plants. Plants transformed with these plasmids can be selected with kanamycin.

(2) Transformation of *Arabidopsis thaliana*

*Agrobacterium tumefaciens* is transformed with a binary vector selected from two plasmids as created in the aforementioned (1). Next, *Arabidopsis thaliana* ecotype Col-0 is transformed by the Floral dip method (as disclosed in Example 8) for *Agrobacterium*-mediated transformation using *Agrobacterium* harboring the aforementioned plasmid. Seeds obtained from *Agrobacterium*-infected floral buds are sterilized with hypochloric acid and sterile water, and seeded in MS medium supplemented with 50 µg/ml kanamycin, and 100 µg/ml carbenicillin. Transgenic plants capable of growing in kanamycin-added medium are selected.

(3) Decrease in Fertility of Transgenic Plants

When the resultant plants, obtained by using the binary vector of the aforementioned (1) in the above step (2), are examined for their seeds formed in the sheaths, it is observed that the number of seeds reduces relative to wild type plants and transgenic plants with decreased fertility are created.

Example 20

Creation of Male-Sterile Plants by Male Reproductive Organ-Specific Expression of NtmybB Plants can be transformed with plasmids for male reproductive organ-specific expressible promoter-driven expression of the NtmybB gene that represses the transcription of G2/M phase-specific expressible genes. The modification of cell growth in the male reproductive organ leads to the inhibition or suppression of normal pollen formation, thereby allowing the production of transgenic plants with decreased seed fertility.

(1) Construction of Plasmids

The applicable gene for detectable male reproductive organ-specific expression includes the *Arabidopsis thaliana* AVP1 gene and the *Arabidopsis thaliana* AtNACK2 gene. The promoter regions of these genes are used to construct plasmids. The available DNA coding for each promoter region of these genes includes inserts of promoter regions in plasmids pENTRAVP1(AVP1) and pENTR0.6(AtNACK2), as disclosed in PCT/JP02/12268 (2002). The NtmybB-encoding DNA can be prepared from OH88. These DNA fragments are inserted into the site, derived by removal of the CaMV 35S promoter and the GUS gene from pBI121 (Clontech), to create plasmids wherein the AVP1 promoter, NtmybB, and the Nos terminator are operably fused, or plasmids wherein the AtNACK2 promoter, NtmybB, and the Nos terminator are operably fused. These plasmids are binary vectors for AVP1 promoter- or AtNACK1 promoter-driven expression of NtmybB, which allow *Agrobacterium*-mediated transformation of plants. The resultant transgenic plants are selectable with kanamycin.

(2) Transformation of *Arabidopsis thaliana*

The resulting plasmids from the aforementioned step (1) are used to transform *Agrobacterium tumefaciens*. Next, *Arabidopsis thaliana* ecotype Col-0 is transformed by the Floral dip method (in the same manner as in Example 8) for *Agrobacterium*-mediated transformation using *Agrobacterium* harboring the aforementioned plasmid. Seeds obtained from *Agrobacterium*-infected floral buds are sterilized with hypochloric acid and sterile water, and seeded in MS medium supplemented with 50 µg/ml kanamycin, and 100 µg/ml carbenicillin. Transgenic plants capable of growing in kanamycin-added medium are selected.

(3) Decrease in Fertility of Transgenic Plants

When the resultant plants, obtained by using the binary vector of the aforementioned (1) in the above step (2), are examined for their seeds formed in the sheaths, it is observed that the number of seeds reduces relative to wild type plants and transgenic plants with decreased fertility are created.

Example 21

Modification of Growth and Development in Transgenic Tobacco Plants with Repressed Expression of NtmybA1 and NtmybA2

RNAi is used to repress the expression of endogenous NtmybA1 and tmybA2 in transgenic tobacco plants with suppressed growth and development.

(1) Construction of Plasmids

DNA is constructed by linking part of DNA for NtmybA1 or NtmybA2, or DNA for both NtmybA1 and NtmybA2 in an inverted repeat configuration. When the elements are linked in an inverted repeat, DNA coding for GUS is inserted as a spacer between the repeats. The resultant inverted repeat DNAs are used as RNAi DNAs. Operably fused DNA carrying the CaMV 35S promoter, RNAi DNA, and the Nos terminator is inserted into plasmid pBI-RHL. These plasmids are those for CaMV 35S promoter-driven expression of double-stranded form RNA coding for NtmybA1, NtmybA2, or both NtmybA1 and NtmybA2, which allow *Agrobacterium*-mediated transformation of plants. The resultant transgenic plants are selectable with hygromycin. In the resultant transgenic plants, the expression of endogenous NtmybA1, or NtmybA2, or both of endogenous NtmybA1 and NtmybA2 decreases, triggered by expressed double-stranded RNA. That is, RNAi machinery is obtainable in plants.

(2) Transformation of Tobacco Plants

The resultant constructed plasmids from the aforementioned step (1) are used to transform *Agrobacterium tumefaciens*. Next, *Nicotiana tabacum* ver. SR1 is transformed by the leaf disc method using *Agrobacterium* harboring each plasmid. The resulting hygromycin-resistant calli are differentiated to regenerate transgenic plant individuals which allow production of self-fertilized seeds.

(3) Modification of Growth and Development in Transgenic Plants

The self-fertilized seeds of the resulting transgenic plants, obtained by using the binary vector of the aforementioned (1) in the above step (2), are sown and grown. When their growth and development states are examined, it is observed that the growth and development of the resultant transgenic tobacco plants is suppressed, relative to that of wild type plants.

Example 22

Modulation in the Growth and Development of Ntmyb-Transformed Tobacco Plants In transgenic tobacco plants which express a member selected from endogenous NtmybA2, NtmybA2T5, NtmybA2T2, and NtmybB, their growth and development is inhibited or suppressed.

In transgenic tobacco plants wherein the expression of a transcription activator form member selected from endogenous NtmybA1, endogenous NtmybA2, and both of endogenous NtmybA1 and NtmybA2, is silenced or suppressed with RNAi, their growth and development is inhibited or suppressed.

(1) Construction of Plasmids

The plasmid, pRHL (disclosed in PCT/JP02/12268 (2002)), was cleaved with ApaI, blunt-ended with T4 DNA polymerase at the protruded end, and then subjected to self-ligation to create pRHL2. The plasmid, pRHL2, was cleaved with XhoI, blunt-ended with the Klenow fragment at the protruded end, and then subjected to self-ligation to create pRHL3. The plasmid, pRHL3, was cleaved with SpeI, blunt-ended with the Klenow fragment at the protruded end, and then subjected to self-ligation to create pRHL4.

A DNA fragment carrying the ccdB cassette, cut out by EcoRI cleavage of pENTR2B (Invitrogen), was blunt-ended with the Klenow fragment at the protruded end, and inserted into the XmnI-BsaAI site of pDONR201 (Invitrogen) to create pDONR201ΔCm1. The plasmid carrying an insert of the DNA fragment in a reverse direction to pDONR201ΔCm1 is designated as "pDONR201ΔCm3".

A DNA fragment, cut out by ApaI-SmaI cleavage of pDONR201ΔCm1, was inserted into the ApaI-SmaI site of pBluescript™II (Stratagene) to create pBS-attP.

A DNA fragment, cut out by EcoRI cleavage of pDHu1-1 (presented by courtesy of Yoshihisa UENO, Graduate School of Science, Nagoya University, Japan), was blunt-ended with the Klenow fragment at the protruded end, and then inserted into the SmaI site of pRHL4 to create pRHGUSRiL.

A DNA fragment, cut out by cleavage with ApaI and NruI of pDONR201ΔCm3, was inserted into the site, derived by cleavage with ApaI and SmaI from pRHGUSRiL, to create pRHGUSRiP1.

A DNA fragment, cut out by ApaI cleavage of pBS-attP, blunt-ending with T4 DNA polymerase at the protruded end followed by cleavage with SpeI, was inserted into the site, derived by XhoI cleavage of pRHGUSRiP1, blunt-ending with the Klenow fragment at the protruded end followed by cleavage with SpeI, to create pRHGUSRiP2.

A DNA fragment, cut out by BglII cleavage of pRHGUSRiP2, was inserted into the site, derived by BglII cleavage of pBI121 followed by removal of the cut out DNA fragment, to create pBI-GUSRiP1.

PCR was performed with as a template pBS-VA1A2 as disclosed in Example 10 (1), in combination with

```
primer B1T3:
                                                    (SEQ ID NO: 41)
5'-GGGGACAAGTTTGTACAAAAAAGCAGGCTCAATTAACCCTCACTAAAGGG-3'
and primer B2T7:
                                                    (SEQ ID NO: 42)
5'-GGGGACCACTTTGTACAAGAAAGCTGGGTCGTAATACGACTCACTATAGGGC-3'
``` to provide a DNA fragment carrying a tandem linked DNA segment coding for part of NtmybA1 and a tandem linked DNA segment coding for part of NtmybA2, wherein the sequence attB1 (Gateway™ system, Invitrogen) was added to one end and the sequence attB2 (Gateway™ system, Invitrogen) to another end. A mixture of this DNA fragment and plasmid pBI-GUSRiP1 (Invitrogen) is subjected to BP reaction using BP Clonase™ (Invitrogen) to generate pBIHm-A1A2RNAi wherein the DNA carrying the tandem linked DNA segment coding for part of NtmybA1 and the tandem linked DNA fragment coding for part of NtmybA2 is inserted in an inverted repeat configuration into pBI-GUSRiP1

PCR is performed with as a template pBS-VA1 as disclosed in Example 10 (1), in combination with

```
primer B1T3:
                                                    (SEQ ID NO: 41)
5'-GGGGACAAGTTTGTACAAAAAAGCAGGCTCAATTAACCCTCACTAAAGGG-3'
and primer B2T7:
                                                    (SEQ ID NO: 42)
5'-GGGGACCACTTTGTACAAGAAAGCTGGGTCGTAATACGACTCACTATAGGGC-3'
``` to provide a DNA fragment carrying a DNA segment coding for part of NtmybA1, wherein the sequence attB1 (Gateway™ system, Invitrogen) is added to one end and the sequence attB2 (Gateway™ system, Invitrogen) to another end. A mixture of this DNA fragment and plasmid pBI-GUSRiP1 (Invitrogen) is subjected to BP reaction using BP Clonase™ (Invitrogen) to generate pBIHm-A1RNAi wherein the DNA carrying the DNA segment coding for part of NtmybA1 is inserted in an inverted repeat configuration into pBI-GUSRiP1.

PCR is performed with as a template pBS-VA2 as disclosed in Example 10 (1), in combination with primer B1T3:
(SEQ ID NO: 41)
(5'-GGGGACAAGTTTGTACAAAAAAGCAGGCTCAATTAACCCTCACTAAAGGG-3'
and primer B2T7:
(SEQ ID NO: 42)
5'-GGGGACCACTTTGTACAAGAAAGCTGGGTCGTAATACGACTCACTATAGGGC-3' to provide a DNA fragment carrying a DNA segment coding for part of NtmybA2, wherein the sequence attB1 (Gateway™ system, Invitrogen) is added to one end and the sequence attB2 (Gateway™ system, Invitrogen) to another end. A mixture of this DNA fragment and plasmid pBI-GUS-RiP1 (Invitrogen) is subjected to BP reaction using BP Clonase™ (Invitrogen) to generate pBIHm-A2RNAi wherein the DNA carrying the DNA segment coding for part of NtmybA2 is inserted in an inverted repeat configuration into pBI-GUS-RiP1.

That is, the plasmids, (i) pBIHm-A1A2RNAi, (ii) pBIHm-A1RNAi, and (iii) pBIHm-A2RNAi, are binary vectors for CaMV 35S promoter-driven expression of double-stranded form (i) RNA encoding both of NtmybA1 and NtmybA2, (ii) RNA encoding NtmybA1, and (iii) RNA encoding NtmybA2, respectively, which allows Agrobacterium-mediated transformation of plants. The resultant transgenic plants are selectable with hygromycin. In the resulting transgenic plants by transformation with a member selected from binary vectors (i) to (iii), the in vivo levels of expressed both of endogenous NtmybA1 and NtmybA2 for the vector (i), expressed endogenous NtmybA1 for the vector (ii), and expressed endogenous NtmybA2 for the vector (iii), decrease, triggered by expressed double-stranded RNA. That is, RNAi machinery is obtainable in plants.

(2) Transformation of Tobacco Plants
Tobacco plants are transformed with the following plasmids:
(i) plasmid pBIHm-A1A2RNAi (the foregoing (1))
(ii) plasmid pBIHm-A1RNAi (the foregoing (1))
(iii) plasmid pBIHm-A2RNAi (the foregoing (1))
(iv) plasmid pBIHm-NtmybA2 (Example 8 (1))
(v) plasmid pBIHm-NtmybA2T2 (Example 8 (1))
(vi) plasmid pBIHm-NtmybB (Example 8 (1))
(vii) plasmid pDBIHm-NtmybA2T5 (Example 9 (1))
(viii) plasmid pBIHm-GFP (Example 8 (1))
(ix) plasmid pPZP211 (Example 9 (1))
(x) plasmid pPCYM-NtmybA2T2 (Example 9 (1))
(xi) plasmid pPZP211-35S:A2RNAi (Example 11 (1))
(xii) plasmid pPZP-35S:A2 (Example 12 (1))
(xiii) plasmid pPZP-35S:A2T2 (Example 12 (1))

The plasmids (i) to (xiii) are used to transform Agrobacterium tumefaciens. Next, Nicotiana tabacum ver. SR1 is transformed by the leaf disc method using Agrobacterium harboring each plasmid. Hygromycin-resistant transgenic plants are produced when the plasmids (i) to (viii) are used, while kanamycin-resistant transgenic plants are produced when the plasmids (ix) to (xiii) are used. The resulting calli are differentiated to regenerate transgenic plant individuals which allow production of self-fertilized seeds.

(3) Modification of Growth and Development in Transgenic Plants

The self-fertilized seeds of the resulting transgenic plants, obtained in the above step (2), are sown and grown. When their growth and development states are examined, it is observed that the growth and development of the resultant transgenic tobacco plants obtained by using a member selected from the vectors (i) to (vii) of the aforementioned (2) is inhibited or suppressed, relative to that of the transgenic plants obtained by using the vector (viii) of the above (2), or wild type plants. It is also observed that the growth and development of the resultant transgenic tobacco plants obtained by using a member selected from the vectors (x) to (xiii) of the aforementioned (2) is inhibited or suppressed, relative to that of the transgenic plants obtained by using the vector (ix) of the above (2), or wild type plants.

Example 23

Creation of NtmybA1, Os3RmybA1, AtMYB3R1, and AtMYB3R4 Mutants with Altered Transcription Activating Ability Transcription activator form plant 3Rmyb members, NtmybA1, Os3RmybA1, AtMYB3R1, and AtMYB3R4, can be C-terminally truncated to generate molecules with enhanced transcription activating ability or molecules with reduced transcription activating ability. Sites or regions to be deleted can be determined on Example 14, and FIGS. 15 to 18, or Example 15 and FIGS. 19 to 25.

That is, for NtmybA1, the amino acid deletion of residues ranging from positions 579 to 1003, 641 to 1003, or 715 to 1003, of the NtmybA1 amino acid sequence will allow the creation of NtmybA1 mutants having enhanced transcription activating ability. For Os3RmybA1, the amino acid deletion of residues ranging from positions 575 to 993, 635 to 993, or 709 to 993, of the Os3RmybA1 amino acid sequence will allow the creation of Os3RmybA1 mutants having enhanced transcription activating ability. For AtMYB3R1, the amino acid deletion of residues ranging from positions 583 to 776, 621 to 776, or 691 to 776, of the AtMYB3R1 amino acid sequence will allow the creation of AtMYB3R1 mutants having enhanced transcription activating ability. For AtMYB3R4, the amino acid deletion of residues ranging from positions 570 to 961, 608 to 961, or 667 to 961, of the AtMYB3R4 amino acid sequence will allow the creation of AtMYB3R4 mutants having enhanced transcription activating ability.

Further, for NtmybA1, the amino acid deletion of residues ranging from positions 186 to 1003, or 299 to 1003, of the NtmybA1 amino acid sequence will allow the creation of NtmybA1 mutants having reduced transcription activating ability. For Os3RmybA1, the amino acid deletion of residues ranging from positions 203 to 993, or 257 to 993, of the Os3RmybA1 amino acid sequence will allow the creation of Os3RmybA1 mutants having reduced transcription activating ability. For AtMYB3R1, the amino acid deletion of residues ranging from positions 187 to 776, or 241 to 776, of the AtMYB3R1 amino acid sequence will allow the creation of AtMYB3R1 mutants having reduced transcription activating ability. For AtMYB3R4, the amino acid deletion of residues ranging from positions 181 to 961, or 235 to 961, of the AtMYB3R4 amino acid sequence will allow the creation of AtMYB3R4 mutants having reduced transcription activating ability.

The transcription activating ability exerted by the aforementioned mutants can be determined according to the methods as disclosed in Examples 3 and 18 by monitoring levels of NACK1 promoter-driven transcription under transient expression conditions in BY2 protoplasts. Each transcription activating ability of these deletion mutants is elevated or decreased, relative to that of the wild type species.

Example 24

Dwarfing of Transgenic Tobacco Plants which Overexpress NtmybA2

(1) Transformation of Tobacco Plants

*Agrobacterium tumefaciens* strain EHA101 was transformed with a member selected from the aforementioned plasmids, pBIHm-NtmybA2, and pBIHm-GFP. Next, *Nicotiana tabacum* ver. SR1 plants were transformed by the leaf disc method using *Agrobacterium* harboring each plasmid.

(2) Expression Levels of Transferred Genes in Transgenic Tobacco Plants

The resulting hygromycin-resistant plant individuals were cultivated to produce self-fertilized seeds. The resultant self-fertilized seeds from NtmybA2-transformed lines, AW#3 and AW#23, and GFP-transformed line, G#3, were sown in a plastic pot (13 cm) filled with a soil composite (Kureha-Engei-Baido, Kureha Chemical Industry Co., Ltd.), and cultivated at 27° C. The lighting conditions included cultivation for 18 hr under continuous light, and cultivation for 6 hr in the dark. The expression of transferred genes was checked by RT-PCR in these lines. Unexpanded terminal leaves were sampled from 5 plant individuals per line, and the amplification of NtmybA2 was performed according to the method of the aforementioned Example 10 (2). The resultant PCR products were analyzed by agarose electrophoretic techniques. As a result, the levels of expressed NtmybA2 increased in the lines, AW#3, and AW#23, relative to the line, G#3, and the overexpression of transferred genes were verified in the lines, AW#3, and AW#23.

(3) Dwarfing of NtmybA2-Transformed Tobacco Plants

Figure 32:
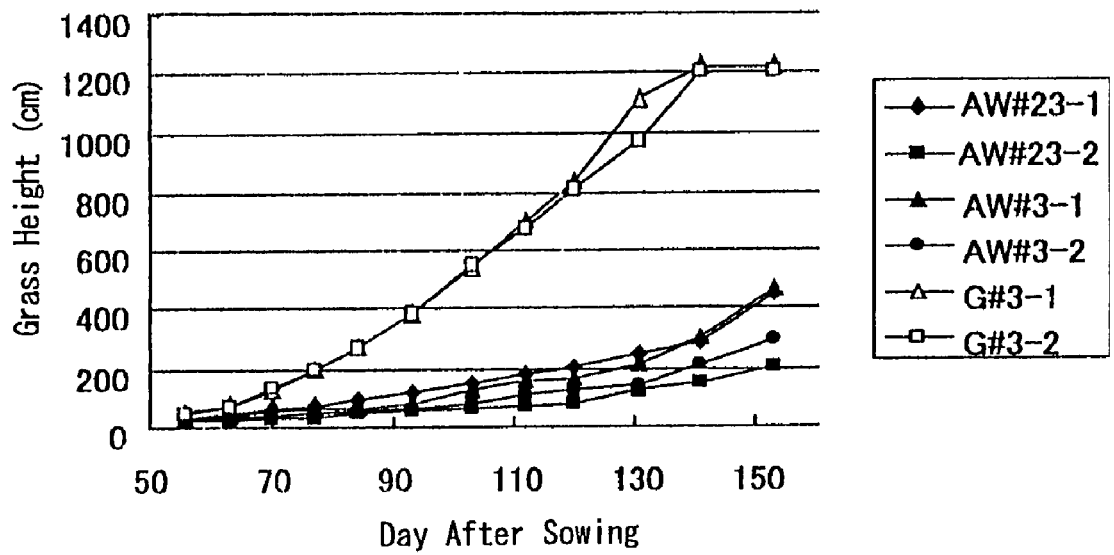
FIG. 32 shows comparison results for growth and development states (grass height) between cultivated NtmybA2 gene-transferred plants (tobacco with high NtmybA2 expression) and NtmybA2 gene-nontransferred plants.
Figure 33:
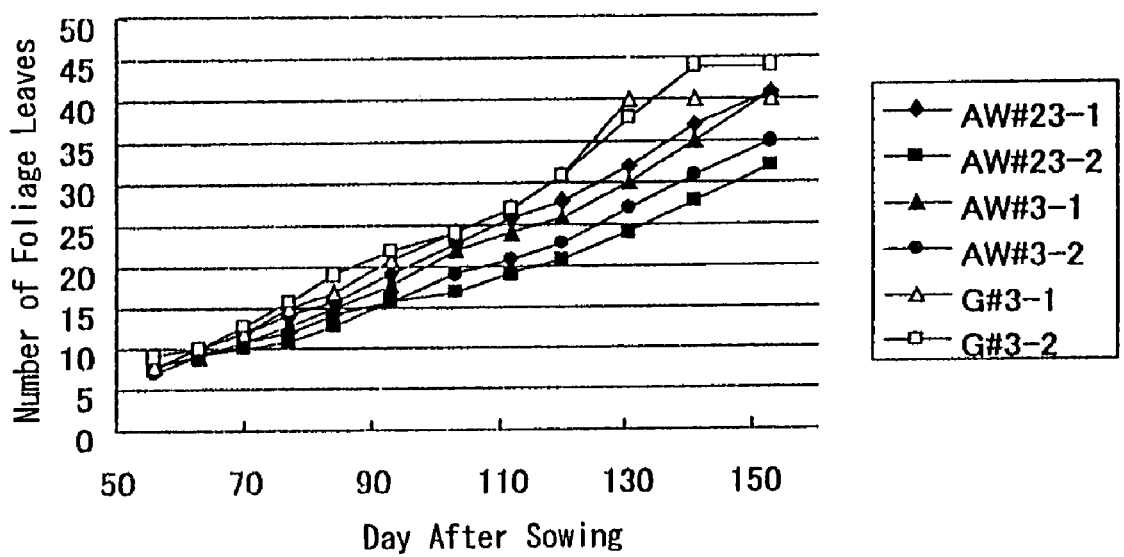
FIG. 33 shows comparison results for growth and development states (true leaf number) between cultivated NtmybA2 gene-transferred plants (tobacco with high NtmybA2 expression) and NtmybA2 gene-nontransferred plants.

Cultivation of respective plant individuals with overexpressed NtmybA2, verified in the aforementioned step (2), was continued and the grass height and foliage leaf number thereof were examined successively. As a result, the plant individuals with elevated levels of expressed NtmybA2, AW#3, and AW#23, had a reduced grass height (FIG. 32), and a smaller leaf size, relative to G#3. It was observed that, in AW#3 and AW#23, true leaf numbers show a tendency to slightly decline (FIG. 33). Their internodes were also significantly shortened. These facts indicate that transgenic tobacco plants with CaMV 35S promoter-driven expression of NtmybA2 are dwarfed.

(4) Decreased Cell Number and Undersized Cell in NtmybA2-Transformed Tobacco Plants The transgenic plant line AW#23, cultivated in the above step (3), was compared with the wild type tobacco for their foliage leaf size and epidermis cell. For the foliage leaves to be observed, completely expanded leaves were used which were located at the same leaf position between the wild type tobacco and AW#23. When these leaves were compared in size, the leaf size of AW#23 was made about 80% smaller than that of the wild type tobacco. In order to examine epidermis cells in this leaf, leaf-disc samples were prepared and decolored-fixed with an ethanol acetic acid (9:1) mixture. The resulting leaf-disc samples were photographed with a differential interference contrast microscope, and the area of 50 epidermis cells per sample was measured. As a result, the cell area was made about 45% smaller in AW#23 than that in the wild type plant, it was disclosed that the size of cells was reduced in AW#23. From the above results, the size of constituent cells for leaves is made 45% smaller in AW#23, the size of leaves is further reduced at a higher miniaturizing rate, i.e., is made 80% smaller, and it is therefore thought that the cause of dwarfed leaves is a decrease in cell number besides a reduction in cell size. It is also thought that the number of cells is decreased due to a delay in the cell cycle.

Example 25

Dwarfing of Transgenic Tobacco Plants for *Arabidopsis thaliana* AtHB8 Promoter-Driven Expression of NtmybA2

Transgenic tobacco plants for *Arabidopsis thaliana* AtHB8 gene promoter-driven expression of NtmybA2 were created, and their growth and development states were compared.

(1) Construction of Plasmids for Transformation

Construction of Plasmid pDBIHm-PAtHB8-NtmybA2

PCR was performed using *Arabidopsis thaliana* genome DNA as a template in combination with

```
primer PAtHB8-1F:
                                      (SEQ ID NO: 96)
5'-AACTGCAGCGGATAAACCAATTTTCAAATGATA-3'
and primer PAtHB8-1700R:
                                      (SEQ ID NO: 97)
5'-CGGGATCCCTTTGATCCTCTCCGATCTCTCTAT-3'
``` to provide a DNA fragment carrying the *Arabidopsis thaliana* AtHB8 gene promoter region (SEQ ID NO: 98, AtHB8 promoter GenBank Accession # AL161582; used nucleotides 89580 to 91279)). PCR was performed using OH60 as a template in combination with primer A2-ATG-Bam:
(SEQ ID NO: 99)
5'-CGGGATCCATGGAAAGTGATAGAATAAGCAC-3'
and primer A2T2-TAA-Not:
(SEQ ID NO: 100)
5'-TTTTCCTTTTGCGGCCGCTTAACAGCCTAAATGGAGTAAGACAG-3' to provide a DNA fragment carrying a segment for part of NtmybA2.

The PCR product, AtHB8 promoter DNA, was cleaved with PstI and BamHI. The DNA fragment carrying a segment for part of NtmybA2 was cleaved with BamHI and NotI. These two DNA fragments were inserted into the site, derived by PstI-NotI cleavage of pBluescript (Stratagene), to create plasmid pBS-PAtHB8-NtmybA2T2.

Plasmid pTH2 (Chiu et al., Curr Biol 1996 Mar. 1; 6 (3): 325-30) was cleaved with EcoRI, blunt-ended with the Klenow fragment at the protruded end, and then cleaved with NotI to cut out a DNA fragment carrying the NOS terminator. The resultant DNA fragment was inserted into the site, derived by NotI-EcoRV cleavage of plasmid pENTR2B (Invitrogen), to create plasmid pENTR-NOST1.

A DNA fragment, cut out by SalI-NotI cleavage of pBS-PAtHB8-NtmybA2T2, was inserted into the site, derived by SalI-NotI cleavage of pENTR-NOST1, to create plasmid pENTR-PAtHB8-NtmybA2T2.

OH60 was cleaved with SalI, blunt-ended with the Klenow fragment at the protruded end, and then cleaved with SpeI to cut out a DNA fragment carrying the C-terminal region of NtmybA2. This DNA fragment was inserted into the site, derived by SpeI-SmaI cleavage of pENTR-PAtHB8-NtmybA2T2, to create plasmid pENTR-PAtHB8-NtmybA2.

A mixture of plasmid pDESTBI-1 (as constructed in Example 9) and pENTR-PAtHB8-NtmybA2 is subjected to site-specific recombination with Gateway™ LR Clonase™ mix (Invitrogen) to generate pDBIHm-HB8-NtmybA2. The reaction with Gateway™ LR Clonase™ mix was done according to protocols enclosed in the reagent. The vector, pDBIHm-HB8-NtmybA2, is a plasmid vector for AtHB8 promoter-driven expression of full-length NtmybA2. It is also a binary vector allowing *Agrobacterium*-mediated transformation of plants. Transgenic plants are selectable with hygromycin from plants transformed with these plasmids.

(2) Transformation of Tobacco Plants

The aforementioned plasmid, pDBIHm-HB8-NtmybA2, was used to transform *Agrobacterium tumefaciens* strain EHA101. Next, *Nicotiana tabacum* ver. SR1 and *Nicotiana bentamiana* plants were transformed by the leaf disc method using *Agrobacterium* harboring each of these plasmids.

(3) Dwarfing of Transgenic Tobacco Plants Which Express NtmybA2, Driven by the AtHB8 Promoter The self-fertilized seeds of respective transformant lines, obtained from the above (2), are produced. These seeds are sown in a plastic pot (13 cm) filled with a soil composite (Kureha-Engei-Baido, Kureha Chemical Industry Co., Ltd.), and cultivated at 27° C. The lighting conditions include cultivation for 18 hr under continuous light, and cultivation for 6 hr in the dark. These transgenic plants are dwarfed, as compared to wild type tobacco plants and control vector-transformed plants.

Example 26

Modification in Polyploidy of Transgenic *Arabidopsis thaliana* Plants with Repressed Expression of Atmyb3R1 and Atmyb3R4

(1) Construction of Plasmids for Expression of Atmyb3R1, and Atmyb3R4 RNAi

In order to create transgenic *Arabidopsis thaliana* plants for induction of RNAi for Atmyb3R1 and Atmyb3R4, suitable plasmids are constructed. DNA sequences containing 250 or more base pairs are amplified by PCR from Atmyb3R1 cDNA as shown in SEQ ID NO: 75 and Atmyb3R4 cDNA as shown in SEQ ID NO: 76. These two DNA fragments are linked in a tandem fashion to generate a DNA construct. Plasmid are constructed by ligating the resultant DNA construct in an inverted repeat configuration having GUS inserted between the repeats according to the same manner for construction of plasmids as in Example 11. This plasmid is a binary vector which allows not only CaMV 35S promoter-controlled expression of inserted DNA but also *Agrobacterium*-mediated transformation of *Arabidopsis thaliana* plants, wherein the resultant transformants are selectable with kanamycin. The RNAi machinery is obtained with RNA expressed by the transferred gene in *Arabidopsis thaliana* plants transformed with this plasmid, thereby leading to reduction in levels of expressed Atmyb3R1 and Atmyb3R4.

(2) Transformation of *Arabidopsis thaliana* Plants

*Arabidopsis thaliana* ecotype Col-0 is transformed by the Floral dip method (similarly in Example 8) using *Agrobacterium* harboring the plasmid constructed in the aforementioned step (1). Self-fertilized seeds obtained from *Agrobacterium*-infected plants are sterilized with ethanol and hypochloric acid, and rinsed well with sterile distilled water. These seeds are cultured in MS agar medium supplemented with kanamycin at a concentration of 50 μg/ml. Transgenic plants are selectable as kanamycin-resistant individuals.

(3) Change in the Endopolyploidy of Transgenic *Arabidopsis thaliana* Plants

The resultant plant transformants selected in the aforementioned step (2) are planted in a pot and cultivated. Self-fertilized seeds obtained from these transgenic plants are sterilized with ethanol and hypochloric acid, and rinsed well with sterile distilled water. These seeds are cultured in MS agar medium supplemented with kanamycin at a concentration of 50 μg/ml. Content levels of nuclear DNA are measured using rosette leaves from grown kanamycin-resistant plant individuals in the same fashion as in Example 11. Since *Arabidopsis thaliana* is a diploid plant, 2C & 4C peaks, and further 8C & 16 C peaks indicating an increased nuclear DNA content level due to endoreduplication are observed when the content level of DNA is measured in wild type *Arabidopsis thaliana*. Plant individuals with increased endopolyploidy can be identified by assaying the content level of nuclear DNA in transgenic *Arabidopsis thaliana* plants with reduced levels of expressed Atmyb3R1 and Atmyb3R4, affected by RNAi machinery. Plant individuals wherein 2C peaks (detectable in the wild type) are not observed can be determined to be tetraploid. Plant individuals wherein 2C & 4C peaks disappear and 8C & 16 C peaks are detectable can be determined to be octaploid.

INDUSTRIAL APPLICABILITY

Techniques for regulating the cell cycle which is important for plant breeding, and for modifying proliferation of plant cells, and techniques for modifying development/differentiation of plant individuals are provided. Plant genes useful for regulation of the plant cell growth and regulation of individual plant development and differentiation and their application technologies are provided. Novel plant lines and plant breeding techniques can be developed by utilizing the technologies. In particular, technologies for modifying or regulating functions of plant 3Rmyb genes, new 3Rmyb mutant genes having modified functions, their gene products, and relating molecules are provided. Plant 3Rmyb protein variants which are dramatically improved in transcription activator functions and molecules which dominant-negatively function against transcripts of plant 3Rmyb genes are also provided, and technologies utilizing the same can be developed. Furthermore, by targeting on said genes, technologies for modifying proliferation of plant cells and technologies for modifying development/differentiation of plant individuals are provided. Thus, plant cells and plants retaining modified cell growth and development/differentiation can be obtained, and plants having desirable properties, such as specific organ enlargement, male sterility, or improved stress resistance, can be developed.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

<Sequence Listing Free Text>

SEQ ID NO: 1, Oligonucleotide to act as a primer for PCR, n stands for inosine in positions 3, 6 and 15 and for any base in position 21
SEQ ID NO: 2, Oligonucleotide to act as a primer for PCR, n stands for inosine
SEQ ID NO: 3, Oligonucleotide to act as a primer for PCR, n stands for inosine
SEQ ID NO: 4, Oligonucleotide to act as a primer for PCR, n stands for inosine
SEQ ID NO: 5, Oligonucleotide to act as a primer for PCR, n stands for inosine
SEQ ID NO: 6, Oligonucleotide to act as a primer for PCR, n stands for inosine
SEQ ID NO: 7, Oligonucleotide to act as a primer for PCR, T7 Primer
SEQ ID NO: 11, Oligonucleotide to act as a primer for PCR
SEQ ID NO: 12, Oligonucleotide to act as a primer for PCR
SEQ ID NO: 13, Oligonucleotide to act as a primer for PCR
SEQ ID NO: 14, Oligonucleotide to act as a primer for PCR
SEQ ID NO: 15, Oligonucleotide to act as a primer for PCR, T3 primer
SEQ ID NO: 16, n stands for any base
SEQ ID NO: 18, Oligonucleotide to act as a primer for PCR
SEQ ID NO: 19, Oligonucleotide to act as a primer for PCR
SEQ ID NO: 20, Oligonucleotide to act as a primer for PCR
SEQ ID NO: 21, Oligonucleotide to act as a primer for PCR
SEQ ID NO: 24, Oligonucleotide to act as a primer for PCR
SEQ ID NO: 25, Oligonucleotide to act as a primer for PCR
SEQ ID NO: 26, Oligonucleotide to act as a primer for PCR
SEQ ID NO: 27, Oligonucleotide to act as a primer for PCR
SEQ ID NO: 28, Oligonucleotide to act as a primer for PCR
SEQ ID NO: 29, Oligonucleotide to act as a primer for PCR
SEQ ID NO: 30, Oligonucleotide to act as a primer for PCR
SEQ ID NO: 31, Os3RmybA1 ORF
SEQ ID NO: 33, RT-PCR Primer for NtmybA1/A2
SEQ ID NO: 34, RT-PCR Primer for NtmybA1/A2
SEQ ID NO: 35, RT-PCR Primer for EF1α
SEQ ID NO: 36, RT-PCR Primer for EF1α
SEQ ID NO: 37, PCR Primer for VIGS A1 DNA
SEQ ID NO: 38, PCR Primer for VIGS A1 DNA
SEQ ID NO: 39, PCR Primer for VIGS A2 DNA
SEQ ID NO: 40, PCR Primer for VIGS A2 DNA
SEQ ID NO: 41, Oligonucleotide to act as a primer for PCR
SEQ ID NO: 42, Oligonucleotide to act as a primer for PCR
SEQ ID NO: 43, Oligonucleotide to act as a primer for PCR
SEQ ID NO: 44, Oligonucleotide to act as a primer for PCR
SEQ ID NO: 45, Oligonucleotide to act as a primer for PCR
SEQ ID NO: 46, Oligonucleotide to act as a primer for PCR
SEQ ID NO: 47, Oligonucleotide to act as a primer for PCR
SEQ ID NO: 48, Oligonucleotide to act as a primer for PCR
SEQ ID NO: 50, DDBJ Accession# AB056122, NtmybA1 (DDBJ Accession# BAB70510)
SEQ ID NO: 52, DDBJ Accession# AB056123, NtmybA2 (DDBJ Accession# BAB70511)
SEQ ID NO: 54, DDBJ Accession# AB056124, NtmybB (DDBJ Accession# BAB70512)
SEQ ID NO: 56, Oligonucleotide to act as a primer for PCR
SEQ ID NO: 57, Oligonucleotide to act as a primer for PCR
SEQ ID NO: 58, Oligonucleotide to act as a primer for PCR
SEQ ID NO: 59, Oligonucleotide to act as a primer for PCR
SEQ ID NO: 60, Oligonucleotide to act as a primer for PCR
SEQ ID NO: 61, Oligonucleotide to act as a primer for PCR
SEQ ID NO: 62, Oligonucleotide to act as a primer for PCR
SEQ ID NO: 63, Oligonucleotide to act as a primer for PCR
SEQ ID NO: 64, Oligonucleotide to act as a primer for PCR
SEQ ID NO: 65, Oligonucleotide to act as a primer for PCR
SEQ ID NO: 66, Oligonucleotide to act as a primer for PCR
SEQ ID NO: 67, Oligonucleotide to act as a primer for PCR
SEQ ID NO: 68, Oligonucleotide to act as a primer for PCR
SEQ ID NO: 69, Oligonucleotide to act as a primer for PCR
SEQ ID NO: 70, Oligonucleotide to act as a primer for PCR
SEQ ID NO: 71, Oligonucleotide to act as a primer for PCR
SEQ ID NO: 72, Oligonucleotide to act as a primer for PCR
SEQ ID NO: 73, Oligonucleotide to act as a primer for PCR
SEQ ID NO: 74, Oligonucleotide to act as a primer for PCR
SEQ ID NO: 84, Oligonucleotide to act as a primer for PCR
SEQ ID NO: 85, Oligonucleotide to act as a primer for PCR
SEQ ID NO: 86, Oligonucleotide to act as a primer for PCR
SEQ ID NO: 87, Oligonucleotide to act as a primer for PCR
SEQ ID NO: 89, Designed amino acid sequence
SEQ ID NO: 90, Designed amino acid sequence, X stands for any amino acid residue
SEQ ID NO: 91, Designed amino acid sequence, X stands for any amino acid residue
SEQ ID NO: 92, Designed amino acid sequence, X stands for any amino acid residue in positions 3, 4, 7 and 8, for S or T in position 2, for D or E in position 6, and for L or I or V in position 9
SEQ ID NO: 93, Designed amino acid sequence, X stands for H, W, Y or F in 16 & 93, for K, H or R in 19, 67, 102, 123, 129, 134 & 150, for S, T, G, C or A in 32, 54, 77, 135, 138 & 146, for D or E in 33 & 110, for L, I or V in 34, 49, 61, 65, 76 & 127, and for any residue in others
SEQ ID NO: 94, Designed amino acid sequence, X stands for K or R in 4 & 17, for L or V in 11, for S or T in 12, for L, I or V in 14, for D or E in 16 & 20, and for any amino acid residue in others
SEQ ID NO: 95, Designed amino acid sequence, X stands for K or R or D or E or H in position 7 and for any amino acid residue in position 5

SEQ ID NO: 96, Oligonucleotide to act as a primer for PCR
SEQ ID NO: 97, Oligonucleotide to act as a primer for PCR
SEQ ID NO: 99, Oligonucleotide to act as a primer for PCR
SEQ ID NO: 100, Oligonucleotide to act as a primer for PCR

SEQUENCE LISTING

<160> NUMBER OF SEQ ID NOS: 100

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide to act as a primer for PCR, n
      stands for inosine in positions 3, 6 and 15 and for any base in
      position 21
<220> FEATURE:
<221> NAME/KEY: misc_feature
<222> LOCATION: (3)..(3)
<223> OTHER INFORMATION: I
<220> FEATURE:
<221> NAME/KEY: misc_feature
<222> LOCATION: (6)..(6)
<223> OTHER INFORMATION: I
<220> FEATURE:
<221> NAME/KEY: misc_feature
<222> LOCATION: (15)..(15)
<223> OTHER INFORMATION: I
<220> FEATURE:
<221> NAME/KEY: misc_feature
<222> LOCATION: (21)..(21)
<223> OTHER INFORMATION: n stands for any base

<400> SEQUENCE: 1
gangtncart gyywncaymg ntgg                                         24

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide to act as a primer for PCR, n
      stands for inosine
<220> FEATURE:
<221> NAME/KEY: misc_feature
<222> LOCATION: (10)..(10)
<223> OTHER INFORMATION: I
<220> FEATURE:
<221> NAME/KEY: misc_feature
<222> LOCATION: (13)..(13)
<223> OTHER INFORMATION: I

<400> SEQUENCE: 2
yttyttdavn ganswrtkcc a                                            21

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide to act as a primer for PCR, n
      stands for inosine
<220> FEATURE:
<221> NAME/KEY: misc_feature
<222> LOCATION: (9)..(9)
<223> OTHER INFORMATION: I
<220> FEATURE:
<221> NAME/KEY: misc_feature
<222> LOCATION: (15)..(15)
<223> OTHER INFORMATION: I

<400> SEQUENCE: 3
cartgyytnc aymgntggca raarg                                        25

```
<210> SEQ ID NO 4
<211> LENGTH: 23
<212> TYPE: DNA
<213> ORGANISM: Artificial Sequence
<220> FEATURE:
<223> OTHER INFORMATION: Oligonucleotide to act as a primer for PCR, n
      stands for inosine
<220> FEATURE:
<221> NAME/KEY: misc_feature
<222> LOCATION: (3)..(3)
<223> OTHER INFORMATION: I
<220> FEATURE:
<221> NAME/KEY: misc_feature
<222> LOCATION: (6)..(6)
<223> OTHER INFORMATION: I

<400> SEQUENCE: 4
acnswnswrt tccarttrtg ytt                                             23

<210> SEQ ID NO 5
<211> LENGTH: 26
<212> TYPE: DNA
<213> ORGANISM: Artificial Sequence
<220> FEATURE:
<223> OTHER INFORMATION: Oligonucleotide to act as a primer for PCR, n
      stands for inosine
<220> FEATURE:
<221> NAME/KEY: misc_feature
<222> LOCATION: (6)..(6)
<223> OTHER INFORMATION: I
<220> FEATURE:
<221> NAME/KEY: misc_feature
<222> LOCATION: (18)..(18)
<223> OTHER INFORMATION: I
<220> FEATURE:
<221> NAME/KEY: misc_feature
<222> LOCATION: (21)..(21)
<223> OTHER INFORMATION: I

<400> SEQUENCE: 5
caymgntggc araargtnyt nraycc                                          26

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide to act as a primer for PCR, n
      stands for inosine
<220> FEATURE:
<221> NAME/KEY: misc_feature
<222> LOCATION: (2)..(2)
<223> OTHER INFORMATION: I
<220> FEATURE:
<221> NAME/KEY: misc_feature
<222> LOCATION: (8)..(8)
<223> OTHER INFORMATION: I
<220> FEATURE:
<221> NAME/KEY: misc_feature
<222> LOCATION: (11)..(11)
<223> OTHER INFORMATION: I
<220> FEATURE:
<221> NAME/KEY: misc_feature
<222> LOCATION: (14)..(14)
<223> OTHER INFORMATION: I
<220> FEATURE:
<221> NAME/KEY: misc_feature
<222> LOCATION: (17)..(17)
<223> OTHER INFORMATION: I
<220> FEATURE:
<221> NAME/KEY: misc_feature
<222> LOCATION: (20)..(20)
<223> OTHER INFORMATION: I
```

```
<220> FEATURE:
<221> NAME/KEY: misc_feature
<222> LOCATION: (23)..(23)
<223> OTHER INFORMATION: I

<400> SEQUENCE: 6
hngcrttntc nswnckncen kgna                                           24

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide to act as a primer for PCR, T7
      Primer

<400> SEQUENCE: 7
taatacgact cactataggg                                                20

<210> SEQ ID NO 8
<211> LENGTH: 228
<212> TYPE: DNA
<213> ORGANISM: Oryza sativa

<400> SEQUENCE: 8
cacaggtggc aaaaggttct aaaccctgaa ttagtcaaag ggccatggtc caaagaagaa     60
gatgaaatca ttgttcagat ggtaaacaaa cttggaccaa agaaatggtc aaccattgct    120
caagctttgc ctggacgtat aggaaagcaa tgtcgagaac ggtggtacaa ccatcttaac    180
cctggcataa acaaggaggc atggacacaa gaagaggaaa ttaccctc                 228

<210> SEQ ID NO 9
<211> LENGTH: 305
<212> TYPE: DNA
<213> ORGANISM: Oryza sativa

<400> SEQUENCE: 9
caccggtggc agaaagtgct ggatcctgaa ttggtcaaag ggccatggtc caaagaagaa     60
gatgacatca ttgttcagat ggtaaacaaa cttgggccaa agaaatggtc aaccattgct    120
caagctttgc ctggacgtat aggaaagcaa tgtcgggaac ggtggcacaa ccatcttaac    180
cctggcataa acaaggaggc atggacacaa gaagaggaaa ttaccctcat acatgctcat    240
cgaatgtatg gaaataaatg ggctgagttg acagaatttt tccacggccg ctccgacaac    300
gccga                                                               305

<210> SEQ ID NO 10
<211> LENGTH: 305
<212> TYPE: DNA
<213> ORGANISM: Oryza sativa

<400> SEQUENCE: 10
cataggtggc agaaggtgct ggaccctgaa ttggtcaaag ggccatggtc caaagaagaa     60
gatgacatca ttgttcagat ggtaaacaaa cttggaccaa agaaatggtc aaccattgct    120
caagctttgc ctggacgtat aggaaagcaa tgtcggggac ggtggcacaa ccatcttaac    180
cctggcgtaa acaaggaggc atggacacaa gaagaggaaa ttaccctcat acatgctcat    240
cgaatgtatg gaaataaatg ggctgagctg acaaaatttt tccacggccg taccgacaac    300
gccta                                                               305
```

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 11
cagctcggcc catttatttc catacatt                                              28

<210> SEQ ID NO 12
<211> LENGTH: 23
<212> TYPE: DNA
<213> ORGANISM: Artificial Sequence
<220> FEATURE:
<223> OTHER INFORMATION: Oligonucleotide to act as a primer for PCR

<400> SEQUENCE: 12
cgactggagc acgaggacac tga                                                   23

<210> SEQ ID NO 13
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 13
cttcttgtgt ccatgcctcc ttgtttat                                              28

<210> SEQ ID NO 14
<211> LENGTH: 26
<212> TYPE: DNA
<213> ORGANISM: Artificial Sequence
<220> FEATURE:
<223> OTHER INFORMATION: Oligonucleotide to act as a primer for PCR

<400> SEQUENCE: 14
ggacactgac atggactgaa ggagta                                                26

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide to act as a primer for PCR, T3
      primer

<400> SEQUENCE: 15
aattaaccct cactaaaggg                                                       20

<210> SEQ ID NO 16
<211> LENGTH: 726
<212> TYPE: DNA
<213> ORGANISM: Oryza sativa
<220> FEATURE:
<221> NAME/KEY: misc_feature
<222> LOCATION: (542)..(542)
<223> OTHER INFORMATION: n stands for any base

<400> SEQUENCE: 16
acgctctgaa atttgaaatc gcagacgagg cgagacgaag acgaagagga agagcaagag           60
ctagggttag gaggaggcga tttgctccgc ccgcagatcg gatcccccac ctcgtctcgc          120
ccccgatctc gctgtattcc ttgaagcaac tccctgaagg ccttactcag gcttgaccgt          180
ataatgattt ttatatccct tagaggtttc tattgcaaag tgaggattga atgtcttcag          240

```
tcatgatgac aagcgacaac ggaaaggctc cagagaaggg tggagaagct tctggacctt    300
catcagctcc ccaagaaggt gaaatcagca atgaaccaca aaggcgccgg ccgctcagtg    360
ggaggaccac tggtccaaca cggcgttcca cgaaaggaaa ttggacccct gaagaggatt    420
ccatattgtc cagagctgtt cagacatata aagggaggaa ttggaaaaaa atagcggaat    480
gttttccgga tagaaccgat gtacaatgct tgcacaggtg gcaaaaggtt ctaaaccctg    540
anttggtcaa agggccatgg tccaagaag aagatgacat cattgttcag atggtaaaca    600
aacttggacc aaagaaatgg tcaaccattg ctcaagcttt gcctggacgt ataggaaagc    660
aatgtcggga acggtggcac aaccatctta accctggcat aaacaaggag gcatggacac    720
aagaag                                                                726
```

<210> SEQ ID NO 17
<211> LENGTH: 574
<212> TYPE: DNA
<213> ORGANISM: Oryza sativa

<400> SEQUENCE: 17

```
cctgaaggcc tcactgaggc ttgacagtat aatgattttt atatcccttg gaggtttcta     60
ctgcaaagtg aggattgatt gtcttcactc atgatgacaa gcgataacgg aaaggctcca    120
gataaggatg gagagccttc tggacctccg tcggctcctc aagaaggaga atcagcaat    180 gaaccaaaaa ggcgacgacc tctcaatggg aggaccaccg gtccgacacg gcgttccacc    240
aaaggaaatt ggaccoctga agaggatgcc atattgtcca gagctgttca gacatacaac    300
gggaagaact ggaaaaaaat agcggaatgc tttccggata gaaccgatgt acaatgcttg    360
cacaggtggc aaaaggttct aaaccctgaa ttagtcaaag ggccatggtc caagaagaa    420 gatgaaatca ttgttcagat ggtaaacaaa cttggaccaa agaaatggtc aaccattgct    480
caagctttgc ctggacgtat aggaaagcaa tgtcgagaac ggtggtacaa ccatcttaac    540
cctggcataa acaaggaggc atggacacaa gaag                                574
```

<210> SEQ ID NO 18
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 18

```
aggaggcatg gacacaagaa gaggaaat                                         28
```

<210> SEQ ID NO 19
<211> LENGTH: 25
<212> TYPE: DNA
<213> ORGANISM: Artificial Sequence
<220> FEATURE:
<223> OTHER INFORMATION: Oligonucleotide to act as a primer for PCR

<400> SEQUENCE: 19

```
gctgtcaacg atacgctacg taacg                                            25
```

<210> SEQ ID NO 20
<211> LENGTH: 28
<212> TYPE: DNA
<213> ORGANISM: Artificial Sequence
<220> FEATURE:
<223> OTHER INFORMATION: Oligonucleotide to act as a primer for PCR

```
<400> SEQUENCE: 20
ggaaataaat gggccgagct gacaaaat                                        28

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide to act as a primer for PCR

<400> SEQUENCE: 21
cgctacgtaa cggcatgaca gtc                                             23

<210> SEQ ID NO 22
<211> LENGTH: 757
<212> TYPE: DNA
<213> ORGANISM: Oryza sativa

<400> SEQUENCE: 22
ggaaataaat gggccgagct gacaaaattt ttaccaggaa ggacggacaa ttcaattaaa     60
aatcactgga acagttcagt aaagaagaaa gtcaattcat acatgtcatc aggtttactt   120
acccaagttt cgtgtctccc tctaaatgaa tattctgcaa attgtaattc ctcaccagcg   180
atgacccgac aaaacagtga agatagtggt tgttttgctg tccgagaggt tgaaaattca   240
tcagggtgta gtcaatcatc acttgccaag gtttcttgct cccaagtgca tgatactact   300
gtgccattgg gctgtgattt gcaagtaaac gcgaattttg acaagaatga agcacatgat   360
tctcaatctt ccatgggtcc ccaagcatgc tatacttctg cggaggctgt tgcatctgct   420
ttgcctgctg tgcattgcca tgtttcttcc tctaacttgg atccagatca acacttgcaa   480
gaggactttg ctcaaggact gaatttggac atgactatag atgaaatgcc aactgttcct   540
agttttgcag acaaccagac tgtttgtagt atagaaaatc atgaaagatc tctggagcca   600
tatgatgtag caatggaggt gcctctctct atgttatcaa gtgattctgg agctgagcaa   660
aaactacatt tcatgtctga ggctgacttc aacagtccta actgtctgaa atctgaactc   720
tggcaggata tttccttaca gggccttctt tctggac                             757

<210> SEQ ID NO 23
<211> LENGTH: 209
<212> TYPE: DNA
<213> ORGANISM: Oryza sativa

<400> SEQUENCE: 23
ggcagagggt agagtcctgg atttcgagtg taccacacct gaaagatcat cagacaaaaa    60
tgctggcagc aatctgggaa gatatctgag ctcacctatt ccttcgtccc atcttctgaa   120
aagttttaga tagcttgata taccatgtga ggaatacacc tcagacttgc tgtaacaatc   180
attatgcgaa cgatcttgtt cattaccgt                                     209

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide to act as a primer for PCR

<400> SEQUENCE: 24
tgtcttcagt catgatgaca agcga                                          25
```

```
<210> SEQ ID NO 25
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 25
caagctatct aaaactttc agaagatgg                                         29

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide to act as a primer for PCR

<400> SEQUENCE: 26
gatcaacact tgcaagagga                                                  20

<210> SEQ ID NO 27
<211> LENGTH: 21
<212> TYPE: DNA
<213> ORGANISM: Artificial Sequence
<220> FEATURE:
<223> OTHER INFORMATION: Oligonucleotide to act as a primer for PCR

<400> SEQUENCE: 27
acagggcctt cttttctgga c                                                21

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide to act as a primer for PCR

<400> SEQUENCE: 28
agcatacctg aatgtgggga                                                  20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide to act as a primer for PCR

<400> SEQUENCE: 29
tactcatgat gaaagcacgg                                                  20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide to act as a primer for PCR

<400> SEQUENCE: 30
atctccttca catggaagtc                                                  20

<210> SEQ ID NO 31
<211> LENGTH: 2996
<212> TYPE: DNA
<213> ORGANISM: Oryza sativa
<220> FEATURE:
<221> NAME/KEY: CDS
<222> LOCATION: (11)..(2992)
```

<223> OTHER INFORMATION: Os3RmybA1 ORF

<400> SEQUENCE: 31

```
tgtcttcgtc atg atg aca agc gat aac gga aag gct cca gat aag gat        49
           Met Met Thr Ser Asp Asn Gly Lys Ala Pro Asp Lys Asp
             1               5                  10 gga gag cct tct gga cct ccg tcg gct cct caa gaa gga gaa atc agc        97
Gly Glu Pro Ser Gly Pro Pro Ser Ala Pro Gln Glu Gly Glu Ile Ser
 15              20                  25 aat gaa cca aaa agg cga cga cct ctc aat ggg agg acc acc ggt ccg       145
Asn Glu Pro Lys Arg Arg Arg Pro Leu Asn Gly Arg Thr Thr Gly Pro
 30              35                  40                  45 aca cgg cgt tcc acc aaa gga aat tgg acc cct gaa gag gat gcc ata       193
Thr Arg Arg Ser Thr Lys Gly Asn Trp Thr Pro Glu Glu Asp Ala Ile
                 50                  55                  60 ttg tcc aga gct gtt cag aca tac aac ggg aag aac tgg aaa aaa ata       241
Leu Ser Arg Ala Val Gln Thr Tyr Asn Gly Lys Asn Trp Lys Lys Ile
                 65                  70                  75 gcg gaa tgc ttt ccg gat aga acc gat gta caa tgc ttg cac agg tgg       289
Ala Glu Cys Phe Pro Asp Arg Thr Asp Val Gln Cys Leu His Arg Trp
             80                  85                  90 caa aag gtt cta aac cct gaa tta gtc aaa ggg cca tgg tcc aaa gaa       337
Gln Lys Val Leu Asn Pro Glu Leu Val Lys Gly Pro Trp Ser Lys Glu
 95                 100                 105 gaa gat gaa atc att gtt cag atg gta aac aaa ctt gga cca aag aaa       385
Glu Asp Glu Ile Ile Val Gln Met Val Asn Lys Leu Gly Pro Lys Lys
110             115                 120                 125 tgg tca acc att gct caa gct ttg cct gga cgt ata gga aag caa tgt       433
Trp Ser Thr Ile Ala Gln Ala Leu Pro Gly Arg Ile Gly Lys Gln Cys
                130                 135                 140 cga gaa cgg tgg tac aac cat ctt aac cct ggc ata aac aag gag gca       481
Arg Glu Arg Trp Tyr Asn His Leu Asn Pro Gly Ile Asn Lys Glu Ala
                145                 150                 155 tgg aca caa gaa gag gaa att acc ctc ata cat gct cat cga acg tat       529
Trp Thr Gln Glu Glu Glu Ile Thr Leu Ile His Ala His Arg Thr Tyr
                160                 165                 170 gga aat aaa tgg gcc gag ctg aca aaa ttt tta cca gga agg acg gac       577
Gly Asn Lys Trp Ala Glu Leu Thr Lys Phe Leu Pro Gly Arg Thr Asp
            175                 180                 185 aat tca att aaa aat cac tgg aac agt tca gta aag aag aaa gtc aat       625
Asn Ser Ile Lys Asn His Trp Asn Ser Ser Val Lys Lys Lys Val Asn
190             195                 200                 205 tca tac atg tca tca ggt tta ctt acc caa gtt tcg tgt ctc cct cta       673
Ser Tyr Met Ser Ser Gly Leu Leu Thr Gln Val Ser Cys Leu Pro Leu
                210                 215                 220 aat gaa tat tct gca aat tgt aat tcc tca cca gcg atg acc caa caa       721
Asn Glu Tyr Ser Ala Asn Cys Asn Ser Ser Pro Ala Met Thr Gln Gln
                225                 230                 235 aac agt gaa gat agt ggt tgt ttt gct gtc cga gag gtt gaa aat tca       769
Asn Ser Glu Asp Ser Gly Cys Phe Ala Val Arg Glu Val Glu Asn Ser
            240                 245                 250 tca ggg tgt agt caa tca tca ctt gcc aag gtt tct tgc tcc caa gtg       817
Ser Gly Cys Ser Gln Ser Ser Leu Ala Lys Val Ser Cys Ser Gln Val
        255                 260                 265 cat gat act act gtg cca ttg ggc tgt gat ttg caa gta aac gcg aat       865
His Asp Thr Thr Val Pro Leu Gly Cys Asp Leu Gln Val Asn Ala Asn
270                 275                 280                 285 ttt gac aag aat gaa gca cat gat tct caa tct tcc atg ggt ccc caa       913
Phe Asp Lys Asn Glu Ala His Asp Ser Gln Ser Ser Met Gly Pro Gln
                290                 295                 300
```

| | | | | | | | | | | | | | | | |
|---|---|---|---|---|---|---|---|---|---|---|---|---|---|---|---|
| gca | tgc | tat | act | tct | gcg | gag | gct | gtt | gca | tct | gct | ttg | cct | gct | gtg | 961 |
| Ala | Cys | Tyr | Thr | Ser | Ala | Glu | Ala | Val | Ala | Ser | Ala | Leu | Pro | Ala | Val | |
| | | | 305 | | | | | 310 | | | | | 315 | | | |
| cat | tgc | cat | gtt | tct | tcc | tct | aac | ttg | gat | cca | gat | caa | cac | ttg | caa | 1009 |
| His | Cys | His | Val | Ser | Ser | Ser | Asn | Leu | Asp | Pro | Asp | Gln | His | Leu | Gln | |
| | | 320 | | | | | 325 | | | | | 330 | | | | |
| gag | gac | ttt | gct | caa | gga | ctg | aat | ttg | gac | atg | act | ata | gat | gaa | atg | 1057 |
| Glu | Asp | Phe | Ala | Gln | Gly | Leu | Asn | Leu | Asp | Met | Thr | Ile | Asp | Glu | Met | |
| 335 | | | | | 340 | | | | | 345 | | | | | | |
| cca | act | gtt | cct | agt | ttt | gca | gac | aac | cag | act | gtt | tgt | agt | ata | gaa | 1105 |
| Pro | Thr | Val | Pro | Ser | Phe | Ala | Asp | Asn | Gln | Thr | Val | Cys | Ser | Ile | Glu | |
| 350 | | | | | 355 | | | | | 360 | | | | | 365 | |
| aat | cat | gaa | aga | tct | ctg | gag | cca | tat | gat | gta | gca | atg | gag | gtg | cct | 1153 |
| Asn | His | Glu | Arg | Ser | Leu | Glu | Pro | Tyr | Asp | Val | Ala | Met | Glu | Val | Pro | |
| | | | | 370 | | | | | 375 | | | | | 380 | | |
| ctc | tct | atg | tta | tca | agt | gat | tct | gga | gct | gag | caa | aaa | cta | cat | ttc | 1201 |
| Leu | Ser | Met | Leu | Ser | Ser | Asp | Ser | Gly | Ala | Glu | Gln | Lys | Leu | His | Phe | |
| | | | 385 | | | | | 390 | | | | | 395 | | | |
| atg | tct | gag | gct | gac | ttc | aac | agt | cct | aac | tgt | ctg | aaa | tct | gaa | ctc | 1249 |
| Met | Ser | Glu | Ala | Asp | Phe | Asn | Ser | Pro | Asn | Cys | Leu | Lys | Ser | Glu | Leu | |
| | | 400 | | | | | 405 | | | | | 410 | | | | |
| tgg | cag | gat | att | tcc | tta | cag | ggc | ctt | ctt | tct | gga | cct | gat | gca | gtt | 1297 |
| Trp | Gln | Asp | Ile | Ser | Leu | Gln | Gly | Leu | Leu | Ser | Gly | Pro | Asp | Ala | Val | |
| 415 | | | | | 420 | | | | | 425 | | | | | | |
| gaa | gct | gat | tca | att | tca | aga | tca | aat | cac | caa | tcg | gat | gta | tat | tcc | 1345 |
| Glu | Ala | Asp | Ser | Ile | Ser | Arg | Ser | Asn | His | Gln | Ser | Asp | Val | Tyr | Ser | |
| 430 | | | | | 435 | | | | | 440 | | | | | 445 | |
| tct | gaa | gca | gat | acc | cat | ttt | tta | gca | cca | ccc | tac | atg | cca | cag | aca | 1393 |
| Ser | Glu | Ala | Asp | Thr | His | Phe | Leu | Ala | Pro | Pro | Tyr | Met | Pro | Gln | Thr | |
| | | | | 450 | | | | | 455 | | | | | 460 | | |
| tca | aat | tct | tca | agt | gtg | atg | ggg | ctt | gct | gat | gac | cag | agt | cca | cag | 1441 |
| Ser | Asn | Ser | Ser | Ser | Val | Met | Gly | Leu | Ala | Asp | Asp | Gln | Ser | Pro | Gln | |
| | | | 465 | | | | | 470 | | | | | 475 | | | |
| atg | tca | gta | cct | cca | tct | ctt | att | tgt | tca | aat | gct | atg | act | gat | gat | 1489 |
| Met | Ser | Val | Pro | Pro | Ser | Leu | Ile | Cys | Ser | Asn | Ala | Met | Thr | Asp | Asp | |
| | | 480 | | | | | 485 | | | | | 490 | | | | |
| gca | cct | ttc | gat | aat | aga | cca | ggg | cgg | aag | gaa | atg | cca | ctt | tct | cag | 1537 |
| Ala | Pro | Phe | Asp | Asn | Arg | Pro | Gly | Arg | Lys | Glu | Met | Pro | Leu | Ser | Gln | |
| | 495 | | | | | 500 | | | | | 505 | | | | | |
| gca | gaa | gtg | gtt | acc | caa | tct | tcc | agt | tct | tct | ggt | gat | gct | gaa | atg | 1585 |
| Ala | Glu | Val | Val | Thr | Gln | Ser | Ser | Ser | Ser | Ser | Gly | Asp | Ala | Glu | Met | |
| 510 | | | | | 515 | | | | | 520 | | | | | 525 | |
| ttt | gct | aac | cct | ggt | tgt | agc | aat | gac | aga | cat | gtt | cct | tct | tca | acg | 1633 |
| Phe | Ala | Asn | Pro | Gly | Cys | Ser | Asn | Asp | Arg | His | Val | Pro | Ser | Ser | Thr | |
| | | | | 530 | | | | | 535 | | | | | 540 | | |
| atg | gaa | agc | ata | cct | gaa | tgt | ggg | gac | caa | cag | gtt | act | aat | gcg | gaa | 1681 |
| Met | Glu | Ser | Ile | Pro | Glu | Cys | Gly | Asp | Gln | Gln | Val | Thr | Asn | Ala | Glu | |
| | | | 545 | | | | | 550 | | | | | 555 | | | |
| gaa | cct | gaa | gcc | agt | cta | gag | aaa | gaa | cca | tcg | ctt | aca | cag | agt | gtg | 1729 |
| Glu | Pro | Glu | Ala | Ser | Leu | Glu | Lys | Glu | Pro | Ser | Leu | Thr | Gln | Ser | Val | |
| | | 560 | | | | | 565 | | | | | 570 | | | | |
| act | gca | cca | gat | gaa | cag | gac | aag | gga | gcc | ctc | ttc | tac | gaa | cct | cct | 1777 |
| Thr | Ala | Pro | Asp | Glu | Gln | Asp | Lys | Gly | Ala | Leu | Phe | Tyr | Glu | Pro | Pro | |
| | 575 | | | | | 580 | | | | | 585 | | | | | |
| cgt | ttt | cca | agc | ctg | gat | gtt | cca | ttt | gtc | agt | tgc | gat | ctt | gta | acc | 1825 |
| Arg | Phe | Pro | Ser | Leu | Asp | Val | Pro | Phe | Val | Ser | Cys | Asp | Leu | Val | Thr | |
| 590 | | | | | 595 | | | | | 600 | | | | | 605 | |
| tct | ggt | gat | ctc | caa | gag | ttt | agt | ccc | ctt | ggc | att | cgg | cag | tta | atg | 1873 |
| Ser | Gly | Asp | Leu | Gln | Glu | Phe | Ser | Pro | Leu | Gly | Ile | Arg | Gln | Leu | Met | |

```
                      610                 615                 620
cat tca acc atg aat gtc tgc acg cca atg aga ttg tgg ggc tcc cct      1921
His Ser Thr Met Asn Val Cys Thr Pro Met Arg Leu Trp Gly Ser Pro
                625                 630                 635 act cat gat gaa agc acg ggc gtt ttg ctg aag agt gct gcc aaa agc      1969
Thr His Asp Glu Ser Thr Gly Val Leu Leu Lys Ser Ala Ala Lys Ser
                640                 645                 650 ttc ata tgc acg cca tca ata ctg aag aaa cgt cac aga gat ctc ttg      2017
Phe Ile Cys Thr Pro Ser Ile Leu Lys Lys Arg His Arg Asp Leu Leu
            655                 660                 665 tct cct att cca gat aaa aga atc gag aag aaa tat ggg act gaa aag      2065
Ser Pro Ile Pro Asp Lys Arg Ile Glu Lys Lys Tyr Gly Thr Glu Lys
670                 675                 680                 685 gat cgt ggg gta tca gac aca tcc tcc acc ggc att caa aca agt tgt      2113
Asp Arg Gly Val Ser Asp Thr Ser Ser Thr Gly Ile Gln Thr Ser Cys
                690                 695                 700 atc aat gcc act aaa gat gat gca ctt ata act aca gtt ttg cgt att      2161
Ile Asn Ala Thr Lys Asp Asp Ala Leu Ile Thr Thr Val Leu Arg Ile
            705                 710                 715 gag cga tct gct tct tct aaa tct ctg gaa aag aaa ctt gtt ttc tct      2209
Glu Arg Ser Ala Ser Ser Lys Ser Leu Glu Lys Lys Leu Val Phe Ser
            720                 725                 730 gat gaa aac aag gaa aat ttg ggc tac aca act gaa cag aca aaa gat      2257
Asp Glu Asn Lys Glu Asn Leu Gly Tyr Thr Thr Glu Gln Thr Lys Asp
735                 740                 745 gga cag agt gct gga aat gac gaa cac atg gac gag cag aca aca ggg      2305
Gly Gln Ser Ala Gly Asn Asp Glu His Met Asp Glu Gln Thr Thr Gly
750                 755                 760                 765 gaa cgc agt tct gca aca aat gta gct act aat gat gac ctg tca ggc      2353
Glu Arg Ser Ser Ala Thr Asn Val Ala Thr Asn Asp Asp Leu Ser Gly
                770                 775                 780 aat tta caa cct gca ggt att ctt att gaa cac agc ggc gat gat ccc      2401
Asn Leu Gln Pro Ala Gly Ile Leu Ile Glu His Ser Gly Asp Asp Pro
                785                 790                 795 att tcc cca gat tat ggc aaa aat acc atg aat cag aag ctg aac aca      2449
Ile Ser Pro Asp Tyr Gly Lys Asn Thr Met Asn Gln Lys Leu Asn Thr
            800                 805                 810 aat gtg aaa tct tta tca gtc tgt aag gag gga gtg tgt gct aaa tca      2497
Asn Val Lys Ser Leu Ser Val Cys Lys Glu Gly Val Cys Ala Lys Ser
            815                 820                 825 aag ccc act gaa ctc atc gtg gag aaa tct tca cca tgt ata aat gtg      2545
Lys Pro Thr Glu Leu Ile Val Glu Lys Ser Ser Pro Cys Ile Asn Val
830                 835                 840                 845 gat tat gaa tat gtg aac ata ttg gct gat acc cca ggt atc aaa aga      2593
Asp Tyr Glu Tyr Val Asn Ile Leu Ala Asp Thr Pro Gly Ile Lys Arg
                850                 855                 860 gga cta gaa tct cct tca gca tgg aag tcc cct tgg ttc gtc gat atg      2641
Gly Leu Glu Ser Pro Ser Ala Trp Lys Ser Pro Trp Phe Val Asp Met
            865                 870                 875 cat ttt cag ggt tca tac ttc acc agc cca gct gat agt tac gac gca      2689
His Phe Gln Gly Ser Tyr Phe Thr Ser Pro Ala Asp Ser Tyr Asp Ala
            880                 885                 890 cta gga ttg atg aag cag ata aat gtg cag act gct gct gct ttg gtg      2737
Leu Gly Leu Met Lys Gln Ile Asn Val Gln Thr Ala Ala Ala Leu Val
            895                 900                 905 gaa gcc cgt gag gta ctg gca agc ggc ggc caa tgt gac aac ata agc      2785
Glu Ala Arg Glu Val Leu Ala Ser Gly Gly Gln Cys Asp Asn Ile Ser
910                 915                 920                 925 tct gat aag gaa aac acg ggg aat cca gat gcc aag aag gaa cca ggg      2833
```

```
Ser Asp Lys Glu Asn Thr Gly Asn Pro Asp Ala Lys Lys Glu Pro Gly
            930                 935                 940 aca acc aaa ttg caa aca aaa atc atg gca gag ggt aga gtc ctg gat    2881
Thr Thr Lys Leu Gln Thr Lys Ile Met Ala Glu Gly Arg Val Leu Asp
            945                 950                 955 ttc gag tgt acc aca cct gaa aga tca tca gac aaa aat gct ggc agc    2929
Phe Glu Cys Thr Thr Pro Glu Arg Ser Ser Asp Lys Asn Ala Gly Ser
        960                 965                 970 aat ctg gga aga tat ctg agc tca cct att cct tcg tcc cat ctt ctg    2977
Asn Leu Gly Arg Tyr Leu Ser Ser Pro Ile Pro Ser Ser His Leu Leu
    975                 980                 985 aaa agt ttt aga tag cttg                                           2996
Lys Ser Phe Arg
990

<210> SEQ ID NO 32
<211> LENGTH: 993
<212> TYPE: PRT
<213> ORGANISM: Oryza sativa

<400> SEQUENCE: 32

Met Met Thr Ser Asp Asn Gly Lys Ala Pro Asp Lys Asp Gly Glu Pro
1               5                   10                  15

Ser Gly Pro Pro Ser Ala Pro Gln Glu Gly Glu Ile Ser Asn Glu Pro
            20                  25                  30

Lys Arg Arg Arg Pro Leu Asn Gly Arg Thr Thr Gly Pro Thr Arg Arg
        35                  40                  45

Ser Thr Lys Gly Asn Trp Thr Pro Glu Glu Asp Ala Ile Leu Ser Arg
    50                  55                  60

Ala Val Gln Thr Tyr Asn Gly Lys Asn Trp Lys Lys Ile Ala Glu Cys
65                  70                  75                  80

Phe Pro Asp Arg Thr Asp Val Gln Cys Leu His Arg Trp Gln Lys Val
                85                  90                  95

Leu Asn Pro Glu Leu Val Lys Gly Pro Trp Ser Lys Glu Glu Asp Glu
            100                 105                 110

Ile Ile Val Gln Met Val Asn Lys Leu Gly Pro Lys Lys Trp Ser Thr
        115                 120                 125

Ile Ala Gln Ala Leu Pro Gly Arg Ile Gly Lys Gln Cys Arg Glu Arg
    130                 135                 140

Trp Tyr Asn His Leu Asn Pro Gly Ile Asn Lys Glu Ala Trp Thr Gln
145                 150                 155                 160

Glu Glu Glu Ile Thr Leu Ile His Ala His Arg Thr Tyr Gly Asn Lys
                165                 170                 175

Trp Ala Glu Leu Thr Lys Phe Leu Pro Gly Arg Thr Asp Asn Ser Ile
            180                 185                 190

Lys Asn His Trp Asn Ser Ser Val Lys Lys Lys Val Asn Ser Tyr Met
        195                 200                 205

Ser Ser Gly Leu Leu Thr Gln Val Ser Cys Leu Pro Leu Asn Glu Tyr
    210                 215                 220

Ser Ala Asn Cys Asn Ser Ser Pro Ala Met Thr Gln Gln Asn Ser Glu
225                 230                 235                 240

Asp Ser Gly Cys Phe Ala Val Arg Glu Val Glu Asn Ser Ser Gly Cys
                245                 250                 255

Ser Gln Ser Ser Leu Ala Lys Val Ser Cys Ser Gln Val His Asp Thr
            260                 265                 270

Thr Val Pro Leu Gly Cys Asp Leu Gln Val Asn Ala Asn Phe Asp Lys
```

-continued

```
              275                 280                 285
Asn Glu Ala His Asp Ser Gln Ser Ser Met Gly Pro Gln Ala Cys Tyr
        290                 295                 300
Thr Ser Ala Glu Ala Val Ala Ser Ala Leu Pro Ala Val His Cys His
305                 310                 315                 320
Val Ser Ser Ser Asn Leu Asp Pro Asp Gln His Leu Gln Glu Asp Phe
                325                 330                 335
Ala Gln Gly Leu Asn Leu Asp Met Thr Ile Asp Glu Met Pro Thr Val
                340                 345                 350
Pro Ser Phe Ala Asp Asn Gln Thr Val Cys Ser Ile Glu Asn His Glu
        355                 360                 365
Arg Ser Leu Glu Pro Tyr Asp Val Ala Met Glu Val Pro Leu Ser Met
    370                 375                 380
Leu Ser Ser Asp Ser Gly Ala Glu Gln Lys Leu His Phe Met Ser Glu
385                 390                 395                 400
Ala Asp Phe Asn Ser Pro Asn Cys Leu Lys Ser Glu Leu Trp Gln Asp
                405                 410                 415
Ile Ser Leu Gln Gly Leu Leu Ser Gly Pro Asp Ala Val Glu Ala Asp
                420                 425                 430
Ser Ile Ser Arg Ser Asn His Gln Ser Asp Val Tyr Ser Ser Glu Ala
            435                 440                 445
Asp Thr His Phe Leu Ala Pro Pro Tyr Met Pro Gln Thr Ser Asn Ser
    450                 455                 460
Ser Ser Val Met Gly Leu Ala Asp Asp Gln Ser Pro Gln Met Ser Val
465                 470                 475                 480
Pro Pro Ser Leu Ile Cys Ser Asn Ala Met Thr Asp Asp Ala Pro Phe
                485                 490                 495
Asp Asn Arg Pro Gly Arg Lys Glu Met Pro Leu Ser Gln Ala Glu Val
            500                 505                 510
Val Thr Gln Ser Ser Ser Ser Gly Asp Ala Glu Met Phe Ala Asn
            515                 520                 525
Pro Gly Cys Ser Asn Asp Arg His Val Pro Ser Ser Thr Met Glu Ser
    530                 535                 540
Ile Pro Glu Cys Gly Asp Gln Gln Val Thr Asn Ala Glu Glu Pro Glu
545                 550                 555                 560
Ala Ser Leu Glu Lys Glu Pro Ser Leu Thr Gln Ser Val Thr Ala Pro
                565                 570                 575
Asp Glu Gln Asp Lys Gly Ala Leu Phe Tyr Glu Pro Pro Arg Phe Pro
            580                 585                 590
Ser Leu Asp Val Pro Phe Val Ser Cys Asp Leu Val Thr Ser Gly Asp
        595                 600                 605
Leu Gln Glu Phe Ser Pro Leu Gly Ile Arg Gln Leu Met His Ser Thr
    610                 615                 620
Met Asn Val Cys Thr Pro Met Arg Leu Trp Gly Ser Pro Thr His Asp
625                 630                 635                 640
Glu Ser Thr Gly Val Leu Leu Lys Ser Ala Lys Ser Phe Ile Cys
                645                 650                 655
Thr Pro Ser Ile Leu Lys Lys Arg His Arg Asp Leu Leu Ser Pro Ile
            660                 665                 670
Pro Asp Lys Arg Ile Glu Lys Lys Tyr Gly Thr Glu Lys Asp Arg Gly
        675                 680                 685
Val Ser Asp Thr Ser Ser Thr Gly Ile Gln Thr Ser Cys Ile Asn Ala
    690                 695                 700
```

```
Thr Lys Asp Asp Ala Leu Ile Thr Thr Val Leu Arg Ile Glu Arg Ser
705                 710                 715                 720

Ala Ser Ser Lys Ser Leu Glu Lys Lys Leu Val Phe Ser Asp Glu Asn
            725                 730                 735

Lys Glu Asn Leu Gly Tyr Thr Thr Glu Gln Thr Lys Asp Gly Gln Ser
            740                 745                 750

Ala Gly Asn Asp Glu His Met Asp Glu Gln Thr Thr Gly Glu Arg Ser
            755                 760                 765

Ser Ala Thr Asn Val Ala Thr Asn Asp Asp Leu Ser Gly Asn Leu Gln
770                 775                 780

Pro Ala Gly Ile Leu Ile Glu His Ser Gly Asp Asp Pro Ile Ser Pro
785                 790                 795                 800

Asp Tyr Gly Lys Asn Thr Met Asn Gln Lys Leu Asn Thr Asn Val Lys
                805                 810                 815

Ser Leu Ser Val Cys Lys Glu Gly Val Cys Ala Lys Ser Lys Pro Thr
                820                 825                 830

Glu Leu Ile Val Glu Lys Ser Ser Pro Cys Ile Asn Val Asp Tyr Glu
            835                 840                 845

Tyr Val Asn Ile Leu Ala Asp Thr Pro Gly Ile Lys Arg Gly Leu Glu
850                 855                 860

Ser Pro Ser Ala Trp Lys Ser Pro Trp Phe Val Asp Met His Phe Gln
865                 870                 875                 880

Gly Ser Tyr Phe Thr Ser Pro Ala Asp Ser Tyr Asp Ala Leu Gly Leu
                885                 890                 895

Met Lys Gln Ile Asn Val Gln Thr Ala Ala Ala Leu Val Glu Ala Arg
            900                 905                 910

Glu Val Leu Ala Ser Gly Gly Gln Cys Asp Asn Ile Ser Ser Asp Lys
            915                 920                 925

Glu Asn Thr Gly Asn Pro Asp Ala Lys Lys Glu Pro Gly Thr Thr Lys
            930                 935                 940

Leu Gln Thr Lys Ile Met Ala Glu Gly Arg Val Leu Asp Phe Glu Cys
945                 950                 955                 960

Thr Thr Pro Glu Arg Ser Ser Asp Lys Asn Ala Gly Ser Asn Leu Gly
                965                 970                 975

Arg Tyr Leu Ser Ser Pro Ile Pro Ser Ser His Leu Leu Lys Ser Phe
            980                 985                 990

Arg

<210> SEQ ID NO 33
<211> LENGTH: 21
<212> TYPE: DNA
<213> ORGANISM: Artificial Sequence
<220> FEATURE:
<223> OTHER INFORMATION: RT-PCR Primer for NtmybA1/A2

<400> SEQUENCE: 33
gtacaatgct tgcaccggtg g                                            21

<210> SEQ ID NO 34
<211> LENGTH: 21
<212> TYPE: DNA
<213> ORGANISM: Artificial Sequence
<220> FEATURE:
<223> OTHER INFORMATION: RT-PCR Primer for NtmybA1/A2

<400> SEQUENCE: 34
```

```
tgtagactgg aacagccag c                                         21

<210> SEQ ID NO 35
<211> LENGTH: 20
<212> TYPE: DNA
<213> ORGANISM: Artificial Sequence
<220> FEATURE:
<223> OTHER INFORMATION: RT-PCR Primer for EF1Y"

<400> SEQUENCE: 35
agaccaccaa gtactactgc                                          20

<210> SEQ ID NO 36
<211> LENGTH: 20
<212> TYPE: DNA
<213> ORGANISM: Artificial Sequence
<220> FEATURE:
<223> OTHER INFORMATION: RT-PCR Primer for EF1Y"

<400> SEQUENCE: 36
gtcaagagcc tcaaggagag                                          20

<210> SEQ ID NO 37
<211> LENGTH: 23
<212> TYPE: DNA
<213> ORGANISM: Artificial Sequence
<220> FEATURE:
<223> OTHER INFORMATION: PCR Primer for VIGS A1 DNA

<400> SEQUENCE: 37
atagttctgt taaaaagaaa ctg                                      23

<210> SEQ ID NO 38
<211> LENGTH: 24
<212> TYPE: DNA
<213> ORGANISM: Artificial Sequence
<220> FEATURE:
<223> OTHER INFORMATION: PCR Primer for VIGS A1 DNA

<400> SEQUENCE: 38
taacattgaa caagaaacat cttg                                     24

<210> SEQ ID NO 39
<211> LENGTH: 21
<212> TYPE: DNA
<213> ORGANISM: Artificial Sequence
<220> FEATURE:
<223> OTHER INFORMATION: PCR Primer for VIGS A2 DNA

<400> SEQUENCE: 39
acaaagtctt ctctaactac g                                        21

<210> SEQ ID NO 40
<211> LENGTH: 19
<212> TYPE: DNA
<213> ORGANISM: Artificial Sequence
<220> FEATURE:
<223> OTHER INFORMATION: PCR Primer for VIGS A2 DNA

<400> SEQUENCE: 40
agcttcgagt cgtctagcg                                           19

<210> SEQ ID NO 41
<211> LENGTH: 50
<212> TYPE: DNA
<213> ORGANISM: Artificial Sequence
```

```
<220> FEATURE:
<223> OTHER INFORMATION: Oligonucleotide to act as a primer for PCR

<400> SEQUENCE: 41
ggggacaagt ttgtacaaaa aagcaggctc aattaaccct cactaaaggg                50

<210> SEQ ID NO 42
<211> LENGTH: 52
<212> TYPE: DNA
<213> ORGANISM: Artificial Sequence
<220> FEATURE:
<223> OTHER INFORMATION: Oligonucleotide to act as a primer for PCR

<400> SEQUENCE: 42
ggggaccact ttgtacaaga aagctgggtc gtaatacgac tcactatagg gc              52

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide to act as a primer for PCR

<400> SEQUENCE: 43
ccgtcgacta tgcagcctcg tcaaacataa                                      30

<210> SEQ ID NO 44
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 44
ccgtcgacta ccacagccta aatggagta                                       29

<210> SEQ ID NO 45
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 45
ccgtcgacta tatgctcgaa ttttcgttca c                                    31

<210> SEQ ID NO 46
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 46
ccgtcgacta gcattctgaa gcttcctcc                                       29

<210> SEQ ID NO 47
<211> LENGTH: 30
<212> TYPE: DNA
<213> ORGANISM: Artificial Sequence
<220> FEATURE:
<223> OTHER INFORMATION: Oligonucleotide to act as a primer for PCR

<400> SEQUENCE: 47
ccgtcgacta cttttgacg gaactattcc                                       30
```

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide to act as a primer for PCR

<400> SEQUENCE: 48
tatccttcgc aagacccttc                                              20

<210> SEQ ID NO 49
<211> LENGTH: 788
<212> TYPE: PRT
<213> ORGANISM: Oryza sativa

<400> SEQUENCE: 49

```
Met Thr Ser Asp Asn Gly Lys Ala Pro Asp Lys Asp Gly Glu Pro Ser
1               5                   10                  15

Gly Pro Pro Ser Ala Pro Gln Glu Gly Glu Ile Ser Asn Glu Pro Lys
            20                  25                  30

Arg Arg Arg Pro Leu Asn Gly Arg Thr Thr Gly Pro Thr Arg Arg Ser
        35                  40                  45

Thr Lys Gly Asn Trp Thr Pro Glu Glu Asp Ala Ile Leu Ser Arg Ala
    50                  55                  60

Val Gln Thr Tyr Asn Gly Lys Asn Trp Lys Lys Ile Ala Glu Cys Phe
65                  70                  75                  80

Pro Asp Arg Thr Asp Val Gln Cys Leu His Arg Trp Gln Lys Val Leu
                85                  90                  95

Asn Pro Glu Leu Val Lys Gly Pro Trp Ser Lys Glu Glu Asp Glu Ile
            100                 105                 110

Ile Val Gln Met Val Asn Lys Leu Gly Pro Lys Lys Trp Ser Thr Ile
        115                 120                 125

Ala Gln Ala Leu Pro Gly Arg Ile Gly Lys Gln Cys Arg Glu Arg Trp
    130                 135                 140

Tyr Asn His Leu Asn Pro Gly Ile Asn Lys Glu Ala Trp Thr Gln Glu
145                 150                 155                 160

Glu Glu Ile Thr Leu Ile His Ala His Arg Met Tyr Gly Asn Lys Trp
                165                 170                 175

Ala Glu Leu Thr Lys Phe Leu Pro Gly Arg Thr Asp Asn Ser Ile Lys
            180                 185                 190

Asn His Trp Asn Ser Ser Val Lys Lys Val Asn Ser Tyr Met Ser
        195                 200                 205

Ser Gly Leu Leu Thr Gln Val Ser Cys Leu Pro Leu Asn Glu Tyr Ser
    210                 215                 220

Ala Asn Cys Asn Ser Ser Pro Ala Met Thr Gln Gln Asn Ser Glu Asp
225                 230                 235                 240

Ser Gly Cys Phe Ala Val Arg Glu Val Glu Asn Ser Ser Gly Cys Ser
                245                 250                 255

Gln Ser Ser Leu Ala Lys Val Ser Cys Ser Gln Val His Asp Thr Thr
            260                 265                 270

Val Pro Leu Gly Cys Asp Leu Gln Val Asn Ala Asn Phe Asp Lys Asn
        275                 280                 285

Glu Ala His Asp Ser Gln Ser Ser Met Gly Pro Gln Ala Cys Tyr Thr
    290                 295                 300

Ser Ala Glu Ala Val Ala Ser Ala Leu Pro Ala Val His Cys His Val
305                 310                 315                 320
```

-continued

```
Ser Ser Ser Asn Leu Asp Pro Asp Gln His Leu Gln Glu Asp Phe Ala
            325                 330                 335

Gln Gly Leu Asn Leu Asp Met Thr Ile Asp Glu Met Pro Thr Val Pro
            340                 345                 350

Ser Phe Ala Asp Asn Gln Thr Val Cys Ser Ile Glu Asn His Glu Arg
            355                 360                 365

Ser Leu Glu Pro Tyr Asp Val Ala Met Glu Val Pro Leu Ser Met Leu
            370                 375                 380

Ser Ser Asp Ser Gly Ala Glu Gln Lys Leu His Phe Met Ser Glu Ala
385                 390                 395                 400

Asp Phe Asn Ser Pro Asn Cys Leu Lys Ser Glu Leu Trp Gln Asp Ile
            405                 410                 415

Ser Leu Gln Gly Leu Leu Ser Gly Pro Asp Ala Val Glu Ala Asp Ser
            420                 425                 430

Ile Ser Arg Ser Asn His Gln Ser Asp Val Tyr Ser Ser Glu Ala Asp
            435                 440                 445

Thr His Phe Leu Ala Pro Pro Tyr Met Pro Gln Thr Ser Asn Ser Ser
            450                 455                 460

Ser Val Met Gly Leu Ala Asp Asp Gln Ser Pro Gln Met Ser Val Pro
465                 470                 475                 480

Pro Ser Leu Ile Cys Ser Asn Ala Met Thr Asp Asp Ala Pro Phe Asp
            485                 490                 495

Asn Arg Pro Gly Arg Lys Glu Met Pro Leu Ser Gln Ala Glu Val Val
            500                 505                 510

Thr Gln Ser Ser Ser Ser Gly Asp Ala Glu Met Phe Ala Asn Pro
            515                 520                 525

Gly Cys Ser Asn Asp Arg His Val Pro Ser Ser Thr Met Glu Ser Ile
            530                 535                 540

Pro Glu Cys Gly Asp Gln Gln Val Thr Asn Ala Glu Glu Pro Glu Ala
545                 550                 555                 560

Ser Leu Glu Lys Glu Pro Ser Leu Thr Gln Ser Val Thr Ala Pro Asp
            565                 570                 575

Glu Gln Asp Lys Gly Ala Leu Phe Tyr Glu Pro Pro Arg Phe Pro Ser
            580                 585                 590

Leu Asp Val Pro Phe Val Ser Cys Asp Leu Val Thr Ser Gly Asp Leu
            595                 600                 605

Gln Glu Phe Ser Pro Leu Gly Ile Arg Gln Leu Met His Ser Thr Met
            610                 615                 620

Asn Val Cys Thr Pro Met Arg Leu Trp Gly Ser Pro Thr His Asp Glu
625                 630                 635                 640

Ser Thr Gly Val Leu Leu Lys Ser Ala Ala Lys Ser Phe Ile Cys Thr
            645                 650                 655

Pro Ser Ile Leu Lys Lys Arg His Arg Asp Leu Leu Ser Pro Ile Pro
            660                 665                 670

Asp Lys Arg Ile Glu Lys Lys Tyr Gly Thr Glu Lys Asp Arg Gly Val
            675                 680                 685

Ser Asp Thr Ser Ser Thr Gly Ile Gln Thr Ser Cys Ile Asn Ala Thr
            690                 695                 700

Lys Asp Asp Ala Leu Ile Thr Thr Val Leu Arg Ile Glu Arg Ser Ala
705                 710                 715                 720

Ser Ser Lys Ser Leu Glu Lys Lys Leu Val Phe Ser Asp Glu Asn Lys
            725                 730                 735
```

-continued

```
Glu Asn Leu Gly Tyr Thr Thr Glu Gln Thr Lys Asp Gly Gln Ser Ala
                740                 745                 750
Gly Asn Asp Glu His Met Asp Glu Gln Thr Thr Gly Glu Arg Ser Ser
            755                 760                 765
Ala Thr Asn Val Ala Thr Asn Asp Asp Leu Ser Gly Asn Leu Val Ser
        770                 775                 780
Thr Ser Ser Phe
785

<210> SEQ ID NO 50
<211> LENGTH: 3012
<212> TYPE: DNA
<213> ORGANISM: Nicotiana tabacum
<220> FEATURE:
<221> NAME/KEY: CDS
<222> LOCATION: (1)..(3012)
<223> OTHER INFORMATION: DDBJ Acsession# AB056122, NtmybA1 (DDBJ
      Acsession# BAB70510)

<400> SEQUENCE: 50 atg gaa agt gat aaa acc agc acg acg cct tca gat gat atc agt agt        48
Met Glu Ser Asp Lys Thr Ser Thr Thr Pro Ser Asp Asp Ile Ser Ser
1               5                   10                  15 ctg caa aga gtt cag cct tcg cac ggg agg acg agt ggt cct aag aga        96
Leu Gln Arg Val Gln Pro Ser His Gly Arg Thr Ser Gly Pro Lys Arg
                20                  25                  30 cgt tcc agt cag tgg act ccc gag gag gat gaa atc ttg cgc caa gct       144
Arg Ser Ser Gln Trp Thr Pro Glu Glu Asp Glu Ile Leu Arg Gln Ala
            35                  40                  45 gtc caa cag ttt aag ggg aaa agc tgg aaa agg att gcg gaa tgt ttt       192
Val Gln Gln Phe Lys Gly Lys Ser Trp Lys Arg Ile Ala Glu Cys Phe
        50                  55                  60 aag gac cgg aca gat gtg caa tgc ttg cac agg tgg cag aaa gtt ctt       240
Lys Asp Arg Thr Asp Val Gln Cys Leu His Arg Trp Gln Lys Val Leu
65                  70                  75                  80 gat cct gaa ctt gtc aaa ggc tca tgg act aag gag gag gat gat aaa       288
Asp Pro Glu Leu Val Lys Gly Ser Trp Thr Lys Glu Glu Asp Asp Lys
                85                  90                  95 cta atc gaa tta gtg aac aga tat ggc ccc aaa aaa tgg tcc acc att       336
Leu Ile Glu Leu Val Asn Arg Tyr Gly Pro Lys Lys Trp Ser Thr Ile
                100                 105                 110 gca caa gag tta gca gga cgt att gga aag caa tgc cgg gaa agg tgg       384
Ala Gln Glu Leu Ala Gly Arg Ile Gly Lys Gln Cys Arg Glu Arg Trp
            115                 120                 125 cac aat cat ctg aat cct gca ata aac aaa gaa cct tgg aca caa gag       432
His Asn His Leu Asn Pro Ala Ile Asn Lys Glu Pro Trp Thr Gln Glu
        130                 135                 140 gag gaa ttg act cta att cgt gcc cac caa gtt tat gga aac aag tgg       480
Glu Glu Leu Thr Leu Ile Arg Ala His Gln Val Tyr Gly Asn Lys Trp
145                 150                 155                 160 gca gag tta gca aaa gtt ttg cat gga agg agt gac aat gca ata aag       528
Ala Glu Leu Ala Lys Val Leu His Gly Arg Ser Asp Asn Ala Ile Lys
                165                 170                 175 aat cat tgg cat agt tct gtt aaa aag aaa ctg gac tca tat ttg gca       576
Asn His Trp His Ser Ser Val Lys Lys Lys Leu Asp Ser Tyr Leu Ala
            180                 185                 190 tca ggt tta ctt gca cag ttc cct gct cta cct aat gtc aac cat cag       624
Ser Gly Leu Leu Ala Gln Phe Pro Ala Leu Pro Asn Val Asn His Gln
        195                 200                 205 aac caa tca gtc cct tct tct tct atg acg ttg caa caa aat agt gaa       672
Asn Gln Ser Val Pro Ser Ser Ser Met Thr Leu Gln Gln Asn Ser Glu
```

```
                 210                 215                 220
gat gaa agc gtt cac aaa gaa gga aca gaa gcg gag gat agt tct gtt      720
Asp Glu Ser Val His Lys Glu Gly Thr Glu Ala Glu Asp Ser Ser Val
225                 230                 235                 240 aaa aag aaa ctg gac tca tat tcg gca tca ggt cta ctt gga cag ttc      768
Lys Lys Lys Leu Asp Ser Tyr Ser Ala Ser Gly Leu Leu Gly Gln Phe
                    245                 250                 255 tct gct ctg cct aat gtc aac cat cag aac caa tca gtc cct tct tct      816
Ser Ala Leu Pro Asn Val Asn His Gln Asn Gln Ser Val Pro Ser Ser
                260                 265                 270 tct atg acg ttg caa caa aat agt gaa gat gaa agc gtt cac aaa gaa      864
Ser Met Thr Leu Gln Gln Asn Ser Glu Asp Glu Ser Val His Lys Glu
            275                 280                 285 gga atg gaa gcg gag gaa gtg cct gaa tgc agt caa ggc tcg aat ttt      912
Gly Met Glu Ala Glu Glu Val Pro Glu Cys Ser Gln Gly Ser Asn Phe
        290                 295                 300 gct ggc tgt tct cag tct aca agt gac ttg ggc aac aca ttt gtg cat      960
Ala Gly Cys Ser Gln Ser Thr Ser Asp Leu Gly Asn Thr Phe Val His
305                 310                 315                 320 ata aga gag aac ggt ggg atg tcg gag gaa tca att tgt aaa aag gat     1008
Ile Arg Glu Asn Gly Gly Met Ser Glu Glu Ser Ile Cys Lys Lys Asp
                    325                 330                 335 gca acc tcc agc act gct cca tgt tgt agg aac tat agc cca gtt ttt     1056
Ala Thr Ser Ser Thr Ala Pro Cys Cys Arg Asn Tyr Ser Pro Val Phe
                340                 345                 350 caa gat gtt tct tgt tca atg tta aaa gtt cct agt gaa ctt gcg gat     1104
Gln Asp Val Ser Cys Ser Met Leu Lys Val Pro Ser Glu Leu Ala Asp
            355                 360                 365 tcc aag ttc ctt gag cat aat tta tca cat gac tgg ggc aat tcc atg     1152
Ser Lys Phe Leu Glu His Asn Leu Ser His Asp Trp Gly Asn Ser Met
        370                 375                 380 gaa gaa gat tgg cag ttt aat agg gat gac ata cct aat att tct cct     1200
Glu Glu Asp Trp Gln Phe Asn Arg Asp Asp Ile Pro Asn Ile Ser Pro
385                 390                 395                 400 ccg gag ttt att cag gaa tct tca ggg att tcc gtg cac tgt tta act     1248
Pro Glu Phe Ile Gln Glu Ser Ser Gly Ile Ser Val His Cys Leu Thr
                    405                 410                 415 ggc aac gac aac cat gac atg gta gca act gct aat gta gga aac gtg     1296
Gly Asn Asp Asn His Asp Met Val Ala Thr Ala Asn Val Gly Asn Val
                420                 425                 430 gtt gag gat cca tat aag ccc aac gaa atg ttt gtt tct gtg gac ggt     1344
Val Glu Asp Pro Tyr Lys Pro Asn Glu Met Phe Val Ser Val Asp Gly
            435                 440                 445 tcc atg atg gta tac ccc gag gaa gga att cct caa tgc tct ccg tct     1392
Ser Met Met Val Tyr Pro Glu Glu Gly Ile Pro Gln Cys Ser Pro Ser
        450                 455                 460 gaa act ggg gtt aat ggc tgt ggt caa cct tca tac tct tta ttt tac     1440
Glu Thr Gly Val Asn Gly Cys Gly Gln Pro Ser Tyr Ser Leu Phe Tyr
465                 470                 475                 480 caa tca tca aac tat cag atc cct gaa gca gga gat atg gtt cca caa     1488
Gln Ser Ser Asn Tyr Gln Ile Pro Glu Ala Gly Asp Met Val Pro Gln
                    485                 490                 495 aac tgc aat gct tta aat ttt gat gat ttt gaa gct tca ttc cat cag     1536
Asn Cys Asn Ala Leu Asn Phe Asp Asp Phe Glu Ala Ser Phe His Gln
                500                 505                 510 cca ttt tct gtt cct tca caa ttt tct tca gag gat aga tcg tct gtg     1584
Pro Phe Ser Val Pro Ser Gln Phe Ser Ser Glu Asp Arg Ser Ser Val
            515                 520                 525 ttt gac att gtt tta aat cag ttc cat aat cct ccg ctt gaa ggc cca     1632
```

```
                Phe Asp Ile Val Leu Asn Gln Phe His Asn Pro Pro Leu Glu Gly Pro
                    530                 535                 540 gat cat atg aaa gat tcc tca agg ata gtt ccc gtg aat gat att ggc      1680
Asp His Met Lys Asp Ser Ser Arg Ile Val Pro Val Asn Asp Ile Gly
545                 550                 555                 560 tca act aca tca aac act gtt caa aca tgt ctg ctg aat gaa aat tca      1728
Ser Thr Thr Ser Asn Thr Val Gln Thr Cys Leu Leu Asn Glu Asn Ser
                    565                 570                 575 ttt gta caa gaa gag cag aaa gat gga gga gct tta tgc tat gac cct      1776
Phe Val Gln Glu Glu Gln Lys Asp Gly Gly Ala Leu Cys Tyr Asp Pro
                580                 585                 590 cct cgt ttt cca agc tcg gat gtt cct ttc ttt tgt tgt gat ctt ata      1824
Pro Arg Phe Pro Ser Ser Asp Val Pro Phe Phe Cys Cys Asp Leu Ile
            595                 600                 605 caa tct ggt tca gat aca cag gaa gag tat agc cct ttt ggc atc cgg      1872
Gln Ser Gly Ser Asp Thr Gln Glu Glu Tyr Ser Pro Phe Gly Ile Arg
        610                 615                 620 cag ttg atg atg act tcg gcg aac tgc ctt act cca tta agg ttg tgg      1920
Gln Leu Met Met Thr Ser Ala Asn Cys Leu Thr Pro Leu Arg Leu Trp
625                 630                 635                 640 gat tca cca tca aga gat gat agt cca gat gct atc ttg aaa agt gct      1968
Asp Ser Pro Ser Arg Asp Asp Ser Pro Asp Ala Ile Leu Lys Ser Ala
                    645                 650                 655 gcc aaa act ttt aca ggg aca cct tct ata cta aag aag cga cat cgt      2016
Ala Lys Thr Phe Thr Gly Thr Pro Ser Ile Leu Lys Lys Arg His Arg
                660                 665                 670 cat tta ctg tcg cct ttg tca gaa aag aga tgt gag aaa aag ctt gaa      2064
His Leu Leu Ser Pro Leu Ser Glu Lys Arg Cys Glu Lys Lys Leu Glu
            675                 680                 685 agc aat ctc aat cag gaa tca ttc tat aat atg tct aca aac ttt tcc      2112
Ser Asn Leu Asn Gln Glu Ser Phe Tyr Asn Met Ser Thr Asn Phe Ser
        690                 695                 700 cga cca gac gat atg ttt gat gag tca gca aat gaa aaa gca tct atg      2160
Arg Pro Asp Asp Met Phe Asp Glu Ser Ala Asn Glu Lys Ala Ser Met
705                 710                 715                 720 gaa gac aaa gaa aat cta cat cca tcc tca gaa gat gga aga aaa gag      2208
Glu Asp Lys Glu Asn Leu His Pro Ser Ser Glu Asp Gly Arg Lys Glu
                    725                 730                 735 gag ggc gaa att tct gga gcc aat gat gca acg gga atg gta aaa cag      2256
Glu Gly Glu Ile Ser Gly Ala Asn Asp Ala Thr Gly Met Val Lys Gln
                740                 745                 750 cat cct gga gtg ctg gtt gag ctt agc tca aat gac ttg ttc ttt tct      2304
His Pro Gly Val Leu Val Glu Leu Ser Ser Asn Asp Leu Phe Phe Ser
            755                 760                 765 cct gat cgt ttc tta atc aag tgt gat aga gct aca agt cta agt aat      2352
Pro Asp Arg Phe Leu Ile Lys Cys Asp Arg Ala Thr Ser Leu Ser Asn
        770                 775                 780 aaa gct ctg ggt agg cag tat gct aga cga ctt gaa gct gca tca aat      2400
Lys Ala Leu Gly Arg Gln Tyr Ala Arg Arg Leu Glu Ala Ala Ser Asn
785                 790                 795                 800 caa gtt act gtt tcg tcc tct ttt gaa act tca tgc ttg tct gtt gta      2448
Gln Val Thr Val Ser Ser Ser Phe Glu Thr Ser Cys Leu Ser Val Val
                    805                 810                 815 tgc tct cct gac ata tgt ggg aag cat aga ggc agt gtt gtc ata gct      2496
Cys Ser Pro Asp Ile Cys Gly Lys His Arg Gly Ser Val Val Ile Ala
                820                 825                 830 aca tca act gct ttg gag aat aca gct gaa gat tct gaa aat gga ttt      2544
Thr Ser Thr Ala Leu Glu Asn Thr Ala Glu Asp Ser Glu Asn Gly Phe
            835                 840                 845
```

```
ggt gct gag act tta agc ata ttt gga gag aca cct ttt aaa agg agt     2592
Gly Ala Glu Thr Leu Ser Ile Phe Gly Glu Thr Pro Phe Lys Arg Ser
    850                 855                 860 ttt gaa tct cct tca gca tgg aaa tct cca tgg ttc atg agt tct ttt     2640
Phe Glu Ser Pro Ser Ala Trp Lys Ser Pro Trp Phe Met Ser Ser Phe
865                 870                 875                 880 ccg cca agc aca aga tat gat aca gaa ctt gaa ttt gag gat ttt gcc     2688
Pro Pro Ser Thr Arg Tyr Asp Thr Glu Leu Glu Phe Glu Asp Phe Ala
                885                 890                 895 ctt ttt atg agc ccg ggt gac aga agc tat gat gct att ggg tta atg     2736
Leu Phe Met Ser Pro Gly Asp Arg Ser Tyr Asp Ala Ile Gly Leu Met
            900                 905                 910 aag caa tta agt gag cag aca gca cct tca att gca gat gcc cat cag     2784
Lys Gln Leu Ser Glu Gln Thr Ala Pro Ser Ile Ala Asp Ala His Gln
        915                 920                 925 atc ttg gga agt gaa act cca gaa aca aac ttg tcg aaa agg aat tcc     2832
Ile Leu Gly Ser Glu Thr Pro Glu Thr Asn Leu Ser Lys Arg Asn Ser
    930                 935                 940 aaa aaa ccg aaa gca gat gaa aat tgt acc ctt ctg gct tca aat gct     2880
Lys Lys Pro Lys Ala Asp Glu Asn Cys Thr Leu Leu Ala Ser Asn Ala
945                 950                 955                 960 acg agt gag aga cga aca ctc gat ttt aat gaa tgt gga att cca gga     2928
Thr Ser Glu Arg Arg Thr Leu Asp Phe Asn Glu Cys Gly Ile Pro Gly
                965                 970                 975 aag gga aag gaa act acc aaa ttt ggc agc aac aac aac agc ttt tca     2976
Lys Gly Lys Glu Thr Thr Lys Phe Gly Ser Asn Asn Asn Ser Phe Ser
            980                 985                 990 agt cct tcc tcc tac ctg ttg aaa  tat tgc aga taa                    3012
Ser Pro Ser Ser Tyr Leu Leu Lys  Tyr Cys Arg
        995                 1000
```

<210> SEQ ID NO 51
<211> LENGTH: 1003
<212> TYPE: PRT
<213> ORGANISM: Nicotiana tabacum

<400> SEQUENCE: 51

```
Met Glu Ser Asp Lys Thr Ser Thr Thr Pro Ser Asp Asp Ile Ser Ser
1               5                   10                  15

Leu Gln Arg Val Gln Pro Ser His Gly Arg Thr Ser Gly Pro Lys Arg
            20                  25                  30

Arg Ser Ser Gln Trp Thr Pro Glu Glu Asp Glu Ile Leu Arg Gln Ala
        35                  40                  45

Val Gln Gln Phe Lys Gly Lys Ser Trp Lys Arg Ile Ala Glu Cys Phe
    50                  55                  60

Lys Asp Arg Thr Asp Val Gln Cys Leu His Arg Trp Gln Lys Val Leu
65                  70                  75                  80

Asp Pro Glu Leu Val Lys Gly Ser Trp Thr Lys Glu Glu Asp Asp Lys
                85                  90                  95

Leu Ile Glu Leu Val Asn Arg Tyr Gly Pro Lys Lys Trp Ser Thr Ile
            100                 105                 110

Ala Gln Glu Leu Ala Gly Arg Ile Gly Lys Gln Cys Arg Glu Arg Trp
        115                 120                 125

His Asn His Leu Asn Pro Ala Ile Asn Lys Glu Pro Trp Thr Gln Glu
    130                 135                 140

Glu Glu Leu Thr Leu Ile Arg Ala His Gln Val Tyr Gly Asn Lys Trp
145                 150                 155                 160

Ala Glu Leu Ala Lys Val Leu His Gly Arg Ser Asp Asn Ala Ile Lys
```

-continued

```
                165                 170                 175
Asn His Trp His Ser Ser Val Lys Lys Leu Asp Ser Tyr Leu Ala
            180                 185                 190
Ser Gly Leu Leu Ala Gln Phe Pro Ala Leu Pro Asn Val Asn His Gln
            195                 200                 205
Asn Gln Ser Val Pro Ser Ser Met Thr Leu Gln Gln Asn Ser Glu
    210                 215                 220
Asp Glu Ser Val His Lys Glu Gly Thr Glu Ala Glu Asp Ser Ser Val
225                 230                 235                 240
Lys Lys Lys Leu Asp Ser Tyr Ser Ala Ser Gly Leu Leu Gly Gln Phe
                245                 250                 255
Ser Ala Leu Pro Asn Val Asn His Gln Asn Gln Ser Val Pro Ser Ser
            260                 265                 270
Ser Met Thr Leu Gln Gln Asn Ser Glu Asp Glu Ser Val His Lys Glu
        275                 280                 285
Gly Met Glu Ala Glu Val Pro Glu Cys Ser Gln Gly Ser Asn Phe
    290                 295                 300
Ala Gly Cys Ser Gln Ser Thr Ser Asp Leu Gly Asn Thr Phe Val His
305                 310                 315                 320
Ile Arg Glu Asn Gly Gly Met Ser Glu Ser Ile Cys Lys Lys Asp
                325                 330                 335
Ala Thr Ser Ser Thr Ala Pro Cys Cys Arg Asn Tyr Ser Pro Val Phe
            340                 345                 350
Gln Asp Val Ser Cys Ser Met Leu Lys Val Pro Ser Glu Leu Ala Asp
        355                 360                 365
Ser Lys Phe Leu Glu His Asn Leu Ser His Asp Trp Gly Asn Ser Met
    370                 375                 380
Glu Glu Asp Trp Gln Phe Asn Arg Asp Asp Ile Pro Asn Ile Ser Pro
385                 390                 395                 400
Pro Glu Phe Ile Gln Glu Ser Ser Gly Ile Ser Val His Cys Leu Thr
                405                 410                 415
Gly Asn Asp Asn His Asp Met Val Ala Thr Ala Asn Val Gly Asn Val
            420                 425                 430
Val Glu Asp Pro Tyr Lys Pro Asn Glu Met Phe Val Ser Val Asp Gly
        435                 440                 445
Ser Met Met Val Tyr Pro Glu Glu Gly Ile Pro Gln Cys Ser Pro Ser
    450                 455                 460
Glu Thr Gly Val Asn Gly Cys Gly Gln Pro Ser Tyr Ser Leu Phe Tyr
465                 470                 475                 480
Gln Ser Ser Asn Tyr Gln Ile Pro Glu Ala Gly Asp Met Val Pro Gln
                485                 490                 495
Asn Cys Asn Ala Leu Asn Phe Asp Asp Phe Glu Ala Ser Phe His Gln
            500                 505                 510
Pro Phe Ser Val Pro Ser Gln Phe Ser Ser Glu Asp Arg Ser Ser Val
        515                 520                 525
Phe Asp Ile Val Leu Asn Gln Phe His Asn Pro Pro Leu Glu Gly Pro
    530                 535                 540
Asp His Met Lys Asp Ser Ser Arg Ile Val Pro Val Asn Asp Ile Gly
545                 550                 555                 560
Ser Thr Thr Ser Asn Thr Val Gln Thr Cys Leu Leu Asn Glu Asn Ser
                565                 570                 575
Phe Val Gln Glu Glu Gln Lys Asp Gly Gly Ala Leu Cys Tyr Asp Pro
            580                 585                 590
```

```
Pro Arg Phe Pro Ser Ser Asp Val Pro Phe Cys Cys Asp Leu Ile
            595                 600                 605

Gln Ser Gly Ser Asp Thr Gln Glu Glu Tyr Ser Pro Phe Gly Ile Arg
            610                 615                 620

Gln Leu Met Met Thr Ser Ala Asn Cys Leu Thr Pro Leu Arg Leu Trp
625                 630                 635                 640

Asp Ser Pro Ser Arg Asp Asp Ser Pro Asp Ala Ile Leu Lys Ser Ala
                645                 650                 655

Ala Lys Thr Phe Thr Gly Thr Pro Ser Ile Leu Lys Lys Arg His Arg
                660                 665                 670

His Leu Leu Ser Pro Leu Ser Glu Lys Arg Cys Glu Lys Lys Leu Glu
            675                 680                 685

Ser Asn Leu Asn Gln Glu Ser Phe Tyr Asn Met Ser Thr Asn Phe Ser
            690                 695                 700

Arg Pro Asp Asp Met Phe Asp Glu Ser Ala Asn Glu Lys Ala Ser Met
705                 710                 715                 720

Glu Asp Lys Glu Asn Leu His Pro Ser Glu Asp Gly Arg Lys Glu
                725                 730                 735

Glu Gly Glu Ile Ser Gly Ala Asn Asp Ala Thr Gly Met Val Lys Gln
                740                 745                 750

His Pro Gly Val Leu Val Glu Leu Ser Ser Asn Asp Leu Phe Phe Ser
            755                 760                 765

Pro Asp Arg Phe Leu Ile Lys Cys Asp Arg Ala Thr Ser Leu Ser Asn
            770                 775                 780

Lys Ala Leu Gly Arg Gln Tyr Ala Arg Arg Leu Glu Ala Ala Ser Asn
785                 790                 795                 800

Gln Val Thr Val Ser Ser Phe Glu Thr Ser Cys Leu Ser Val Val
                805                 810                 815

Cys Ser Pro Asp Ile Cys Gly Lys His Arg Gly Ser Val Val Ile Ala
                820                 825                 830

Thr Ser Thr Ala Leu Glu Asn Thr Ala Glu Asp Ser Glu Asn Gly Phe
            835                 840                 845

Gly Ala Glu Thr Leu Ser Ile Phe Gly Glu Thr Pro Phe Lys Arg Ser
850                 855                 860

Phe Glu Ser Pro Ser Ala Trp Lys Ser Pro Trp Phe Met Ser Ser Phe
865                 870                 875                 880

Pro Pro Ser Thr Arg Tyr Asp Thr Glu Leu Glu Phe Glu Asp Phe Ala
                885                 890                 895

Leu Phe Met Ser Pro Gly Asp Arg Ser Tyr Asp Ala Ile Gly Leu Met
                900                 905                 910

Lys Gln Leu Ser Glu Gln Thr Ala Pro Ser Ile Ala Asp Ala His Gln
            915                 920                 925

Ile Leu Gly Ser Glu Thr Pro Glu Thr Asn Leu Ser Lys Arg Asn Ser
            930                 935                 940

Lys Lys Pro Lys Ala Asp Glu Asn Cys Thr Leu Leu Ala Ser Asn Ala
945                 950                 955                 960

Thr Ser Glu Arg Arg Thr Leu Asp Phe Asn Glu Cys Gly Ile Pro Gly
                965                 970                 975

Lys Gly Lys Glu Thr Thr Lys Phe Gly Ser Asn Asn Ser Phe Ser
                980                 985                 990

Ser Pro Ser Ser Tyr Leu Leu Lys Tyr Cys Arg
            995                 1000
```

-continued

```
<210> SEQ ID NO 52
<211> LENGTH: 3129
<212> TYPE: DNA
<213> ORGANISM: Nicotiana tabacum
<220> FEATURE:
<221> NAME/KEY: CDS
<222> LOCATION: (1)..(3129)
<223> OTHER INFORMATION: DDBJ Acsession# AB056123, NtmybA2 (DDBJ
      Acsession# BAB70511)

<400> SEQUENCE: 52
```

| | | | | | | | | | | | | | | | | |
|---|---|---|---|---|---|---|---|---|---|---|---|---|---|---|---|---|
| atg | gaa | agt | gat | aga | ata | agc | act | cct | tca | gat | ggc | act | agc | agt | agt | 48 |
| Met | Glu | Ser | Asp | Arg | Ile | Ser | Thr | Pro | Ser | Asp | Gly | Thr | Ser | Ser | Ser | |
| 1 | | | | 5 | | | | | 10 | | | | | 15 | | |
| ctc | caa | aga | gtt | cgg | cct | ttg | cat | ggg | aga | act | agt | ggt | cct | acg | aga | 96 |
| Leu | Gln | Arg | Val | Arg | Pro | Leu | His | Gly | Arg | Thr | Ser | Gly | Pro | Thr | Arg | |
| | | | 20 | | | | | 25 | | | | | 30 | | | |
| cgt | tca | aca | aag | ggg | cag | tgg | act | act | gaa | gaa | gac | gag | atc | cta | cgc | 144 |
| Arg | Ser | Thr | Lys | Gly | Gln | Trp | Thr | Thr | Glu | Glu | Asp | Glu | Ile | Leu | Arg | |
| | | 35 | | | | | 40 | | | | | 45 | | | | |
| aaa | gct | gtc | caa | cgt | ttt | aag | ggc | aaa | aac | tgg | aaa | aaa | ata | gcg | gaa | 192 |
| Lys | Ala | Val | Gln | Arg | Phe | Lys | Gly | Lys | Asn | Trp | Lys | Lys | Ile | Ala | Glu | |
| | 50 | | | | | 55 | | | | | 60 | | | | | |
| tgt | ttt | aaa | gac | cgg | act | gat | gta | caa | tgc | ttg | cac | cgg | tgg | cag | aaa | 240 |
| Cys | Phe | Lys | Asp | Arg | Thr | Asp | Val | Gln | Cys | Leu | His | Arg | Trp | Gln | Lys | |
| 65 | | | | | 70 | | | | | 75 | | | | | 80 | |
| gtt | ctt | aat | cct | gaa | ctt | gtc | aaa | ggt | cca | tgg | tct | aaa | gag | gag | gat | 288 |
| Val | Leu | Asn | Pro | Glu | Leu | Val | Lys | Gly | Pro | Trp | Ser | Lys | Glu | Glu | Asp | |
| | | | | 85 | | | | | 90 | | | | | 95 | | |
| gaa | gta | ata | gtt | gaa | tta | gtt | aag | aaa | tat | ggc | ccc | aaa | aag | tgg | tcc | 336 |
| Glu | Val | Ile | Val | Glu | Leu | Val | Lys | Lys | Tyr | Gly | Pro | Lys | Lys | Trp | Ser | |
| | | | 100 | | | | | 105 | | | | | 110 | | | |
| acc | atc | gct | caa | cat | ttg | ccg | gga | cgt | att | gga | aaa | caa | tgt | cga | gaa | 384 |
| Thr | Ile | Ala | Gln | His | Leu | Pro | Gly | Arg | Ile | Gly | Lys | Gln | Cys | Arg | Glu | |
| | | 115 | | | | | 120 | | | | | 125 | | | | |
| agg | tgg | cac | aat | cat | ctg | aat | cct | gga | ata | aac | aag | gaa | gct | tgg | acg | 432 |
| Arg | Trp | His | Asn | His | Leu | Asn | Pro | Gly | Ile | Asn | Lys | Glu | Ala | Trp | Thr | |
| | 130 | | | | | 135 | | | | | 140 | | | | | |
| cag | gag | gag | gag | ttg | act | ctg | att | cgt | gcc | cat | caa | att | tac | ggg | aat | 480 |
| Gln | Glu | Glu | Glu | Leu | Thr | Leu | Ile | Arg | Ala | His | Gln | Ile | Tyr | Gly | Asn | |
| 145 | | | | | 150 | | | | | 155 | | | | | 160 | |
| aaa | tgg | gca | gag | tta | acg | aag | tat | ttg | cct | gga | agg | aca | gat | aat | gca | 528 |
| Lys | Trp | Ala | Glu | Leu | Thr | Lys | Tyr | Leu | Pro | Gly | Arg | Thr | Asp | Asn | Ala | |
| | | | | 165 | | | | | 170 | | | | | 175 | | |
| ata | aaa | aat | cac | tgg | aat | agt | tcc | gtc | aaa | aag | aaa | ttg | gac | tcg | tat | 576 |
| Ile | Lys | Asn | His | Trp | Asn | Ser | Ser | Val | Lys | Lys | Lys | Leu | Asp | Ser | Tyr | |
| | | | 180 | | | | | 185 | | | | | 190 | | | |
| ttg | gca | tca | ggt | tta | ctt | gca | cag | ttc | cct | gct | ttg | cct | aat | gtc | aac | 624 |
| Leu | Ala | Ser | Gly | Leu | Leu | Ala | Gln | Phe | Pro | Ala | Leu | Pro | Asn | Val | Asn | |
| | | 195 | | | | | 200 | | | | | 205 | | | | |
| cgt | cag | aac | caa | tca | atc | cct | tct | tcg | gcg | aag | ttg | caa | cag | agt | agt | 672 |
| Arg | Gln | Asn | Gln | Ser | Ile | Pro | Ser | Ser | Ala | Lys | Leu | Gln | Gln | Ser | Ser | |
| | 210 | | | | | 215 | | | | | 220 | | | | | |
| gaa | gat | gat | agt | gtt | cgt | aaa | gaa | gga | acc | gaa | atg | gag | gaa | gct | tca | 720 |
| Glu | Asp | Asp | Ser | Val | Arg | Lys | Glu | Gly | Thr | Glu | Met | Glu | Glu | Ala | Ser | |
| 225 | | | | | 230 | | | | | 235 | | | | | 240 | |
| gaa | tgc | agt | caa | ggg | tca | aat | ctt | gct | ggc | tgt | tcc | cag | tct | aca | agt | 768 |
| Glu | Cys | Ser | Gln | Gly | Ser | Asn | Leu | Ala | Gly | Cys | Ser | Gln | Ser | Thr | Ser | |
| | | | | 245 | | | | | 250 | | | | | 255 | | |
| gac | atg | ggc | aac | aaa | ttt | gta | cat | aca | aga | gag | gag | ggc | aag | ttg | ctg | 816 |
| Asp | Met | Gly | Asn | Lys | Phe | Val | His | Thr | Arg | Glu | Glu | Gly | Lys | Leu | Leu | |

-continued

```
                260                 265                 270
gag gat tca aat tat agg aag gac cca agc tcc agt tca gca cca tgc      864
Glu Asp Ser Asn Tyr Arg Lys Asp Pro Ser Ser Ser Ser Ala Pro Cys
        275                 280                 285 tct gaa tac tat acc cca gcc ttt gaa gat att acc ttt tca atg gca      912
Ser Glu Tyr Tyr Thr Pro Ala Phe Glu Asp Ile Thr Phe Ser Met Ala
    290                 295                 300 gaa gtg cct agt gaa ctt gac gaa tcc aag ctc ctg gag cat acc ttc      960
Glu Val Pro Ser Glu Leu Asp Glu Ser Lys Leu Leu Glu His Thr Phe
305                 310                 315                 320 tca cat gac tgg gca gca tcc att gga aaa gaa tgg cag ttt aat cca     1008
Ser His Asp Trp Ala Ala Ser Ile Gly Lys Glu Trp Gln Phe Asn Pro
                325                 330                 335 gat gac ata cct aat att tct ccg ctg gag ttg atg cag gat tct tca     1056
Asp Asp Ile Pro Asn Ile Ser Pro Leu Glu Leu Met Gln Asp Ser Ser
            340                 345                 350 ggg ctc ttc atg cag tgt tta act ggt aat ggg aat cac gat atg gtt     1104
Gly Leu Phe Met Gln Cys Leu Thr Gly Asn Gly Asn His Asp Met Val
        355                 360                 365 acc ttt cca cag caa aat gca gtg aag ttt gaa acg act aat gtc ggg     1152
Thr Phe Pro Gln Gln Asn Ala Val Lys Phe Glu Thr Thr Asn Val Gly
    370                 375                 380 agc atg gtt gtg ggt ttt gat aag ccc aat gag atg ttt acc tct gtg     1200
Ser Met Val Val Gly Phe Asp Lys Pro Asn Glu Met Phe Thr Ser Val
385                 390                 395                 400 gag ggt tgc agg atg gta tac cct gag gca gga att cca caa tac att     1248
Glu Gly Cys Arg Met Val Tyr Pro Glu Ala Gly Ile Pro Gln Tyr Ile
                405                 410                 415 ccc tct gaa gct ggt acg aac ggt gct gat gaa act gca gat tct ttg     1296
Pro Ser Glu Ala Gly Thr Asn Gly Ala Asp Glu Thr Ala Asp Ser Leu
            420                 425                 430 att tgc caa tca tcg aac tat cag atc tct gaa ggt gga aat atg tct     1344
Ile Cys Gln Ser Ser Asn Tyr Gln Ile Ser Glu Gly Gly Asn Met Ser
        435                 440                 445 ata gag aat tgc aac cct ctc tgt tca gat gtt atg gga act tca tcc     1392
Ile Glu Asn Cys Asn Pro Leu Cys Ser Asp Val Met Gly Thr Ser Ser
    450                 455                 460 ggc caa cca ttt tcc att cct tca cag ttt tct tca gag caa agc tca     1440
Gly Gln Pro Phe Ser Ile Pro Ser Gln Phe Ser Ser Glu Gln Ser Ser
465                 470                 475                 480 ctc atg ttt ggt act gcc gca aat cag ttt cat aat cca ttg cag gga     1488
Leu Met Phe Gly Thr Ala Ala Asn Gln Phe His Asn Pro Leu Gln Gly
                485                 490                 495 aac cca gca cag gag tcc cac aca agt aac tct gat ggt ttt cta tat     1536
Asn Pro Ala Gln Glu Ser His Thr Ser Asn Ser Asp Gly Phe Leu Tyr
            500                 505                 510 ccc ttt gaa tct ggt act cct tgt gac aac ata atg gac gat cct ctc     1584
Pro Phe Glu Ser Gly Thr Pro Cys Asp Asn Ile Met Asp Asp Pro Leu
        515                 520                 525 ctg gaa gag caa ctg gat caa act aaa gat tct cta cag cta gtt tct     1632
Leu Glu Glu Gln Leu Asp Gln Thr Lys Asp Ser Leu Gln Leu Val Ser
    530                 535                 540 gtc aat gat ttt cgc aca act cct tca aat act att caa aca tgt cca     1680
Val Asn Asp Phe Arg Thr Thr Pro Ser Asn Thr Ile Gln Thr Cys Pro
545                 550                 555                 560 ttg gtg aac gaa aat tcg agc ata cca gta gag cag aag gat gga gga     1728
Leu Val Asn Glu Asn Ser Ser Ile Pro Val Glu Gln Lys Asp Gly Gly
                565                 570                 575 gcc tta tac tat gag cct cct cgt ttt ccg agc ttg gac att cca ttt     1776
```

```
Ala Leu Tyr Tyr Glu Pro Pro Arg Phe Pro Ser Leu Asp Ile Pro Phe
            580                 585                 590 ttc agt tgt gat ctt ata caa tct ggt aca gat gca cag caa gag tac    1824
Phe Ser Cys Asp Leu Ile Gln Ser Gly Thr Asp Ala Gln Gln Glu Tyr
        595                 600                 605 agc cct ctt ggc atc cgc cag ttg atg atg act tct gtg aac tgt ctt    1872
Ser Pro Leu Gly Ile Arg Gln Leu Met Met Thr Ser Val Asn Cys Leu
    610                 615                 620 act cca ttt agg ctg tgg gat tca cca tct aga gat gga agt aca gat    1920
Thr Pro Phe Arg Leu Trp Asp Ser Pro Ser Arg Asp Gly Ser Thr Asp
625                 630                 635                 640 gcc gtc ctg aga agt gct gcc aaa act ttc acc agc aca cct tct ata    1968
Ala Val Leu Arg Ser Ala Ala Lys Thr Phe Thr Ser Thr Pro Ser Ile
                645                 650                 655 tta aag aag cga cac cgt gat ttg gtg tca cct ttg tca gaa aag aga    2016
Leu Lys Lys Arg His Arg Asp Leu Val Ser Pro Leu Ser Glu Lys Arg
            660                 665                 670 tgt gaa aag aag ctt gga agt gat ttc cgt caa gaa tca ttc tct gat    2064
Cys Glu Lys Lys Leu Gly Ser Asp Phe Arg Gln Glu Ser Phe Ser Asp
        675                 680                 685 ctg tct aag gat ttt tct cga cta gat gtt atg ttt gac gag gct gca    2112
Leu Ser Lys Asp Phe Ser Arg Leu Asp Val Met Phe Asp Glu Ala Ala
    690                 695                 700 aat gaa aaa gca aca aag tct tct cta act acg gat caa aca ttg gaa    2160
Asn Glu Lys Ala Thr Lys Ser Ser Leu Thr Thr Asp Gln Thr Leu Glu
705                 710                 715                 720 ctt gaa gct tca tct gaa gat aaa gaa aac ata aat cca act gaa gat    2208
Leu Glu Ala Ser Ser Glu Asp Lys Glu Asn Ile Asn Pro Thr Glu Asp
                725                 730                 735 gga agt aag gag gag gac aag gta cgt aat gga ctt tcc aac gag aga    2256
Gly Ser Lys Glu Glu Asp Lys Val Arg Asn Gly Leu Ser Asn Glu Arg
            740                 745                 750 cag tta gat gga ggt gaa gtt cac tat aaa gag aaa gga aca agg gag    2304
Gln Leu Asp Gly Gly Glu Val His Tyr Lys Glu Lys Gly Thr Arg Glu
        755                 760                 765 ggc aca aag ggt gga gcc aat agt gca att gga aag ata aaa caa cct    2352
Gly Thr Lys Gly Gly Ala Asn Ser Ala Ile Gly Lys Ile Lys Gln Pro
    770                 775                 780 tct gga gtt ctg gtt gaa ctg aac gca agt gac ctg ttc ttc tct cct    2400
Ser Gly Val Leu Val Glu Leu Asn Ala Ser Asp Leu Phe Phe Ser Pro
785                 790                 795                 800 gat cgt ttt gga gcc aag tct ggt aga gct aca tat ctc agc agt aaa    2448
Asp Arg Phe Gly Ala Lys Ser Gly Arg Ala Thr Tyr Leu Ser Ser Lys
                805                 810                 815 gct cta gga aat cag tac gct aga cga ctc gaa gct gca tca aat caa    2496
Ala Leu Gly Asn Gln Tyr Ala Arg Arg Leu Glu Ala Ala Ser Asn Gln
            820                 825                 830 ggt tct gtt tca tct tca ttt gag act tca tgt ttt tct gtt att tgc    2544
Gly Ser Val Ser Ser Ser Phe Glu Thr Ser Cys Phe Ser Val Ile Cys
        835                 840                 845 tct cct cgt ata cgt gga aag aaa gac gga agt agt ttt atc atc act    2592
Ser Pro Arg Ile Arg Gly Lys Lys Asp Gly Ser Ser Phe Ile Ile Thr
    850                 855                 860 aca tca atg caa tct gct cca gca cca aca gcc ttg gac aac tca gct    2640
Thr Ser Met Gln Ser Ala Pro Ala Pro Thr Ala Leu Asp Asn Ser Ala
865                 870                 875                 880 gaa act tca gga aat gga gtt ggc gcg gag act gta agc ata tct gga    2688
Glu Thr Ser Gly Asn Gly Val Gly Ala Glu Thr Val Ser Ile Ser Gly
                885                 890                 895
```

-continued

```
gaa acg cct tat aaa agg agt att gaa tct cct tca gct tgg aaa tct       2736
Glu Thr Pro Tyr Lys Arg Ser Ile Glu Ser Pro Ser Ala Trp Lys Ser
        900                 905                 910 cca tgg ttc atc aac tct ctt ctg tca agc cca aga ctt gat aat gaa       2784
Pro Trp Phe Ile Asn Ser Leu Leu Ser Ser Pro Arg Leu Asp Asn Glu
    915                 920                 925 ctt aat ttt gag gat ctt gca ctg ttt atg agt cca ggt gac aga agc       2832
Leu Asn Phe Glu Asp Leu Ala Leu Phe Met Ser Pro Gly Asp Arg Ser
930                 935                 940 tat gat gct att gga ttg atg aag caa ttg agt gag cag act gca ggg       2880
Tyr Asp Ala Ile Gly Leu Met Lys Gln Leu Ser Glu Gln Thr Ala Gly
945                 950                 955                 960 gca ttt gca gac gca cag gag gtc ttg gga ggt gaa act cca gag tca       2928
Ala Phe Ala Asp Ala Gln Glu Val Leu Gly Gly Glu Thr Pro Glu Ser
                965                 970                 975 atc cta cgg ggg agg aac tcc aaa aac cag aaa gca gat gaa aat cat       2976
Ile Leu Arg Gly Arg Asn Ser Lys Asn Gln Lys Ala Asp Glu Asn His
            980                 985                 990 tca ctt ttg tct gca aat gtt atg agt gag agg cgt act ctt gat ttc       3024
Ser Leu Leu Ser Ala Asn Val Met Ser Glu Arg Arg Thr Leu Asp Phe
        995                 1000                1005 agt gaa tgt gga tca cct gga aag gga aag gaa act gaa aat ttt           3069
Ser Glu Cys Gly Ser Pro Gly Lys Gly Lys Glu Thr Glu Asn Phe
    1010                1015                1020 tgc acg agc aac aac agc ttt tca agt cct tcc tcc tac cta ttg           3114
Cys Thr Ser Asn Asn Ser Phe Ser Ser Pro Ser Ser Tyr Leu Leu
1025                1030                1035 aaa ggc tgc agg tag                                                   3129
Lys Gly Cys Arg
1040

<210> SEQ ID NO 53
<211> LENGTH: 1042
<212> TYPE: PRT
<213> ORGANISM: Nicotiana tabacum

<400> SEQUENCE: 53

Met Glu Ser Asp Arg Ile Ser Thr Pro Ser Asp Gly Thr Ser Ser Ser
1               5                   10                  15

Leu Gln Arg Val Arg Pro Leu His Gly Arg Thr Ser Gly Pro Thr Arg
            20                  25                  30

Arg Ser Thr Lys Gly Gln Trp Thr Thr Glu Glu Asp Glu Ile Leu Arg
        35                  40                  45

Lys Ala Val Gln Arg Phe Lys Gly Lys Asn Trp Lys Lys Ile Ala Glu
    50                  55                  60

Cys Phe Lys Asp Arg Thr Asp Val Gln Cys Leu His Arg Trp Gln Lys
65                  70                  75                  80

Val Leu Asn Pro Glu Leu Val Lys Gly Pro Trp Ser Lys Glu Glu Asp
                85                  90                  95

Glu Val Ile Val Glu Leu Val Lys Lys Tyr Gly Pro Lys Lys Trp Ser
            100                 105                 110

Thr Ile Ala Gln His Leu Pro Gly Arg Ile Gly Lys Gln Cys Arg Glu
        115                 120                 125

Arg Trp His Asn His Leu Asn Pro Gly Ile Asn Lys Glu Ala Trp Thr
    130                 135                 140

Gln Glu Glu Glu Leu Thr Leu Ile Arg Ala His Gln Ile Tyr Gly Asn
145                 150                 155                 160

Lys Trp Ala Glu Leu Thr Lys Tyr Leu Pro Gly Arg Thr Asp Asn Ala
```

-continued

```
                165                 170                 175
Ile Lys Asn His Trp Asn Ser Ser Val Lys Lys Leu Asp Ser Tyr
            180                 185                 190
Leu Ala Ser Gly Leu Leu Ala Gln Phe Pro Ala Leu Pro Asn Val Asn
        195                 200                 205
Arg Gln Asn Gln Ser Ile Pro Ser Ser Ala Lys Leu Gln Gln Ser Ser
    210                 215                 220
Glu Asp Asp Ser Val Arg Lys Glu Gly Thr Glu Met Glu Glu Ala Ser
225                 230                 235                 240
Glu Cys Ser Gln Gly Ser Asn Leu Ala Gly Cys Ser Gln Ser Thr Ser
                245                 250                 255
Asp Met Gly Asn Lys Phe Val His Thr Arg Glu Glu Gly Lys Leu Leu
            260                 265                 270
Glu Asp Ser Asn Tyr Arg Lys Asp Pro Ser Ser Ser Ala Pro Cys
        275                 280                 285
Ser Glu Tyr Tyr Thr Pro Ala Phe Glu Asp Ile Thr Phe Ser Met Ala
    290                 295                 300
Glu Val Pro Ser Glu Leu Asp Glu Ser Lys Leu Leu Glu His Thr Phe
305                 310                 315                 320
Ser His Asp Trp Ala Ala Ser Ile Gly Lys Glu Trp Gln Phe Asn Pro
                325                 330                 335
Asp Asp Ile Pro Asn Ile Ser Pro Leu Glu Leu Met Gln Asp Ser Ser
            340                 345                 350
Gly Leu Phe Met Gln Cys Leu Thr Gly Asn Gly Asn His Asp Met Val
        355                 360                 365
Thr Phe Pro Gln Gln Asn Ala Val Lys Phe Glu Thr Thr Asn Val Gly
    370                 375                 380
Ser Met Val Val Gly Phe Asp Lys Pro Asn Glu Met Phe Thr Ser Val
385                 390                 395                 400
Glu Gly Cys Arg Met Val Tyr Pro Glu Ala Gly Ile Pro Gln Tyr Ile
                405                 410                 415
Pro Ser Glu Ala Gly Thr Asn Gly Ala Asp Glu Thr Ala Asp Ser Leu
            420                 425                 430
Ile Cys Gln Ser Ser Asn Tyr Gln Ile Ser Glu Gly Gly Asn Met Ser
        435                 440                 445
Ile Glu Asn Cys Asn Pro Leu Cys Ser Asp Val Met Gly Thr Ser Ser
    450                 455                 460
Gly Gln Pro Phe Ser Ile Pro Ser Gln Phe Ser Ser Glu Gln Ser Ser
465                 470                 475                 480
Leu Met Phe Gly Thr Ala Ala Asn Gln Phe His Asn Pro Leu Gln Gly
                485                 490                 495
Asn Pro Ala Gln Glu Ser His Thr Ser Asn Ser Asp Gly Phe Leu Tyr
            500                 505                 510
Pro Phe Glu Ser Gly Thr Pro Cys Asp Asn Ile Met Asp Pro Leu
        515                 520                 525
Leu Glu Glu Gln Leu Asp Gln Thr Lys Asp Ser Leu Gln Leu Val Ser
    530                 535                 540
Val Asn Asp Phe Arg Thr Thr Pro Ser Asn Thr Ile Gln Thr Cys Pro
545                 550                 555                 560
Leu Val Asn Glu Asn Ser Ser Ile Pro Val Glu Gln Lys Asp Gly Gly
                565                 570                 575
Ala Leu Tyr Tyr Glu Pro Pro Arg Phe Pro Ser Leu Asp Ile Pro Phe
            580                 585                 590
```

-continued

```
Phe Ser Cys Asp Leu Ile Gln Ser Gly Thr Asp Ala Gln Gln Glu Tyr
        595                 600                 605

Ser Pro Leu Gly Ile Arg Gln Leu Met Met Thr Ser Val Asn Cys Leu
        610                 615                 620

Thr Pro Phe Arg Leu Trp Asp Ser Pro Ser Arg Asp Gly Ser Thr Asp
625                 630                 635                 640

Ala Val Leu Arg Ser Ala Ala Lys Thr Phe Thr Ser Thr Pro Ser Ile
                645                 650                 655

Leu Lys Lys Arg His Arg Asp Leu Val Ser Pro Leu Ser Glu Lys Arg
                660                 665                 670

Cys Glu Lys Lys Leu Gly Ser Asp Phe Arg Gln Ser Phe Ser Asp
        675                 680                 685

Leu Ser Lys Asp Phe Ser Arg Leu Asp Val Met Phe Asp Glu Ala Ala
        690                 695                 700

Asn Glu Lys Ala Thr Lys Ser Ser Leu Thr Thr Asp Gln Thr Leu Glu
705                 710                 715                 720

Leu Glu Ala Ser Ser Glu Asp Lys Glu Asn Ile Asn Pro Thr Glu Asp
                725                 730                 735

Gly Ser Lys Glu Glu Asp Lys Val Arg Asn Gly Leu Ser Asn Glu Arg
                740                 745                 750

Gln Leu Asp Gly Gly Glu Val His Tyr Lys Lys Gly Thr Arg Glu
        755                 760                 765

Gly Thr Lys Gly Gly Ala Asn Ser Ala Ile Gly Lys Ile Lys Gln Pro
        770                 775                 780

Ser Gly Val Leu Val Glu Leu Asn Ala Ser Asp Leu Phe Phe Ser Pro
785                 790                 795                 800

Asp Arg Phe Gly Ala Lys Ser Gly Arg Ala Thr Tyr Leu Ser Ser Lys
                805                 810                 815

Ala Leu Gly Asn Gln Tyr Ala Arg Arg Leu Glu Ala Ala Ser Asn Gln
                820                 825                 830

Gly Ser Val Ser Ser Ser Phe Glu Thr Ser Cys Phe Ser Val Ile Cys
        835                 840                 845

Ser Pro Arg Ile Arg Gly Lys Lys Asp Gly Ser Ser Phe Ile Ile Thr
        850                 855                 860

Thr Ser Met Gln Ser Ala Pro Ala Pro Thr Ala Leu Asp Asn Ser Ala
865                 870                 875                 880

Glu Thr Ser Gly Asn Gly Val Gly Ala Glu Thr Val Ser Ile Ser Gly
                885                 890                 895

Glu Thr Pro Tyr Lys Arg Ser Ile Glu Ser Pro Ser Ala Trp Lys Ser
                900                 905                 910

Pro Trp Phe Ile Asn Ser Leu Leu Ser Ser Pro Arg Leu Asp Asn Glu
        915                 920                 925

Leu Asn Phe Glu Asp Leu Ala Leu Phe Met Ser Pro Gly Asp Arg Ser
        930                 935                 940

Tyr Asp Ala Ile Gly Leu Met Lys Gln Leu Ser Glu Gln Thr Ala Gly
945                 950                 955                 960

Ala Phe Ala Asp Ala Gln Glu Val Leu Gly Gly Thr Pro Glu Ser
                965                 970                 975

Ile Leu Arg Gly Arg Asn Ser Lys Asn Gln Lys Ala Asp Glu Asn His
                980                 985                 990

Ser Leu Leu Ser Ala Asn Val Met  Ser Glu Arg Arg Thr  Leu Asp Phe
        995                 1000                1005
```

-continued

```
Ser Glu Cys Gly Ser Pro Gly Lys Gly Lys Glu Thr Glu Asn Phe
    1010                1015                1020

Cys Thr Ser Asn Asn Ser Phe Ser Ser Pro Ser Ser Tyr Leu Leu
    1025                1030                1035

Lys Gly Cys Arg
    1040

<210> SEQ ID NO 54
<211> LENGTH: 1767
<212> TYPE: DNA
<213> ORGANISM: Nicotiana tabacum
<220> FEATURE:
<221> NAME/KEY: CDS
<222> LOCATION: (1)..(1767)
<223> OTHER INFORMATION: DDBJ Acsession# AB056124, NtmybB (DDBJ
      Acsession# BAB70512)

<400> SEQUENCE: 54 atg ata caa gtt aag gag gaa tct cag act ctg gac ttc agt gga ttt        48
Met Ile Gln Val Lys Glu Glu Ser Gln Thr Leu Asp Phe Ser Gly Phe
1               5                   10                  15 gct tct tgt tca tct ttc tct gat agc agt tac gag gct agc act ccg        96
Ala Ser Cys Ser Ser Phe Ser Asp Ser Ser Tyr Glu Ala Ser Thr Pro
                20                  25                  30 aga tac tcc tcc gaa cct ggt tct agt tat cga agg agc tct ggt cca       144
Arg Tyr Ser Ser Glu Pro Gly Ser Ser Tyr Arg Arg Ser Ser Gly Pro
            35                  40                  45 act aaa cgt tct tcc cag gca ggc tgg acg gaa gaa gag gat aat ctg       192
Thr Lys Arg Ser Ser Gln Ala Gly Trp Thr Glu Glu Glu Asp Asn Leu
        50                  55                  60 ttg act gaa gtg gtg aaa agg ttc aaa ggg aga aac tgg aaa aag ata       240
Leu Thr Glu Val Val Lys Arg Phe Lys Gly Arg Asn Trp Lys Lys Ile
65                  70                  75                  80 gct gag tgc atg aat gga agg act gat gtg cag tgc ttg cat cgc tgg       288
Ala Glu Cys Met Asn Gly Arg Thr Asp Val Gln Cys Leu His Arg Trp
                85                  90                  95 cag aag gtt ctg aat cct gaa ctt gta aag ggt cct tgg tca aag gag       336
Gln Lys Val Leu Asn Pro Glu Leu Val Lys Gly Pro Trp Ser Lys Glu
            100                 105                 110 gag gat gac ctg att gtt gag tta gtt gag aaa tat ggc tgt aag aag       384
Glu Asp Asp Leu Ile Val Glu Leu Val Glu Lys Tyr Gly Cys Lys Lys
        115                 120                 125 tgg tct ttt att gct aag tct atg cct ggt cgc att ggc aag caa tgt       432
Trp Ser Phe Ile Ala Lys Ser Met Pro Gly Arg Ile Gly Lys Gln Cys
    130                 135                 140 cgg gaa agg tgg cac aac cat ctt gac cca aca ata aaa aga gat gct       480
Arg Glu Arg Trp His Asn His Leu Asp Pro Thr Ile Lys Arg Asp Ala
145                 150                 155                 160 tgg acg gaa cag gaa gaa tca gtc cta tgc cac tat cac caa ata tac       528
Trp Thr Glu Gln Glu Glu Ser Val Leu Cys His Tyr His Gln Ile Tyr
                165                 170                 175 ggg aac aag tgg gca gaa att gcg agg ttt ctg cct gga agg act gat       576
Gly Asn Lys Trp Ala Glu Ile Ala Arg Phe Leu Pro Gly Arg Thr Asp
            180                 185                 190 aat gca att aaa aat cat tgg aat tcc tca gta aag aaa aga ttg aac       624
Asn Ala Ile Lys Asn His Trp Asn Ser Ser Val Lys Lys Arg Leu Asn
        195                 200                 205 ttg aat ttg cct agt agg tta gtg ctg gat aca gaa agt gag gga tct       672
Leu Asn Leu Pro Ser Arg Leu Val Leu Asp Thr Glu Ser Glu Gly Ser
    210                 215                 220 cct aat ttc tct agt gac aag aaa aaa ata gag atc aag aag cat ccg       720
```

```
Pro Asn Phe Ser Ser Asp Lys Lys Ile Glu Ile Lys Lys His Pro
225                 230                 235                 240 gta caa gct caa aat gca gaa caa aca atc ttt tta ggc aag cag aca    768
Val Gln Ala Gln Asn Ala Glu Gln Thr Ile Phe Leu Gly Lys Gln Thr
                245                 250                 255 gga ttg gat aat gct gct gtt gct ttg tca act gat ctg aga att gga    816
Gly Leu Asp Asn Ala Ala Val Ala Leu Ser Thr Asp Leu Arg Ile Gly
                260                 265                 270 tat gct tat tct gct gga aat gct aag cat aag gat act tct tta ttt    864
Tyr Ala Tyr Ser Ala Gly Asn Ala Lys His Lys Asp Thr Ser Leu Phe
                275                 280                 285 gga gcc tgt ata tca gca gaa gaa aat gtg agg gat ctg ata aag cca    912
Gly Ala Cys Ile Ser Ala Glu Glu Asn Val Arg Asp Leu Ile Lys Pro
        290                 295                 300 ctt ggt gga ata caa ttt ggc aag gca gat gtt ctt ccg att ggt gag    960
Leu Gly Gly Ile Gln Phe Gly Lys Ala Asp Val Leu Pro Ile Gly Glu
305                 310                 315                 320 aca gat aaa cca tgc caa tcc aat tta agt cgc act aaa ata tca tat    1008
Thr Asp Lys Pro Cys Gln Ser Asn Leu Ser Arg Thr Lys Ile Ser Tyr
                325                 330                 335 cca ctc tca gcc tct tct tca gat ttt cct ttg gat cag ttg cac cac    1056
Pro Leu Ser Ala Ser Ser Ser Asp Phe Pro Leu Asp Gln Leu His His
                340                 345                 350 aca agt tgg agt act tct caa gtt gag gct gtt cat cct act act ttt    1104
Thr Ser Trp Ser Thr Ser Gln Val Glu Ala Val His Pro Thr Thr Phe
            355                 360                 365 agg agc atg tat gaa tct ccc aaa agg tct agg cac gat act gtt aat    1152
Arg Ser Met Tyr Glu Ser Pro Lys Arg Ser Arg His Asp Thr Val Asn
370                 375                 380 gat cct aac tgt gat ttt ttg agt ttg tca ttg gct agc ttt act gag    1200
Asp Pro Asn Cys Asp Phe Leu Ser Leu Ser Leu Ala Ser Phe Thr Glu
385                 390                 395                 400 gtt cat tcc caa agt acc aag aag aat aaa gca tat gat aca caa tct    1248
Val His Ser Gln Ser Thr Lys Lys Asn Lys Ala Tyr Asp Thr Gln Ser
                405                 410                 415 tct ttg ggt ctc aag cag cag ggc tcc tta tat tat gaa cca cca cag    1296
Ser Leu Gly Leu Lys Gln Gln Gly Ser Leu Tyr Tyr Glu Pro Pro Gln
            420                 425                 430 tta aag gac atg atg att cct tta aca gat gaa aac ctt agt aga gac    1344
Leu Lys Asp Met Met Ile Pro Leu Thr Asp Glu Asn Leu Ser Arg Asp
                435                 440                 445 gac ctt atc agg caa caa aat ggt cat cca ttt tgc tct aca cct cct    1392
Asp Leu Ile Arg Gln Gln Asn Gly His Pro Phe Cys Ser Thr Pro Pro
        450                 455                 460 agt ctt aaa tta aca gtc tct gct aat ggt agc agt cca gaa tct gtc    1440
Ser Leu Lys Leu Thr Val Ser Ala Asn Gly Ser Ser Pro Glu Ser Val
465                 470                 475                 480 tta agg aat tcc gca atg agt tac aca aga act cct tca atc ata aga    1488
Leu Arg Asn Ser Ala Met Ser Tyr Thr Arg Thr Pro Ser Ile Ile Arg
                485                 490                 495 aag aag aat tcc aga ttt cct gaa gct gca acg cat tct aga tgc aca    1536
Lys Lys Asn Ser Arg Phe Pro Glu Ala Ala Thr His Ser Arg Cys Thr
                500                 505                 510 ggt acc acc agt ccc aca cat att ttc cca aga gca tct gac agg gaa    1584
Gly Thr Thr Ser Pro Thr His Ile Phe Pro Arg Ala Ser Asp Arg Glu
            515                 520                 525 gac acc tca aac ctg aag gac aga ttt tct gga tgt aaa tca tca gct    1632
Asp Thr Ser Asn Leu Lys Asp Arg Phe Ser Gly Cys Lys Ser Ser Ala
530                 535                 540
```

```
tcg gga aaa tct ctt gga aga cgg ttg gaa tat gcc ttt gat atg gaa    1680
Ser Gly Lys Ser Leu Gly Arg Arg Leu Glu Tyr Ala Phe Asp Met Glu
545                 550                 555                 560 tgg gat gcc tct aga tgt tgc aca cca gtt tct gca gct tca cct tgt    1728
Trp Asp Ala Ser Arg Cys Cys Thr Pro Val Ser Ala Ala Ser Pro Cys
            565                 570                 575 gca ctt aga ctt ggt ggt aat acc atg ctg aca cca taa                1767
Ala Leu Arg Leu Gly Gly Asn Thr Met Leu Thr Pro
        580                 585

<210> SEQ ID NO 55
<211> LENGTH: 588
<212> TYPE: PRT
<213> ORGANISM: Nicotiana tabacum

<400> SEQUENCE: 55

Met Ile Gln Val Lys Glu Glu Ser Gln Thr Leu Asp Phe Ser Gly Phe
1               5                   10                  15

Ala Ser Cys Ser Ser Phe Ser Asp Ser Ser Tyr Glu Ala Ser Thr Pro
            20                  25                  30

Arg Tyr Ser Ser Glu Pro Gly Ser Ser Tyr Arg Arg Ser Ser Gly Pro
        35                  40                  45

Thr Lys Arg Ser Ser Gln Ala Gly Trp Thr Glu Glu Asp Asn Leu
    50                  55                  60

Leu Thr Glu Val Val Lys Arg Phe Lys Gly Arg Asn Trp Lys Lys Ile
65                  70                  75                  80

Ala Glu Cys Met Asn Gly Arg Thr Asp Val Gln Cys Leu His Arg Trp
                85                  90                  95

Gln Lys Val Leu Asn Pro Glu Leu Val Lys Gly Pro Trp Ser Lys Glu
            100                 105                 110

Glu Asp Asp Leu Ile Val Glu Leu Val Glu Lys Tyr Gly Cys Lys Lys
        115                 120                 125

Trp Ser Phe Ile Ala Lys Ser Met Pro Gly Arg Ile Gly Lys Gln Cys
    130                 135                 140

Arg Glu Arg Trp His Asn His Leu Asp Pro Thr Ile Lys Arg Asp Ala
145                 150                 155                 160

Trp Thr Glu Gln Glu Glu Ser Val Leu Cys His Tyr His Gln Ile Tyr
                165                 170                 175

Gly Asn Lys Trp Ala Glu Ile Ala Arg Phe Leu Pro Gly Arg Thr Asp
            180                 185                 190

Asn Ala Ile Lys Asn His Trp Asn Ser Ser Val Lys Arg Leu Asn
        195                 200                 205

Leu Asn Leu Pro Ser Arg Leu Val Leu Asp Thr Glu Ser Glu Gly Ser
    210                 215                 220

Pro Asn Phe Ser Ser Asp Lys Lys Ile Glu Ile Lys Lys His Pro
225                 230                 235                 240

Val Gln Ala Gln Asn Ala Glu Gln Thr Ile Phe Leu Gly Lys Gln Thr
                245                 250                 255

Gly Leu Asp Asn Ala Val Ala Leu Ser Thr Asp Leu Arg Ile Gly
            260                 265                 270

Tyr Ala Tyr Ser Ala Gly Asn Ala Lys His Lys Asp Thr Ser Leu Phe
        275                 280                 285

Gly Ala Cys Ile Ser Ala Glu Glu Asn Val Arg Asp Leu Ile Lys Pro
    290                 295                 300

Leu Gly Gly Ile Gln Phe Gly Lys Ala Asp Val Leu Pro Ile Gly Glu
305                 310                 315                 320
```

-continued

```
Thr Asp Lys Pro Cys Gln Ser Asn Leu Ser Arg Thr Lys Ile Ser Tyr
            325                 330                 335
Pro Leu Ser Ala Ser Ser Asp Phe Pro Leu Asp Gln Leu His His
            340                 345                 350
Thr Ser Trp Ser Thr Ser Gln Val Glu Ala Val His Pro Thr Thr Phe
            355                 360                 365
Arg Ser Met Tyr Glu Ser Pro Lys Arg Ser Arg His Asp Thr Val Asn
        370                 375                 380
Asp Pro Asn Cys Asp Phe Leu Ser Leu Ser Leu Ala Ser Phe Thr Glu
385                 390                 395                 400
Val His Ser Gln Ser Thr Lys Lys Asn Lys Ala Tyr Asp Thr Gln Ser
            405                 410                 415
Ser Leu Gly Leu Lys Gln Gln Gly Ser Leu Tyr Tyr Glu Pro Pro Gln
            420                 425                 430
Leu Lys Asp Met Met Ile Pro Leu Thr Asp Glu Asn Leu Ser Arg Asp
            435                 440                 445
Asp Leu Ile Arg Gln Gln Asn Gly His Pro Phe Cys Ser Thr Pro Pro
450                 455                 460
Ser Leu Lys Leu Thr Val Ser Ala Asn Gly Ser Ser Pro Glu Ser Val
465                 470                 475                 480
Leu Arg Asn Ser Ala Met Ser Tyr Thr Arg Thr Pro Ser Ile Ile Arg
            485                 490                 495
Lys Lys Asn Ser Arg Phe Pro Glu Ala Ala Thr His Ser Arg Cys Thr
                500                 505                 510
Gly Thr Thr Ser Pro Thr His Ile Phe Pro Arg Ala Ser Asp Arg Glu
            515                 520                 525
Asp Thr Ser Asn Leu Lys Asp Arg Phe Ser Gly Cys Lys Ser Ser Ala
        530                 535                 540
Ser Gly Lys Ser Leu Gly Arg Arg Leu Glu Tyr Ala Phe Asp Met Glu
545                 550                 555                 560
Trp Asp Ala Ser Arg Cys Cys Thr Pro Val Ser Ala Ala Ser Pro Cys
                565                 570                 575
Ala Leu Arg Leu Gly Gly Asn Thr Met Leu Thr Pro
            580                 585

<210> SEQ ID NO 56
<211> LENGTH: 27
<212> TYPE: DNA
<213> ORGANISM: Artificial Sequence
<220> FEATURE:
<223> OTHER INFORMATION: Oligonucleotide to act as a primer for PCR

<400> SEQUENCE: 56
ccggatcctt caatagaatt tcttcca                                          27

<210> SEQ ID NO 57
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 57
ccaagcttac ccataaattg ttggtaaa                                         28

<210> SEQ ID NO 58
<211> LENGTH: 33
```

```
<212> TYPE: DNA
<213> ORGANISM: Artificial Sequence
<220> FEATURE:
<223> OTHER INFORMATION: Oligonucleotide to act as a primer for PCR

<400> SEQUENCE: 58
ccggatcctc tagatttgcg cctgagatct gag                                    33

<210> SEQ ID NO 59
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 59
ccaagcttca taagccgata gaattcacc                                         29

<210> SEQ ID NO 60
<211> LENGTH: 30
<212> TYPE: DNA
<213> ORGANISM: Artificial Sequence
<220> FEATURE:
<223> OTHER INFORMATION: Oligonucleotide to act as a primer for PCR

<400> SEQUENCE: 60
aactgcagtc ttcaatagaa tttcttccag                                        30

<210> SEQ ID NO 61
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 61
ggaattcgtg tgatatctac ccgcttcg                                          28

<210> SEQ ID NO 62
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 62
cgggatccgt ttttcaccga agttcatgc                                         29

<210> SEQ ID NO 63
<211> LENGTH: 32
<212> TYPE: DNA
<213> ORGANISM: Artificial Sequence
<220> FEATURE:
<223> OTHER INFORMATION: Oligonucleotide to act as a primer for PCR

<400> SEQUENCE: 63
ttgaattcca agtcttgggc ttgacagaag ag                                     32

<210> SEQ ID NO 64
<211> LENGTH: 38
<212> TYPE: DNA
<213> ORGANISM: Artificial Sequence
<220> FEATURE:
<223> OTHER INFORMATION: Oligonucleotide to act as a primer for PCR

<400> SEQUENCE: 64
```

-continued ttctcgagaa gcttcgtcaa gaatcattct ctgatctg   38

<210> SEQ ID NO 65
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 65
ttggatccaa gtcttgggct tgacagaaga g   31

<210> SEQ ID NO 66
<211> LENGTH: 43
<212> TYPE: DNA
<213> ORGANISM: Artificial Sequence
<220> FEATURE:
<223> OTHER INFORMATION: Oligonucleotide to act as a primer for PCR

<400> SEQUENCE: 66
cctctagact agtgtcgacc gtcaagaatc attctctgat ctg   43

<210> SEQ ID NO 67
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 67
ttgaattctt gttgcctgat aaggtcgtct c   31

<210> SEQ ID NO 68
<211> LENGTH: 37
<212> TYPE: DNA
<213> ORGANISM: Artificial Sequence
<220> FEATURE:
<223> OTHER INFORMATION: Oligonucleotide to act as a primer for PCR

<400> SEQUENCE: 68
ttctcgagaa gcttgaattt gcctagtagg ttagtgc   37

<210> SEQ ID NO 69
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 69
ttggatcctt gttgcctgat aaggtcgtct c   31

<210> SEQ ID NO 70
<211> LENGTH: 42
<212> TYPE: DNA
<213> ORGANISM: Artificial Sequence
<220> FEATURE:
<223> OTHER INFORMATION: Oligonucleotide to act as a primer for PCR

<400> SEQUENCE: 70
cctctagact agtgtcgacg aatttgccta gtaggttagt gc   42

<210> SEQ ID NO 71
<211> LENGTH: 36
<212> TYPE: DNA
<213> ORGANISM: Artificial Sequence

```
<220> FEATURE:
<223> OTHER INFORMATION: Oligonucleotide to act as a primer for PCR

<400> SEQUENCE: 71
ccggatcctt cctcagtaaa gaaaagattg aacttg                                36

<210> SEQ ID NO 72
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 72
ccgtcgactt aacagttagg atcattaaca g                                     31

<210> SEQ ID NO 73
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 73
ccggatcctt ccagttcagc accatgctct g                                     31

<210> SEQ ID NO 74
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 74
ccgtcgacct aagagatctg atagttcgat g                                     31

<210> SEQ ID NO 75
<211> LENGTH: 776
<212> TYPE: PRT
<213> ORGANISM: Arabidopsis thaliana

<400> SEQUENCE: 75

Met Lys Arg Glu Met Lys Ala Pro Thr Thr Pro Leu Glu Ser Leu Gln
1               5                   10                  15

Gly Asp Leu Lys Gly Lys Gln Gly Arg Thr Ser Gly Pro Ala Arg Arg
            20                  25                  30

Ser Thr Lys Gly Gln Trp Thr Pro Glu Glu Asp Glu Val Leu Cys Lys
        35                  40                  45

Ala Val Glu Arg Phe Gln Gly Lys Asn Trp Lys Lys Ile Ala Glu Cys
    50                  55                  60

Phe Lys Asp Arg Thr Asp Val Gln Cys Leu His Arg Trp Gln Lys Val
65                  70                  75                  80

Leu Asn Pro Glu Leu Val Lys Gly Pro Trp Ser Lys Glu Glu Asp Asn
                85                  90                  95

Thr Ile Ile Asp Leu Val Glu Lys Tyr Gly Pro Lys Lys Trp Ser Thr
            100                 105                 110

Ile Ser Gln His Leu Pro Gly Arg Ile Gly Lys Gln Cys Arg Glu Arg
        115                 120                 125

Trp His Asn His Leu Asn Pro Gly Ile Asn Lys Asn Ala Trp Thr Gln
    130                 135                 140

Glu Glu Glu Leu Thr Leu Ile Arg Ala His Gln Ile Tyr Gly Asn Lys
```

-continued

```
            145                 150                 155                 160
    Trp Ala Glu Leu Met Lys Phe Leu Pro Gly Arg Ser Asp Asn Ser Ile
                    165                 170                 175
    Lys Asn His Trp Asn Ser Ser Val Lys Lys Leu Asp Ser Tyr Tyr
                180                 185                 190
    Ala Ser Gly Leu Leu Asp Gln Cys Gln Ser Pro Leu Ile Ala Leu
                195                 200                 205
    Gln Asn Lys Ser Ile Ala Ser Ser Ser Trp Met His Ser Asn Gly
                210                 215                 220
    Asp Glu Gly Ser Ser Arg Pro Gly Val Asp Ala Glu Ser Glu Cys
    225                 230                 235                 240
    Ser Gln Ala Ser Thr Val Phe Ser Gln Ser Thr Asn Asp Leu Gln Asp
                    245                 250                 255
    Glu Val Gln Arg Gly Asn Glu Glu Tyr Tyr Met Pro Glu Phe His Ser
                    260                 265                 270
    Gly Thr Glu Gln Gln Ile Ser Asn Ala Ala Ser His Ala Glu Pro Tyr
                    275                 280                 285
    Tyr Pro Ser Phe Lys Asp Val Lys Ile Val Pro Glu Ile Ser Cys
                290                 295                 300
    Glu Thr Glu Cys Ser Lys Lys Phe Gln Asn Leu Asn Cys Ser His Glu
    305                 310                 315                 320
    Leu Arg Thr Thr Thr Ala Thr Glu Asp Gln Leu Pro Gly Val Ser Asn
                    325                 330                 335
    Asp Ala Lys Gln Asp Arg Gly Leu Glu Leu Leu Thr His Asn Met Asp
                340                 345                 350
    Asn Gly Gly Lys Asn Gln Ala Leu Gln Gln Asp Phe Gln Ser Ser Val
                355                 360                 365
    Arg Leu Ser Asp Gln Pro Phe Leu Ser Asn Ser Asp Thr Asp Pro Glu
                370                 375                 380
    Ala Gln Thr Leu Ile Thr Asp Glu Glu Cys Cys Arg Val Leu Phe Pro
    385                 390                 395                 400
    Asp Asn Met Lys Asp Ser Ser Thr Ser Ser Gly Glu Gln Gly Arg Asn
                    405                 410                 415
    Met Val Asp Pro Gln Asn Gly Lys Gly Ser Leu Cys Ser Gln Ala Ala
                420                 425                 430
    Glu Thr His Ala His Glu Thr Gly Lys Val Pro Ala Leu Pro Trp His
                435                 440                 445
    Pro Ser Ser Ser Glu Gly Leu Ala Gly His Asn Cys Val Pro Leu Leu
                450                 455                 460
    Asp Ser Asp Leu Lys Asp Ser Leu Leu Pro Arg Asn Asp Ser Asn Ala
    465                 470                 475                 480
    Pro Ile Gln Gly Cys Arg Leu Phe Gly Ala Thr Glu Leu Glu Cys Lys
                    485                 490                 495
    Thr Asp Thr Asn Asp Gly Phe Ile Asp Thr Tyr Gly His Val Thr Ser
                500                 505                 510
    His Gly Asn Asp Asp Asn Gly Gly Phe Pro Glu Gln Gln Gly Leu Ser
                515                 520                 525
    Tyr Ile Pro Lys Asp Ser Leu Lys Leu Val Pro Leu Asn Ser Phe Ser
                530                 535                 540
    Ser Pro Ser Arg Val Asn Lys Ile Tyr Phe Pro Ile Asp Asp Lys Pro
    545                 550                 555                 560
    Ala Glu Lys Asp Lys Gly Ala Leu Cys Tyr Glu Pro Pro Arg Phe Pro
                    565                 570                 575
```

```
Ser Ala Asp Ile Pro Phe Phe Ser Cys Asp Leu Val Pro Ser Asn Ser
            580                 585                 590

Asp Leu Arg Gln Glu Tyr Ser Pro Phe Gly Ile Arg Gln Leu Met Ile
        595                 600                 605

Ser Ser Met Asn Cys Thr Thr Pro Leu Arg Leu Trp Asp Ser Pro Cys
    610                 615                 620

His Asp Arg Ser Pro Asp Val Met Leu Asn Asp Thr Ala Lys Ser Phe
625                 630                 635                 640

Ser Gly Ala Pro Ser Ile Leu Lys Lys Arg His Arg Asp Leu Leu Ser
                645                 650                 655

Pro Val Leu Asp Arg Arg Lys Asp Lys Lys Leu Lys Arg Ala Ala Thr
            660                 665                 670

Ser Ser Leu Ala Asn Asp Phe Ser Arg Leu Asp Val Met Leu Asp Glu
        675                 680                 685

Gly Asp Asp Cys Met Thr Ser Arg Pro Ser Glu Ser Pro Glu Asp Lys
    690                 695                 700

Asn Ile Cys Ala Ser Pro Ser Ile Ala Arg Asp Asn Arg Asn Cys Ala
705                 710                 715                 720

Ser Ala Arg Leu Tyr Gln Glu Met Ile Pro Ile Asp Glu Pro Lys
                725                 730                 735

Glu Thr Leu Glu Ser Gly Gly Val Thr Ser Met Gln Asn Glu Asn Gly
            740                 745                 750

Cys Asn Asp Gly Gly Ala Ser Ala Lys Asn Val Ser Pro Ser Leu Ser
        755                 760                 765

Leu His Ile Ile Trp Tyr Gln Leu
    770                 775

<210> SEQ ID NO 76
<211> LENGTH: 961
<212> TYPE: PRT
<213> ORGANISM: Arabidopsis thaliana

<400> SEQUENCE: 76

Met Glu Ala Glu Ser Ser Thr Pro Gln Glu Arg Ile Pro Lys Leu Arg
1               5                   10                  15

His Gly Arg Thr Ser Gly Pro Ala Arg Arg Ser Thr Arg Gly Gln Trp
            20                  25                  30

Thr Ala Glu Glu Asp Glu Ile Leu Arg Lys Ala Val His Ser Phe Lys
        35                  40                  45

Gly Lys Asn Trp Lys Lys Ile Ala Glu Tyr Phe Lys Asp Arg Thr Asp
    50                  55                  60

Val Gln Cys Leu His Arg Trp Gln Lys Val Leu Asn Pro Glu Leu Val
65                  70                  75                  80

Lys Gly Pro Trp Thr Lys Glu Glu Asp Glu Met Ile Val Gln Leu Ile
                85                  90                  95

Glu Lys Tyr Gly Pro Lys Lys Trp Ser Thr Ile Ala Arg Phe Leu Pro
            100                 105                 110

Gly Arg Ile Gly Lys Gln Cys Arg Glu Arg Trp His Asn His Leu Asn
        115                 120                 125

Pro Ala Ile Asn Lys Glu Ala Trp Thr Gln Glu Glu Leu Leu Leu
    130                 135                 140

Ile Arg Ala His Gln Ile Tyr Gly Asn Arg Trp Ala Glu Leu Thr Lys
145                 150                 155                 160

Phe Leu Pro Gly Arg Ser Asp Asn Gly Ile Lys Asn His Trp His Ser
```

-continued

```
                165                 170                 175
Ser Val Lys Lys Lys Leu Asp Ser Tyr Met Ser Ser Gly Leu Leu Asp
            180                 185                 190

Gln Tyr Gln Ala Met Pro Leu Ala Pro Tyr Glu Arg Ser Ser Thr Leu
            195                 200                 205

Gln Ser Thr Phe Met Gln Ser Asn Ile Asp Gly Asn Gly Cys Leu Asn
            210                 215                 220

Gly Gln Ala Glu Asn Glu Ile Asp Ser Arg Gln Asn Ser Ser Met Val
225                 230                 235                 240

Gly Cys Ser Leu Ser Ala Arg Asp Phe Gln Asn Gly Thr Ile Asn Ile
            245                 250                 255

Gly His Asp Phe His Pro Cys Gly Asn Ser Gln Glu Asn Glu Gln Thr
            260                 265                 270

Ala Tyr His Ser Glu Gln Phe Tyr Pro Glu Leu Glu Asp Ile Ser
            275                 280                 285

Val Ser Ile Ser Glu Val Ser Tyr Asp Met Glu Asp Cys Ser Gln Phe
            290                 295                 300

Pro Asp His Asn Val Ser Thr Ser Pro Ser Gln Asp Tyr Gln Phe Asp
305                 310                 315                 320

Phe Gln Glu Leu Ser Asp Ile Ser Leu Glu Met Arg His Asn Met Ser
            325                 330                 335

Glu Ile Pro Met Pro Tyr Thr Lys Glu Ser Lys Glu Ser Thr Leu Gly
            340                 345                 350

Ala Pro Asn Ser Thr Leu Asn Ile Asp Val Ala Thr Tyr Thr Asn Ser
            355                 360                 365

Ala Asn Val Leu Thr Pro Glu Thr Glu Cys Cys Arg Val Leu Phe Pro
370                 375                 380

Asp Gln Glu Ser Glu Gly His Ser Val Ser Arg Ser Leu Thr Gln Glu
385                 390                 395                 400

Pro Asn Glu Phe Asn Gln Val Asp Arg Arg Asp Pro Ile Leu Tyr Ser
            405                 410                 415

Ser Ala Ser Asp Arg Gln Ile Ser Glu Ala Thr Lys Ser Pro Thr Gln
            420                 425                 430

Ser Ser Ser Ser Arg Phe Thr Ala Thr Ala Ala Ser Gly Lys Gly Thr
            435                 440                 445

Leu Arg Pro Ala Pro Leu Ile Ile Ser Pro Asp Lys Tyr Ser Lys Lys
450                 455                 460

Ser Ser Gly Leu Ile Cys His Pro Phe Glu Val Glu Pro Lys Cys Thr
465                 470                 475                 480

Thr Asn Gly Asn Gly Ser Phe Ile Cys Ile Gly Asp Pro Ser Ser Ser
            485                 490                 495

Thr Cys Val Asp Glu Gly Thr Asn Asn Ser Glu Glu Asp Gln Ser
            500                 505                 510

Tyr His Val Asn Asp Pro Lys Lys Leu Val Pro Val Asn Asp Phe Ala
            515                 520                 525

Ser Leu Ala Glu Asp Arg Pro His Ser Leu Pro Lys His Glu Pro Asn
530                 535                 540

Met Thr Asn Glu Gln His His Glu Asp Met Gly Ala Ser Ser Ser Leu
545                 550                 555                 560

Gly Phe Pro Ser Phe Asp Leu Pro Val Phe Asn Cys Asp Leu Leu Gln
            565                 570                 575

Ser Lys Asn Asp Pro Leu His Asp Tyr Ser Pro Leu Gly Ile Arg Lys
            580                 585                 590
```

```
Leu Leu Met Ser Thr Met Thr Cys Met Ser Pro Leu Arg Leu Trp Glu
            595                 600                 605

Ser Pro Thr Gly Lys Lys Thr Leu Val Gly Ala Gln Ser Ile Leu Arg
        610                 615                 620

Lys Arg Thr Arg Asp Leu Leu Thr Pro Leu Ser Glu Lys Arg Ser Asp
625                 630                 635                 640

Lys Lys Leu Glu Ile Asp Ile Ala Ala Ser Leu Ala Lys Asp Phe Ser
                645                 650                 655

Arg Leu Asp Val Met Phe Asp Glu Thr Glu Asn Arg Gln Ser Asn Phe
            660                 665                 670

Gly Asn Ser Thr Gly Val Ile His Gly Asp Arg Glu Asn His Phe His
        675                 680                 685

Ile Leu Asn Gly Asp Gly Glu Glu Trp Ser Gly Lys Pro Ser Ser Leu
690                 695                 700

Phe Ser His Arg Met Pro Glu Glu Thr Met His Ile Arg Lys Ser Leu
705                 710                 715                 720

Glu Lys Val Asp Gln Ile Cys Met Glu Ala Asn Val Arg Glu Lys Asp
                725                 730                 735

Asp Ser Glu Gln Asp Val Glu Asn Val Glu Phe Ser Gly Ile Leu
            740                 745                 750

Ser Glu His Asn Thr Gly Lys Pro Val Leu Ser Thr Pro Gly Gln Ser
        755                 760                 765

Val Thr Lys Ala Glu Lys Ala Gln Val Ser Thr Pro Arg Asn Gln Leu
770                 775                 780

Gln Arg Thr Leu Met Ala Thr Ser Asn Lys Glu His His Ser Pro Ser
785                 790                 795                 800

Ser Val Cys Leu Val Ile Asn Ser Pro Ser Arg Ala Arg Asn Lys Glu
                805                 810                 815

Gly His Leu Val Asp Asn Gly Thr Ser Asn Glu Asn Phe Ser Ile Phe
            820                 825                 830

Cys Gly Thr Pro Phe Arg Arg Gly Leu Glu Ser Pro Ser Ala Trp Lys
        835                 840                 845

Ser Pro Phe Tyr Ile Asn Ser Leu Leu Pro Ser Pro Arg Phe Asp Thr
850                 855                 860

Asp Leu Thr Ile Glu Asp Met Gly Tyr Ile Phe Ser Pro Gly Glu Arg
865                 870                 875                 880

Ser Tyr Glu Ser Ile Gly Val Met Thr Gln Ile Asn Glu His Thr Ser
                885                 890                 895

Ala Phe Ala Ala Phe Ala Asp Ala Met Glu Val Ser Ile Ser Pro Thr
            900                 905                 910

Asn Asp Asp Ala Arg Gln Lys Lys Glu Leu Asp Lys Glu Asn Asn Asp
        915                 920                 925

Pro Leu Leu Ala Glu Arg Val Leu Asp Phe Asn Asp Cys Glu Ser
930                 935                 940

Pro Ile Lys Ala Thr Glu Glu Val Ser Ser Tyr Leu Leu Lys Gly Cys
945                 950                 955                 960

Arg

<210> SEQ ID NO 77
<211> LENGTH: 505
<212> TYPE: PRT
<213> ORGANISM: Arabidopsis thaliana

<400> SEQUENCE: 77
```

```
Met Ser Ser Thr Phe Asn Pro Ala Ala Ser Pro Asp Glu Glu Gly
1               5                   10                  15

Thr Gly Glu Val Lys Ile Glu Asp Gln Cys Val Glu Asn Lys Gln Ser
            20                  25                  30

Thr Pro Ala Ser Cys Ser Ser Val Ser Glu Gly Ser Ala Gly Ser Ser
            35                  40                  45

His Lys Ser Pro Thr Ile Ala Ser Pro Ala Thr Val Ser Pro Thr His
    50                  55                  60

Arg Tyr Leu Gly Arg Thr Ser Gly Pro Ile Arg Arg Ala Lys Gly Gly
65                  70                  75                  80

Trp Thr Pro Glu Glu Asp Glu Thr Leu Arg Gln Ala Val Asp Thr Phe
                85                  90                  95

Lys Gly Lys Ser Trp Lys Asn Ile Ala Lys Ser Phe Pro Asp Arg Thr
                100                 105                 110

Glu Val Gln Cys Leu His Arg Trp Gln Lys Val Leu Asn Pro Asp Leu
            115                 120                 125

Ile Lys Gly Pro Trp Thr His Glu Glu Asp Glu Lys Ile Val Glu Leu
130                 135                 140

Val Glu Lys Tyr Gly Pro Ala Lys Trp Ser Ile Ile Ala Gln Ser Leu
145                 150                 155                 160

Pro Gly Arg Ile Gly Lys Gln Cys Arg Glu Arg Trp His Asn His Leu
                165                 170                 175

Asn Pro Asp Ile Asn Lys Asp Ala Trp Thr Thr Glu Glu Val Ala
                180                 185                 190

Leu Met Asn Ala His Arg Ser His Gly Asn Lys Trp Ala Glu Ile Ala
        195                 200                 205

Lys Val Leu Pro Gly Arg Thr Asp Asn Ala Ile Lys Asn His Trp Asn
            210                 215                 220

Ser Ser Leu Lys Lys Lys Ser Glu Phe Tyr Leu Leu Thr Gly Arg Leu
225                 230                 235                 240

Pro Pro Pro Thr Thr Thr Arg Asn Gly Val Pro Asp Ser Val Thr Lys
                245                 250                 255

Arg Ser Ser Ser Ala Gln Lys Arg Val Phe Gly Ser Val Ala Gln Thr
            260                 265                 270

Ser Ser Val Thr Thr Asp Val Asn Asn Leu Ala Glu Asp Gly Asn Gly
            275                 280                 285

Gln Ile Asn Ser Ser Val Pro Val Glu Glu Val Val Ala Ala Ser Arg
    290                 295                 300

Met Thr Ser Leu Asn Glu Tyr Ala Arg Ser Pro Gln Leu Pro Asn Pro
305                 310                 315                 320

Glu Pro Leu Pro Glu Asn Gly Gly Ala Ala Asn Asn Gly Tyr His Leu
                325                 330                 335

Tyr Tyr Thr Pro Gln Ile Asp Tyr Tyr Arg Ala Ser Glu Val Asp Thr
            340                 345                 350

Gln Arg Met Tyr Gly Asn Glu Cys Gly Cys Ser Pro Ser Ala Ser Pro
            355                 360                 365

Val Ser Phe Phe Thr Pro Pro Cys Arg Asn Val His Ser Asn Gly
            370                 375                 380

Ser Thr Pro Arg Ser Pro Glu Ser Tyr Leu Arg Glu Ala Gly Arg Thr
385                 390                 395                 400

Tyr Pro Asn Thr Pro Ser Ile Phe Arg Lys Arg Pro Arg Val Val
                405                 410                 415
```

```
Val Gln Asp Asn Asn Ala Lys Lys Thr Asp Glu Ala Lys Glu Val
            420                 425                 430

Asp Gln Lys Val Asn Asp Gly Lys Asp Ser Ser Glu Ile Gln Asn Asn
            435                 440                 445

Gly Ser Asn Ala Tyr Asn Leu Ser Pro Pro Tyr Arg Ile Arg Ser Lys
            450                 455                 460

Arg Thr Ala Val Phe Lys Ser Arg Gln Leu Glu Phe Ile Ser Arg Glu
465                 470                 475                 480

Glu Glu Lys Ala Asp Asp Glu Thr Lys Ser Ser Glu Lys Asp Met Leu
            485                 490                 495

Ile Asp Gly Asp Ser Gln Leu Leu Gly
            500                 505

<210> SEQ ID NO 78
<211> LENGTH: 548
<212> TYPE: PRT
<213> ORGANISM: Arabidopsis thaliana

<400> SEQUENCE: 78

Met Ser Leu Ser Ser Asn Pro Pro Val Cys Ser Pro Glu Lys Glu Glu
1               5                   10                  15

Arg Ser Glu Met Lys Ile Glu Ile Gln Cys Met Glu Asn Lys Gln Pro
            20                  25                  30

Leu Ala Ala Ser Cys Ser Ser Ala Ser Glu Gly Ser Gly Cys Phe Phe
            35                  40                  45

Leu Lys Ser Pro Glu Ile Ala Thr Pro Ala Thr Val Ser Ser Phe Pro
            50                  55                  60

Arg Arg Thr Ser Gly Pro Met Arg Arg Ala Lys Gly Gly Trp Thr Pro
65                  70                  75                  80

Glu Glu Asp Glu Thr Leu Arg Arg Ala Val Glu Lys Tyr Lys Gly Lys
            85                  90                  95

Arg Trp Lys Lys Ile Ala Glu Phe Phe Pro Glu Arg Thr Glu Val Gln
            100                 105                 110

Cys Leu His Arg Trp Gln Lys Val Leu Asn Pro Glu Leu Val Lys Gly
            115                 120                 125

Pro Trp Thr Gln Glu Glu Asp Asp Lys Ile Val Glu Leu Val Lys Lys
            130                 135                 140

Tyr Gly Pro Ala Lys Trp Ser Val Ile Ala Lys Ser Leu Pro Gly Arg
145                 150                 155                 160

Ile Gly Lys Gln Cys Arg Glu Arg Trp His Asn His Leu Asn Pro Gly
            165                 170                 175

Ile Arg Lys Asp Ala Trp Thr Val Glu Glu Ser Ala Leu Met Asn
            180                 185                 190

Ser His Arg Met Tyr Gly Asn Lys Trp Ala Glu Ile Ala Lys Val Leu
            195                 200                 205

Pro Gly Arg Thr Asp Asn Ala Ile Lys Asn His Trp Asn Ser Ser Leu
            210                 215                 220

Lys Lys Lys Leu Glu Phe Tyr Leu Ala Thr Gly Asn Leu Pro Pro Pro
225                 230                 235                 240

Ala Ser Lys Phe Ile Val Leu Lys Asp Ile Ala Asp Gly Asp Arg Asp
            245                 250                 255

Ser Lys Gln Ser Ser Ala Thr Lys Pro Phe Lys Asp Ser Asp Ser Leu
            260                 265                 270

Thr Gln Thr Ser Ser Gly Asn Thr Asp Ser Asn Glu Val Gly Arg Asp
            275                 280                 285
```

```
His Phe Asp Ser Ser Ser Ala Leu Leu Glu Glu Val Ala Ala Ser Arg
    290                 295                 300

Arg Ile Gly Val Asn Glu Tyr Ala Cys Ser Pro Val Glu Tyr Lys Pro
305                 310                 315                 320

Gln Leu Pro Asn Leu Glu Pro Ile Ser Glu Glu Val Arg Ile Asn Ser
                325                 330                 335

Lys Ala Tyr Phe Glu Arg Ser Ile Gln Arg Lys Val Glu Asn Gly Phe
            340                 345                 350

Gly Thr Pro Lys His Gly Asn Leu Tyr Tyr Lys Ser Pro Leu Asp Tyr
        355                 360                 365

Tyr Phe Pro Ser Glu Ala Asp Leu Gln His Met Tyr Gly Tyr Glu Cys
    370                 375                 380

Gly Cys Ser Pro Gly Ala Ala Ser Pro Val Ser Leu Met Thr Thr Pro
385                 390                 395                 400

Cys Asn Lys Asp Ser Gly Leu Thr Ala Thr Arg Ser Pro Glu Ser Phe
                405                 410                 415

Leu Arg Glu Ala Ala Arg Thr Phe Pro Asn Thr Pro Ser Ile Phe Arg
            420                 425                 430

Lys Arg Arg Lys Val Val Leu Ala Ala Lys Thr Asp Ala Val Val Val
        435                 440                 445

Val Asn Gly Val Val Lys Glu Val Asp Arg Lys Glu Glu Ser Lys Asp
    450                 455                 460

Met Arg Lys Ser Leu Leu Leu Glu Thr Thr Asp Asn Cys Ser Asp Asp
465                 470                 475                 480

Glu Glu Leu Gly Leu Asn Gly Asn Ala Phe Asn Leu Ser Pro Pro Tyr
                485                 490                 495

Arg Leu Arg Ala Lys Arg Thr Ala Val Ile Lys Ser Arg Gln Leu Glu
            500                 505                 510

Phe Thr Ser Glu Lys Glu Lys Gln Pro Asp Asn Glu Ile Glu Phe Thr
        515                 520                 525

Ser Ala Lys Glu Lys Gln Pro Asp Asn Glu Ile Lys Thr Ser Glu Glu
    530                 535                 540

Asp Lys Pro Val
545

<210> SEQ ID NO 79
<211> LENGTH: 599
<212> TYPE: PRT
<213> ORGANISM: Physcomitrella patens

<400> SEQUENCE: 79

Met Ser Asp Thr Val Glu Phe Tyr Leu Ile Thr Arg Ser Ile Ile Lys
1               5                   10                  15

Val Lys Asn Phe Arg Arg Thr Gly Gly Pro Thr Arg Arg Ser Ser Lys
            20                  25                  30

Gly Gly Trp Thr Pro Glu Glu Asp Glu Thr Leu Arg Arg Ala Val Gln
        35                  40                  45

Cys Phe Asn Gly Lys Asn Trp Lys Lys Ile Ala Glu Phe Phe Thr Asp
    50                  55                  60

Arg Thr Asp Val Gln Cys Leu His Arg Trp Gln Lys Val Leu Asn Pro
65                  70                  75                  80

Asp Leu Val Lys Gly Ala Trp Thr Lys Glu Glu Asp Asp Arg Ile Met
                85                  90                  95

Glu Leu Val Asn Lys Tyr Gly Ala Lys Lys Trp Ser Val Ile Ala Gln
```

-continued

```
                100                 105                 110
Asn Leu Pro Gly Arg Ile Gly Lys Gln Cys Arg Glu Arg Trp His Asn
            115                 120                 125

His Leu Asn Pro Ser Ile Lys Arg Glu Ala Trp Thr Gln Gln Glu Asp
        130                 135                 140

Leu Ala Leu Ile Arg Ala His Gln Leu Tyr Gly Asn Lys Trp Ala Glu
145                 150                 155                 160

Ile Ala Lys Phe Leu Pro Gly Arg Thr Asp Asn Ser Ile Lys Asn His
                165                 170                 175

Trp Asn Ser Thr Met Lys Lys Val Asp Pro Leu Thr Ala Asn Asp
            180                 185                 190

Pro Ile Ser Arg Ala Leu Ala Ala Tyr Gln Ala Gln Gln Glu Gln Ser
                195                 200                 205

Met Asn Ser Gly Ser Gly Val Gly Gln Val Asp Ser Gly Ser Ile Gly
        210                 215                 220

Gly Arg Thr Gly Pro Pro Met Ser Glu Thr Thr Thr Ser Ser Asp Pro
225                 230                 235                 240

Ser Arg His Asn Ser Asn Thr Arg Gly Leu Gly Arg Thr Ser His Tyr
                245                 250                 255

Val Glu Gln Asp Thr Lys Ser Thr Gly Ser Ala Pro Pro Pro Tyr
            260                 265                 270

Pro Asp Thr Tyr Pro Asn Arg Gly Lys Asp Gln Gln Arg Asn Ala Ser
        275                 280                 285

His Leu Gln Pro Lys Lys Glu Glu Ser Asp His Asp Leu Ile Gly Gln
290                 295                 300

Ser Leu Gly Phe Ser Gly Trp Ser Ser Gly Gln Leu Pro Val Tyr Ser
305                 310                 315                 320

Gly Gly Phe Ser Gly Val Ser Leu Gly Thr Ser Ser Leu Ser Asn Ser
                325                 330                 335

Val Thr Glu Gln Leu Val Pro Ser Val Gln His Lys Arg Ala Met Ser
            340                 345                 350

Asn Ile Glu Leu Thr Arg Ile Ala Ser Phe Ser Asn Ser Phe Pro Arg
        355                 360                 365

Ile Pro Ala Pro Glu Ser Ser Ser Gln Ala Tyr Arg Ser Ser Ser Met
    370                 375                 380

Ser Val Pro Leu Pro Asp Leu Gly Ser Leu Phe Ala Ser Ser His Met
385                 390                 395                 400

Pro Met Ala Ala His Asn Asp Thr Gln Pro Leu Ser Ser Phe Asn Gly
                405                 410                 415

Thr Gly Val Pro Pro Gly Glu Glu Thr Leu Ala Met Met Gly Ser Lys
            420                 425                 430

Gln Asn Tyr Glu Pro Leu Arg Arg Cys Asn Leu Pro Pro Ser Gln Pro
        435                 440                 445

Ser Glu Gly Asp Ala Ala Phe Glu Asp Ser Gly Ala Ser Val Arg Cys
    450                 455                 460

Asp Ser Gln Met Ala Glu Pro Met Asp Lys Ala Met Asp Gln Asp Val
465                 470                 475                 480

Ser Glu Phe Pro Ser Asp Asn Leu Leu Arg Asp Ser Ser Glu Ala Val
                485                 490                 495

Asn Glu Tyr Gln Ser Gln Ser Pro Met Leu Thr Glu Glu Asp Leu Glu
            500                 505                 510

Asp Lys Gly Asp Ser Ser Arg Val Gln Asp Arg Asp Gly Leu Phe Tyr
        515                 520                 525
```

Glu Pro Pro Arg Ile Val Asp Pro Pro Phe Met Asn Tyr Asp Leu Val
530                 535                 540

Ser Ser Leu Asn Ala Tyr Ser Pro Leu Gly Val Arg Gln Met Ile Met
545                 550                 555                 560

Pro Ala Gly Asn Cys Ile Thr Pro Pro Asn Tyr Leu Gln Ser Pro Phe
                565                 570                 575

Gln Gly Lys Ser Pro Gln Ser Lys Leu Arg Ser Ala Ala Lys Ser Phe
            580                 585                 590

Ser Gly Ser Pro Ser Ile Leu
            595

<210> SEQ ID NO 80
<211> LENGTH: 254
<212> TYPE: PRT
<213> ORGANISM: Adiantum raddianum

<400> SEQUENCE: 80

Asp Leu Leu Lys Asp Arg Ser Asp Val Gln Cys Leu His Arg Trp Gln
1               5                   10                  15

Lys Val Leu Asn Pro Asn Leu Val Lys Gly Pro Trp Thr Lys Glu Glu
            20                  25                  30

Asp Glu Lys Ile Ala Glu Leu Val Asn Lys Asn Gly Pro Lys Lys Trp
        35                  40                  45

Ser Val Val Ala Arg Ser Leu Pro Gly Arg Ile Gly Lys Gln Cys Arg
    50                  55                  60

Glu Arg Trp His Asn His Leu Asp Pro His Ile Lys Lys Asp Ala Trp
65                  70                  75                  80

Thr Pro Glu Glu Glu Gln Ala Leu Ile Glu Ala His Gln Arg Asn Gly
                85                  90                  95

Asn Lys Trp Ala Glu Ile Ala Lys Ser Leu Pro Gly Arg Thr Asp Asn
            100                 105                 110

Ala Ile Lys Asn His Trp Asn Ser Ser Leu Lys Lys Lys Leu Glu Phe
        115                 120                 125

Thr Asn Leu His Arg Pro Val Leu Asp Arg Leu Lys Glu Leu Glu Gly
    130                 135                 140

Val Ser Ser Gly Val Gly Ser Thr Ile Gly Val Ser Arg Ser Asp Cys
145                 150                 155                 160

His Thr Glu Leu Ala Glu Arg Val Gly Ala Ser Ala Gly Phe Ser Lys
                165                 170                 175

Pro Gly Gln Ser Glu Lys Ala Gly Glu Asn Ser Phe Asn Arg Ile Arg
            180                 185                 190

Asp Thr Asn Arg Asn Arg His Leu Ala Gly Pro Gly Ala Leu Gly Gly
        195                 200                 205

Ser Asn Cys Leu Ser Pro Phe Arg Thr Glu Ser Val Met Leu Ser Asn
    210                 215                 220

Gln Arg Cys Ser Ser Ile Arg Asn Gly Ser Thr Leu Leu Val Ala Ala
225                 230                 235                 240

Arg Leu Asn Gln Val Ala Ala Glu Asn Asp Val Ala Ser Thr
                245                 250

<210> SEQ ID NO 81
<211> LENGTH: 197
<212> TYPE: PRT
<213> ORGANISM: Hordeum vulgare

<400> SEQUENCE: 81

```
Glu Cys Phe Pro Gly Arg Thr Asp Val Gln Cys Leu His Arg Trp Gln
1               5                   10                  15

Lys Val Leu Asn Pro Glu Leu Ile Lys Gly Pro Trp Ser Lys Glu Glu
            20                  25                  30

Asp Asp Ile Ile Val Glu Met Val Lys Lys Tyr Gly Pro Lys Lys Trp
        35                  40                  45

Ser Thr Ile Ala Gln Ala Leu Pro Gly Arg Ile Gly Lys Gln Cys Arg
    50                  55                  60

Glu Arg Trp His Asn His Leu Asn Pro Gly Ile Asn Lys Asp Ala Trp
65                  70                  75                  80

Thr Gln Glu Glu Glu Ile Thr Leu Ile His Ala His Arg Met Tyr Gly
                85                  90                  95

Asn Lys Trp Ala Glu Leu Thr Lys Phe Leu Pro Gly Lys Thr Asp Asn
            100                 105                 110

Ser Ile Lys Asn His Trp Asn Ser Val Lys Lys Ile Gly Ser
            115                 120                 125

Tyr Met Ser Ser Gly Leu Leu Ala Gln Val Ser Arg Leu Pro Leu Val
130                 135                 140

Glu His His Ala His Phe Ser Ser Pro Ala Ile Thr Gln Gln Asn
145                 150                 155                 160

Ser Glu Asp Ser Glu Ser Asn Ala Val Arg Glu Val Glu Asp Ser Ser
                165                 170                 175

Gly Cys Ser Gln Ser Ser Leu Gly Ile Val Ser Arg Lys Cys Arg
                180                 185                 190

His Ala Ser Leu Gly
            195

<210> SEQ ID NO 82
<211> LENGTH: 98
<212> TYPE: PRT
<213> ORGANISM: Secale cereale

<400> SEQUENCE: 82

Pro Glu Leu Val Lys Gly Pro Trp Ser Lys Glu Glu Asp Val Ile
1               5                   10                  15

Ile Gln Met Val Lys Lys Tyr Gly Pro Thr Lys Trp Ser Thr Ile Ala
            20                  25                  30

Gln Ala Leu Pro Gly Arg Ile Gly Lys Gln Cys Arg Glu Arg Trp His
        35                  40                  45

Asn His Leu Asn Pro Gly Ile Asn Lys Asp Ala Trp Thr Gln Glu Glu
    50                  55                  60

Glu Ile Arg Leu Ile Gln Ala His Arg Ile Tyr Gly Asn Lys Trp Ala
65                  70                  75                  80

Glu Leu Ser Lys Phe Leu Pro Gly Arg Thr Asp Asn Ala Ile Lys Asn
                85                  90                  95

His Trp

<210> SEQ ID NO 83
<211> LENGTH: 566
<212> TYPE: PRT
<213> ORGANISM: Papaver rhoeas

<400> SEQUENCE: 83

Ser Ser Pro Ser Pro Ala Ile Lys Ser Ser Asp Glu Ser Glu Lys Ile
1               5                   10                  15
```

```
Val Asp Met Asp Asp Ala Glu Met Met Val Asp Val Asp
         20                  25                  30

Val Asp Val Asp Val Glu Val Arg Cys Leu Glu Asn Lys Gln Glu Thr
             35                  40                  45

Pro Asn Ser Ser Ser Val Ser Asp Glu Glu Glu Asp Leu Asn
 50                  55                  60

Cys Ser Gly Ser Ser Leu Ser Val Arg Ser Ala Ser Ser Asn Arg Arg
 65                  70                  75                  80

Ile Ser Gly Pro Ile Arg Arg Ala Lys Gly Gly Trp Thr Pro Glu Glu
                 85                  90                  95

Asp Glu Lys Leu Arg Lys Ala Val Glu Ser Phe Lys Gly Lys Asn Trp
             100                 105                 110

Lys Lys Ile Ala Ala Cys Leu Pro His Arg Thr Glu Leu Gln Cys Leu
             115                 120                 125

His Arg Trp Gln Lys Val Leu His Pro Asp Leu Val Lys Gly Pro Trp
130                 135                 140

Thr Leu Glu Glu Asp Asp Lys Ile Met Glu Leu Val Ser Lys Tyr Gly
145                 150                 155                 160

Pro Ser Lys Trp Ser Leu Ile Ala Lys Glu Leu Pro Gly Arg Ile Gly
                165                 170                 175

Lys Gln Cys Arg Glu Arg Trp His Asn His Leu Asn Pro Glu Ile Lys
             180                 185                 190

Arg Asp Ala Trp Thr Val Glu Glu Val Ala Leu Met Asn Ala His
             195                 200                 205

Arg Leu Tyr Gly Asn Lys Trp Ala Glu Ile Ala Lys Val Leu Pro Gly
             210                 215                 220

Arg Thr Asp Asn Ala Ile Lys Asn Leu Trp Asn Ser Ser Leu Lys Lys
225                 230                 235                 240

Lys Leu Asp Phe Tyr Leu Ser Ser Gly Gln Leu Pro Pro Leu Gly Pro
                245                 250                 255

Val Leu Lys Thr Glu Asp Tyr Ala Leu Ala Met Ser Arg Ser Ser Ala
             260                 265                 270

Ala Gly Asn Ser Ile Ile Cys Leu Asp Glu Glu Ile Asn Thr Gly Thr
             275                 280                 285

Gln Arg Ser Leu Glu Lys Asp Asp Ser Asn Lys Phe Gly Glu Gly Thr
             290                 295                 300

Met Val Leu Val Gln Pro Ser Thr Pro Glu Phe Leu Asp Arg Glu Val
305                 310                 315                 320

Pro Thr Gly Val Arg Ala Ile Lys Ser Ser Asn Ser Asp Asp Ile Glu
                325                 330                 335

Gly Lys Gln Leu Ala Ser Glu Asn Tyr Tyr Ser Cys Ser Lys Ser Phe
             340                 345                 350

Ser Thr Pro Asn Pro Val Gln Tyr Arg Ser Ser Ala Val Ala Asp Pro
             355                 360                 365

Glu Lys Asn Ile Ala Ala Thr Thr Leu Gln Met Ala Val Pro Val Ser
             370                 375                 380

Ser Pro Ser Leu Phe Glu Met Ser Asp Ser Asn Ser Val Leu Ser Pro
385                 390                 395                 400

Ser Ser Phe Leu Thr Pro Pro Arg Ile Arg Asn Asn Gly Leu Asp Leu
                405                 410                 415

Gln Ser Ala Glu Ser Ile Leu Lys Asn Ala Ala Lys Ser Phe Gln Asn
             420                 425                 430

Thr Pro Ser Ile Leu Arg Lys Arg Arg Arg Glu Ala Gly Gly Thr Pro
```

```
                    435                 440                 445
Asn Arg Ile Val Gln Thr Asn Gly Leu Thr Ala Glu Asp Lys Leu His
        450                 455                 460

Ser Leu Glu Arg Glu Lys Ile Glu Asp Cys Lys Glu Thr Pro Gly Ser
465                 470                 475                 480

Met Glu Ser Asn Ser Ser Thr Gly Arg Val Asn Ser Thr Ile Arg Leu
                485                 490                 495

Phe Tyr Thr Arg Lys Lys His Arg Pro Cys Arg Ser Arg Val Glu Arg
            500                 505                 510

Pro Asp Ala Cys Lys Ser Leu Glu Lys Gln Leu Glu Ser Thr Leu Asp
        515                 520                 525

Gly Val Asn Thr Gly Asn Ser Gln Tyr Glu Ser Met Lys Ser Ala Ser
    530                 535                 540

Asp Gln Gln Gly Lys Ser Thr Thr Lys Glu Asp Gly His Asp Pro Leu
545                 550                 555                 560

Gln Asn Ser Val Ala Ser
                565

<210> SEQ ID NO 84
<211> LENGTH: 37
<212> TYPE: DNA
<213> ORGANISM: Artificial Sequence
<220> FEATURE:
<223> OTHER INFORMATION: Oligonucleotide to act as a primer for PCR

<400> SEQUENCE: 84
cccaagctta aattcggaca aatagagcgt agtcaac                              37

<210> SEQ ID NO 85
<211> LENGTH: 26
<212> TYPE: DNA
<213> ORGANISM: Artificial Sequence
<220> FEATURE:
<223> OTHER INFORMATION: Oligonucleotide to act as a primer for PCR

<400> SEQUENCE: 85
gccatcttct ctcctccgta taagag                                         26

<210> SEQ ID NO 86
<211> LENGTH: 29
<212> TYPE: DNA
<213> ORGANISM: Artificial Sequence
<220> FEATURE:
<223> OTHER INFORMATION: Oligonucleotide to act as a primer for PCR

<400> SEQUENCE: 86
cccaagcttc tcgttaagaa cccttgatc                                      29

<210> SEQ ID NO 87
<211> LENGTH: 28
<212> TYPE: DNA
<213> ORGANISM: Artificial Sequence
<220> FEATURE:
<223> OTHER INFORMATION: Oligonucleotide to act as a primer for PCR

<400> SEQUENCE: 87
gccatcttct acacacaaaa tcgaaacc                                       28

<210> SEQ ID NO 88
<211> LENGTH: 640
<212> TYPE: PRT
<213> ORGANISM: Homo sapiens
```

```
<400> SEQUENCE: 88

Met Ala Arg Arg Pro Arg His Ser Ile Tyr Ser Ser Asp Glu Asp
1               5                   10                  15

Glu Asp Phe Glu Met Cys Asp His Asp Tyr Asp Gly Leu Leu Pro Lys
            20                  25                  30

Ser Gly Lys Arg His Leu Gly Lys Thr Arg Trp Thr Arg Glu Glu Asp
        35                  40                  45

Glu Lys Leu Lys Lys Leu Val Glu Gln Asn Gly Thr Asp Asp Trp Lys
    50                  55                  60

Val Ile Ala Asn Tyr Leu Pro Asn Arg Thr Asp Val Gln Cys Gln His
65                  70                  75                  80

Arg Trp Gln Lys Val Leu Asn Pro Glu Leu Ile Lys Gly Pro Trp Thr
                85                  90                  95

Lys Glu Glu Asp Gln Arg Val Ile Glu Leu Val Gln Lys Tyr Gly Pro
            100                 105                 110

Lys Arg Trp Ser Val Ile Ala Lys His Leu Lys Gly Arg Ile Gly Lys
        115                 120                 125

Gln Cys Arg Glu Arg Trp His Asn His Leu Asn Pro Glu Val Lys Lys
130                 135                 140

Thr Ser Trp Thr Glu Glu Asp Arg Ile Ile Tyr Gln Ala His Lys
145                 150                 155                 160

Arg Leu Gly Asn Arg Trp Ala Glu Ile Ala Lys Leu Leu Pro Gly Arg
                165                 170                 175

Thr Asp Asn Ala Ile Lys Asn His Trp Asn Ser Thr Met Arg Arg Lys
            180                 185                 190

Val Glu Gln Glu Gly Tyr Leu Gln Glu Ser Ser Lys Ala Ser Gln Pro
        195                 200                 205

Ala Val Ala Thr Ser Phe Gln Lys Asn Ser His Leu Met Gly Phe Ala
    210                 215                 220

Gln Ala Pro Pro Thr Ala Gln Leu Pro Ala Thr Gly Gln Pro Thr Val
225                 230                 235                 240

Asn Asn Asp Tyr Ser Tyr Tyr His Ile Ser Glu Ala Gln Asn Val Ser
                245                 250                 255

Ser His Val Pro Tyr Pro Val Ala Leu His Val Asn Ile Val Asn Val
            260                 265                 270

Pro Gln Pro Ala Ala Ala Ile Gln Arg His Tyr Asn Asp Glu Asp
        275                 280                 285

Pro Glu Lys Glu Lys Arg Ile Lys Glu Leu Glu Leu Leu Met Ser
290                 295                 300

Thr Glu Asn Glu Leu Lys Gly Gln Gln Val Leu Pro Thr Gln Asn His
305                 310                 315                 320

Thr Cys Ser Tyr Pro Gly Trp His Ser Thr Thr Ile Ala Asp His Thr
                325                 330                 335

Arg Pro His Gly Asp Ser Ala Pro Val Ser Cys Leu Gly Glu His His
            340                 345                 350

Ser Thr Pro Ser Leu Pro Ala Asp Pro Gly Ser Leu Pro Glu Glu Ser
        355                 360                 365

Ala Ser Pro Ala Arg Cys Met Ile Val His Gln Gly Thr Ile Leu Asp
    370                 375                 380

Asn Val Lys Asn Leu Leu Glu Phe Ala Glu Thr Leu Gln Phe Ile Asp
385                 390                 395                 400

Ser Phe Leu Asn Thr Ser Ser Asn His Glu Asn Ser Asp Leu Glu Met
```

```
                            405                 410                 415

Pro Ser Leu Thr Ser Thr Pro Leu Ile Gly His Lys Leu Thr Val Thr
            420                 425                 430

Thr Pro Phe His Arg Asp Gln Thr Val Lys Thr Gln Lys Glu Asn Thr
            435                 440                 445

Val Phe Arg Thr Pro Ala Ile Lys Arg Ser Ile Leu Glu Ser Ser Pro
            450                 455                 460

Arg Thr Pro Thr Pro Phe Lys His Ala Leu Ala Ala Gln Glu Ile Lys
465                 470                 475                 480

Tyr Gly Pro Leu Lys Met Leu Pro Gln Thr Pro Ser His Leu Val Glu
                485                 490                 495

Asp Leu Gln Asp Val Ile Lys Gln Glu Ser Asp Glu Ser Gly Ile Val
            500                 505                 510

Ala Glu Phe Gln Glu Asn Gly Pro Pro Leu Leu Lys Lys Ile Lys Gln
            515                 520                 525

Glu Val Glu Ser Pro Thr Asp Lys Ser Gly Asn Phe Phe Cys Ser His
            530                 535                 540

His Trp Glu Gly Asp Ser Leu Asn Thr Gln Leu Phe Thr Gln Thr Ser
545                 550                 555                 560

Pro Val Ala Asp Ala Pro Asn Ile Leu Thr Ser Ser Val Leu Met Ala
            565                 570                 575

Pro Ala Ser Glu Asp Glu Asp Asn Val Leu Lys Ala Phe Thr Val Pro
            580                 585                 590

Lys Asn Arg Ser Leu Ala Ser Pro Leu Gln Pro Cys Ser Ser Thr Trp
            595                 600                 605

Glu Pro Ala Ser Cys Gly Lys Met Glu Glu Gln Met Thr Ser Ser Ser
610                 615                 620

Gln Ala Arg Lys Tyr Val Asn Ala Phe Ser Ala Arg Thr Leu Val Met
625                 630                 635                 640

<210> SEQ ID NO 89
<211> LENGTH: 10
<212> TYPE: PRT
<213> ORGANISM: Artificial Sequence
<220> FEATURE:
<223> OTHER INFORMATION: Designed amino acid sequence

<400> SEQUENCE: 89

Thr Pro Ser Ile Leu Lys Lys Arg His Arg
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Designed amino acid sequence, X stands for any
      amino acid residue
<220> FEATURE:
<221> NAME/KEY: MISC_FEATURE
<222> LOCATION: (2)..(2)
<223> OTHER INFORMATION: X stands for any amino acid residue
<220> FEATURE:
<221> NAME/KEY: MISC_FEATURE
<222> LOCATION: (3)..(3)
<223> OTHER INFORMATION: X stands for any amino acid residue
<220> FEATURE:
<221> NAME/KEY: MISC_FEATURE
<222> LOCATION: (6)..(6)
<223> OTHER INFORMATION: X stands for any amino acid residue
<220> FEATURE:
<221> NAME/KEY: MISC_FEATURE
```

```
<222> LOCATION: (10)..(10)
<223> OTHER INFORMATION: X stands for any amino acid residue

<400> SEQUENCE: 90

Asn Xaa Xaa Thr Pro Xaa Arg Leu Trp Xaa
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Designed amino acid sequence, X stands for any
      amino acid residue
<220> FEATURE:
<221> NAME/KEY: MISC_FEATURE
<222> LOCATION: (7)..(7)
<223> OTHER INFORMATION: X stands for any amino acid residue
<220> FEATURE:
<221> NAME/KEY: MISC_FEATURE
<222> LOCATION: (9)..(9)
<223> OTHER INFORMATION: X stands for any amino acid residue

<400> SEQUENCE: 91

Pro Pro Arg Phe Pro Ser Xaa Asp Xaa Pro Phe
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Designed amino acid sequence, X stands for any
      amino acid residue in positions 3, 4, 7 and 8, for S or T in
      position 2, for D or E in position 6, and for L or I or V in
      position 9
<220> FEATURE:
<221> NAME/KEY: MISC_FEATURE
<222> LOCATION: (2)..(2)
<223> OTHER INFORMATION: X stands for S or T
<220> FEATURE:
<221> NAME/KEY: MISC_FEATURE
<222> LOCATION: (3)..(3)
<223> OTHER INFORMATION: X stands for any amino acid residue
<220> FEATURE:
<221> NAME/KEY: MISC_FEATURE
<222> LOCATION: (4)..(4)
<223> OTHER INFORMATION: X stands for any amino acid residue
<220> FEATURE:
<221> NAME/KEY: MISC_FEATURE
<222> LOCATION: (7)..(7)
<223> OTHER INFORMATION: X stands for any amino acid residue
<220> FEATURE:
<221> NAME/KEY: MISC_FEATURE
<222> LOCATION: (8)..(8)
<223> OTHER INFORMATION: X stands for any amino acid residue
<220> FEATURE:
<221> NAME/KEY: MISC_FEATURE
<222> LOCATION: (6)..(6)
<223> OTHER INFORMATION: X stands for D or E
<220> FEATURE:
<221> NAME/KEY: MISC_FEATURE
<222> LOCATION: (9)..(9)
<223> OTHER INFORMATION: X stands for L or I or V

<400> SEQUENCE: 92

Trp Xaa Xaa Xaa Glu Xaa Xaa Xaa Xaa
1               5

<210> SEQ ID NO 93
<211> LENGTH: 150
<212> TYPE: PRT
<213> ORGANISM: Artificial Sequence
```

```
<220> FEATURE:
<223> OTHER INFORMATION: Designed amino acid sequence, X stands for H,
      W, Y or F in 16 & 9 3, for K, H or R in 19, 67, 102, 123, 129, 134
      & 150, for S, T, G , C or A in 32, 54, 77, 135, 138 & 146, for D
      or E in 33 & 110, for L, I or V in 34, 49, 61, 65, 76 & 127, and
      for any residue in others
<220> FEATURE:
<221> NAME/KEY: MISC_FEATURE
<222> LOCATION: (3)..(3)
<223> OTHER INFORMATION: X stands for any amino acid residue
<220> FEATURE:
<221> NAME/KEY: MISC_FEATURE
<222> LOCATION: (7)..(8)
<223> OTHER INFORMATION: X stands for any amino acid residue
<220> FEATURE:
<221> NAME/KEY: MISC_FEATURE
<222> LOCATION: (10)..(12)
<223> OTHER INFORMATION: X stands for any amino acid residue
<220> FEATURE:
<221> NAME/KEY: MISC_FEATURE
<222> LOCATION: (14)..(15)
<223> OTHER INFORMATION: X stands for any amino acid residue
<220> FEATURE:
<221> NAME/KEY: MISC_FEATURE
<222> LOCATION: (17)..(17)
<223> OTHER INFORMATION: X stands for any amino acid residue
<220> FEATURE:
<221> NAME/KEY: MISC_FEATURE
<222> LOCATION: (20)..(20)
<223> OTHER INFORMATION: X stands for any amino acid residue
<220> FEATURE:
<221> NAME/KEY: MISC_FEATURE
<222> LOCATION: (23)..(23)
<223> OTHER INFORMATION: X stands for any amino acid residue
<220> FEATURE:
<221> NAME/KEY: MISC_FEATURE
<222> LOCATION: (26)..(30)
<223> OTHER INFORMATION: X stands for any amino acid residue
<220> FEATURE:
<221> NAME/KEY: MISC_FEATURE
<222> LOCATION: (45)..(45)
<223> OTHER INFORMATION: X stands for any amino acid residue
<220> FEATURE:
<221> NAME/KEY: MISC_FEATURE
<222> LOCATION: (47)..(47)
<223> OTHER INFORMATION: X stands for any amino acid residue
<220> FEATURE:
<221> NAME/KEY: MISC_FEATURE
<222> LOCATION: (52)..(52)
<223> OTHER INFORMATION: X stands for any amino acid residue
<220> FEATURE:
<221> NAME/KEY: MISC_FEATURE
<222> LOCATION: (55)..(55)
<223> OTHER INFORMATION: X stands for any amino acid residue
<220> FEATURE:
<221> NAME/KEY: MISC_FEATURE
<222> LOCATION: (59)..(60)
<223> OTHER INFORMATION: X stands for any amino acid residue
<220> FEATURE:
<221> NAME/KEY: MISC_FEATURE
<222> LOCATION: (62)..(64)
<223> OTHER INFORMATION: X stands for any amino acid residue
<220> FEATURE:
<221> NAME/KEY: MISC_FEATURE
<222> LOCATION: (66)..(66)
<223> OTHER INFORMATION: X stands for any amino acid residue
<220> FEATURE:
<221> NAME/KEY: MISC_FEATURE
<222> LOCATION: (68)..(68)
<223> OTHER INFORMATION: X stands for any amino acid residue
<220> FEATURE:
<221> NAME/KEY: MISC_FEATURE
<222> LOCATION: (70)..(71)
<223> OTHER INFORMATION: X stands for any amino acid residue
<220> FEATURE:
<221> NAME/KEY: MISC_FEATURE
<222> LOCATION: (75)..(75)
<223> OTHER INFORMATION: X stands for any amino acid residue
<220> FEATURE:
```

```
<221> NAME/KEY: MISC_FEATURE
<222> LOCATION: (78)..(81)
<223> OTHER INFORMATION: X stands for any amino acid residue
<220> FEATURE:
<221> NAME/KEY: MISC_FEATURE
<222> LOCATION: (97)..(97)
<223> OTHER INFORMATION: X stands for any amino acid residue
<220> FEATURE:
<221> NAME/KEY: MISC_FEATURE
<222> LOCATION: (99)..(99)
<223> OTHER INFORMATION: X stands for any amino acid residue
<220> FEATURE:
<221> NAME/KEY: MISC_FEATURE
<222> LOCATION: (101)..(101)
<223> OTHER INFORMATION: X stands for any amino acid residue
<220> FEATURE:
<221> NAME/KEY: MISC_FEATURE
<222> LOCATION: (103)..(104)
<223> OTHER INFORMATION: X stands for any amino acid residue
<220> FEATURE:
<221> NAME/KEY: MISC_FEATURE
<222> LOCATION: (107)..(108)
<223> OTHER INFORMATION: X stands for any amino acid residue
<220> FEATURE:
<221> NAME/KEY: MISC_FEATURE
<222> LOCATION: (111)..(112)
<223> OTHER INFORMATION: X stands for any amino acid residue
<220> FEATURE:
<221> NAME/KEY: MISC_FEATURE
<222> LOCATION: (114)..(116)
<223> OTHER INFORMATION: X stands for any amino acid residue
<220> FEATURE:
<221> NAME/KEY: MISC_FEATURE
<222> LOCATION: (118)..(120)
<223> OTHER INFORMATION: X stands for any amino acid residue
<220> FEATURE:
<221> NAME/KEY: MISC_FEATURE
<222> LOCATION: (128)..(128)
<223> OTHER INFORMATION: X stands for any amino acid residue
<220> FEATURE:
<221> NAME/KEY: MISC_FEATURE
<222> LOCATION: (130)..(130)
<223> OTHER INFORMATION: X stands for any amino acid residue
<220> FEATURE:
<221> NAME/KEY: MISC_FEATURE
<222> LOCATION: (132)..(132)
<223> OTHER INFORMATION: X stands for any amino acid residue
<220> FEATURE:
<221> NAME/KEY: MISC_FEATURE
<222> LOCATION: (142)..(142)
<223> OTHER INFORMATION: X stands for any amino acid residue
<220> FEATURE:
<221> NAME/KEY: MISC_FEATURE
<222> LOCATION: (144)..(144)
<223> OTHER INFORMATION: X stands for any amino acid residue
<220> FEATURE:
<221> NAME/KEY: MISC_FEATURE
<222> LOCATION: (147)..(147)
<223> OTHER INFORMATION: X stands for any amino acid residue
<220> FEATURE:
<221> NAME/KEY: MISC_FEATURE
<222> LOCATION: (16)..(16)
<223> OTHER INFORMATION: X stands for H or W or Y or F
<220> FEATURE:
<221> NAME/KEY: MISC_FEATURE
<222> LOCATION: (93)..(93)
<223> OTHER INFORMATION: X stands for H or W or Y or F
<220> FEATURE:
<221> NAME/KEY: MISC_FEATURE
<222> LOCATION: (19)..(19)
<223> OTHER INFORMATION: X stands for K or H or R
<220> FEATURE:
<221> NAME/KEY: MISC_FEATURE
<222> LOCATION: (123)..(123)
<223> OTHER INFORMATION: X stands for K or H or R
<220> FEATURE:
<221> NAME/KEY: MISC_FEATURE
<222> LOCATION: (102)..(102)
<223> OTHER INFORMATION: X stands for K or H or R
```

```
<220> FEATURE:
<221> NAME/KEY: MISC_FEATURE
<222> LOCATION: (67)..(67)
<223> OTHER INFORMATION: X stands for K or H or R
<220> FEATURE:
<221> NAME/KEY: MISC_FEATURE
<222> LOCATION: (129)..(129)
<223> OTHER INFORMATION: X stands for K or H or R
<220> FEATURE:
<221> NAME/KEY: MISC_FEATURE
<222> LOCATION: (134)..(134)
<223> OTHER INFORMATION: X stands for K or H or R
<220> FEATURE:
<221> NAME/KEY: MISC_FEATURE
<222> LOCATION: (150)..(150)
<223> OTHER INFORMATION: X stands for K or H or R
<220> FEATURE:
<221> NAME/KEY: MISC_FEATURE
<222> LOCATION: (32)..(32)
<223> OTHER INFORMATION: X stands for S or T or G or C or A
<220> FEATURE:
<221> NAME/KEY: MISC_FEATURE
<222> LOCATION: (135)..(135)
<223> OTHER INFORMATION: X stands for S or T or G or C or A
<220> FEATURE:
<221> NAME/KEY: MISC_FEATURE
<222> LOCATION: (138)..(138)
<223> OTHER INFORMATION: X stands for S or T or G or C or A
<220> FEATURE:
<221> NAME/KEY: MISC_FEATURE
<222> LOCATION: (146)..(146)
<223> OTHER INFORMATION: X stands for S or T or G or C or A
<220> FEATURE:
<221> NAME/KEY: MISC_FEATURE
<222> LOCATION: (33)..(33)
<223> OTHER INFORMATION: X stands for D or E
<220> FEATURE:
<221> NAME/KEY: MISC_FEATURE
<222> LOCATION: (110)..(110)
<223> OTHER INFORMATION: X stands for D or E
<220> FEATURE:
<221> NAME/KEY: MISC_FEATURE
<222> LOCATION: (34)..(34)
<223> OTHER INFORMATION: X stands for L or I or V
<220> FEATURE:
<221> NAME/KEY: MISC_FEATURE
<222> LOCATION: (49)..(49)
<223> OTHER INFORMATION: X stands for L or I or V
<220> FEATURE:
<221> NAME/KEY: MISC_FEATURE
<222> LOCATION: (76)..(76)
<223> OTHER INFORMATION: X stands for L or I or V
<220> FEATURE:
<221> NAME/KEY: MISC_FEATURE
<222> LOCATION: (127)..(127)
<223> OTHER INFORMATION: X stands for L or I or V
<220> FEATURE:
<221> NAME/KEY: MISC_FEATURE
<222> LOCATION: (54)..(54)
<223> OTHER INFORMATION: X stands for S or T or G or C or A
<220> FEATURE:
<221> NAME/KEY: MISC_FEATURE
<222> LOCATION: (77)..(77)
<223> OTHER INFORMATION: X stands for S or T or G or C or A
<220> FEATURE:
<221> NAME/KEY: MISC_FEATURE
<222> LOCATION: (61)..(61)
<223> OTHER INFORMATION: X stands for L or I or V
<220> FEATURE:
<221> NAME/KEY: MISC_FEATURE
<222> LOCATION: (65)..(65)
<223> OTHER INFORMATION: X stands for L or I or V

<400> SEQUENCE: 93

Trp Thr Xaa Glu Glu Asp Xaa Xaa Leu Xaa Xaa Xaa Val Xaa Xaa Xaa
1               5                   10                  15

Xaa Gly Xaa Xaa Trp Lys Xaa Ile Ala Xaa Xaa Xaa Xaa Xaa Arg Xaa
```

```
                   20                  25                  30
Xaa Xaa Gln Cys Leu His Arg Trp Gln Lys Val Leu Xaa Pro Xaa Leu
        35                  40                  45

Xaa Lys Gly Xaa Trp Xaa Xaa Glu Glu Asp Xaa Xaa Xaa Xaa Xaa Xaa
 50                  55                  60

Xaa Xaa Xaa Xaa Gly Xaa Xaa Lys Trp Ser Xaa Xaa Xaa Xaa Xaa Xaa
 65                  70                  75                  80

Xaa Gly Arg Ile Gly Lys Gln Cys Arg Glu Arg Trp Xaa Asn His Leu
                 85                  90                  95

Xaa Pro Xaa Ile Xaa Xaa Xaa Xaa Trp Thr Xaa Xaa Glu Xaa Xaa Xaa
            100                 105                 110

Leu Xaa Xaa Xaa His Xaa Xaa Xaa Gly Asn Xaa Trp Ala Glu Xaa Xaa
        115                 120                 125

Xaa Xaa Leu Xaa Gly Xaa Xaa Asp Asn Xaa Ile Lys Asn Xaa Trp Xaa
    130                 135                 140

Ser Xaa Xaa Lys Lys Xaa
145                 150

<210> SEQ ID NO 94
<211> LENGTH: 22
<212> TYPE: PRT
<213> ORGANISM: Artificial Sequence
<220> FEATURE:
<223> OTHER INFORMATION: Designed amino acid sequence, X stands for K or
      R in 4, for L or V in 11, for S or T in 12, for L, I or V in 14,
      for D or E in 16 & 20, and for any amino acid residue in others
<220> FEATURE:
<221> NAME/KEY: MISC_FEATURE
<222> LOCATION: (7)..(7)
<223> OTHER INFORMATION: X stands for any amino acid residue
<220> FEATURE:
<221> NAME/KEY: MISC_FEATURE
<222> LOCATION: (9)..(9)
<223> OTHER INFORMATION: X stands for any amino acid residue
<220> FEATURE:
<221> NAME/KEY: MISC_FEATURE
<222> LOCATION: (15)..(15)
<223> OTHER INFORMATION: X stands for any amino acid residue
<220> FEATURE:
<221> NAME/KEY: MISC_FEATURE
<222> LOCATION: (19)..(19)
<223> OTHER INFORMATION: X stands for any amino acid residue
<220> FEATURE:
<221> NAME/KEY: MISC_FEATURE
<222> LOCATION: (4)..(4)
<223> OTHER INFORMATION: X stands for K or R
<220> FEATURE:
<221> NAME/KEY: MISC_FEATURE
<222> LOCATION: (17)..(17)
<223> OTHER INFORMATION: X stands for K or R
<220> FEATURE:
<221> NAME/KEY: MISC_FEATURE
<222> LOCATION: (11)..(11)
<223> OTHER INFORMATION: X stands for L or V
<220> FEATURE:
<221> NAME/KEY: MISC_FEATURE
<222> LOCATION: (12)..(12)
<223> OTHER INFORMATION: X stands for S or T
<220> FEATURE:
<221> NAME/KEY: MISC_FEATURE
<222> LOCATION: (14)..(14)
<223> OTHER INFORMATION: X stands for L or I or V
<220> FEATURE:
<221> NAME/KEY: MISC_FEATURE
<222> LOCATION: (16)..(16)
<223> OTHER INFORMATION: X stands for D or E
<220> FEATURE:
<221> NAME/KEY: MISC_FEATURE
<222> LOCATION: (20)..(20)
<223> OTHER INFORMATION: X stands for D or E
```

```
<400> SEQUENCE: 94

Ser Ile Leu Xaa Lys Arg Xaa Arg Xaa Leu Xaa Xaa Pro Xaa Xaa Xaa
1               5                   10                  15

Xaa Arg Xaa Xaa Lys Lys
            20

<210> SEQ ID NO 95
<211> LENGTH: 7
<212> TYPE: PRT
<213> ORGANISM: Artificial Sequence
<220> FEATURE:
<223> OTHER INFORMATION: Designed amino acid sequence, X stands for K or
      R or D or E or H in position 7 and for any amino acid residue in
      position 5
<220> FEATURE:
<221> NAME/KEY: MISC_FEATURE
<222> LOCATION: (5)..(5)
<223> OTHER INFORMATION: X stands for any amino acid residue
<220> FEATURE:
<221> NAME/KEY: MISC_FEATURE
<222> LOCATION: (7)..(7)
<223> OTHER INFORMATION: X stands for K or R or D or E or H

<400> SEQUENCE: 95

Ser Cys Ser Ser Xaa Ser Xaa
1               5

<210> SEQ ID NO 96
<211> LENGTH: 33
<212> TYPE: DNA
<213> ORGANISM: Artificial Sequence
<220> FEATURE:
<223> OTHER INFORMATION: Oligonucleotide to act as a primer for PCR

<400> SEQUENCE: 96
aactgcagcg gataaaccaa ttttcaaatg ata                                33

<210> SEQ ID NO 97
<211> LENGTH: 33
<212> TYPE: DNA
<213> ORGANISM: Artificial Sequence
<220> FEATURE:
<223> OTHER INFORMATION: Oligonucleotide to act as a primer for PCR

<400> SEQUENCE: 97
cgggatccct ttgatcctct ccgatctctc tat                                33

<210> SEQ ID NO 98
<211> LENGTH: 1700
<212> TYPE: DNA
<213> ORGANISM: Arabidopsis thaliana

<400> SEQUENCE: 98
cggataaacc aattttcaaa tgataatatt tgtatataat gtttctgtat acagggggcgg    60 acccacgtta gtcttgggtg gggcatgtgc ccgatactca attctataaa tcttatataa   120
gtttgcatta tgtaattaaa aatgtattta gtttagtggt ttttacttaa atggtgcccc   180
acattaaccc aagtttaaac cttgctgatg tcttttttatt gattttttat aactgtaccc   240
atataagatt atttcctgga ttagccatct gtatattaat aaatcgtttc ctgtggttgt   300
gcgatgcata accgtccaag aaagtcgtat attttttaata catgtgttaa aataggtttt   360
aagtgagaat ttttttaact tgtggagtgt ggagtgtaga gtgtagatgt acattaccta   420
tatatttatc caattctgtg taataaagat gttggggcgg cgcctgctgc cacatacaca   480
```

```
ttggattaga agggcaaaag aagttctaat aaggagcaaa ctaatagcca tgaaaattat      540
gaatttacca tactgaaaac aaaggaatta aggttttgaa ttcaatactt gttttgttat      600
atatgatgtt gatgtgacgt atttgtgcgt ttctcatagt gactttgaaa ggaaggctaa      660
acgaatttgc agtaaaagta acagaagaaa cacttcaaaa ttgaattaaa atgaagaaaa      720
aaaagaatga gaaaagtgaa gaagtggtgg ttgtctggta ttaagggtac tcacttctct      780 cctttcaac acagcccgac acacatgtct cttttttttt ttttcataca cacatttcta      840
tttattagtt tcctaaaata aaaattataa aacaaaaagc acacccaccc ataaactaaa      900
gcttttctct ctcatcccac tacaaatctt atatacaagt ttcgcaaatc ttgactcttc      960
acgttgtgga tctatctaga gagataagta agagagagga agagtaagga agaaagtggt     1020
tgaactgtag cagagtctga ggtttgaatc ttgtagttcc cattgaagca tgcttcaccg     1080
ttttttccga aggaagttac tcatccactg agagagaaag agggatttgg agatagagaa     1140
agaaatttct cagatgggtt tgtgagaatt cacagcaaga gcaagaaact cctatatctt     1200
cctttgcttc cagagaccag cgtgatcaaa aacaaatatt tttacggtat ctataagaat     1260
cctcccctct ttttcttttt ccttaaagag aattttttg catctttctt aggttccaat      1320
aaatatgcag aagaaagtta aaattttgt accgtcgttg aaccttttaa agacctaatt      1380
aagagacaag atcatactaa gctcataaat cactttctat ttacacatat ataggttatt     1440
aatcttaaac aagatctata ttttatcttt gagattttc aagatttcat caagtgtcac      1500
gttcattcat tgattacatt tcaaatttca ctaagaaagt taaaacacgg atcttttga      1560 gaatatcaag aaagttcttt gaaatatacc aaaagaaatc agtactttca agaatacata     1620 acttttagg ttgtgttaaa taatatttgc ttttgtaata aaggaacaaa attaaataga      1680
gagatcggag aggatcaaag                                                 1700

<210> SEQ ID NO 99
<211> LENGTH: 31
<212> TYPE: DNA
<213> ORGANISM: Artificial Sequence
<220> FEATURE:
<223> OTHER INFORMATION: Oligonucleotide to act as a primer for PCR

<400> SEQUENCE: 99
cgggatccat ggaaagtgat agaataagca c                                     31

<210> SEQ ID NO 100
<211> LENGTH: 44
<212> TYPE: DNA
<213> ORGANISM: Artificial Sequence
<220> FEATURE:
<223> OTHER INFORMATION: Oligonucleotide to act as a primer for PCR

<400> SEQUENCE: 100
ttttcctttt gcggccgctt aacagcctaa atggagtaag acag                       44
```

What is claimed is:

1. A plant comprising an isolated polynucleotide encoding the amino acid sequence of SEQ ID NO:53, wherein the polynucleotide is operably linked to a promoter.

* * * * *